US008114887B2

(12) United States Patent
Barrow et al.

(10) Patent No.: US 8,114,887 B2

(45) Date of Patent: Feb. 14, 2012

(54) SPIROPIPERIDINE COMPOUNDS USEFUL AS BETA-SECRETASE INHIBITORS FOR THE TREATMENT OF ALZHEIMER'S DISEASE

(75) Inventors: James C. Barrow, Harleysville, PA (US); Craig A. Coburn, Royersford, PA (US); Melissa S. Egbertson, Ambler, PA (US); Georgia B. McGaughey, Harleysville, PA (US); Melody A. McWherter, Boyertown, PA (US); Lou Anne Neilson, Sellersville, PA (US); Kenneth E. Rittle, Green Lane, PA (US); Harold G. Selnick, Ambler, PA (US); Shaun R. Stauffer, Schwenksville, PA (US); Zhi-Qiang Yang, Schwenksville, PA (US); Wenjin Yang, Foster City, CA (US); Wanli Lu, Burlingame, CA (US); Bruce Fahr, Foster City, CA (US)

(73) Assignees: Merck, Sharp & Dohme Corp., Rahway, NJ (US); Sunesis Pharmaceuticals, Inc., South San Francisco, CA (US)

( * ) Notice: Subject to any disclaimer, the term of this patent is extended or adjusted under 35 U.S.C. 154(b) by 976 days.

(21) Appl. No.: 11/663,388

(22) PCT Filed: Oct. 12, 2005

(86) PCT No.: PCT/US2005/036752

§ 371 (c)(1),
(2), (4) Date: Mar. 21, 2007

(87) PCT Pub. No.: WO2006/044497

PCT Pub. Date: Apr. 27, 2006

(65) Prior Publication Data

US 2007/0197571 A1 Aug. 23, 2007

Related U.S. Application Data

(60) Provisional application No. 60/618,420, filed on Oct. 13, 2004.

(51) Int. Cl.
*A61K 31/438* (2006.01)
*C07D 411/02* (2006.01)

(52) U.S. Cl. .......................................... 514/278; 546/18

(58) Field of Classification Search .................... 546/18; 514/290
See application file for complete search history.

(56) References Cited

U.S. PATENT DOCUMENTS

| | | | | |
|---|---|---|---|---|
| 3,542,729 | A | 11/1970 | Murayama et al. | |
| 3,639,409 | A | 2/1972 | Murayama et al. | |
| 4,066,615 | A | 1/1978 | Murayama et al. | |
| 5,221,675 | A * | 6/1993 | Chung et al. | 514/278 |
| 5,534,520 | A | 7/1996 | Fisher et al. | |
| 5,852,029 | A | 12/1998 | Fisher et al. | |
| 7,049,321 | B2 | 5/2006 | Fisher et al. | |
| 2004/0067950 | A1 | 4/2004 | Tulshian et al. | |
| 2006/0052406 | A1 | 3/2006 | Fisher et al. | |

FOREIGN PATENT DOCUMENTS

| | | |
|---|---|---|
| DE | 2126187 | 12/1971 |
| DE | 10012859 | 9/2000 |
| EP | 0 272 589 A2 | 12/1987 |
| GB | 1354313 | 5/1974 |
| JP | 46022105 | 6/1971 |
| JP | 48016984 | 7/1973 |
| JP | 03191344 | 8/1991 |
| WO | WO 95/03303 | 2/1995 |
| WO | WO 99/65494 | 12/1999 |
| WO | WO 03/057698 | 7/2003 |
| WO | WO 2004/037800 | 5/2004 |

OTHER PUBLICATIONS

Dorwald, Side Reactions in Organic Synthesis, Preface 2005.*
Dorwald , Side reactions, pp. 8 and 9 , 2005.*
"Neuroscience Drug Discovery," presented at Vanderbilt University Pharmacology Department Seminar (Feb. 18, 2008).
Brana, et al., J. Heterocyclic Chem., 27, 397 "Reaction of N-[(a-acetoxy)-4-pyridylmethyl]-3,5-dimethylbenzamide with Alkyl Isocyanates" 1988.
Chem Registry No. 29096-07-9 (1984).
Chem Registry No. 128221-95-4 (1990).
CAS Registry No. 150358-83-1 (Interchim Intermediates) (Jul. 2002).

* cited by examiner

*Primary Examiner* — Rita Desai
(74) *Attorney, Agent, or Firm* — Keith D. MacMillan; Gerard M. Devlin

(57) ABSTRACT

The present invention is directed to spiropiperidine compounds of formula (I)

(I)

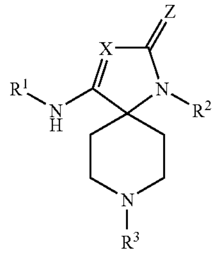

which are inhibitors of the beta-secretase enzyme and that are useful in the treatment of diseases in which the beta-secretase enzyme is involved, such as Alzheimer's disease. The invention is also directed to pharmaceutical compositions comprising these compounds and the use of these compounds and compositions in the treatment of such diseases in which the beta-secretase enzyme is involved.

11 Claims, No Drawings

SPIROPIPERIDINE COMPOUNDS USEFUL AS BETA-SECRETASE INHIBITORS FOR THE TREATMENT OF ALZHEIMER'S DISEASE

CROSS-REFERENCE TO RELATED APPLICATIONS

This application claims priority under 35 U.S.C. §119(e) of U.S. provisional application Ser. No. 60/618,420, filed Oct. 13, 2004.

REFERENCE TO JOINT RESEARCH AGREEMENT

This invention was made as a result of activities undertaken within the scope of a Joint Research Agreement between Merck & Co., Inc. and Sunesis Pharmaceuticals, Inc.

FIELD OF THE INVENTION

The invention is directed to compounds useful as inhibitors of the beta secretase enzyme, and useful in the treatment of diseases in which the beta secretase enzyme is involved, such as Alzheimer's Disease.

BACKGROUND OF THE INVENTION

Alzheimer's disease is characterized by the abnormal deposition of amyloid in the brain in the form of extra-cellular plaques and intra-cellular neurofibrillary tangles. The rate of amyloid accumulation is a combination of the rates of formation, aggregation and egress from the brain. It is generally accepted that the main constituent of amyloid plaques is the 4 kD amyloid protein (βA4, also referred to as Aβ, β-protein and βAP) which is a proteolytic product of a precursor protein of much larger size. The amyloid precursor protein (APP or AβPP) has a receptor-like structure with a large ectodomain, a membrane spanning region and a short cytoplasmic tail. The Aβ domain encompasses parts of both extra-cellular and transmembrane domains of APP, thus its release implies the existence of two distinct proteolytic events to generate its $NH_2$- and COOH-termini. At least two secretory mechanisms exist which release APP from the membrane and generate soluble, COOH-truncated forms of APP ($APP_s$). Proteases that release APP and its fragments from the membrane are termed "secretases." Most $APP_s$ is released by a putative α-secretase which cleaves within the Aβ protein to release α-$APP_s$ and precludes the release of intact Aβ. A minor portion of $APP_s$ is released by a β-secretase ("β-secretase"), which cleaves near the $NH_2$-terminus of APP and produces COOH-terminal fragments (CTFs) which contain the whole Aβ domain.

Thus, the activity of β-secretase or β-site amyloid precursor protein-cleaving enzyme ("BACE") leads to the cleavage of APP, production of Aβ, and accumulation of β amyloid plaques in the brain, which is characteristic of Alzheimer's disease (see R. N. Rosenberg, *Arch. Neurol.*, vol. 59, September 2002, pp. 1367-1368; H. Fukumoto et al, *Arch. Neurol., vol.* 59, September 2002, pp. 1381-1389; J. T. Huse et al, *J. Biol. Chem.*, vol 277, No. 18, issue of May 3, 2002, pp. 16278-16284; K. C. Chen and W. J. Howe, *Biochem. Biophys. Res. Comm*, vol. 292, pp 702-708, 2002). Therefore, therapeutic agents that can inhibit β-secretase or BACE may be useful for the treatment of Alzheimer's disease.

The compounds of the present invention are useful for treating Alzheimer's disease by inhibiting the activity of β-secretase or BACE, thus preventing the formation of insoluble Aβ and arresting the production of Aβ.

SUMMARY OF THE INVENTION

The present invention is directed to novel spiropiperidine compounds represented by general formula (I)

(I)

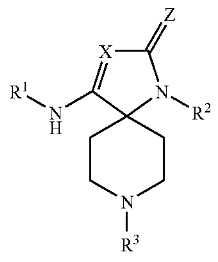

or its tautomer (I')

(I')

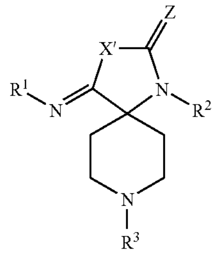

and pharmaceutically acceptable salts thereof, which are useful as inhibitors of the β-secretase enzyme.

The invention is also directed to pharmaceutical compositions which include an effective amount of a compound of formula (I), or pharmaceutically acceptable salts thereof, and a pharmaceutically acceptable carrier. The invention is also directed to methods of treating mammals for diseases in which the β-secretase enzyme is involved, such as Alzheimer's disease, and the use of the compounds and pharmaceutical compositions of the invention in the treatment of such diseases.

DETAILED DESCRIPTION OF THE INVENTION

In one embodiment, the present invention is directed to methods of treating mammals for diseases in which the β-secretase enzyme is involved, such as Alzheimer's disease, by administering a compound of formula (I)

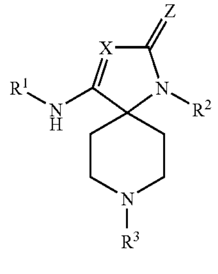

or its tautomer (I')

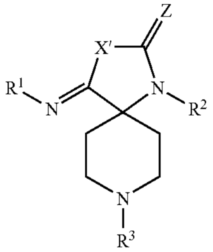

(I')

and pharmaceutically acceptable salts thereof, and individual enantiomers and diastereomers thereof, wherein:

X is $CR^5$ or N;

X' is $CR^5H$ or NH;

Z is O or S;

$R^1$ is selected from the group consisting of (1) hydrogen,
(2) —$C_{1-6}$ alkyl,
(3) —$C_{0-6}$ alkyl-$C_{6-10}$ aryl,
(4) —$C_{0-6}$ alkyl-$C_{5-12}$ heteroaryl,
(5) —$C_{0-6}$ alkyl-$C_{3-12}$ carbocyclic, wherein the carbocyclic group optionally has from one to three ring heteroatoms selected from the group consisting of S, N and O,
(6) —O—$R^6$, and
(7) —$C_{0-6}$ alkyl-$Q^1$-$R^6$, wherein said $R^1$ alkyl moiety is optionally substituted with one or more (a) —$OR^4$,
(b) halogen,
(c) cyano, and
(d) —$NR^4R^{4'}$, said $R^1$ carbocyclic moiety is optionally substituted with one or more (a) —$OR^4$,
(b) =O,
(c) halogen,
(d) cyano,
(e) —C(=O)—$NR^4R^{4'}$,
(f) —$C_{1-6}$ alkyl, wherein said alkyl is optionally substituted with one or more
(I) halogen,
(II) —OH, and
(III) —$C_{6-10}$ aryl,
(g) —$NR^4$—$SO_2$—$R^{4'}$,
(h) —$SO_2$—$R^4$,
(i) —$NR^4$—C(=O)—$R^{4'}$,
(j) —C(=O)—$OR^4$,
(k) —$NR^4R^{4'}$,
(l) —C(=O)—$R^4$, and
(m) —$SO_2$—$NR^4R^{4'}$, and said $R^1$ aryl and heteroaryl moieties are optionally substituted with one or more (a) halogen,
(b) —$C_{1-6}$ alkyl,
(c) —$C_{2-6}$ alkenyl,
(d) —$C_{2-6}$ alkynyl,
(e) —$C_{0-3}$ alkyl-$C_{6-10}$ aryl,
(f) cyano,
(g) —O—$C_{0-3}$ alkyl-$C_{6-10}$ aryl,
(h) —O—$R^4$,
(i) —C(=O)—$NR^4R^{4'}$,
(j)—$NR^4R^{4'}$,
(k) -$Q^2$-$R^7$, and
(l) —$C_{0-3}$ alkyl-$C_{5-12}$ heteroaryl, $Q^1$ and $Q^2$ are selected from the group consisting of (a) —C(=O)—,
(b) —C(=O)—O—,
(c) —C(=O)—$NR^8$—,
(d) —$NR^8$—C(=O)—,
(e) —$S(=O)_n$—,
(f) —$Si(R^8R^9)$—,
(g) —$S(=O)_2$—$R^8$—,
(h) —$R^8$—$S(=O)_2$—,
(i) —O—C(=O)—,
(j) —$NR^8$—C(=O)—O—,
(k) —$SO_2$—$NR^4$—,
(l) —$NR^4SO_2$—,
(m) —$NR^4$ wherein n is 0, 1 or 2;

$R^2$ is selected from the group consisting of (1) hydrogen,
(2) —$C_{1-6}$ alkyl,
(3) —$C_{0-6}$ alkyl-$C_{3-12}$ carbocyclic, wherein the carbocyclic group optionally has from one to three ring heteroatoms selected from the group consisting of S, N and O,
(4) —$C_{0-6}$ alkyl-$C_{6-10}$ aryl,
(5) —$C_{0-6}$ alkyl-$Q^3$-$C_{1-6}$ alkyl,
(6) —$C_{0-6}$ alkyl-$C_{5-12}$ heteroaryl, wherein said $R^2$ alkyl moiety is optionally substituted with one or more (a) halogen
(b) cyano
(c) —$C_{3-8}$ cycloalkyl
(d) —O—$C_{1-6}$alkyl,
(e) OH, and said $R^2$ cycloalkyl moiety is optionally substituted with one or more —$C_{1-6}$ alkyl, and said $R^2$ aryl or heteroaryl moiety is optionally substituted with one or more (a) —$OR^{10}$,
(b) halogen,
(c) -cyano,
(d) —$NO_2$,
(e) -$Q^4$-$C_{1-6}$ alkyl,
(f) —$C_{1-6}$ alkyl, wherein said alkyl is optionally substituted with one or more
(I) halogen, and
(II) cyano,
(g) —$C_{0-3}$ alkyl-$C_{6-10}$ aryl, wherein said aryl is optionally substituted with one or more
(I) halogen,
(II) —$C_{1-6}$ alkyl,
(III) —$C_{2-6}$ alkenyl,
(IV) —$C_{2-6}$ alkynyl,
(V) —O—$C_{1-6}$ alkyl,
(VI) —$SO_2$—$C_{1-6}$ alkyl,
(VII) cyano,
(VIII) —$C_{3-8}$ cycloalkyl,
(IX) —$NO_2$,
(X) —$SO_2$—$NR^4R^4R^{4'}$
(h) —$SO_2$—$C_{1-6}$ alkyl,
(i) —$SO_2$—$NR^4R^{4'}$,
(j) —$NR^4R^{4'}$,
(k) —$C_{3-8}$ cycloalkyl,
(l) —$C_{2-6}$ alkenyl,
(m) —NHC(=O)—$C_{1-6}$ alkyl, wherein said alkyl is optionally substituted with one or more (I) —$NR^4R^{4'}$
(II) OH
(III) —$SO_2R^4$, and
(IV) —$NHSO_2R^4$,
(n) —NHC(=O)—$C_{0-3}$ alkyl-$C_{6-10}$ aryl, wherein said aryl is optionally substituted with one or more
(I) $NR^4R^{4'}$,
(II) OH,
(III) —$SO_2R^4$, and
(IV) —$NHSO_2R^4$,
(o) —$C_{0-3}$ alkyl-$C_{5-12}$ heteroaryl, wherein said heteroaryl is optionally substituted with one or more
(I) halogen,
(II) —$C_{1-6}$ alkyl, and
(III)=O,
(p) —S(=O)$_m$—$C_{0-6}$ alkyl-$C_{6-10}$ aryl,
(q) —$CO_2$—$R^4$,
(r) —C(=O)—$NR^4R^{4'}$,
(s) —$C_{0-6}$ alkyl-$NR^4SO_2$—$R^4$,
(t) —O—$C_{2-6}$ alkenyl,
and m is 0, 1 or 2;
and $Q^3$ and $Q^4$ are selected from the same group as $Q^1$ and $Q^2$;
$R^3$ is selected from the group consisting of
(1) hydrogen,
(2) —$C_{0-3}$ alkyl-$C_{6-10}$ aryl,
(3) —$C_{0-3}$ alkyl-$C_{5-12}$ heteroaryl,
(4) —$C_{0-3}$ alkyl-$C_{3-10}$ carbocyclic, wherein the carbocyclic group optionally has from one to three ring heteroatoms selected from the group consisting of S, N and O,
wherein said $R^3$ alkyl moiety is optionally substituted with one or more
(a) —$OR^{11}$,
(b) halogen,
(c) cyano,
(d) —C(=O)—$NR^4R^{4'}$,
(e) -$Q^5$-$C_{1-6}$ alkyl,
(f) -$Q^5$-H;
and said $R^3$ cycloalkyl moiety is optionally substituted with one or more
(a) —$C_{1-6}$ alkyl,
(b) —$C_{0-3}$ alkyl-$C_{6-10}$ aryl,
and said $R^3$ aryl and heteroaryl moiety is optionally substituted with one or more
(a) —$OR^{12}$,
(b) —$NR^4R^{4'}$,
(c) halogen,
(d) cyano,
(f) —$NO_2$,
(g) $Q^6$-$R^4$, and
(h) —$C_{1-6}$ alkyl, wherein said alkyl is optionally substituted with one or more
(I) halogen,
(II) cyano,
(III) —$C_{1-6}$ alkyl,
(IV) —O—$C_{1-6}$ alkyl,
(V) —$C_{3-8}$ cycloalkyl,
(VI) —C(=O)$C_{1-6}$ alkyl,
(i) —$C_{2-6}$ alkenyl,
(j) —$C_{2-6}$ alkynyl,
(k) —$C_{0-3}$ alkyl-$C_{5-12}$ heteroaryl,
(l) —$C_{2-6}$ alkenyl,
(m) —$C_{0-3}$ alkyl-$C_{6-10}$ aryl, wherein said aryl moiety is optionally substituted with one or more
(I) —$C_{1-6}$ alkyl,
(II) —$C_{2-6}$ alkenyl,
(III) —$C_{2-6}$ alkynyl, (IV) halogen,
(V) cyano,
(VI) —$C_{3-8}$ cycloalkyl, and
(VII) $NO_2$,
and $R^{12}$ is selected from the group consisting of
(I) hydrogen,
(II) —$C_{1-6}$ alkyl,
(III) —$C_{2-6}$ alkenyl,
(IV) —$C_{2-6}$ alkynyl,
(V) —$C_{3-8}$ cycloalkyl, and
(VI) —$C_{0-3}$ alkyl-$C_{6-10}$ aryl,
and said $R^{12}$ alkyl, alkenyl and alkynyl moiety is optionally substituted with one or more
(A) halogen,
(B) hydroxyl,
(C) cyano,
(D) —O—$C_{1-6}$ alkyl, wherein said alkyl is optionally substituted with one or more halogen,
(E) —$NR^4R^{4'}$,
(F) —$NR^4$—S(=O)$_2$—$R^{4'}$,
(G) —$NR^4$—C(=O)—$R^{4'}$,
(H) —$NR^4$—C(=O)—$OR^{4'}$,
(I) —S(=O)$_2$—$NR^4$—,
and said $R^{10}$ cycloalkyl moiety is optionally substituted with one or more
(A) halogen,
(B) hydroxyl,
(C) -cyano,
(D) —O—$C_{1-6}$ alkyl, and
(E) —$C_{1-6}$ alkyl, wherein said alkyl is optionally substituted one or more halogen;
and said $R^{12}$ aryl moiety is optionally substituted with one or more
(A) halogen,
(B) cyano,
(C) —O—$C_{1-6}$ alkyl, and
(D) —$C_{1-6}$ alkyl, wherein said alkyl is optionally substituted one or more halogen;
$Q^5$ and $Q^6$ are selected from the same group as $Q^1$ and $Q^2$;
$R^4$ and $R^{4'}$ are selected from the group consisting of
(1) hydrogen,
(2) —$C_{1-8}$ alkyl, wherein said alkyl is optionally substituted with
(a) halogen,
(b) —$C_{3-8}$ cycloalkyl
(c) —$CO_2C_{1-6}$ alkyl
(d) —$OC_{1-6}$ alkyl, wherein said alkyl is optionally substituted with one or more
(I) halogen, or
(II) cyano,
(3) —$C_{2-8}$ alkenyl, and
(4) —$C_{0-3}$ alkyl-$C_{6-10}$aryl;
$R^5$ is selected from the group consisting of
(1) hydrogen,
(2) —$C_{1-6}$ alkyl,
(3) halogen, and
(4) —$CO_2$—$R^4$,
$R^6$, $R^7$, $R^8$, $R^9$, $R^{10}$ and $R^{11}$ are independently selected from the group consisting of:
(1) hydrogen,
(2) —$C_{1-6}$ alkyl,
(3) —$C_{3-8}$ cycloalkyl,
(4) —$C_{0-3}$ alkyl-$C_{6-10}$ aryl,
wherein said alkyl is optionally substituted with one or more
(A) halogen,
(B) hydroxyl, (C) cyano, (D) —O—$C_{1-6}$ alkyl, wherein said alkyl is optionally substituted with one or more halogen, and said cycloalkyl and aryl are optionally substituted with one or more (A) halogen, (B) hydroxyl, (C) cyano, (D) —O—$C_{1-6}$ alkyl, and (E) —$C_{1-6}$ alkyl, wherein said alkyl is optionally substituted one or more halogen.

The invention is also directed to pharmaceutical compositions which include an effective amount of a compound of formula (I), or pharmaceutically acceptable salts thereof, and a pharmaceutically acceptable carrier.

The present invention is further directed to a method for the manufacture of a medicament or a composition for inhibiting β-secretase enzyme activity in humans and animals. The invention is also directed to a method for the manufacture of a medicament for the treatment of Alzheimer's Disease in humans, comprising combining a compound of the present invention with a pharmaceutical carrier or diluent.

In another embodiment, the invention is directed to novel spiropiperidine compounds of formula (I) above, provided that when X is N; Z is O; $R^1$ is unsubstituted cyclohexyl; and $R^2$ is unsubstituted phenyl, then $R^3$ is not unsubstituted benzyl.

In a preferred embodiment, Z is O.

In one sub-genus of this embodiment, the invention is directed to compounds of formula (I) wherein X is N and X' is NH. In another embodiment, X is $CR^5$, wherein $R^5$ is preferably hydrogen, and X' is $CR^5H$, wherein $R^5$ is preferably hydrogen.

In another embodiment of the compounds of formula (I), $R^1$ is —$C_{1-6}$ alkyl or —$C_{0-3}$ alkyl-$C_{3-12}$ carbocyclic wherein said alkyl or carbocyclic is optionally substituted with one or more (a) —$OR^4$, (b) halogen, (c) cyano, (d) —$NR^4R^{4'}$, and (e) —$C_{1-6}$ alkyl.

Preferred $R^1$ carbocyclic groups include-$C_{3-8}$ carbocyclic groups, including cyclobutyl, cyclopentyl, cyclohexyl, morpholinyl, tetrahydropyran and pyrrolidinyl.

In another embodiment of the compounds of formula (I), $R^1$ is —$C_{0-3}$ alkyl —$C_{6-10}$ aryl, preferably phenyl or benzyl. Preferably, the $R^1$ aryl moiety is optionally substituted with one or more (a) halogen, or (b) —$C_{1-6}$ alkyl.

In another embodiment, $R^1$ is $C_{0-3}$ alkyl-$C_{5-12}$ heteroaryl, wherein the heteroaryl moiety is optionally substituted with one or more (a) halogen, or (b) —$C_{1-6}$ alkyl.

Preferred $R^1$ heteroaryl groups include pyridinyl, thienyl, furanyl and imidazolyl.

In another embodiment, $R^2$ is selected from the group consisting of (1) —$C_{1-6}$ alkyl, (2) —$C_{0-6}$ alkyl-$C_{3-8}$ carbocyclic, and (3) —$C_{0-3}$ alkyl-$C_{6-10}$ aryl, which are optionally substituted as described above.

Preferably, $R^2$ is selected from —$C_{1-6}$ alkyl, phenyl, benzyl, or —$C_{0-3}$ alkyl-$C_{3-8}$ carbocyclic, optionally substituted as described above.

When $R^2$ is —$C_{0-3}$ alkyl-$C_{6-10}$ aryl, preferably the aryl moiety is optionally substituted with one or more (a) —$OR^{10}$, (b) halogen, (c) —$C_{1-6}$ alkyl, wherein said alkyl is optionally substituted with one or more (I) halogen, (II) cyano, (III) —$C_{1-6}$alkyl, (IV) —O—$C_{1-6}$ alkyl, (V) —$C_{3-8}$ cycloalkyl, (VI) —C(═O)—$C_{1-6}$ alkyl, (d) —$C_{0-3}$ alkyl-$C_{6-10}$ aryl, wherein said aryl moiety is optionally substituted with one or more (I) —$C_{1-6}$ alkyl, (II) —$C_{2-6}$ alkenyl, (III) —$C_{2-6}$ alkynyl, (IV) halogen, (V) cyano, (VI) —$C_{3-8}$ cycloalkyl, (VII) $NO_2$, (e) —$SO_2$—$C_{1-6}$ alkyl, and (f) —NHC(═O)—$C_{1-6}$ alkyl, wherein said alkyl is optionally substituted with one or more (I) —$NR^4R^{4'}$, and (II) —OH.

Within this embodiment, there is a sub-genus of compounds of formula (II)

(II)

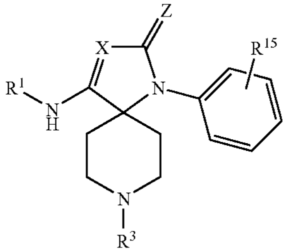

or its tautomer (II')

(II')

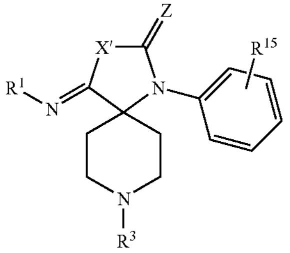

and pharmaceutically acceptable salts thereof, and individual enantiomers and diasteromers thereof, wherein X, X', Z, $R^1$ and $R^3$ are as defined above, and $R^{15}$ is selected from the group consisting of (a) —$OR^{10}$, (b) halogen, (c) -cyano, (d) -$Q^4$-$C_{1-6}$ alkyl, (e) —$C_{1-6}$ alkyl, wherein said alkyl is optionally substituted with one or more (I) halogen, and (II) cyano, (f) —$C_{0-3}$ alkyl-$C_{6-10}$ aryl, wherein said aryl is optionally substituted with one or more (I) halogen, (II) —$C_{1-6}$ alkyl, (V) —O—$C_{1-6}$ alkyl, (VI) —$SO_2$—$C_{1-6}$ alkyl, (VII) cyano, (VII) —$C_{3-8}$ cycloalkyl, (X) —$SO_2$—$NR^4R^{4'}$ (g) —$SO_2$—$C_{1-6}$ alkyl, (h) —$SO_2$—$NR^4R^{4'}$, (i) —$C_{3-8}$ cycloalkyl, (j) —NHC(═O)—$C_{1-6}$ alkyl, wherein said alkyl is optionally substituted with one or more (I) —$NR^4R^{4'}$ (II) OH (III) —$SO_2R^4$, and (IV) —$NHSO_2R^4$, (k) —$C_{0-3}$ alkyl-$C_{5-12}$ heteroaryl, wherein said heteroaryl is optionally substituted with one or more (I) halogen, (II) —$C_{1-6}$ alkyl, and (III)═O, (l) —$S(═O)_m$—$C_{0-6}$ alkyl-$C_{6-10}$ aryl, (m) —$CO_2$—$R^4$, (n) —C(═O)—$NR^4R^{4'}$, (o) —$C_{0-6}$ alkyl-$NR^4SO_2$—$R^4$.

Within this sub-genus of compounds of formula (II), $R^3$ is preferably (1) —$C_{0-3}$ alkyl-$C_{6-10}$ aryl, or (2) —$C_{0-3}$ alkyl-$C_{5-12}$ heteroaryl, and said aryl and heteroaryl are optionally substituted with one or more (a) —$OR^{12}$, (b) —$NR^4R^{4'}$, (c) halogen, (d) cyano, (f) —$NO_2$, (g) -$Q^6$-$R^4$, and (h) —$C_{1-6}$ alkyl, wherein said alkyl is optionally substituted with one or more (I) halogen, (II) cyano, (III) —$C_{1-6}$ alkyl, (IV) —O—$C_{1-6}$ alkyl, (V) —$C_{3-8}$ cycloalkyl, (VI) —C(═O)$C_{1-6}$ alkyl, (i) —$C_{2-6}$ alkenyl, (j) —$C_{2-6}$ alkynyl, (k) —$C_{0-3}$ alkyl-$C_{5-12}$ heteroaryl, (l) —$C_{0-3}$ alkyl-$C_{6-10}$ aryl, and said aryl moiety is optionally substituted with one or more (I) —$C_{1-6}$ alkyl, (II) —$C_{2-6}$ alkenyl, (III) —$C_{2-6}$ alkynyl, (IV) halogen, (V) cyano, (VI) —$C_{3-8}$ cycloalkyl, and (VI) $NO_2$.

When $R^3$ is —$C_{0-3}$ alkyl-heteroaryl, preferably the heteroaryl is selected from the group consisting of pyridyl, pyrrolyl, furanyl, thienyl, dihydrobenzofuran, indolyl, isoquinolinyl, imidazolyl, isoxazolyl, quinolinyl, tetrahydroquinolinyl, dihydroindolyl and pyridyl. Preferably, when $R^3$ is —$C_{0-3}$ alkyl-heteroaryl, the heteroaryl is substituted with one or more (a) —$OR^{12}$, (b) halogen, (c) cyano, (d) —C(═O)—$NR^4R^{4'}$, (e) —$C_{1-6}$ alkyl, and (f) —$NR^4R^{4'}$.

In preferred embodiments of compounds of formula (II), X is N and Z is O.

In another sub-genus of the embodiment of compounds of formula (I), the invention is directed to compounds of formula (III):

(III)

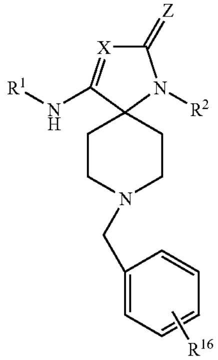

or its tautomer (III')

(III')

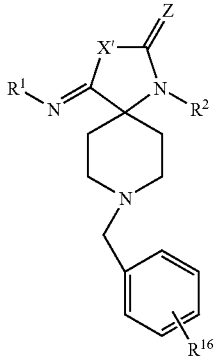

and pharmaceutically acceptable salts thereof, and individual enantiomers and diastereomers thereof, wherein X, X', Z, $R^1$, and $R^2$ are as defined above, and $R^{16}$ is selected from the group consisting of (a) —$OR^{12}$, (b) $NR^4R^{4'}$, (c) halogen, (d) cyano, (f) —$NO_2$, (g) -$Q^6$-$R^4$, and (h) —$C_{1-6}$ alkyl, wherein said alkyl is optionally substituted with one or more (I) halogen, (II) cyano, (III) —$C_{1-6}$ alkyl, (IV) —O—$C_{1-6}$ alkyl, (V) $C_{3-8}$ cycloalkyl, (VI) —C(=O)—$C_{1-6}$ alkyl, (i) —$C_{2-6}$ alkenyl, (j) —$C_{2-6}$ alkynyl, (k) —$C_{0-3}$ alkyl-$C_{5-12}$ heteroaryl, and (l) —$C_{0-3}$ alkyl-$C_{6-10}$ aryl, wherein said aryl moiety is optionally substituted with one or more (I) —$C_{1-6}$ alkyl, (II) —$C_{2-6}$ alkenyl, (III) —$C_{2-6}$ alkynyl, (IV) halogen, (V) cyano, (VI) —$C_{3-8}$ cycloalkyl, and (VII) $NO_2$.

In preferred embodiments of compounds of formula (III), X is N and Z is O.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$ alkyl groups, having from one to six carbon atoms. Exemplary alkyl groups include methyl, ethyl, n-propyl, isopropyl, n-butyl, isobutyl, tert-butyl, pentyl, hexyl, and the like. $C_0$ alkyl means a bond.

As used herein, the term "alkoxy," by itself or as part of another substituent, means the group —O— alkyl, wherein alkyl is defined above, having the number of carbon atoms designated (e.g., $C_{1-10}$ alkoxy means an alkoxy group having from one to ten carbon atoms. Preferred alkoxy groups for use in the invention are $C_{1-6}$ alkoxy groups, having from one to six carbon atoms. Exemplary preferred alkoxy groups include methoxy, ethoxy, propoxy, butoxy, sec-butoxy and pentoxy. Especially preferred alkoxy groups are $C_{1-3}$ alkoxy.

As used herein, the term "alkenyl," by itself or as part of another substituent, means a straight or branched chain hydrocarbon radical having a single carbon-carbon double bond and the number of carbon atoms designated (e.g., $C_{2-10}$ alkenyl means an alkenyl group having from two to ten carbon atoms). Preferred alkenyl groups for use in the invention are $C_{2-6}$ alkenyl groups, having from two to six carbon atoms. Exemplary alkenyl groups include ethenyl and propenyl.

As used herein, the term "alkynyl," by itself or as part of another substituent, means a straight or branched chain hydrocarbon radical having a single carbon-carbon triple bond and the number of carbon atoms designated (e.g., $C_{2-10}$ alkynyl means an alkynyl group having from two to ten carbon atoms). Preferred alkynyl groups for use in the invention are $C_{2-6}$ alkynyl groups, having from two to six carbon atoms. Exemplary alkynyl groups include ethynyl and propynyl.

As used herein, the term "cycloalkyl," by itself or as part of another substituent, means a saturated cyclic hydrocarbon radical having the number of carbon atoms designated (e.g., $C_{3-12}$ cycloalkyl means a cycloalkyl group having from three to twelve carbon atoms). The term cycloalkyl as used herein includes mono-, bi- and tricyclic saturated carbocycles, as well as bridged and fused ring carbocycles, such as spiro fused ring systems.

Preferred cycloalkyl groups for use in the invention are monocyclic $C_{3-8}$ cycloalkyl groups, having from three to eight carbon atoms. Exemplary monocyclic cycloalkyl groups include cyclopropyl, cyclobutyl, cyclopentyl, cyclohexyl and the like. Exemplary bridged cycloalkyl groups include adamantly and norbornyl. Exemplary fused cycloalkyl groups include decahydronaphthalene.

As used herein, the term "carbocyclic," by itself or as part of another substituent, means a cycloalkyl group as defined above, or a non-aromatic heterocyclic group. A non-aromatic heterocyclic group, by itself or as part of another substituent, means a cycloalkyl group as defined above in which one or more of the ring carbon atoms is replaced with a heteroatom (such as N, S or O). Suitable non-aromatic heterocyclic groups for use in the invention include piperidinyl, piperazinyl, morpholinyl, tetrahydrofuranyl, tetrahydrothienyl, pyrrolidinyl, pyrazolidinyl, azetidinyl, tetrahydropyranyl and imidazolidinyl. Preferred non-aromatic heterocyclic groups are piperidinyl, piperazinyl, tetrahydrofuranyl, tetrahydropyranyl, pyrrolidinyl, morpholinyl and azetidinyl.

When a non-aromatic heterocyclic group as defined herein is substituted, the substituent may be bonded to a ring carbon atom of the heterocyclic group, or on a ring heteroatom (i.e., a nitrogen, oxygen or sulfur), which has a valence which permits substitution. Preferably, the substituent is bonded to a ring carbon atom. Similarly, when a non-aromatic heterocyclic group is defined as a substituent herein, the point of attachment may be at a ring carbon atom of the heterocyclic group or on a ring heteroatom (i.e., a nitrogen, oxygen or sulfur), which has a valence which permits substitution. Preferably, the attachment is at a ring carbon atom.

As used herein, the term "aryl," by itself or as part of another substituent, means an aromatic cyclic hydrocarbon radical having the number of carbon atoms designated (e.g., $C_{6-10}$ aryl means an aryl group having from six to ten carbons atoms). The term "aryl" includes multiple ring systems as well as single ring systems. Preferred aryl groups for use in the invention include phenyl and naphthyl.

The term "aryl" also includes fused cyclic hydrocarbon rings which are partially aromatic (i.e., one of the fused rings is aromatic and the other is non-aromatic). An exemplary aryl group which is partially aromatic is indanyl.

The term "halo" or "halogen" includes fluoro, chloro, bromo and iodo.

As used herein, the term "heteroaryl," by itself or as part of another substituent, means an aromatic cyclic group having at least one ring heteroatom (O, N or S).). The term "heteroaryl" includes multiple ring systems as well as single ring systems. Exemplary heteroaryl groups for use in the invention include furyl, pyranyl, benzofuranyl, isobenzofuranyl, chromenyl, thienyl, benzothiophenyl, pyrrolyl, pyrazolyl, imidazolyl, pyridyl, pyrazinyl, pyrimidinyl, pyridazinyl, indolyl, benzimidazolyl, quinolinyl, isoquinolinyl, tetrazolyl, indazolyl, napthyridinyl, triazolyl, oxazolyl, oxadiazolyl, thiazolyl, thiadiazolyl, isoxazolyl, tetrahydroquinolinyl, tetrahydroisoquinolinyl and dihydroindolyl.

The term "heteroaryl" also includes fused aromatic cyclic groups which are partially aromatic (i.e., one of the fused rings is aromatic and the other is non-aromatic). Exemplary heteroaryl groups which are partially aromatic include tetrahydroquinolyl, dihydrobenzofuran and dihydroindolyl.

When a heteroaryl group as defined herein is substituted, the substituent may be bonded to a ring carbon atom of the heteroaryl group, or on a ring heteroatom (i.e., a nitrogen, oxygen or sulfur), which has a valence which permits substitution. Preferably, the substituent is bonded to a ring carbon atom. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment. Preferably, the attachment is at a ring carbon atom.

Some of the compounds of the instant invention have at least one asymmetric center. Additional asymmetric centers may be present depending upon the nature of the various substituents on the molecule. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of these compounds.

As used herein, the term "tautomer" refers to a compound which exists in an equilibrium mixture and which can be isolated in either form and react through either form. The tautomers may differ in linkage, bond, or connections between atoms, and the position or distribution of the atoms in the molecule. One common form of tautomerism occurs when an enamine group, for example a group $R_2C{=}CR{-}NHR$, exists in equilibrium with its tautomeric imine form, for example $R_2CH{-}CR{=}NR$. In the context of this invention, compounds of formula (I) may be present in the enamine form depicted above, or in the tautomeric imine form (I'), as shown below:

(I')

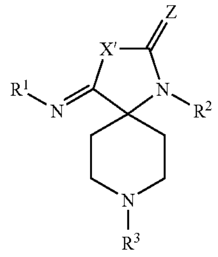

and pharmaceutically acceptable salts thereof, and individual enantiomers and diastereomers thereof, wherein X', Z, $R^1$, $R^2$ and $R^3$ are as defined above.

Additionally, compounds of formula (II) may be present in the enamine form depicted above, or in the tautomeric imine form (II'), as shown below:

(II')

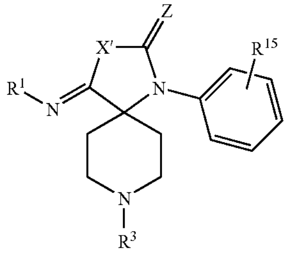

and pharmaceutically acceptable salts thereof, and individual enantiomers and diastereomers thereof, wherein X', Z, $R^1$, $R^3$ and $R^{15}$ are as defined above.

Compounds of formula (III) may be present in the enamine form depicted above, or in the tautomeric imine form (III'), as shown below:

(III')

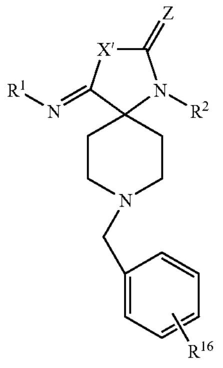

and pharmaceutically acceptable salts thereof, and individual enantiomers and diastereomers thereof, wherein X', Z, $R^1$, $R^2$ and $R^{16}$ are as defined above.

Compounds described herein may contain one or more double bonds, and may thus give rise to cis/trans isomers as well as other conformational isomers. The present invention includes all such possible isomers as well as mixtures of such isomers.

Formulas (I) to (III) are shown above without a definite stereochemistry at certain positions. The present invention includes all stereoisomers of Formulas (I) to (III) and pharmaceutically acceptable salts thereof.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer of a compound may be obtained by stereoselective synthesis using optically pure starting materials or reagents of known configuration by methods well known in the art.

The compounds claimed in this invention can be prepared according to the following general procedure methods (Schemes 1 and 2).

Scheme 1 below depicts an Ugi four-component coupling reaction between a piperidone derivative, amine, isonitrile, and cyanate, which assembles the core structure 1-1. Further elaboration of 1-1 is possible, for example, removal of a temporary $R^3$ group to give 1-2, followed by alkylation with a different $R^3$ to give new structures 1-3.

Scheme 1

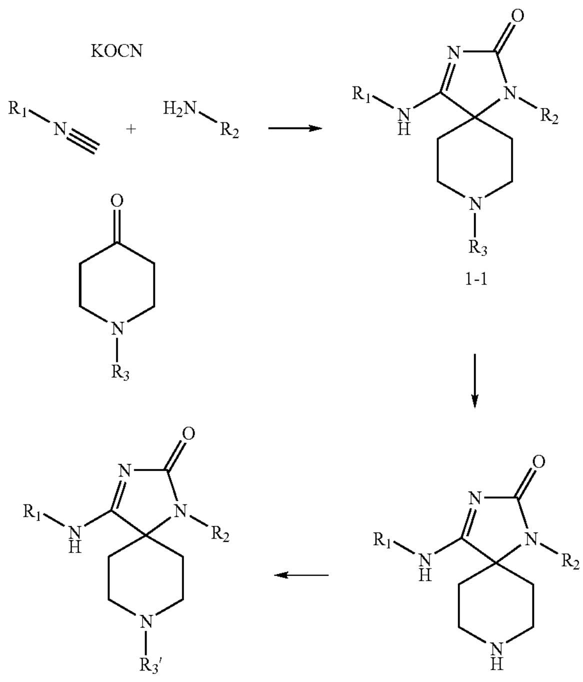

1-1

1-3

1-2

Alternatively, compounds of the invention where X═C may be prepared as shown in Scheme 2, below. Strecker reaction on a suitably configured piperidone gives nitrile 2-1 which can be hydrolyzed and esterified to 2-2. Acylation to 2-3 and ring closure to 2-4 followed by condensation with amines gives compounds 2-5.

Scheme 2

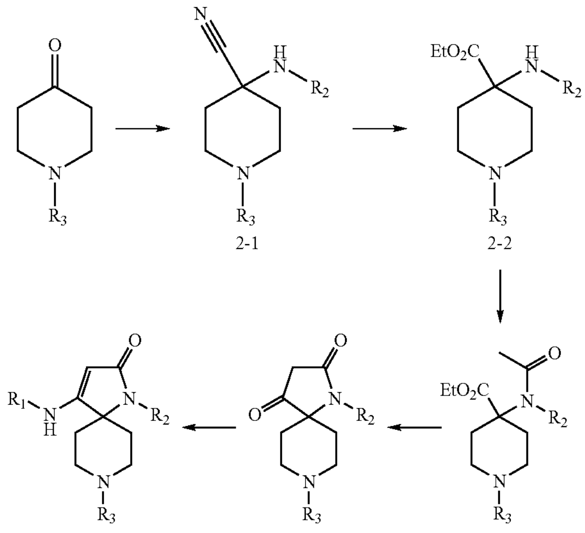

2-1

2-2

2-5

2-4

2-3

Specific embodiments of the compounds of the invention, and methods of making them, are described in Examples (3-1)-(15-45) herein, and in Schemes 3-15.

The term "substantially pure" means that the isolated material is at least 90% pure, and preferably 95% pure, and even more preferably 99% pure as assayed by analytical techniques known in the art.

The term "pharmaceutically acceptable salts" refers to salts prepared from pharmaceutically acceptable non-toxic bases or acids including inorganic or organic bases and inorganic or organic acids. The compounds of the invention may be mono, di or tris salts, depending on the number of acid functionalities present in the free base form of the compound. Free bases and salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, trifluoroacetic, maleic, phosphoric, sulfuric, fumaric, and tartaric acids.

The present invention is directed to the use of the compounds of formulas (I) to (III) disclosed herein as inhibitors of β-secretase enzyme activity or β-site amyloid precursor protein-cleaving enzyme ("BACE") activity, in a patient or subject such as a mammal in need of such inhibition, comprising the administration of an effective amount of the compound. The terms "β-secretase enzyme," "β-site amyloid precursor protein-cleaving enzyme," and "BACE" are used interchangeably in this specification. In addition to humans, a variety of other mammals can be treated according to the method of the present invention.

The compounds of the present invention have utility in treating, ameliorating, controlling or reducing the risk of Alzheimer's disease. For example, the compounds may be useful for the prevention of dementia of the Alzheimer's type, as well as for the treatment of early stage, intermediate stage or late stage dementia of the Alzheimer's type. The compounds may also be useful in treating, ameliorating, controlling or reducing the risk of diseases mediated by abnormal cleavage of amyloid precursor protein (also referred to as APP), and other conditions that may be treated or prevented by inhibition of β-secretase. Such conditions include mild cognitive impairment, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes and atherosclerosis.

The subject or patient to whom the compounds of the present invention is administered is generally a human being, male or female, in whom inhibition of β-secretase enzyme activity is desired, but may also encompass other mammals, such as dogs, cats, mice, rats, cattle, horses, sheep, rabbits, monkeys, chimpanzees or other apes or primates, for which inhibition of β-secretase enzyme activity or treatment of the above noted disorders is desired.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds of the present invention with other drugs in either unit dose or kit form include combinations with anti-Alzheimer's agents, for example other beta-secretase inhibitors or gamma-secretase inhibitors; tau phosphorylation inhibitors; M1 receptor positive allosteric modulators; blockers of Aβ oligomer formation; 5-HT modulators, such as PRX-03140, GSK 742467, SGS-518, FK-962, SL-65.0155, SRA-333 and xaliproden; p25/CDK5 inhibitors; NK1/NK3 receptor antagonists; COX-2 inhibitors; HMG-CoA reductase inhibitors; NSAIDs including ibuprofen; vitamin E; anti-amyloid antibodies, including anti-amyloid humanized monoclonal antibodies; anti-inflammatory compounds such as (R)-flurbiprofen, nitroflurbiprofen, rosiglitazone, ND-1251, VP-025, HT-0712 and EHT-202; CB-1 receptor antagonists or CB-1 receptor inverse agonists; antibiotics such as doxycycline and rifampin; N-methyl-D-aspartate (NMDA) receptor antagonists, such as memantine and neramexane; cholinesterase inhibitors such as galantamine, rivastigmine, donepezil, tacrine, phenserine, ladostigil and ABT-089; growth hormone secretagogues such as ibutamoren, ibutamoren mesylate, and capromorelin; histamine $H_3$ antagonists such as ABT-834, ABT 829 and GSK 189254; AMPA agonists or AMPA modulators, such as CX-717, LY 451395 and S-18986; PDE IV inhibitors; $GABA_A$ inverse agonists; neuronal nicotinic agonists; selective M1 agonists; microtobubule affinity regulating kinase (MARK) ligands; P-450 inhibitors, such as ritonavir, or other drugs that affect receptors or enzymes that either increase the efficacy, safety, convenience, or reduce unwanted side effects or toxicity of the compounds of the present invention. The foregoing list of combinations is illustrative only and not intended to be limiting in any way.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients.

In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound, which is a compound of formulas (I) to (III), is included in an amount sufficient to produce the desired effect upon the process or condition of diseases. Accordingly, the pharmaceutical compositions of the present invention encompass any composition made by admixing a compound of the present invention and a pharmaceutically acceptable carrier.

The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds represented by Formulas (I) to (VII), or pharmaceutically acceptable salts thereof, may also be administered by controlled release means and/or delivery devices.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, or in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can also be in a form suitable for rectal administration wherein the carrier is a solid. It is preferable that the mixture forms unit dose suppositories. Suitable carriers include cocoa butter and other materials commonly used in the art.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician.

As used herein, the term "treatment" or "treating" means any administration of a compound of the present invention and includes (1) inhibiting the disease in an animal that is experiencing or displaying the pathology or symptomotology of the diseased (i.e., arresting further development of the pathology and/or symptomotology), or (2) ameliorating the disease in an animal that is experiencing or displaying the pathology or symptomotology of the diseased (i.e., reversing the pathology and/or symptomotology). The term "controlling" includes preventing treating, eradicating, ameliorating or otherwise reducing the severity of the condition being controlled.

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

The compositions containing compounds of the present invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating, ameliorating, controlling or reducing the risk of Alzheimer's disease or other diseases for which compounds of the present invention are indicated, generally satisfactory results are obtained when the compounds of the present invention are administered at a daily dosage of from about 0.1 mg to about 100 mg per kg of animal body weight, preferably given as a single daily dose or in divided doses two to six times a day, or in sustained release form. The total daily dosage is from about 1.0 mg to about 2000 mg, preferably from about 0.1 mg to about 20 mg per kg of body weight. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The amount of active ingredient that may be combined with the carrier materials to produce a single dosage form will vary depending upon the host treated and the particular mode of administration. For example, a formulation intended for the oral administration to humans may conveniently contain from about 0.005 mg to about 2.5 g of active agent, compounded with an appropriate and convenient amount of carrier material. Unit dosage forms will generally contain between from about 0.005 mg to about 1000 mg of the active ingredient, typically 0.005, 0.01 mg, 0.05 mg, 0.25 mg, 1 mg, 5 mg, 25 mg, 50 mg, 100 mg, 200 mg, 300 mg, 400 mg, 500 mg, 600 mg, 800 mg or 1000 mg, administered once, twice or three times a day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The utility of the compounds in accordance with the present invention as inhibitors of β-secretase enzyme activity may be demonstrated by methodology known in the art. Enzyme inhibition is determined as follows.

ECL Assay: A homogeneous end point electrochemiluminescence (ECL) assay is employed using a biotinylated BACE substrate. The Km of the substrate is greater than 100 μM and can not be determined due to the limit of solubility of the substrate. A typical reaction contains approximately 0.1 nM enzyme, 0.25 μM of the substrate, and buffer (50 mM NaOAc, pH 4.5 or 6.5, 0.1 mg/ml BSA, 0.2% CHAPS, 15 mM EDTA and 1 mM deferoxamine) in a total reaction volume of 100 μl. The reaction proceeds for 30 min and is then stopped by the addition of 25 μL of 1 M Tris-HCl, pH 8.0. The resulting enzymatic product is assayed by adding a ruthenylated antibody which specifically recognizes the C-terminal residue of the product. Streptavidin coated magnetic beads are added into the solution and the samples are subjected to M-384 (Igen Inc., Gaithersburg, Md.) analysis. Under these conditions, less than 10% of substrate is processed by BACE 1. The enzyme used in these studies is soluble (transmembrane domain and cytoplasmic extension excluded) human protein produced in a baculovirus expression system. To measure the inhibitory potency for compounds, 12 concentrations of inhibitors are prepared starting from 100 μM with three fold series dilution. Solutions of the inhibitor in DMSO are included in the reaction mixture (final DMSO concentration is 10%). All experiments are conducted at rt using the standard reaction conditions described above. To determine the $IC_{50}$ of the compound, a four parameter equation is used for curve fitting. The errors in reproducing the dissociation constants are typically less than two-fold.

HPLC assay: A homogeneous end point HPLC assay is used with the substrate (coumarin-CO-REVNFEVEFR), which is cleaved by BACE 1 to release the N-terminal fragment attached with coumarin. The Km of the substrate is greater than 100 μM and can not be determined due to the limit of solubility of the substrate. A typical reaction contains approximately 2 nM enzyme, 1.0 μM of the substrate, and buffer (50 mM NaOAc, pH 4.5 or 6.5, 0.1 mg/ml BSA, 0.2% CHAPS, 15 mM EDTA and 1 mM deferoxamine) in a total reaction volume of 100 μl. The reaction is proceeded for 30 min and the reaction is stopped by the addition of 25 μL of 1 M Tris-HCl, pH 8.0. The resulting reaction mixture is loaded on the HPLC and the product is separated from substrate with 5 min linear gradient. Under these conditions, less than 10% of substrate is processed by BACE 1. The enzyme used in these studies is soluble (transmembrane domain and cytoplasmic extension excluded) human protein produced in a baculovirus expression system. To measure the inhibitory potency for compounds, 12 concentrations of inhibitors are prepared, and the concentration rage is dependent on the potency predicted by ECL. Solutions of inhibitor in DMSO are included in the reaction mixture (final DMSO concentration is 10%). All experiments are conducted at rt using the standard reaction conditions described above. To determine the $IC_{50}$ of the compound, four parameters equation is employed for curve fitting. The errors in reproducing the dissociation constants are typically less than two-fold.

In particular, the compounds of the following examples had activity in inhibiting the beta-secretase enzyme in the aforementioned assays, generally with an $IC_{50}$ from about 1 nM to 500 μM, preferably 1 nM to 100 μM. Such a result is indicative of the intrinsic activity of the compounds in use as inhibitors of beta-secretase enzyme activity.

Several methods for preparing the compounds of this invention are illustrated in the schemes and examples herein. Starting materials are made according to procedures known in the art or as illustrated herein. The following examples are provided so that the invention might be more fully understood. These examples are illustrative only and should not be construed as limiting the invention in any way.

The following abbreviations are used throughout the text:

Me: methyl

Et: ethyl t-Bu: tert-butyl

Ar: aryl

Ph: phenyl

Bn: benzyl

Ac: acetyl

THF: tetrahydrofuran

DMSO: dimethylsulfoxide

EDTA: ethylene diamine tetraacetic acid

Boc: tert-butyloxy carbonyl

CHAPS: 3-[(3-cholamidopropyl)dimethylammonio]-2-hydroxy-1-propanesulfonate

DCM: dichloromethane

DCE: dichloroethane

BSA: bovine serum albumin

TFA: trifluoracetic acid

DMF: N,N-dimethylformamide

TMSCN: trimethylsilylnitrile

PS-DIEA: N,N(diisopropyl)aminomethylpolystyrene

DEA: diethylamine

DMA: N,N dimethylacetamide

LDA: lithium diisopropylamide

DEAD: diethylazole dicarboxylate rt: room temperature

HPLC: high performance liquid chromatography

A representative procedure for the Ugi four-component coupling, as depicted in Scheme 3 below, can be used in the synthesis of various compounds of the invention, including Examples (3-1)-(3-46) below. Examples (3-1)-(3-46) are depicted below in enamine form, but may also exist in tautomeric imine form, as described above.

Scheme 3

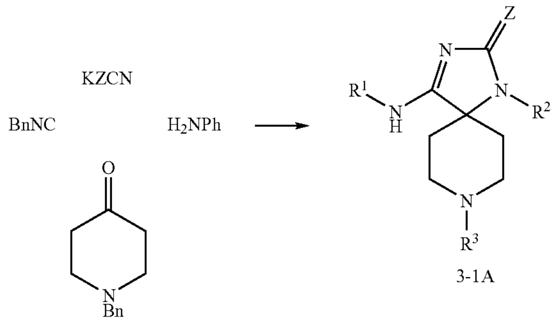

3-1A

Example 3-1

8-benzyl-4-(benzylamino)-1-phenyl-1,3,8-triazaspiro[4.5]dec-3-en-2-one (3-1)

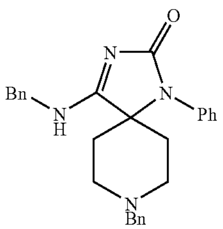

In a 10 mL flask N-benzyl piperidinone (833 mg, 4.41 mmol) and benzyl isocyanide (500 mg, 4.2 mmol) were dissolved in MeOH (2.2 mL). A solution of KOCN (313 mg, 4.41 mmol) in $H_2O$ (0.9 mL) was added in one portion with stirring. Aniline hydrochloride was added in portions over 5 min. After stirring for 1 h the crude product precipitated from solution. The resulting solid was isolated via vacuum filtration, rinsed with $H_2O$ followed by $Et_2O$, and dried in vacuo to give 150 mg of a white solid. A portion of this solid was further purified by RP-HPLC. Product containing fractions were poured onto a biphasic mixture of aq. $NaHCO_3$ and EtOAc. The layers were separated and the organic layer washed with brine. Upon drying the organic layer over $Na_2SO_4$ and solvent removal under reduced pressure, the target compound, 8-benzyl-4-(benzylamino)-1-phenyl-1,3,8-triazaspiro[4.5]dec-3-en-2-one, was obtained as a white solid: $^1H$ NMR (400 MHz, $CDCl_3$) δ 9.05 (br s, 1H), 7.4-7.2 (m, 8H), 6.88 (d, J=6.9 Hz, 2H), 4.66 (d, J=5.2 Hz, 2H), 3.37 (s, 2H), 2.75 (overlapping t's, J=6.8 Hz, 2H), 2.30 (overlapping t's, J=7.2 Hz, 2), 2.03 (m, 4H); LC-MS (M+H)=425.03; HPLC=98.6% (215 nm); 100% (254 nM).

The following examples were prepared in a similar manner, substituting the appropriately substituted isocyanide and/or the amine, to give the products in Table 1. For example 345, potassium thiocyanate was substituted for potassium cyanate. Examples (3-37)-(3-40) were prepare using 4-Boc amino analine followed by deprotection and acylation with an appropriate acylating reagent.

TABLE 1

Compounds (or salts thereof) Synthesized According to Scheme 3

| EX | Structure | Chemical Name | Mass spec |
|---|---|---|---|
| 3-1 | 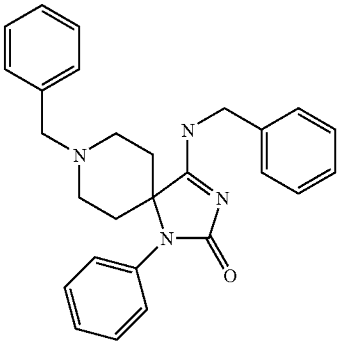 | 8-benzyl-4-(benzylamino)-1-phenyl-1,3,8-triazaspiro[4.5]dec-3-en-2-one | 425 |
| 3-2 | 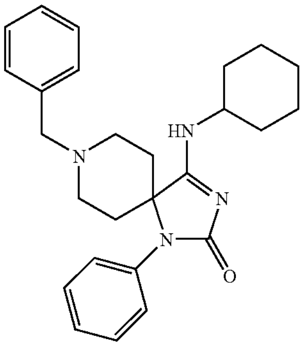 | 8-benzyl-4-(cyclohexylamino)-1-phenyl-1,3,8 triazaspiro[4.5]dec-3-en-2-one | 417 |

TABLE 1-continued

| Compounds (or salts thereof) Synthesized According to Scheme 3 | | | |
|---|---|---|---|
| EX | Structure | Chemical Name | Mass spec |
| 3-3 | 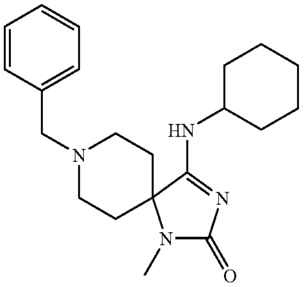 | 8-benzyl-4-(cyclohexylamino)-1-methyl-1,3,8-triazaspiro[4.5]dec-3-en-2-one | 355 |
| 3-4 | 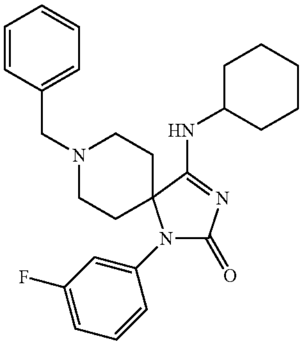 | 8-benzyl-4-(cyclohexylamino)-1-(3-fluorophenyl)-1,3,8-triazaspiro[4.5]dec-3 -en-2-one | 435 |
| 3-5 | 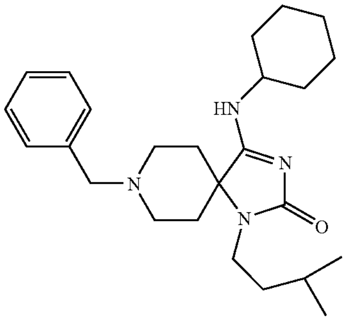 | 8-benzyl-4-(cyclohexylamino)-1-(3-methylbutyl)-2-oxo-1,3-diaza-8-azoniaspiro[4.5]dec-3-ene trifluoroacetate | 411.2 |
| 3-8 | 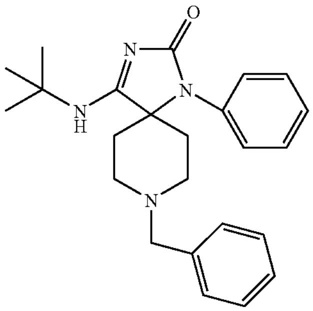 | 8-benzyl-4-(tert-butylamino)-1-phenyl-1,3,8-triazaspiro[4.5]dec-3-en-2-one | 391.2 |

TABLE 1-continued
| Compounds (or salts thereof) Synthesized According to Scheme 3 | | | |
|---|---|---|---|
| EX | Structure | Chemical Name | Mass spec |
| 3-9 | 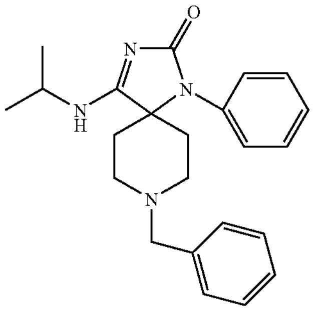 | 8-benzyl-4-(isopropylamino)-1-phenyl-1,3,8-triazaspiro[4.5]dec-3-en-2-one | 377.2 |
| 3-12 | 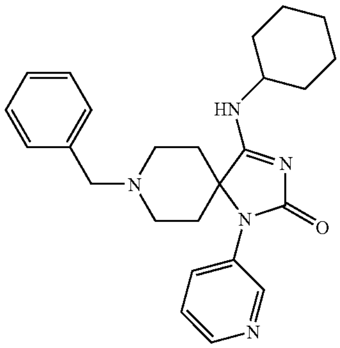 | 8-benzyl-4-(cyclohexylamino)-l-(3-pyridyl)-1,3,8-triazaspiro[4.5]dec-3-en-2-one | 418.1 |
| 3-13 | 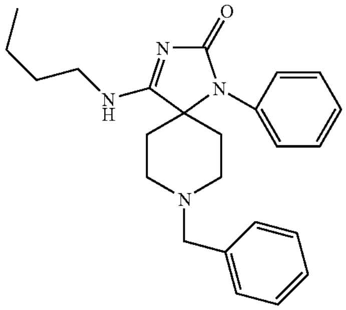 | 8-benzyl-4-(butylamino)-1-phenyl-1,3,8-triazaspiro[4.5]dec-3-en-2-one | 388.2 |
| 3-14 | 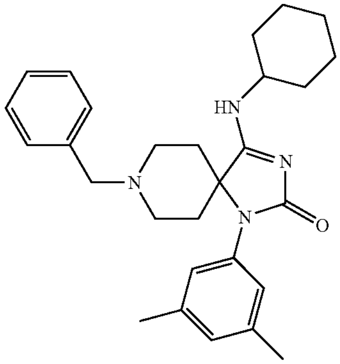 | 8-benzyl-4-(cyclohexylammo)-1-(3,5-dimethylphenyl)-1,3,8-triazaspiro[4.5]dec-3-en-2-one | 445.2 |

TABLE 1-continued

| Compounds (or salts thereof) Synthesized According to Scheme 3 | | | |
|---|---|---|---|
| EX | Structure | Chemical Name | Mass spec |
| 3-15 | 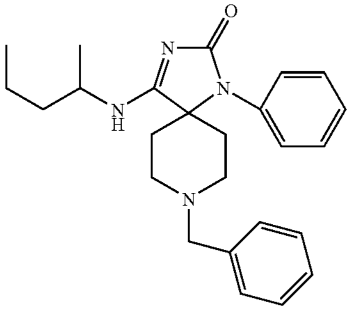 | 8-benzyl-4-(1-methylbutylamino)-1-phenyl-1,3,8-triazaspiro[4.5]dec-3-en-2-one | 405.2 |
| 3-16 | 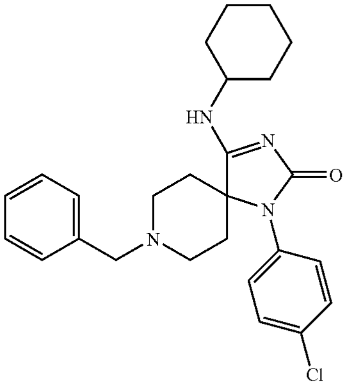 | 8-benzyl-4-(cyclohexylamino)-1-(4-chlorophenyl)-1,3,8-triazaspiro[4.5]dec-3-en-2-one | 451.1 |
| 3-17 | 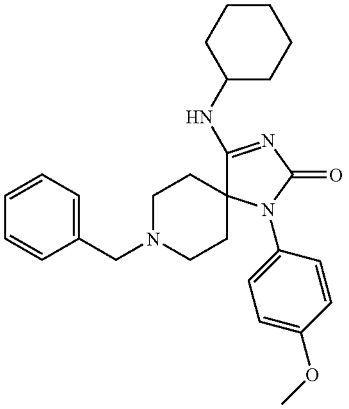 | 8-benzyl-4-(cyclohexylamino)-1-(4-methoxyphenyl)-1,3,8-triazaspiro[4.5]dec-3-en-2-one | 447.2 |
| 3-18 | 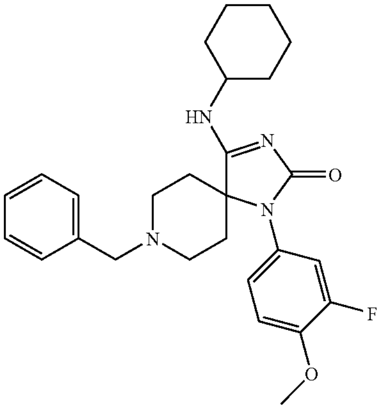 | 8-benzyl-4-(cyclohexylamino)-1-(4-methoxy-3-fluorophenyl)-1,3,8-triazaspiro[4.5]dec-3-en-2-one | 465.1 |

TABLE 1-continued

| Compounds (or salts thereof) Synthesized According to Scheme 3 | | | |
|---|---|---|---|
| EX | Structure | Chemical Name | Mass spec |
| 3-19 | 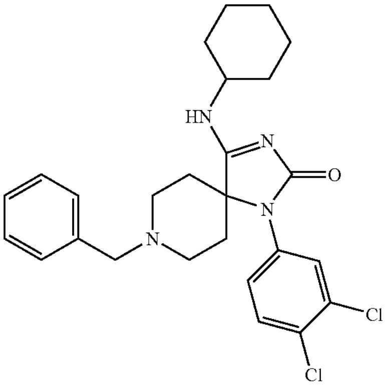 | 8-benzyl-4-(cyclohexylamino)-1-(3,4-difluorophenyl)-1,3,8-triazaspiro[4.5]dec-3-en-2-one | 485.1 |
| 3-20 | 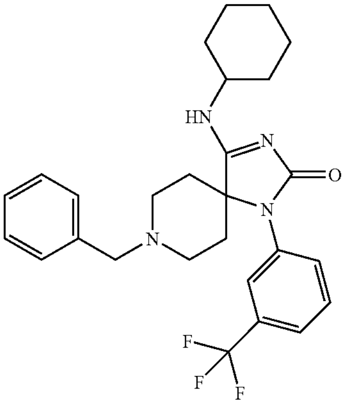 | 8-benzyl-4-(cyclohexylamino)-1-(3-trifluoromethyiphenyl)-1,3,8-triazaspiro[4.5]dec-3-en-2-one | 485.2 |
| 3-23 | 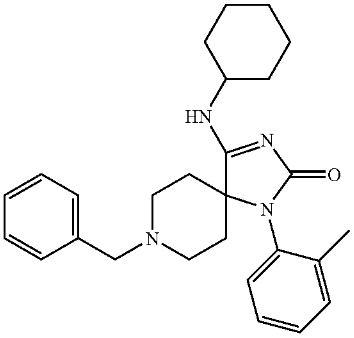 | 8-benzyl-4-(cyclohexylamino)-1-(2-methyiphenyl)-1,3,8-triazaspiro[4.5]dec-3-en-2-one | 431.2 |
| 3-24 | 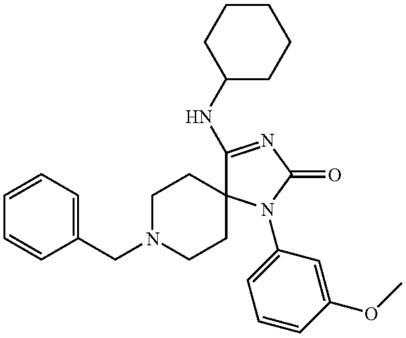 | 8-benzyl-4-(cyclohexylamino)-1-(3-methoxyphenyl)-1,3,8-triazaspiro[4.5]dec-3-en-2-one | 447.3 |

TABLE 1-continued

Compounds (or salts thereof) Synthesized According to Scheme 3

| EX | Structure | Chemical Name | Mass spec |
|---|---|---|---|
| 3-25 | 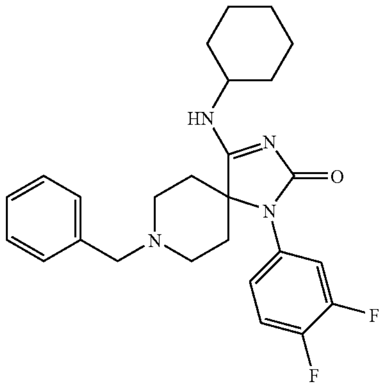 | 8-benzyl-4-(cyclohexylamino)-1-(3,4-dichlorophenyl)-1,3,8-triazaspiro[4.5]dec-3-en-2-one | 453.2 |
| 3-26 | 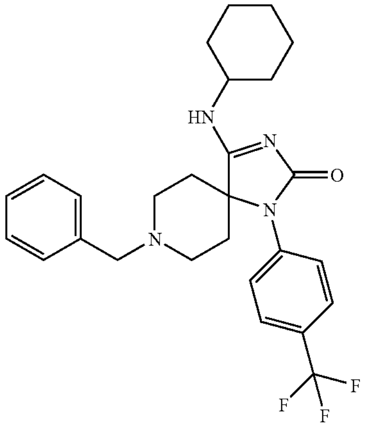 | 8-benzyl-4-(cyclohexylamino)-1-(4-trifluoromethylphenyl)-1,3,8-triazaspiro[4.5]dec-3-en-2-one | 485.2 |
| 3-27 | 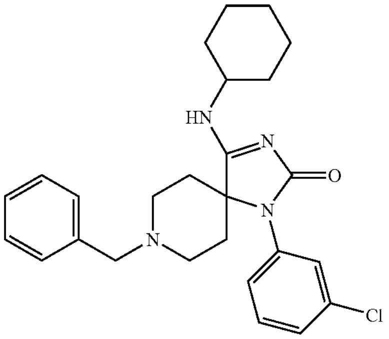 | 8-benzyl-4-(cyclohexylamino)-1-(3-chlorophenyl)-1,3,8-triazaspiro[4.5]dec-3-en-2-one | 451.2 |
| 3-28 | 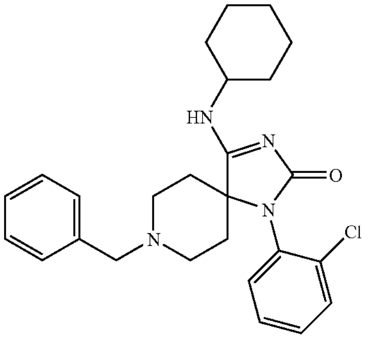 | 8-benzyl-4-(cyclohexylamino)-1-(2-chlorophenyl)-1,3,8-triazaspiro[4.5]dec-3-en-2-one | 451.2 |

TABLE 1-continued

| Compounds (or salts thereof) Synthesized According to Scheme 3 | | | |
|---|---|---|---|
| EX | Structure | Chemical Name | Mass spec |
| 3-29 | 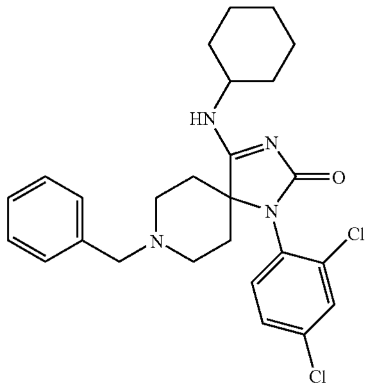 | 8-benzyl-4-(cyclohexylamino)-1-(2,4-dichlorophenyl)-1,3,8-triazaspiro[4.5]dec-3-en-2-one | 485.1 |
| 3-30 | 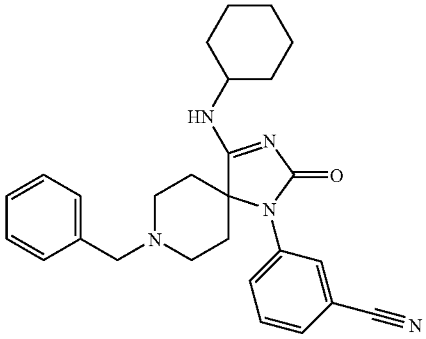 | 8-benzyl-4-(cyclohexylamino)-1-(3-cyanophenyl)-1,3,8-triazaspiro[4.5]dec-3-en-2-one | 442.3 |
| 3-31 | 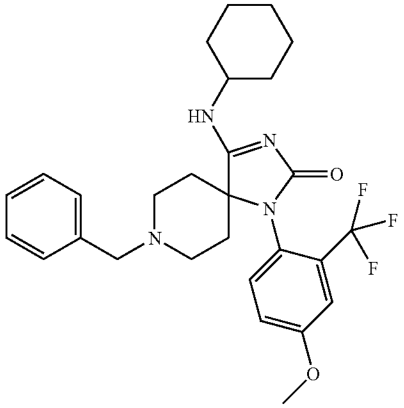 | 8-benzyl-4-(cyclohexylamino)-1-(2-trifluoromethyl-4-methoxyphenyl)-1,3,8-triazaspiro[4.5]dec-3-en-2-one | 515.2 |
| 3-32 | 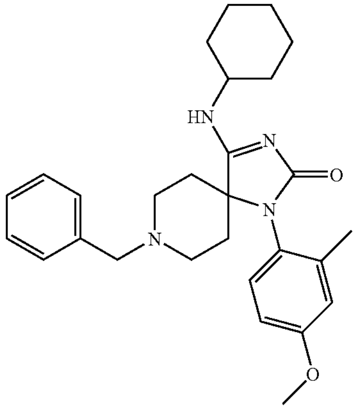 | 8-benzyl-4-(cyclohexylamino)-1-(2-methyl-4-methoxyphenyl)-1,3,8-triazaspiro[4.5]dec-3-en-2-one | 461.2 |

TABLE 1-continued
| Compounds (or salts thereof) Synthesized According to Scheme 3 | | | |
|---|---|---|---|
| EX | Structure | Chemical Name | Mass spec |
| 3-33 | 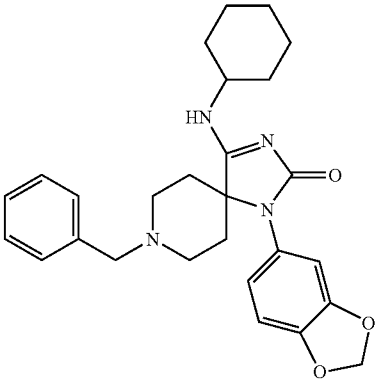 | 8-benzyl-4-(cyclohexylamino)-1-(1,3-benzodioxo-5-yl)-1,3,8-triazaspiro[4.5]dec-3-en-2-one | 461.2 |
| 3-34 | 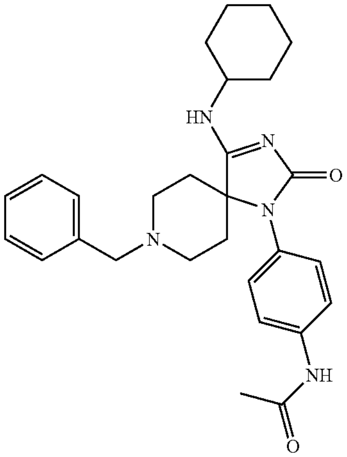 | 8-benzyl-4-(cyclohexylamino)-1-(4-acetylaminophenyl)-1,3,8-triazaspiro[4.5]dec-3-en-2-one | 474.2 |
| 3-35 | 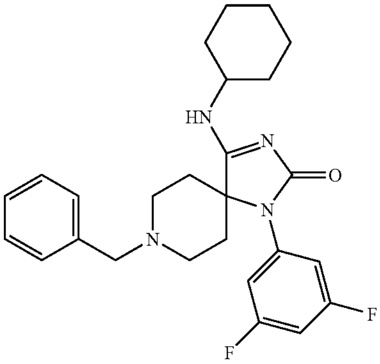 | 8-benzyl-4-(cyclohexylamino)-1-(3,5-difluorophenyl)-1,3,8-triazaspiro[4.5]dec-3-en-2-one | 453.2 |

TABLE 1-continued

| Compounds (or salts thereof) Synthesized According to Scheme 3 | | | |
|---|---|---|---|
| EX | Structure | Chemical Name | Mass spec |
| 3-36 | 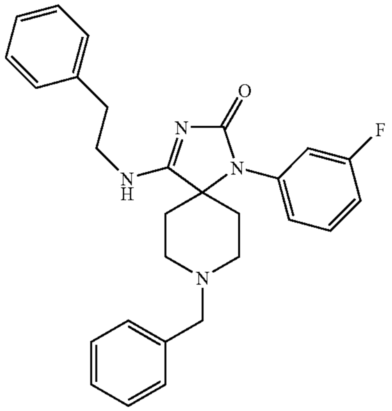 | 8-benzyl-4-((2-phenethyl)amino)-1-(3-fluorophenyl)-1,3,8-triazaspiro[4.5]dec-3-en-2-one | 457.2 |
| 3-37 | 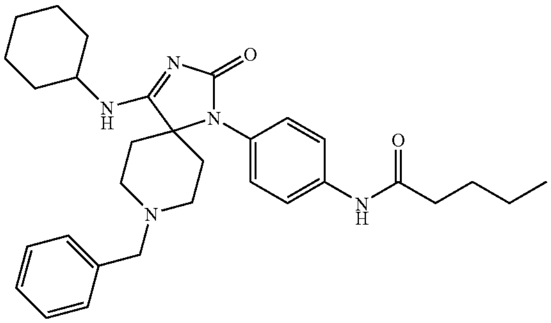 | 8-benzyl-4-(cyclohexylamino)-1-(4-pentanoylaminophenyl)-1,3,8-triazaspiro[4.5]dec-3-en-2-one | 516.3 |
| 3-38 | 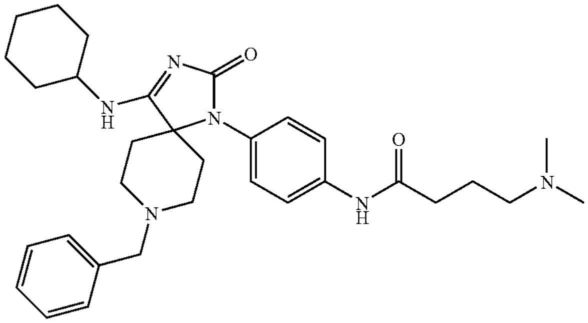 | 8-benzyl-4-(cyclohexylamino)-1-(4-(4-dimethylamino) butanoylaminophenyl)-1,3,8-triazaspiro[4.5]dec-3-en-2-one | 545.4 |
| 3-39 | 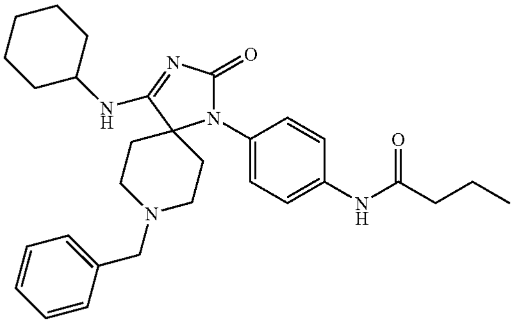 | N-{4-[8-benzyl-4-(cyclohexylamino)-2-oxo-1,3,8-triazaspiro[4.5]dec-3-en-1-yl]phenyl}butanamide | 502.4 |

TABLE 1-continued

| Compounds (or salts thereof) Synthesized According to Scheme 3 | | | |
|---|---|---|---|
| EX | Structure | Chemical Name | Mass spec |
| 3-40 | 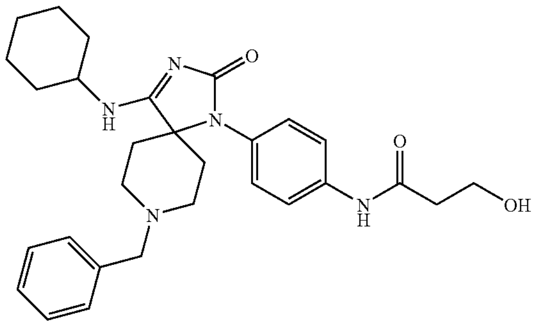 | N-{4-[8-benzyl-4-(cyclohexylamino)-2-oxo-1,3,8-triazaspiro[4.5]dec-3-en-1-yl]phenyl}-3-hydroxypropanamide | 504.3 |
| 3-42 | 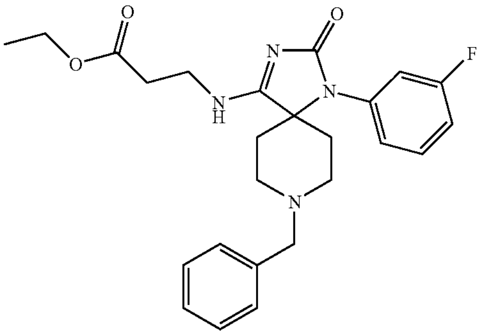 | ethyl N-[8-benzyl-1-(3-fluorophenyl)-2-oxo-1,3,8-triazaspiro[4.5]dec-3-en-4-yl]-beta-alaninate | 453.3 |
| 3-43 | 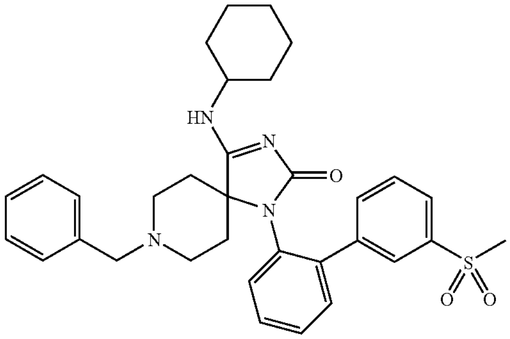 | 8-benzyl-4-(cyclohexylamino)-1-[3'-(methylsulfonyl)biphenyl-2-yl]-1,3,8-triazaspiro[4.5]dec-3-en-2-one | 571.3 |
| 3-44 | 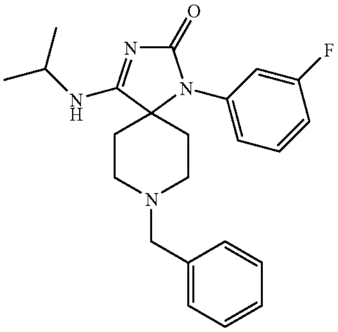 | 8-benzyl-4-(isopropylamino)-1-phenyl-1,3,8-triazaspiro[4.5]dec-3-en-2-one | 395.2 |

TABLE 1-continued

Compounds (or salts thereof) Synthesized According to Scheme 3

| EX | Structure | Chemical Name | Mass spec |
|---|---|---|---|
| 3-45 | 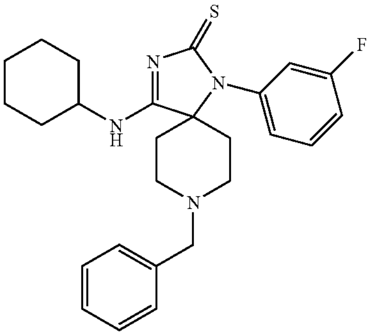 | 8-benzyl-4-(cyclohexylamino)-1-(3-fluorophenyl)-1,3,8-triazaspiro[4.5]dec-3-ene-2-thione | 451.2360 |
| 3-46 | 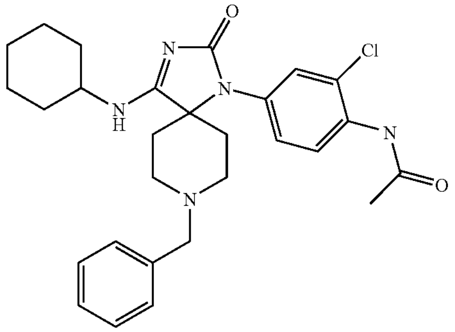 | N-{4-[8-benzyl-4-(cyclohexylamino)-2-oxo-1,3,8-triazaspiro[4.5]dec-3-en-1-yl]-2-chiorophenyl}acetamide | 510.0 |

Scheme 4A, which depicts a method for preparing compounds of the invention wherein X=CH, can be used in the synthesis of various compounds of the invention, including Example 4A-6 below (Example 4A-6 is depicted in enamine form, but may also exist in tautomeric form).

Scheme 4A

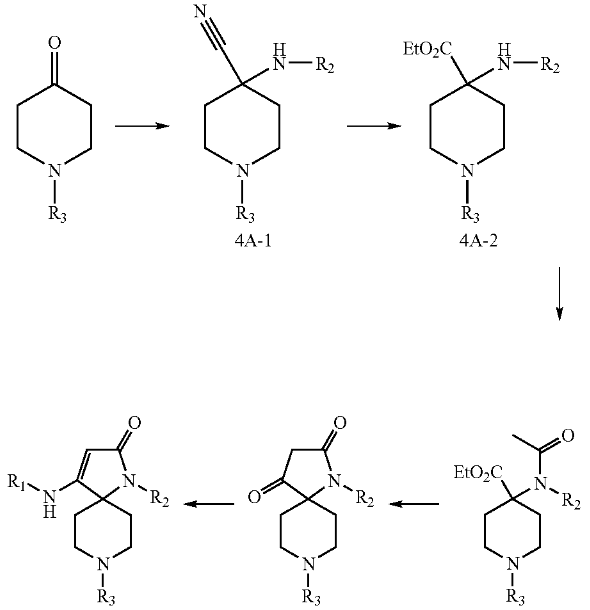

4A-1 4A-2 4A-3 4A-4 4A-5

Example 4A-6

8-benzyl-1-(3-fluorophenyl)-4-[(4-fluorophenyl)amino]-1,8-diazaspiro[4.5]dec-3-en-2-one

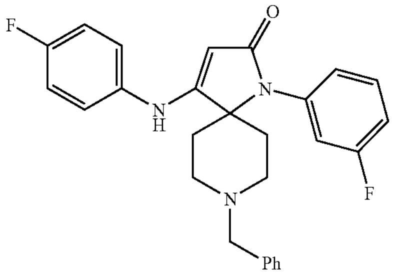

Step 1: 1-benzyl-4-[(3-fluorophenyl)amino]piperidine-4-carbonitrile (4A-1)

To a 0° C. solution of 15 g (79 mmol) N-benzyl piperidone in 80 mL acetic acid was added 7.6 mL (79 mmol) 3-fluoro aniline followed by dropwise addition of 10.5 mL (79 mmol) trimethylsilylnitrile (TMSCN). The reaction mixture was allowed to warm to rt and stirred for 1 hr, then poured onto a mixture of 120 g ice and 120 g concentrated $NH_4OH$. The resulting mixture was extracted 2×300 mL $CH_2Cl_2$ and the combined extracts washed with brine, dried over $MgSO_4$, filtered, and concentrated. The residue was suspended in 100 mL diisopropylether and stirred 30 min and filtered to give 1-benzyl-4-[(3-fluorophenyl)amino]piperidine-4-carbonitrile. $^1$H NMR ($CDCl_3$, 400 MHz) δ 7.26-7.35 (m, 5H); 7.19 (app q, J=8.06 Hz, 1H); 6.55-6.66 (m, 3H); 3.78 (s, 1H); 3.56 (s, 2H); 2.80 (br m, 2H); 2.48 (ddd, J=12.5, 12.5, 2.2 Hz, 2H); 2.35 (ddd, J=13.4, 2.56, 2.56 Hz, 2H); 1.92 (ddd, J=13.2, 13.2, 3.1 Hz, 2H) High resolution mass spec (FT/ICR) calc M+H=310.1714 found 310.1749.

Step 2: ethyl 1-benzyl-4-[(3-fluorophenyl)amino]piperidine-4-carboxylate (4A-2)

A solution of 5 g (16 mmol) 1-benzyl-4-[(3-fluorophenyl)amino]piperidine-4-carbonitrile in 20 mL concentrated $H_2SO_4$ was stirred vigorously for 18 hr, then cooled in an ice bath. The mixture was neutralized by slow addition of concentrated NaOH and ice chips, and the resulting heterogeneous mixture extracted with 500 mL $CH_2Cl_2$. The organic extract was dried over $MgSO_4$, filtered, and concentrated to give 4.6 g 1-benzyl-4-[(3-fluorophenyl)amino]piperidine-4-carbonitrile as a tan solid, of which 3.5 g (10.7 mmol) was dissolved in 25 mL ethylene glycol. To this was added 2.4 g solid KOH and the mixture was heated to 190° C. for 4 hr then cooled to 0° C. Water (100 mL) was added followed by acetic acid until the pH was neutral. The precipitate that formed was filtered, and a second crop was obtained and each crop was dissolved in 75 mL EtOH and 1.5 mL concentrated $H_2SO_4$ was added and the mixture was heated to reflux for 2 days, cooled and concentrated. Purification by automated flash chromatography (40 g silica gel cartridge 0-5% MeOH/$CH_2Cl_2$/(10% $NH_4OH$) over 15 min) afforded ethyl 1-benzyl-4-[(3-fluorophenyl)amino]piperidine-4-carboxylate as a thick oil. $^1$H NMR ($CDCl_3$, 400 MHz) δ 7.31 (m, 4H); 7.25 (m, 1H); 7.05 (app q, J=8.24 Hz, 1H); 6.41 (app dt, J=8.42 and 2.38 Hz, 1H); 6.33 (dd, J=8.24 and 2.20 Hz, 1H); 6.27 (app dt, J=11.5 and 2.20 Hz, 1H); 4.16 (q, J=7.14 Hz, 2H); 3.96 (s, 1H); 3.51 (s, 2H); 2.63 (br m, 2H); 2.38 (ddd, J=12.3, 12.3, 2.01 Hz, 2H); 2.24 (ddd, J=13.7, 3.67, 3.67 Hz, 2H); 2.00 (br d, J=11.3 Hz, 2H); 1.16 (t, J=7.14, 3H). Electrospray mass spectrum M+H=357.1.

Step 3: ethyl 4-[acetyl(3-fluorophenyl)amino]-1-benzylpiperidine-4-carboxylate (4A-3)

A solution of 0.2 g (0.56 mmol) ethyl 1-benzyl-4-[(3-fluorophenyl)amino]piperidine-4-carboxylate in 2.6 mL (28 mmol) acetic anhydride (neat) was heated to 120° C. for 20 hr, then poured into 50 mL of a 1:1 mixture of water and concentrated $NH_4OH$, extracted with 100 mL EtOAc, washed with water then brine, dried over $MgSO_4$, filtered, and concentrated. Purification by automated flash chromatography (40 g silica gel cartridge 0-5% MeOH/$CH_2Cl_2$) over 15 min) afforded ethyl 4-[acetyl(3-fluorophenyl)amino]-1-benzylpiperidine-4-carboxylate. $^1$H NMR ($CDCl_3$, 400 MHz) δ 7.39 (m, 1H); 7.20-7.31 (m, 4H); 7.06-7.15 (m, 4H); 4.25 (q, J=7.14 Hz, 2H); 3.46 (s, 2H); 2.59 (br m, 2H); 2.30-2.48 (m, 3H); 2.22 (m, 2H); 1.72 (s, 3H) 1.63 (m, 2H); 1.31 (t, J=7.15, 3H). Electrospray mass spectrum M+H=399.2

Step 4: 8-benzyl-1-(3-fluorophenyl)-1,8-diazaspiro[4.5]decane-2,4-dione (4A-4)

To a 0° C. solution of 0.86 g (2.2 mmol) ethyl 4-[acetyl(3-fluorophenyl)amino]-1-benzylpiperidine-4-carboxylate in 1 mL THF was added 3.2 mL (6.5 mmol, 2M solution in heptane, THF, ethylbenzene) lithium diisopropylamide solution and the reaction mixture was allowed to slowly warm to rt and stirred for an additional 14 hr. To this mixture was added 50 mL water and 50 mL EtOAc and the pH was adjusted to pH=6 with 1N HCl (approx 11 mL). The aqueous layer was extracted 3×100 mL EtOAc and the combined extracts washed with 100 mL brine, dried over MgSO4, filtered, and concentrated to give 8-benzyl-1-(3-fluorophenyl)-1,8-diazaspiro[4.5]decane-2,4-dione as a solid. $^1$H NMR ($CDCl_3$, 400 MHz) δ 7.44 (ddd, J=8.06, 8.06 and 6.23 Hz, 1H); 7.14-7.30 (m, 6H); 6.95 (br d, J=7.88 Hz, 1H); 6.89 (ddd, J=9.16, 2.02, and 2.02 Hz, 1H); 3.52 (s, 2H); 3.26 (s, 2H); 2.73 (m, 2H); 2.65 (m, 2H); 1.85 (br m, 4H). Electrospray mass spectrum M+H=353.1

Step 6 to give 8-benzyl-1-(3-fluorophenyl)-4-[(4-fluorophenyl)amino]-1,8-diazaspiro[4.5]dec-3-en-2-one. (4A-6)

To a solution of 55 mg (0.156 mmol) 8-benzyl-1-(3-fluorophenyl)-1,8-diazaspiro[4.5]decane-2,4-dione in 2 mL dry toluene was added 36 mg (0.187 mmol)$_p$-toluenesulfonic acid monohydrate and 0.030 mL (0.312 mmol) 4-fluoroaniline. The reaction mixture was refluxed for 24 hrs. The solvent was then removed by concentration in vacuum. The residue was purified by preparative HPLC (5→95% $CH_3CN$/$H_2O$ over 30 min, 0.05% added TFA, C18 PRO YMC 20×150 mm) to afford 8-benzyl-1-(3-fluorophenyl)-4-[(4-fluorophenyl)amino]-1,8-diazaspiro[4.5]dec-3-en-2-one as a white solid. $^1$H NMR ($CD_3OD$, 400 MHz): δ 7.50-7.20 (m, 7H), 7.20-6.98 (m 6H), 5.24 (s, 1H), 3.60 (s, 2H), 2.99-2.80 (m, 2H), 2.36-2.43 (m, 2H), 2.24-1.98 (m, 2H), 2.10 (m, 1H), 1.00 (m, 2H). High resolution mass spec (FT/ICR): calc M+H=446.2039 found 446.2035.

Scheme 4B depicts an alternative procedure for the preparation of compounds of the invention wherein X═$CR^4$ or X'═$CR^4R^{4'}$, including Example 4B-7 below (Example 4B-7 is depicted in enamine form, but may also exist in tautomeric form). Strecker adduct 4A-1 is first acylated to give 4B-2 and then cyclized to 4B-3 using a base such as NaOMe. Structures of type 4B-3 and derivatives thereof are also of use for the intended invention described herein. Decarboxylation of structures of type 4B-3 using a strong acid, such as aqueous 6N HCl, gives initially structures of type 4B-4a, which are also claimed for use in the invention. Upon prolonged heating in acid intermediate 4B-4b (same as 4A-4 in scheme 4A) is generated. 4B-4b may then be treated with a suitable amine to give final compounds of type 4B-5 (4A-4). Additionally, for cases wherein X═$CR^4$ and $R^4$=fluorine, penultimate compounds from either route 4A or 4B, for example 4B-5 can be treated with a fluorinating agent to give compounds of type 4B-6.

Scheme 4B

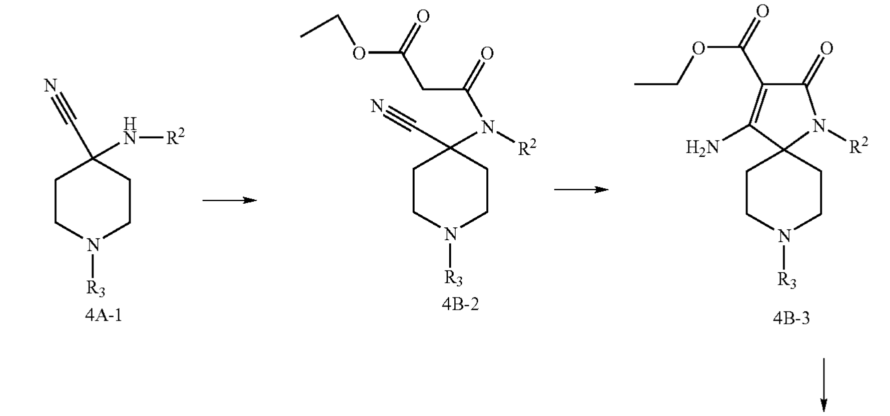

4A-1 4B-2 4B-3

-continued

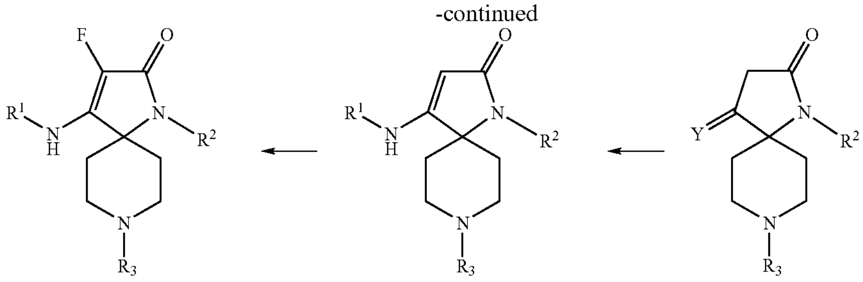

4B-6

4B-5
(4A-4)

4B-4a Y = NH
4B-4b Y = O

Example 4B-7

8-Benzyl-4-[(2-ethylphenyl)amino]-1-(3-fluorophenyl)-1,8-diazaspiro[4.5]dec-3-en-2-one

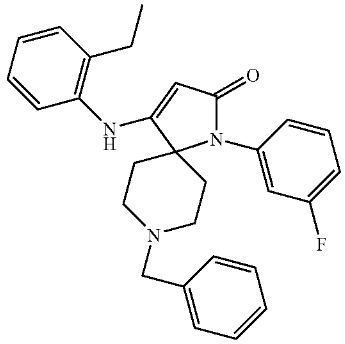

Step 1. Acylation to give Intermediate of type 4B-2. To a rt solution of 9.0 g (29.1 mmol) ethyl 3-[(1-benzyl-4-cyanopiperidin-4-yl)(3-fluorophenyl)amino]-3-oxopropanoate (intermediate 4A-1 as describe above) in 150 mL $CH_2Cl_2$ was added 4.9 mL (37.8 mmol) ethyl malonyl chloride and 5.1 mL (43.6 mmol) 2,6-lutidine. After 3 h, the reaction was diluted with 150 mL $CH_2Cl_2$ and washed with water and brine. The organic portion was dried over $Na_2SO_4$, filtered, and concentrated in vacuo to afford ethyl 3-[(1-benzyl-4-cyanopiperidin-4-yl)(3-fluorophenyl)amino]-3-oxopropanoate. LC/MS [M+H]=424.0.

Step 2. Intermediate of type 4B-3: 8-benzyl-1-(3-fluorophenyl)-1,8-diazaspiro[4.5]decane-2,4-dione To a rt solution of 14.9 g (35.2 mmol) ethyl 3-[(1-benzyl-4-cyanopiperidin-4-yl)(3-fluorophenyl)amino]-3-oxopropanoate in 20 mL methanol was added 7.6 mL (42.2 mmol) 30% w/v sodium methoxide in methanol. After 1 h, the reaction was concentrated to yield a mixture of ethyl 4-amino-8-benzyl-1-(3-fluorophenyl)-2-oxo-1,8-diazaspiro[4.5]dec-3-ene-3-carboxylate and methyl 4-amino-8-benzyl-1-(3-fluorophenyl)-2-oxo-1,8-diazaspiro[4.5]dec-3-ene-3-carboxylate, which was suspended in 200 mL 6N HCl and heated to 80° C. After 18 h the reaction was cooled to 0° C., adjusted to pH=10 with concentrated NaOH, and extracted 9×200 mL EtOAc. The combined extracts were washed with brine, dried over $Na_2SO_4$, filtered, and concentrated to give a red foam. Crystallization from $CH_2Cl_2$ afforded ketoamide intermediate 8-benzyl-1-(3-fluorophenyl)-1,8-diazaspiro[4.5]decane-2,4-dione. LC/MS [M+H]=353.1.

Step C. Condensation with amine to give structures of type 4B-4. 8-benzyl-4-[(2-ethylphenyl)amino]-1-(3-fluorophenyl)-1,8-diazaspiro[4.5]dec-3-en-2-one (4B-7)

To a solution of 100 mg (0.28 mmol) 8-benzyl-1-(3-fluorophenyl)-1,8-diazaspiro[4.5]decane-2,4-dione in 0.71 mL dry toluene was added 70 mg (0.37 mmol)$_p$-toluenesulfonic acid monohydrate and 61 μL (0.50 mmol) 2-ethylaniline. The reaction was heated to reflux for 18 h and then diluted with EtOAc, washed with 1N NaOH, dried over $Na_2SO_4$, filtered, and concentrated in vacuo. The crude material was purified on silica gel with 20-60% EtOAc/hexanes to afford title example 8-benzyl-4-[(2-ethylphenyl)amino]-1-(3-fluorophenyl)-1,8-diazaspiro[4.5]dec-3-en-2-one as a tan foam. $^1H$ NMR ($CD_3OD$, 400 MHz) δ 7.43 (q, J=7.38 Hz, 1H), 7.32 (m, 1H), 7.24 (m, 6H), 7.16 (m, 3H), 7.08 (m, 2H), 4.55 (s, 1H), 3.41 (s, 2H), 2.80 (m, 2H), 2.64 (q, J=7.51 Hz, 2H), 2.38 (m, 2H), 2.19 (m, 2H), 2.10 (dt, J=11.5 and 3.85 Hz, 2H), 1.18 (t, J=7.51 Hz, 3H); LC/MS [M+H]=456.1.

The compounds (or salts thereof) of the following type in Table 1a can be prepared in a manner similar to one of the above mentioned methods described in Schemes 4A and 4B. Table 1a.

| EX | Name | Structure | ES M + 1 |
|---|---|---|---|
| 4B-8 | 4-anilino-8-benzyl-1-(3-fluorophenyl)-1,8-diazaspiro[4.5]dec-3-en-2-one | 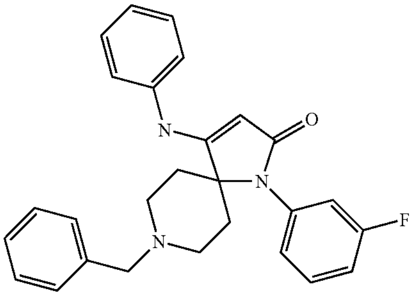 | 428.2 |
| 4B-9 | 8-benzyl-1-(3-fluorophenyl)-4-[(3-fluorophenyl)amino]-1,8-diazaspiro[4.5]dec-3-en-2-one | 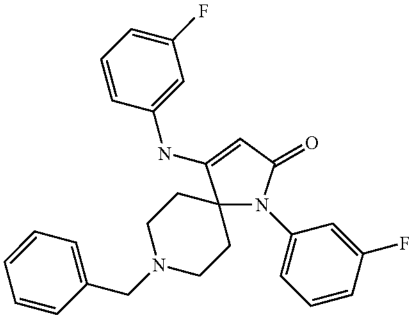 | 446.2 |
| 4B-10 | 8-benzyl-4-(cyclohexylamino)-1-(3-fluorophenyl)-1,8-diazaspiro[4.5]dec-3-en-2-one | 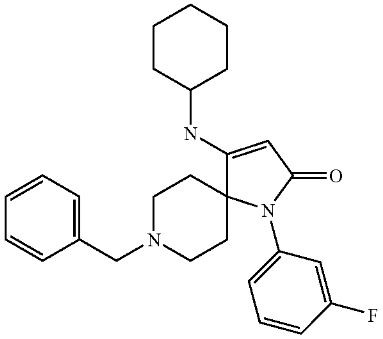 | 434.3 |
| 4B-12 | 4-(cyclohexylamino)-1-(3-fluorophenyl)-8-(3-isopropoxybenzyl)-1,8-diazaspiro[4.5]dec-3-en-2-one | 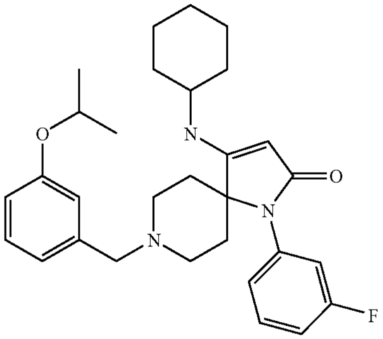 | 492.4 |

-continued
| EX | Name | Structure | ES M + 1 |
|---|---|---|---|
| 4B-13 | 8-benzyl-4-[(3,4-difluorophenyl)amino]-1-(3-fluorophenyl)-1,8-diazaspiro[4.5]dec-3-en-2-one | 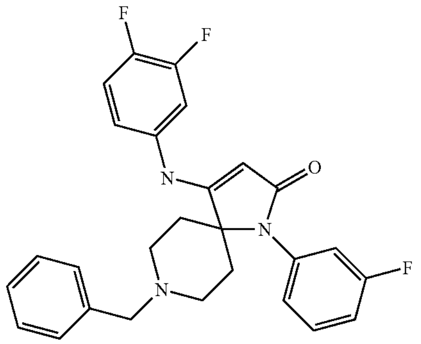 | 464.2 |
| 4B-14 | 8-benzyl-4-[(3,5-difluorophenyl)amino]-1-(3-fluorophenyl)-1,8-diazaspiro[4.5]dec-3-en-2-one | 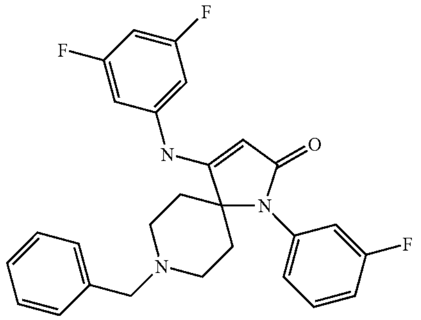 | 464.2 |
| 4B-15 | 8-benzyl-4-[(2,4-difluorophenyl)amino]-1-(3-fluorophenyl)-1,8-diazaspiroll4.5]dec-3-en-2-one | 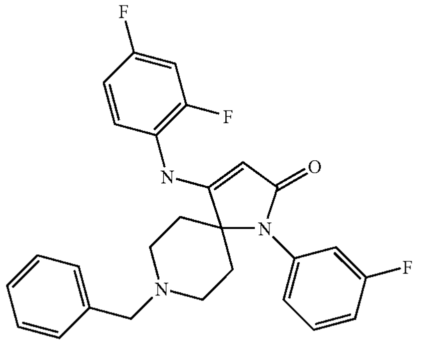 | 464.2 |
| 4B-16 | 8-benzyl-1-(3-fluorophenyl)-4-[(4-methoxyphenyl)amino]-1,8-diazaspiro[4.5]dec-3-en-2-one | 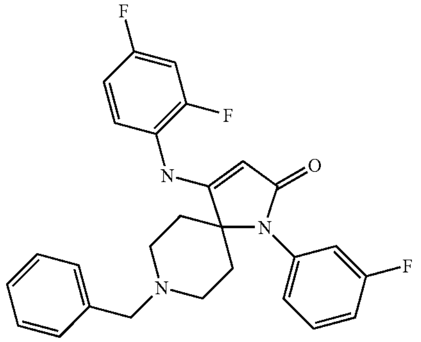 | 458.3 |

-continued

| EX | Name | Structure | ES M + 1 |
|---|---|---|---|
| 4B-17 | 8-benzyl-1-(3-fluorophenyl)-4-[(2-fluorophenyl)amino]-1,8-diazaspiro[4.5]dec-3-en-2-one | 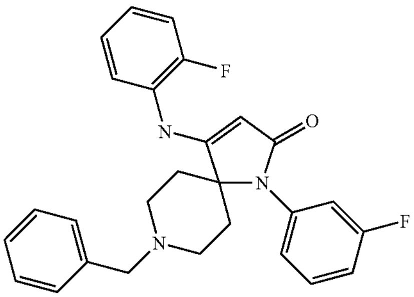 | 446.2 |
| 4B-18 | 8-benzyl-1-(3-fluorophenyl)-4-[(2-propylphenyl)amino]-1,8-diazaspiro[4.5]dec-3-en-2-one | 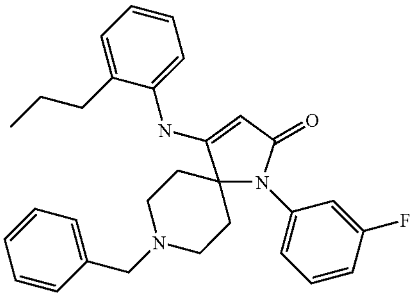 | 484.3 |
| 4B-19 | 8-benzyl-4-[(2-butylphenyl)amino]-1-(3-fluorophenyl)-1,8-diazaspiro[4.5]dec-3-en-2-one | 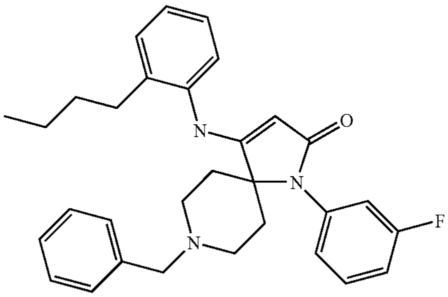 | 470.3 |
| 4B-20 | 8-benzyl-1-(3-fluorophenyl)-4-[(2-isopropylphenyl)amino]-1,8-diazaspiro[4.5]dec-3-en-2-one | 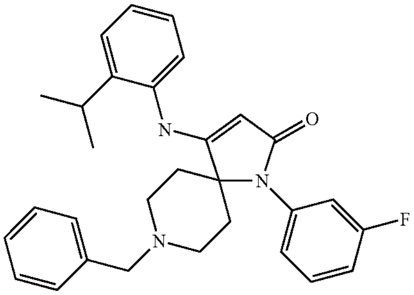 | 484.1 |
| 4B-21 | 8-benzyl-4-[(2-sec-butylphenyl)amino]-1-(3-fluorophenyl)-1,8-diazaspiro[4.5]dec-3-en-2-one | 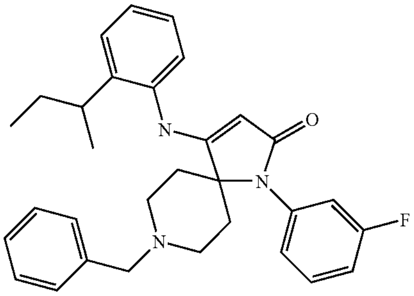 | 518.3 |

-continued

| EX | Name | Structure | ES M + 1 |
|---|---|---|---|
| 4B-22 | 8-benzyl-4-[(2-benzylphenyl)amino]-1-(3-fluorophenyl)-1,8-diazaspiro[4.5]dec-3-en-2-one | 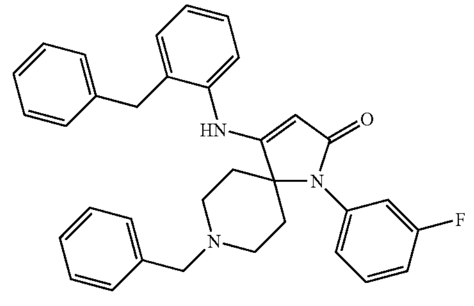 | 618.2 |
| 4B-23 | 8-benzyl-4-[(2,4-difluorophenyl)amino]-1-[4-fluoro-4'-(methylsulfonyl)biphenyl-2-yl]-1,8-diazaspiro[4.5]dec-3-en-2-one | 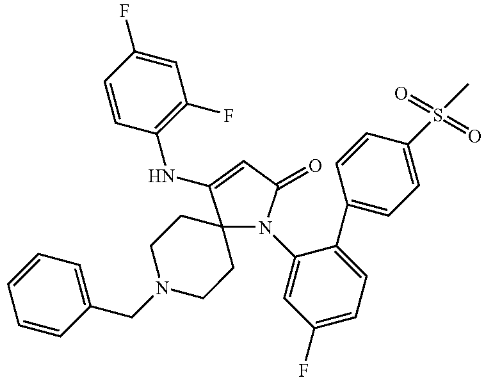 | 618.4 |

Example 4B-24

8-benzyl-4-(cyclohexylamine)-3-fluoro-1-(3-fluorophenyl)-1,8-diazaspiro[4.5]dec-3-en-2-one (4B-24)

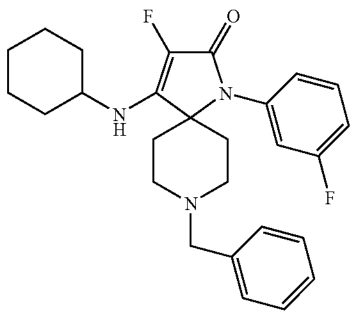

To a solution of vinylogous amide 8-benzyl-4-(cyclohexylamine)-1-(3-fluorophenyl)-1,8-diazaspiro[4.5]dec-3-en-2-one (11 mg 0.025 mmol) in anhydrous DMA was added Selectfluor (9 mg, 0.025 mmol). The solution stirred overnight at rt. Purification by preparative HPLC (5→95% $CH_3CN/H_2O$ over 30 min, 0.05% added TFA, C18 PROYMC 20×150 mm) yielded the product as a solid. $^1H$ NMR ($CD_3OD$, 400 MHz) δ 7.51-7.11 (m, 9H), 4.17 (s, 2H), 3.51-3.41 (m, 3H), 2.54 (m, 3H), 2.34-2.30 (m, 2H), 1.80 (m, 2H), 1.60 (m, 2H), 1.40 (m, 3H), 1.37-1.12 (m, 5H). HRMS (FT/ICR): calc M+H=452.2508. found 452.2513.

Example 4B-25

Ethyl 4-amino-8-benzyl-1-(5-bromo-2-fluorophenyl)-2-oxo-1,8-diazaspiro[4.5]dec-3-ene-3-carboxylate

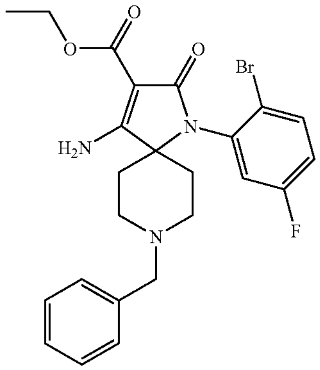

To a solution of 1-benzyl-4-[(2-bromo-5-fluorophenyl)amino]piperidine-4-carbonitrile (100 mg, 0.258 mmol, prepared from Strecker reaction using 2-bromo-4-fluoroaniline) in 2 mL dichloromethane was added ethyl malonyl chloride (43 μL, 0.335 mmol). The solution stirred for 1 hr at rt. The solvent was removed in vacuo and the residue purified by preparative HPLC (5→95% $CH_3CN/H_2O$ over 30 min, 0.05% added TFA, C18 PROYMC 20×150 mm) to afford the product as a white solid. $^1H$ NMR ($CD_3OD$, 400 MHz): δ 7.60-7.05 (m, 8M), 4.29-4.15 (m, 4H), 3.53-3.50 (m, 2H), 2.69-2.53 (m, 4H), 1.30 (m, 3H). LC/MS [M+1]=502.0

Example 4B-26

4-amino-8-benzyl-1-[4-fluoro-4'-(methylsulfonyl)biphenyl-2-yl]-1,8-diazaspiro[4.5]dec-3-en-2-one

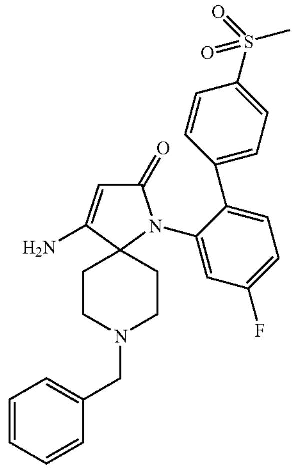

Decarboxylation of 4B-25 and isolation using conditions similar to example 4B-1 followed by Suzuki coupling using [4(methylsulfonyl)phenyl]boronic acid as described for example 15-2 and purification using RP-HPLC provided title compound as a white solid. LC/MS [M+H]=506.3.

Scheme 5 depicts a method for synthesizing compounds with alternative $R^3$ groups, such as Example (5-3) below (Example (5-3) is depicted in enamine form, but may also exist in tautomeric imine form).

Scheme 5

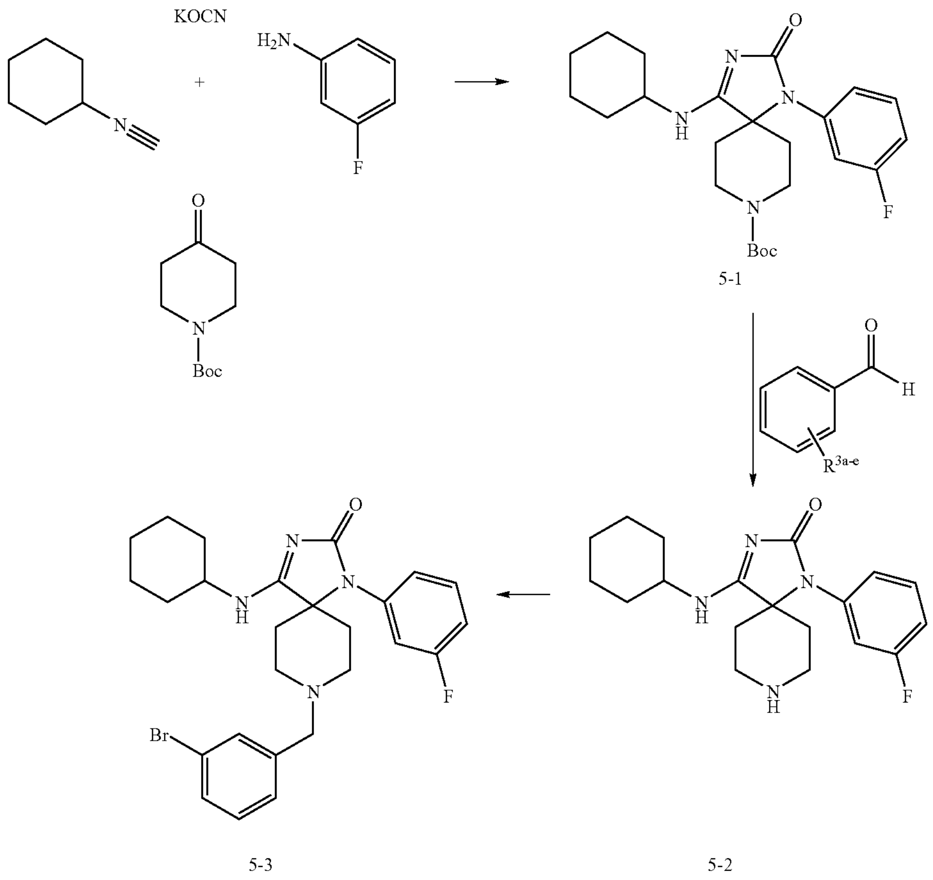

Example 5-3

8-(3-Bromobenzyl)-4-(cyclohexylamino)-1-(3-fluorophenyl)-1,3,8-triazaspiro[4.5]dec-3-en-2-one

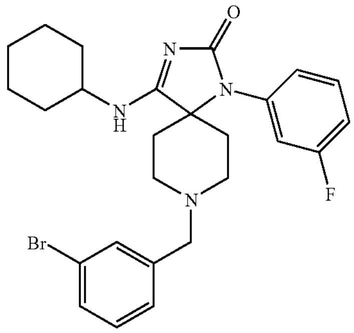

Step 1: tert-Butyl 4-(cyclohexylamino)-1-(3-fluorophenyl)-2-oxo-1,3,8-triazaspiro[4.5]dec-3-ene-8-carboxylate (5-1)

To a 10 mL MeOH suspension of 4.05 g (20.3 mmol) N-boc piperidinone and 2.11 g (19.3 mmol) cyclohexyl isocyanide was added a solution of 2.06 g (25.4 mmol) potassium isocyanate in 2.8 mL $H_2O$ in one portion with stirring followed by 3.0 g (20.3 mmol) 3-fluoroaniline hydrochloride in portions over 5 m. After stirring for 2 h the reaction was treated with 250 ml $CH_2Cl_2$. The organic layer was washed with water (2×50 ml), brine (1×50 ml), dried over $Na_2SO_4$, filtered and concentrated to dryness in vacuo to give a crude oil (9.68 g). Purification by automated flash chromatography (0-5.5% MeOH in $CH_2Cl_2$ over 28 m) afforded tert-butyl 4-(cyclohexylamino)-1-(3-fluorophenyl)-2-oxo-1,3,8-triazaspiro[4.5]dec-3-ene-8-carboxylate as a white solid. $^1H$ NMR ($CDCl_3$, 400 MHz): δ 7.41 (m, 1H), 7.11 (m, 1H), 7.05 (d, J=7.88 Hz, 1H), 6.99 (m, 1H), 5.40 (br s, 1H), 4.02 (m, 1H), 3.58 (m, 2H), 3.27 (m, 2H), 2.05 (m, 4H), 1.92 (m, 2H), 1.71 (m, 4H), 1.44 (m, 12H), 1.24 (m, 2H). Electrospray mass spectrum: M+H=445.2

Step 2: 2: 4-(Cyclohexylamino)-1-(3-fluorophenyl)-2-oxo-1,3,8-triazaspiro[4.5]dec-3-ene dihydrochloride 5-2

To a suspension of 2.74 g (6.16 mmol) tert-butyl 4-(cyclohexylamino)-1-(3-fluorophenyl)-2-oxo-1,3,8-triazaspiro[4.5]dec-3-ene-8-carboxylate in 50 mL EtOAc at 0° C. was bubbled in HCl gas until the solvent was saturated. The reaction was stirred in the cold for 30 m and concentrated in vacuo. The solid residue was reconcentrated to dryness (2× ethyl ether) and dried under high vacuum to give 4-(cyclohexylamino)-1-(3-fluorophenyl)-2-oxo-1,3-triazaspiro[4.5]dec-3-ene as its dihydrochloride salt as a fine white solid. $^1H$ NMR (DMSO, 400 MHz): δ 10.73 (br s, 1H), 9.58 (br s, 1H), 9.21 (s, 1H), 8.36 (br s, 1H), 7.46 (m, 4H), 3.82 (br m, 1H), 3.36 (br s, 2H), 2.92 (br s, 2H), 2.55 (m, 2H), 2.33 (br m, 2H), 1.87 (br s, 2H), 1.75 (br s, 2H), 1.52 (br m, 3H), 1.29 (br m, 2H), 1.16 (m, 1H). Electrospray mass spectrum: M+H=345.2

Step 3: 8-(3-Bromobenzyl)-4-(cyclohexylamino)-1-(3-fluorophenyl)-1,3,8-triazaspiro[4.5]dec-3-en-2-one (5-3)

To a suspension of 600 mg (1.44 mmol) 4-(cyclohexylammonio)-1-(3-fluorophenyl)-2-oxo-1,3-diaza-8-azoniaspiro[4.5]dec-3-ene dihydrochloride, 376 μL (2.16 mmol) diisopropylethylamine, and 427 mg (2.01 mmol) triacetoxy sodium borohydride in 20 mL DCE was added dropwise a 4 mL DCE solution of 251 μL (2.16 mmol) 3-bromobenzaldehyde and the resulting heterogeneous mixture was stirred at rt overnight under a nitrogen atmosphere. The reaction mixture was treated with 50 mL $CH_2Cl_2$ and washed with 20 mL saturated $NaHCO_3$ (aq), 20 mL brine, dried over $Na_2SO_4$, filtered, and concentrated in vacuo. Purification by automated flash chromatography (0-5% MeOH in $CH_2Cl_2$ over 25 m) afforded the product as a white solid. $^1H$ NMR ($CDCl_3$, 400 MHz): δ 7.75 (d, J=8.15 Hz, 1H), 7.45 (m, 2H), 7.36 (m, 1H), 7.22 (m, 1H), 7.15 (d, J=7.69 Hz, 1H), 7.02 (m, 3H), 3.97 (m, 1H), 3.50 (s, 2H), 2.76 (m, 2H), 2.43 (m, 2H), 2.09 (m, 4H), 1.95 (m, 2H), 1.75 (m, 2H), 1.68 (m, 1H), 1.41 (m, 2H), 1.23 (m, 3H). High resolution mass spec (FT/ICR): calc M+H=513.1660. found 513.1697

Example (5-4)

4-(cyclohexylamino)-1-(3-fluorophenyl)-8-{3-[(1-methylprop-2-enyl)oxy]benzyl}-1,3,8-triazaspiro[4.5]dec-3-en-2-one

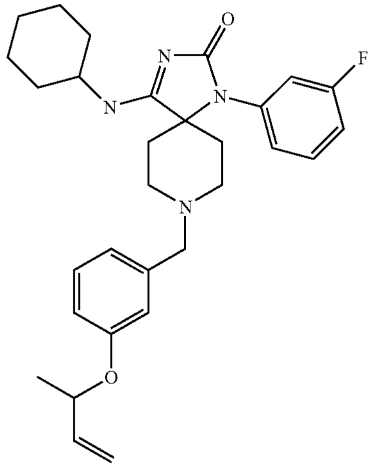

Step 1

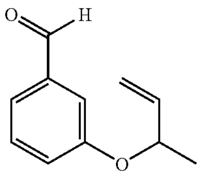

Step 1: 3-[(1-methylprop-2-enyl)oxy]benzaldehyde

Added DEAD (0.964 mL, 6.142 mmole) dropwise to a solution of triphenylphosphine (0.1.611 g, 6.142 mmole), 3-buten-2-ol (Fluka, 0.423 mL, 4.91 mmole), and 3-hydroxy benzaldehyde (0.5 g, 4.09 mmole) in 10 mL dry THF, at rt, under Argon. After 10 min, the reaction was concentrated in vacuo and was purified on a 35 g Redisep column eluting with a gradient of 5%-30% EtOAc in hexanes.

Step 2: 4-(cyclohexylamino)-1-(3-fluorophenyl)-8-{3-[(1-methylprop-2-enyl)oxy]benzyl}-1,3,8-triazaspiro[4.5]dec-3-en-2-one The compound was prepared as described for Example (5-3) using the above aldehyde.

$^1H$ NMR ($CDCl_3$, 400 Mh), δ 8.07 (d, J=7.9 Hz, 1H); 7.34 (m, 1H); 7.23 (t, J=8.24, 8.06 Hz, 1H); 7.00 (m, 3H); 6.84 (m, 3H); 5.89 (ddd, J=6.4, 5.9, 11.0, 21.9 Hz, 1H); 5.25 (dd, J=1.1, 17.4 Hz, 1H); 5.17 (d, J=10.6 Hz, 1H); 4.80 (m, 1H);

3.95 (m, 1H); 3.49 (s, 2H); 2.78 (m, 2H); 2.44 (m, 2H); 2.12 (m, 2H); 2.07 (m, 2H); 1.94 (m, 2H); 1.74 (m, 2H); 1.67 (m, 2H); 1.43 (d, J=6.5 Hz, 3H); 1.39 (m, 1H); 1.22 (m, 3H). Mass spec (m+1)=505.

Example (5-5)

4-(cyclohexylamino)-1-(3-fluorophenyl)-8-(3-isopropoxybenzyl)-1,3,8-triazaspiro[4.5]dec-3-en-2-one

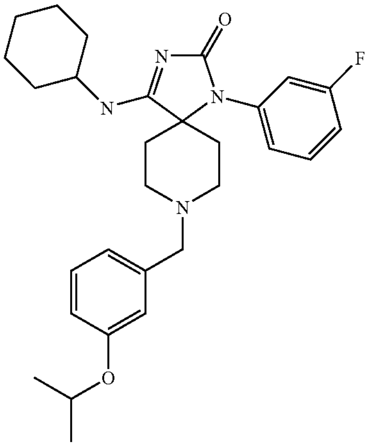

Step 1: 3-isopropoxybenzyaldehyde

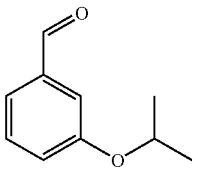

This method of alkylation is similar to that described in *J Med Chem* (2002), 45(18), 3891-3904. Dissolved 3-Hydroxy benzaldehyde (0.500 g, 4.094 mmole) in 10 mL EtOH at rt, under Argon, and magnetically stirred. Added $K_2CO_3$. (1.132 g, 8.189 mmole), then 2-iodopropane (0.819 mL, 8.819 mmole). Warmed to 60° C. After 18 hr, added a second equivalent of alkyl iodide of (0.819 mL, 8.189 mmole) and continued heating at 60° C. After 4 hr, cooled to rt and concentrated in vacuo. Partitioned residue between EtOAc, and $H_2O$. Washed organic layer with 1 M NaOH, 2×20 mL, dried organic layer over $MgSO_4$, filtered and concentrated in vacuo to give the aldehyde.

Step 2: 4-(cyclohexylamino)-1-(3-fluorophenyl)-8-(3-isopropoxybenzyl)-1,3,8-triazaspiro[4.5]dec-3-en-2-one (5-6)

Suspended 4-(cyclohexylamino)-1-(3-fluorophenyl)-2-oxo-1,3-triazaspiro[4.5]dec-3-ene dihydrochloride salt (5-2, 0.500 g, 1.198 mMole) and 3-isopropoxyaldehyde (0.197 g, 1.198 mmole) in 5 mL of CHC13. Added Hunigs Base (0.313 mL, 1.795 mmole). Let stir for 0.5 hr, then added cyanoborohydride silica bound (1 mmole/g, 1.318 g, 1.318 mmole) (Aldrich), then 0.034 mL HOAc. Let sit for 1 hr, then heated in microwave for 20 min at 150° C. Filtered off silica gel and concentrated in vacuo. Purified using a Redi-sep 40 g silica gel column eluting with 0-5% methanol/CH2C12 saturated with NH3 and collected impure product as a solid. Rinsed solid with EtOAc, and collected purified solids to give product.

$^1H$ NMR ($CDCl_3$, 400 Mh), δ 8.11 (d, J=7.4 Hz, 1H); 7.40 (m, 1H); 7.24 (m, 1H); 7.02 (m, 3H); 6.80 (m, 3H); 4.55 (quintet, J=6.04 Hz, 1H); 3.98 (m, 1H); 3.50 (s, 2H); 2.79 (m, 2H); 2.43 (m, 2H); 2.10 (m, 2H); 2.02 (m, 2H); 1.97 (m, 2H); 1.74 (m, 2H); 1.64 (m, 2H); 1.38 (m, 1H); 1.33 (d, J=6.0 Hz, 6H); 1.23 (m, 3H).

Mass Spec (m+1)=493.

Scheme 6 depicts a method for preparing compounds wherein $R^1$ is methyl, such as Examples (6-3)-(6-6) below. Examples (6-3)-(6-6) are depicted in enamine form, but may also exist in tautomeric imine form as described above.

Scheme 6

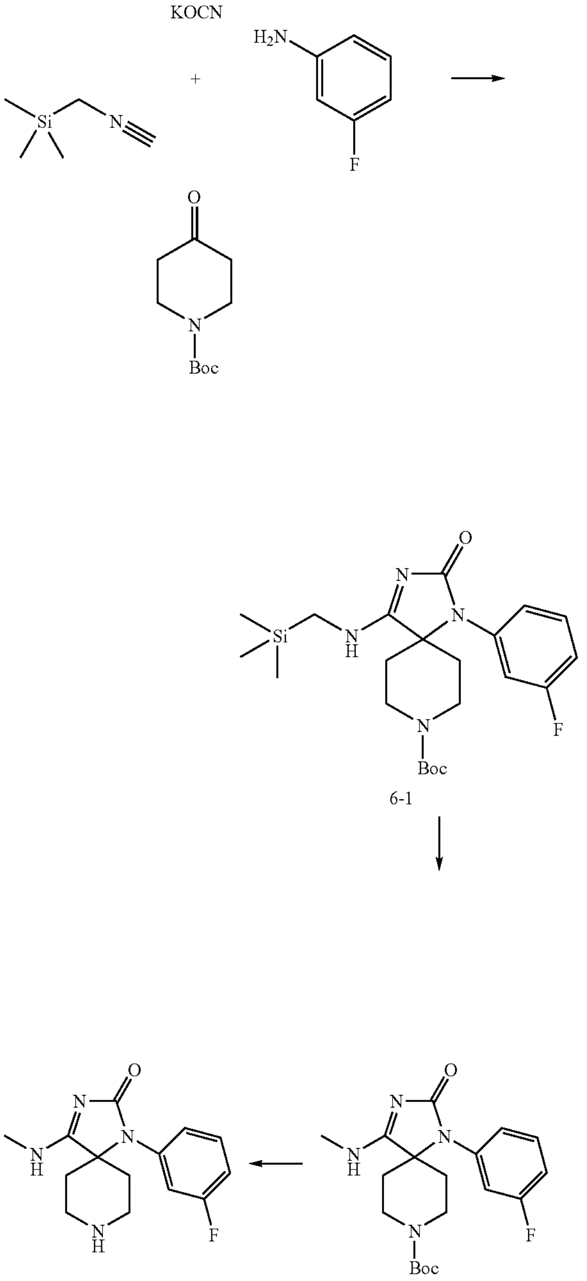

6-1

6-3

6-2

Example 6-3

4-methyl-1-(3-fluorophenyl)-2-oxo-1,3,8-triazaspiro[4.5]dec-3-ene (6-3)

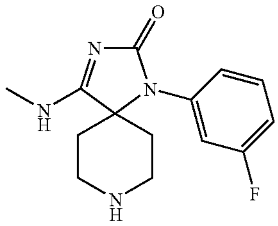

Intermediate 6-1: tert-Butyl 1-(3-fluorophenyl)-2-oxo-4-[(trimethylsilyl)methyl]amino-1,3,8-triazaspiro[4.5]dec-3-ene-8-carboxylate Intermediate 6-1 was prepared in the same manner as Intermediate 5-1 above.

Intermediate 6-2: tert-Butyl 1-(3-fluorophenyl)-4-(methylamino)-2-oxo-1,3,8-triazaspiro[4.5]dec-3-ene-8-carboxylate To a 50 ml THF solution of 1.04 g (2.41 mmol) tert-butyl 1-(3-fluorophenyl)-2-oxo-4-{[(trimethylsilyl)methyl]amino}-1,3,8-triazaspiro[4.5]dec-3-ene-8-carboxylate (prepared in the same manner as Intermediate 5-1 above) was added 3.61 mL (3.61 mmol) of a 1.0M tetrabutylammonium fluoride in THF solution over 5 m and the reaction warmed to 60° C. overnight. The reaction was concentrated to dryness in vacuo and the residue treated with 100 mL $CH_2Cl_2$. The organic layer was washed with water (1×25 mL), brine (1×25 mL), dried over $Na_2SO_4$, filtered and concentrated to dryness in vacuo to give a crude oil (1.6 g). Purification by flash chromatography (0-7.5% MeOH in $CH_2Cl_2$ over 25 m) afforded tert-butyl 1-(3-fluorophenyl)-4-(methylamino)-2-oxo-1,3,8-triazaspiro[4.5]dec-3-ene-8-carboxylate 6-2 as a white solid. $^1H$ NMR ($CDCl_3$, 400 MHz) δ 7.39 (m, 1H), 7.12 (m, 1H), 7.03 (d, J=7.95 Hz, 1H), 6.97 (m, 1H), 5.70 (br s, 1H), 3.54 (m, 2H), 3.11 (d, J=4.76 Hz, 3H), 2.02 (m, 2H), 1.92 (m, 2H), 1.42 (s, 9H). High resolution mass spec (FT/ICR): calc M+H=377.1984. found 377.2010

4-methyl-1-(3-fluorophenyl)-2-oxo-1,3,8-triazaspiro[4.5]dec-3-ene (6-3) was prepared in analogy to Intermediate 5-2 and the following examples in Table 2 and their pharmaceutically acceptable salts were prepared according to Scheme 6 and in analogy to Intermediate 5-3.

TABLE 2

Compounds (or salts thereof) Synthesized According to a manner similar to that described in Scheme 6

| EX | Structure | Chemical Name | Mass spec |
|---|---|---|---|
| 6-4 | 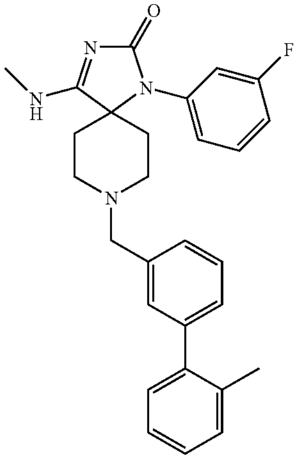 | 1-(3-fluorophenyl)-4-(methylamino)-8-[(2'-methylbiphenyl-3-yl)methyl]-1,3,8-triazaspiro[4.5]dec-3-en-2-one | 457.2 |
| 6-5 | 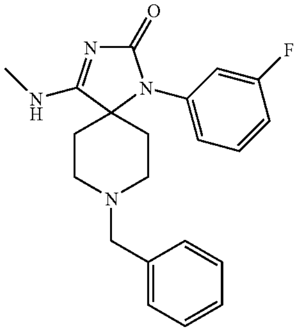 | 8-benzyl-1-(3-fluorophenyl)-4-(methylamino)-1,3,8-triazaspiro[4.5]dec-3-en-2-one | 367.1 |

TABLE 2-continued

| Compounds (or salts thereof) Synthesized According to a manner similar to that described in Scheme 6 | | | |
|---|---|---|---|
| EX | Structure | Chemical Name | Mass spec |
| 6-6 | 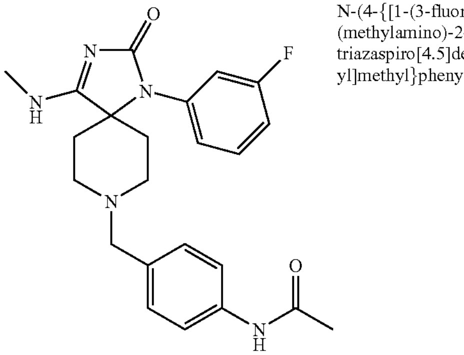 | N-(4-{[1-(3-fluorophenyl)-4-(methylamino)-2-oxo-1,3,8-triazaspiro[4.5]dec-3-en-8-yl]methyl}phenyl)acetamide | 424.2 |

Scheme 7 demonstrates another method for preparing compounds with alternate $R^3$ groups (such as Example (7-2) and (7-3). Example (7-2) and (7-3) are depicted in enamine form but may also exist in tautomeric imine form.

Scheme 7

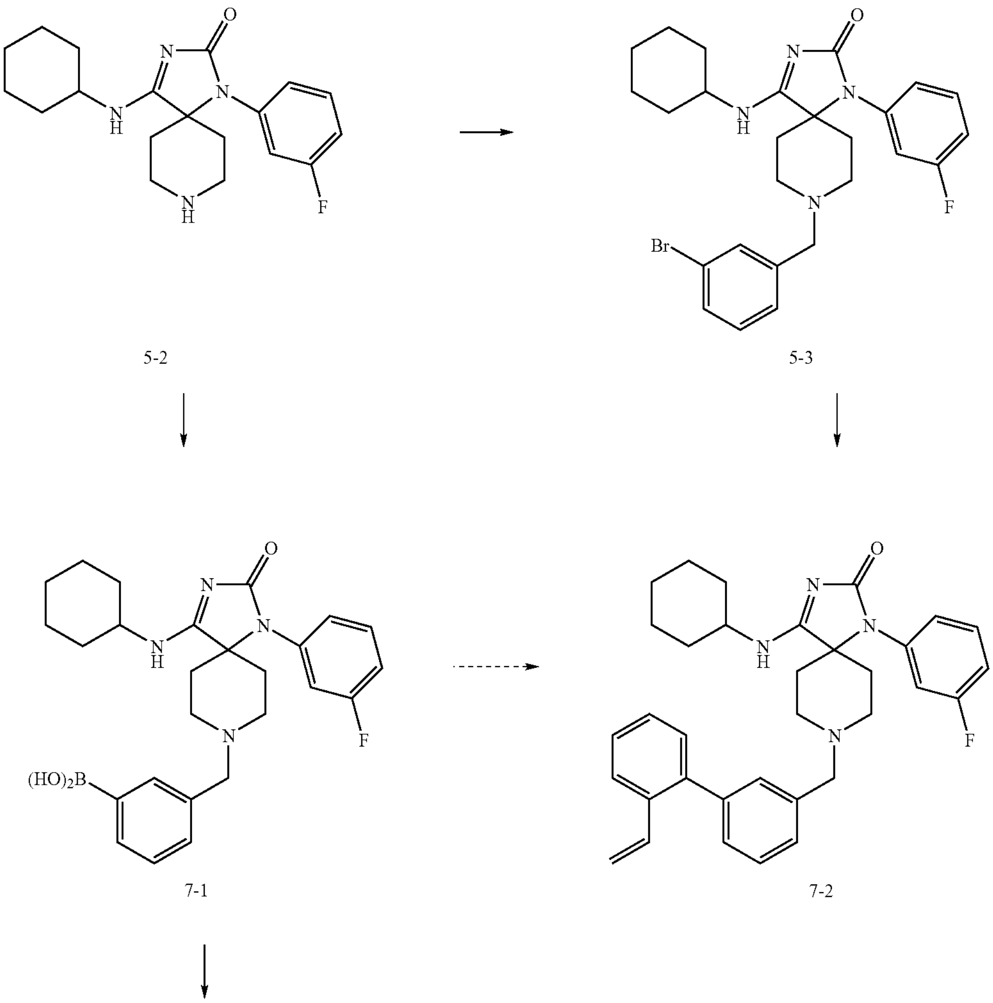

5-2

5-3

7-1

7-2

-continued

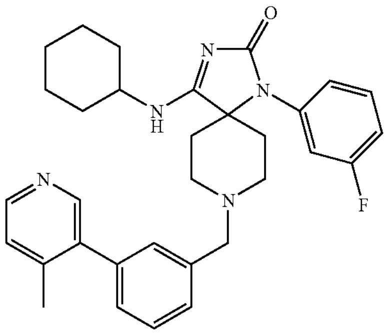

7-3

Example (7-2)

4-(cyclohexylamino)-1-(3-fluorophenyl)-8-[(2'-vinyl-1,1'-biphenyl-3-yl)methyl]-1,3,8-triazaspiro[4.5]dec-3-en-2-one (7-2)

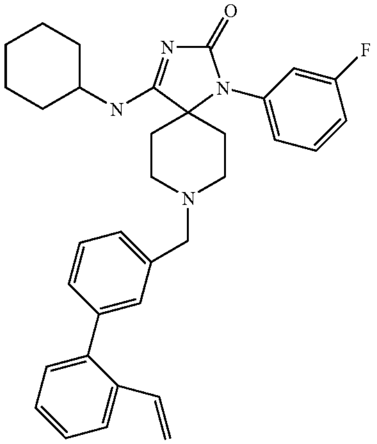

To a solution of 0.020 g (0.039 mmol) 8-(3-bromobenzyl)-4-(cyclohexylamino)-1-(3-fluorophenyl)-1,3,8-triazaspiro[4.5]dec-3-en-2-one (5-3) in 0.5 mL degassed DMF:$H_2O$ (4:1) was added 0.006 g (0.039 mmol) (2-vinylphenyl) boronic acid and 0.003 g (0.006 mmol) 3,3',3"-Phosphinidynetris (benzene sulfonic acid) and 0.001 g (0.002 mmol) palladium II acetate and 16 μL (0.117 mmol) diisopropylamine. The reaction was heated in the microwave at 100° C. for 10 mins. Purification by preparative HPLC (5-95% $CH_3CN$/$H_2O$ over 30 min, 0.05% added TFA, C18 PROYMC 20×150 mm) afforded 4-(cyclohexylamino)-1-(3-fluorophenyl)-8-[(2'-vinyl-1,1'-biphenyl-3-yl)methyl]-1,3,8-triazaspiro[4.5]dec-3-en-2-one as a white solid. NMR $^1H$ NMR ($CD_3OD$) δ 7.65 (dd, J=6.8 Hz, 2.2 Hz, 1H), 7.43 (dt, J=7.96 Hz, 6.32 Hz, 1H), 7.34 (m, 3H) 7.17 (m, 7H), 6.61 (dd, J=17.49 Hz, 10.99 Hz, 1H), 5.70 (d, J=17.58, 1H), 5.15 (d, J=10.99 Hz, 1H), 3.75 (m, 1H), 3.46 (s, 1H), 2.78 (m, 2H), 2.14 (m, 6H), 1.93 (m, 2H), 1.74 (m, 2H), 1.63 (m, 1H), 1.34 (m, 4H), 1.17 (m, 1H). High resolution mass spec (FT/ICR) calc M+H=537.3024 found 537.3038.

Example (7-3)

4-(cyclohexylamino)-1-(3-fluorophenyl)-8-[3-(4-methylpyridin-3-yl)benzyl]-1,3,8-triazaspiro[4.5]dec-3-en-2-one (7-3)

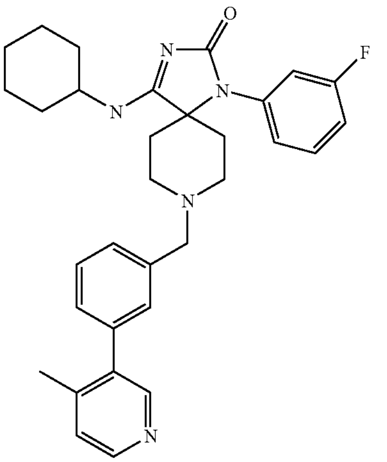

Step 1: 3-{[4-(cyclohexylamino)-1-(3-fluorophenyl)-2-oxo-1,3,8-triazaspiro[4.5]dec-3-en-8-yl]methyl}phenylboronic acid (7-1)

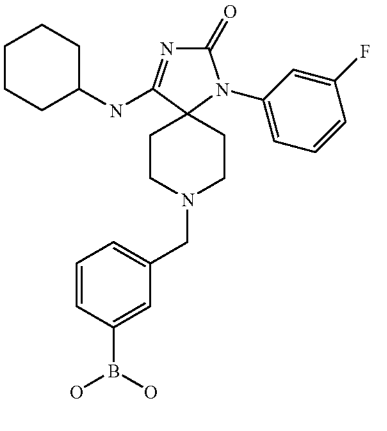

To a solution of 3.0 g (7.188 mmol) 4-(cyclohexylamino)-1-(3-fluorophenyl)-2-oxo-1,3-diaza-8-azoniaspiro[4.5]dec-3-ene dihydrochloride in 30 mL THF:AcOH (9:1) was added 1.8 g (12.005 mmol) 3-formylphenylboronic acid and 5.53 g (21.567 mmol) PS-DIEA resin and 5.97 g (14.388 mmol) MP-cyanoborohydride resin. The heterogeneous reaction mixture was stirred at rt for 24 hrs, then filtered, washed with 100 mL methanol, and concentrated. Purification by automated flash chromatography (8-30% $CH_3CN/H_2O$ over 41 min, 0.05% added TFA reverse phase YMC ODSA 120 Å, 15-30 μM particle size,) afforded 3-{[4-(cyclohexylamino)-1-(3-fluorophenyl)-2-oxo-1,3,8-triazaspiro[4.5]dec-3-en-8-yl]methyl}phenylboronic acid as a solid. $^1H$ NMR ($CD_3OD$, 400 MHz) δ 7.44 (m, 1H), 7.38 (d, J=7.32 Hz, 1H), 7.29 (s, 1H), 7.18 (m, 1H), 7.09 (m, 3H) 6.93 (m, 1H), 3.75 (m, 1H), 3.31 (s, 2H), 2.78 (m, 2H), 2.12 (m, 4H), 1.97 (m, 4H), 1.78 (m, 2H), 1.65 (m, 1H), 1.35 (m, 5H). High resolution mass spec (FT/ICR) calc M+H=478.2661 found 478.2709.

Step 2: 4-(cyclohexylamino)-1-(3-fluorophenyl)-8-[3-(4-methylpyridin-3-yl)benzyl]-1,3,8-triazaspiro[4.5]dec-3-en-2-one (7-3)

To a solution of 0.100 g (0.209 mmol) 3-{[4-(cyclohexylamino)-1-(3-fluorophenyl)-2-oxo-1,3,8-triazaspiro[4.5]dec-3-en-8-yl]methyl}phenylboronic acid (7-1) in 1 mL $CH_3CN:H_2O$ was added 0.030 g (0.174 mmol) 3-bromo-4-methylpyridine and 0.007 g (0.011 mmol) Tris(4,6-dimethyl-3sulfonatophenyl)phosphine and 0.001 g (0.004 mmol) palladium II acetate and 0.037 g (0.349 mmol) sodium carbonate. The reaction was heated in the microwave at 120° C. for 20 mins. Purification by preparative HPLC (5-95% $CH_3CN/H_2O$ over 30 min, 0.05% added TFA, C18 PRO YMC 20×150 mm) afforded 4-(cyclohexylamino)-1-(3-fluorophenyl)-8-[3-(4-methylpyridin-3-yl)benzyl]-1,3,8-triazaspiro[4.5]dec-3-en-2-one as a white solid. NMR $^1H$ NMR ($CD_3OD$) δ 8.37 (d, J=5.04 Hz, 1H), 8.29 (s, 1H), 7.42 (m, 3H) 7.19 (m, 6H), 3.76 (m, 1H), 3.47 (s, 2H), 2.77 (m, 2H), 2.29 (s, 3H), 2.14 (m, 6H), 1.95 (m, 2H), 1.77 (m, 2H), 1.66 (m, 1H), 1.36 (m, 4H), 1.18 (m, 1H). High resolution mass spec (FT/ICR) calc M+H=526.2977 found 526.3012.

Examples (7-4)-(7-109) listed below in Table 3 were prepared in a manner similar to that described in Schemes 3, 5 and 7. Examples (7-4)-(7-109) and their pharmaceutically acceptable salts are depicted in enamine form, but may also exist in tautomeric imine form.

TABLE 3

Compounds (or salts thereof) Synthesized According to Schemes 5 and 7, using methods similar to that described for Examples (5-3)-(5-5) and (7-2)-(7-3).

| EX | Structure | Chemical Name | Mass spec |
|---|---|---|---|
| 7-4 | 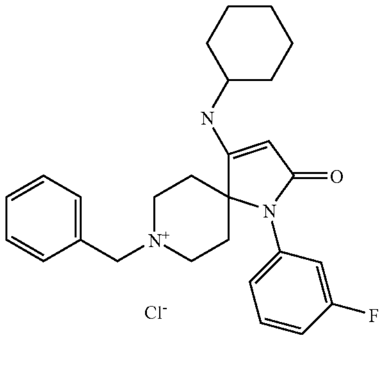 | 8-benzyl-4-(cyclohexylamino)-1-(3-fluorophenyl)-1,3,8-triazaspiro[4.5]dec-3-en-2-one | 435.2 |
| 7-5 | 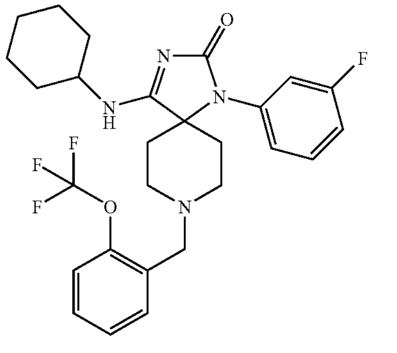 | 8-(2-trifluoromethoxybenzyl)-4-(cyclohexylamino)-1-(3-fluorophenyl)-1,3,8-triazaspiro[4.5]dec-3-en-2-one | 519.2 |

TABLE 3-continued

Compounds (or salts thereof) Synthesized According to Schemes 5 and 7, using methods similar to that described for Examples (5-3)-(5-5) and (7-2)-(7-3).

| EX | Structure | Chemical Name | Mass spec |
|---|---|---|---|
| 7-6 | 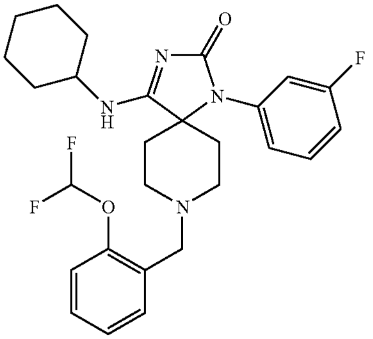 | 4-(cyclohexylamino)-8-[2-(difluoromethoxy)benzyl]-1-(3-fluorophenyl)-1,3,8-triazaspiro[4.5]dec-3-en-2-one | 501.2 |
| 7-7 | 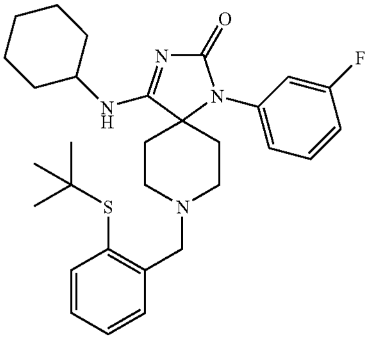 | 8-[2-(tert-butylthio)benzyl]-4-(cyclohexylamino)-1-(3-fluorophenyl)-1,3,8-triazaspiro[4.5]dec-3-en-2-one | 523.2 |
| 7-8 | 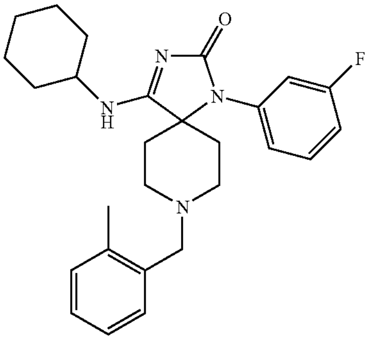 | 8-[2-methylbenzyl]-4-(cyclohexylamino)-1-(3-fluorophenyl)-1,3,8-triazaspiro[4.5]dec-3-en-2-one | 449.2 |
| 7-9 | 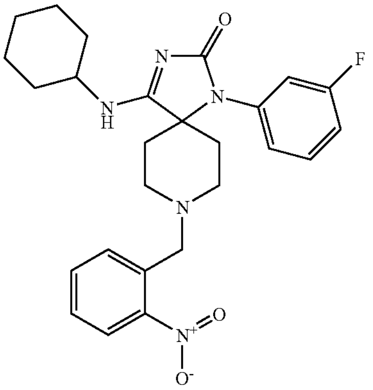 | 8-[2-nitrobenzyl]-4-(cyclohexylamino)-1-(3-fluorophenyl)-1,3,8-triazaspiro[4.5]dec-3-en-2-one | 480.2 |

TABLE 3-continued

Compounds (or salts thereof) Synthesized According to Schemes 5 and 7, using methods similar to that described for Examples (5-3)–(5-5) and (7-2)–(7-3).

| EX | Structure | Chemical Name | Mass spec |
|---|---|---|---|
| 7-10 | 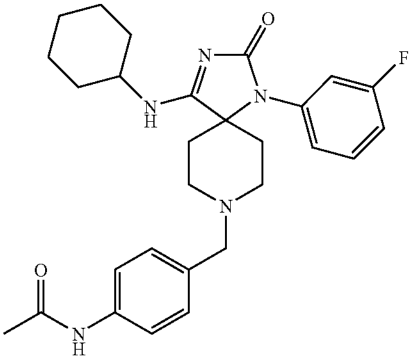 | N-(4-{[4-(cyclohexylamino)-1-(3-fluorophenyl)-2-oxo-1,3,8-triazaspiro[4.5]dec-3-en-8-yl]methyl}phenyl)acetamide | 492.3 |
| 7-11 | 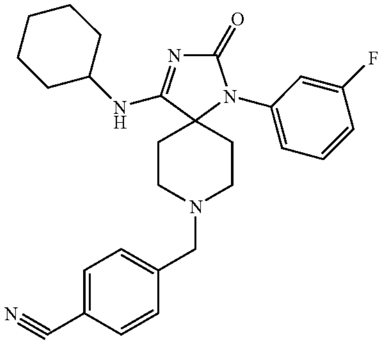 | 8-[4-cyanobenzyl]-4-(cyclohexylamino)-1-(3-fluorophenyl)-1,3,8-triazaspiro[4.5]dec-3-en-2-one | 460.2 |
| 7-12 | 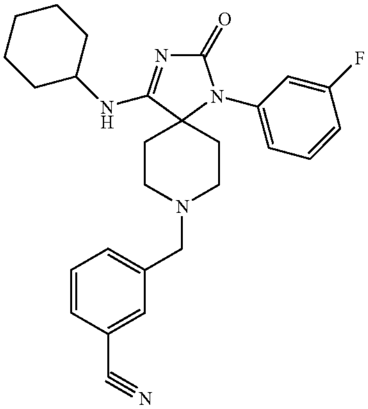 | 8-[3-cyanobenzyl]-4-(cyclohexylamino)-1-(3-fluorophenyl)-1,3,8-triazaspiro[4.5]dec-3-en-2-one | 460.2 |
| 7-13 | 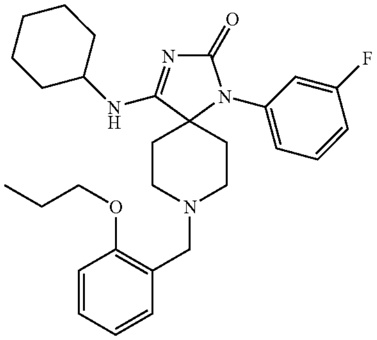 | 8-[2-propoxybenzyl]-4-(cyclohexylamino)-1-(3-fluorophenyl)-1,3,8-triazaspiro[4.5]dec-3-en-2-one | 493.2 |

TABLE 3-continued

Compounds (or salts thereof) Synthesized According to Schemes 5 and 7, using methods similar to that described for Examples (5-3)–(5-5) and (7-2)–(7-3).

| EX | Structure | Chemical Name | Mass spec |
|---|---|---|---|
| 7-14 | 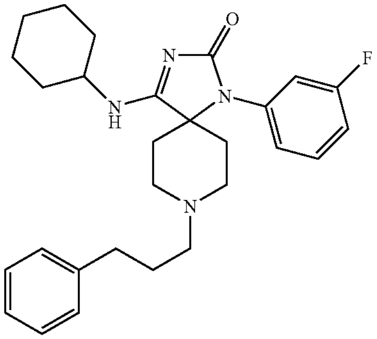 | 8-[3-phenylpropyl]-4-(cyclohexylamino)-1-(3-fluorophenyl)-1,3,8-triazaspiro[4.5]dec-3-en-2-one | 463.3 |
| 7-15 | 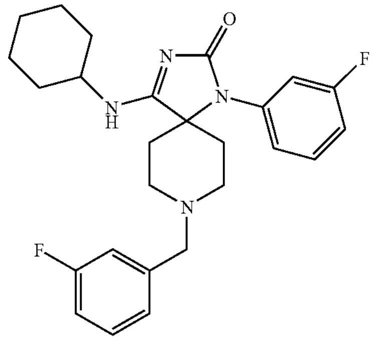 | 8-[3-fluorobenzyl]-4-(cyclohexylamino)-1-(3-fluorophenyl)-1,3,8-triazaspiro[4.5]dec-3-en-2-one | 453.3 |
| 7-16 | 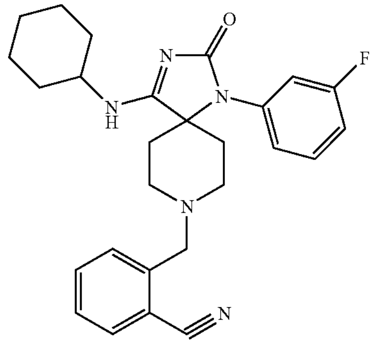 | 8-[2-cyanobenzyl]-4-(cyclohexylamino)-1-(3-fluorophenyl)-1,3,8-triazaspiro[4.5]dec-3-en-2-one | 460.2 |
| 7-17 | 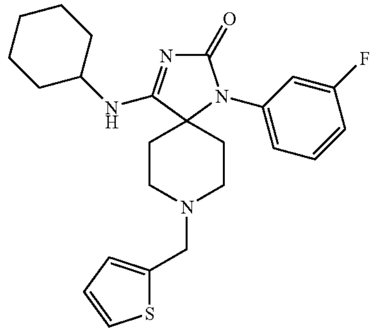 | 4-(cyclohexylamino)-1-(3-fluorophenyl)-8-(2-thienylmethyl)-1,3,8-triazaspiro[4.5]dec-3-en-2-one | 441.2 |

TABLE 3-continued

Compounds (or salts thereof) Synthesized According to Schemes 5 and 7, using methods similar to that described for Examples (5-3)-(5-5) and (7-2)-(7-3).

| EX | Structure | Chemical Name | Mass spec |
|---|---|---|---|
| 7-18 | 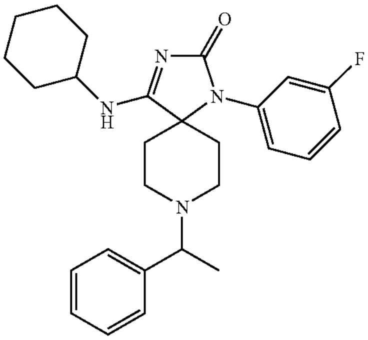 | 4-(cyclohexylamino)-1-(3-fluorophenyl)-8-(1-phenylethyl)-1,3,8-triazaspiro[4.5]dec-3-en-2-one | 449.2 |
| 7-19 | 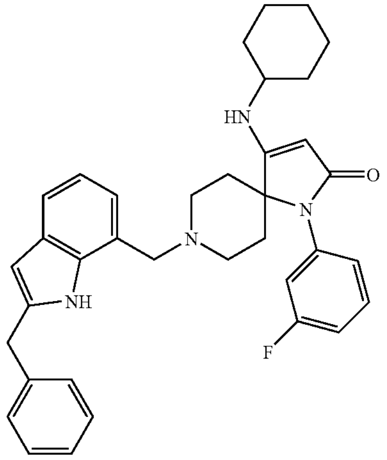 | 8-[(2-benzyl-1H-indol-7-yl)methyl]-4-(cyclohexylamino)-1-(3-fluorophenyl)-1,3,8-triazaspiro[4.5]dec-3-en-2-one | 564.3 |
| 7-20 | 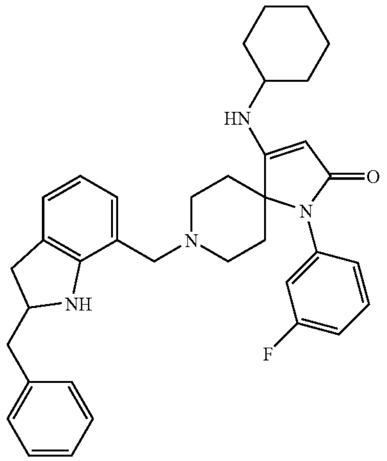 | 8-[(2-benzyl-2,3-dihydro-1H-indol-7-yl)methyl]-4-(cyclohexylamino)-1-(3-fluorophenyl)-1,3,8-triazaspiro[4.5]dec-3-en-2-one | 566.3 |

TABLE 3-continued

| Compounds (or salts thereof) Synthesized According to Schemes 5 and 7, using methods similar to that described for Examples (5-3)-(5-5) and (7-2)-(7-3). | | | |
|---|---|---|---|
| EX | Structure | Chemical Name | Mass spec |
| 7-21 | 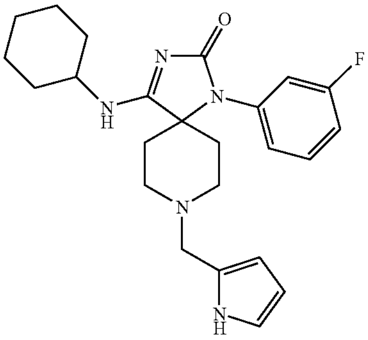 | 4-(cyclohexylamino)-1-(3-fluorophenyl)-8-(1H-pyrrol-2-ylmethyl)-1,3,8-triazaspiro[4.5]dec-3-en-2-one | 424.2 |
| 7-22 | 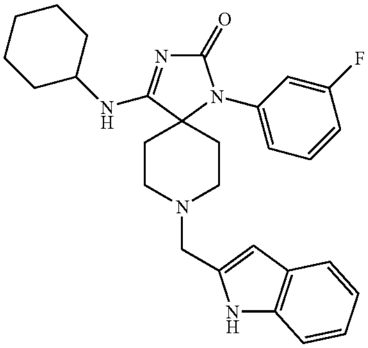 | 4-(cyclohexylamino)-1-(3-fluorophenyl)-8-(1H-indol-2-ylmethyl)-1,3,8-triazaspiro[4.5]dec-3-en-2-one | 474.2 |
| 7-23 | 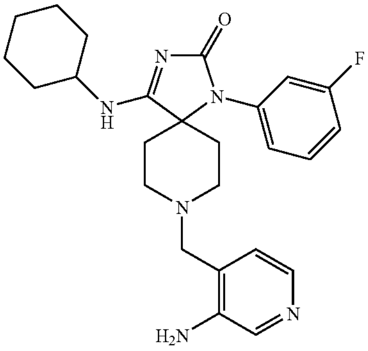 | 8-[(3-aminopyridin-4-yl)methyl]-4-(cyclohexylamino)-1-(3-fluorophenyl)-1,3,8-triazaspiro[4.5]dec-3-en-2 -one | 451.2 |
| 7-24 | 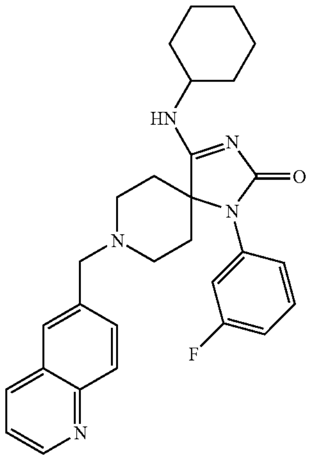 | 4-(cyclohexylamino)-1-(3-fluorophenyl)-8-(quinolin-6-ylmethyl)-1,3,8-triazaspiro[4.5]dec-3-en-2-one | 486.2 |

TABLE 3-continued

Compounds (or salts thereof) Synthesized According to Schemes 5 and 7, using methods similar to that described for Examples (5-3)-(5-5) and (7-2)-(7-3).

| EX | Structure | Chemical Name | Mass spec |
|---|---|---|---|
| 7-25 | 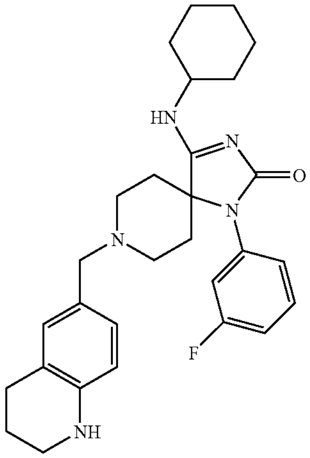 | 4-(cyclohexylamino)-1-(3-fluorophenyl)-8-(1,2,3,4-tetrahydroquinolin-6-ylmethyl)-1,3,8-triazaspiro[4.5]dec-3-en-2-one | 490.3 |
| 7-26 | 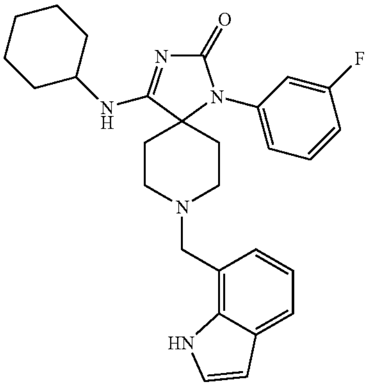 | 4-(cyclohexylamino)-1-(3-fluorophenyl)-8-(1H-indol-7-ylmethyl)-1,3,8-triazaspiro[4.5]dec-3-en-2-one | 474.2 |
| 7-27 | 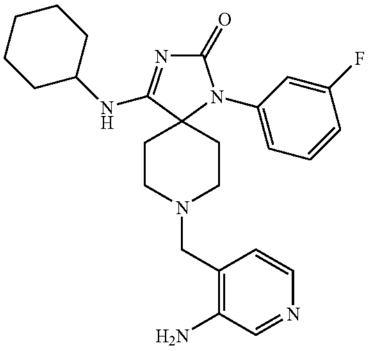 | 8-[(2-aminopyridin-3-yl)methyl]-4-(cyclohexylamino)-1-(3-fluorophenyl)-1,3,8-triazaspiro[4.5]dec-3-en-2-one | 451.2 |
| 7-28 | 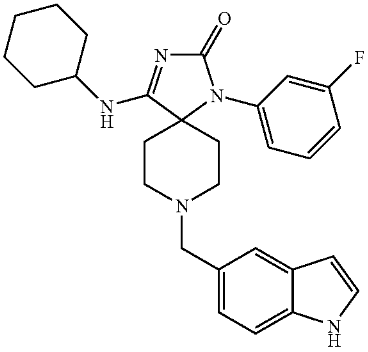 | 4-(cyclohexylamino)-1-(3-fluorophenyl)-8-(1H-indol-5-ylmethyl)-1,3,8-triazaspiro[4.5]dec-3-en-2-one | 474.2 |

TABLE 3-continued

Compounds (or salts thereof) Synthesized According to Schemes 5 and 7, using methods similar to that described for Examples (5-3)-(5-5) and (7-2)-(7-3).

| EX | Structure | Chemical Name | Mass spec |
|---|---|---|---|
| 7-30 | 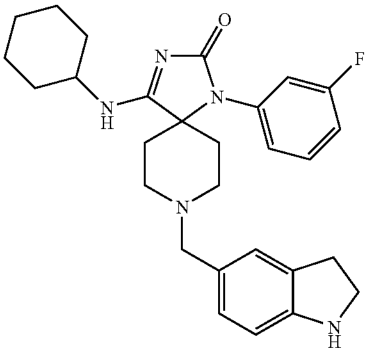 | 4-(cyclohexylamino)-8-(2,3-dihydro-1H-indol-5-ylmethyl)-1-(3-fluorophenyl)-1,3,8-triazaspiro[4.5]dec-3-en-2-one | 476.2 |
| 7-31 | 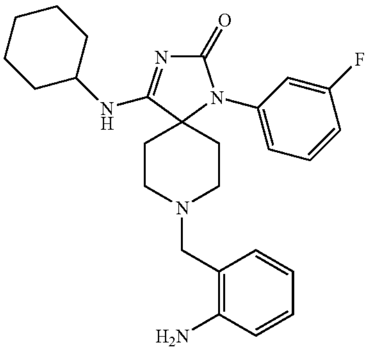 | 8-(2-aminobenzyl)-4-(cyclohexylamino)-1-(3-fluorophenyl)-1,3,8-triazaspiro[4.5]dec-3-en-2-one | 450.2 |
| 7-32 | 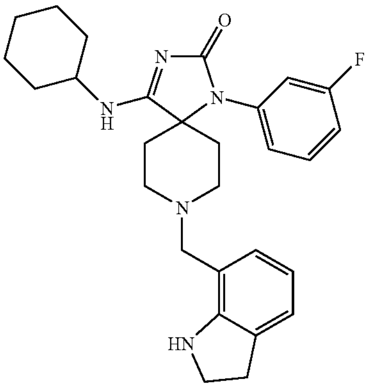 | 4-(cyclohexylamino)-8-(2,3-dihydro-1H-indol-7-ylmethyl)-1-(3-fluorophenyl)-1,3,8-triazaspiro[4.5]dec-3-en-2-one | 476.2 |
| 7-33 | 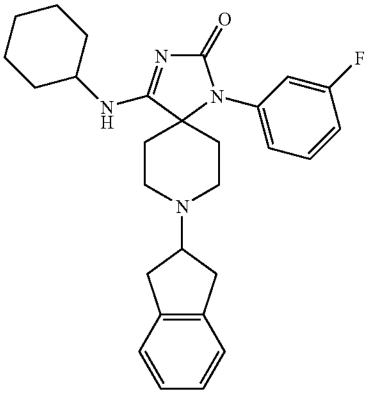 | 4-(cyclohexylamino)-8-(2,3-dihydro-1H-inden-2-yl)-1-(3-fluorophenyl)-1,3,8-triazaspiro[4.5]dec-3-en-2-one | 461.2 |

TABLE 3-continued

Compounds (or salts thereof) Synthesized According to Schemes 5 and 7, using methods similar to that described for Examples (5-3)–(5-5) and (7-2)–(7-3).

| EX | Structure | Chemical Name | Mass spec |
|---|---|---|---|
| 7-34 | 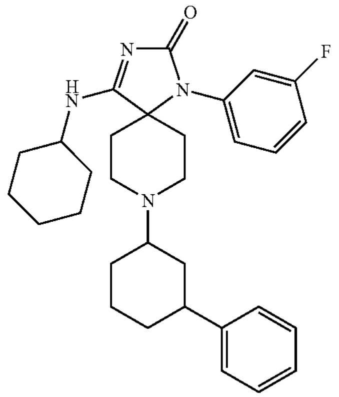 | 4-(cyclohexylamino)-1-(3-fluorophenyl)-8-(3-phenylcyclohexyl)-1,3,8-triazaspiro[4.5]dec-3-en-2-one | 503.4 |
| 7-35 | 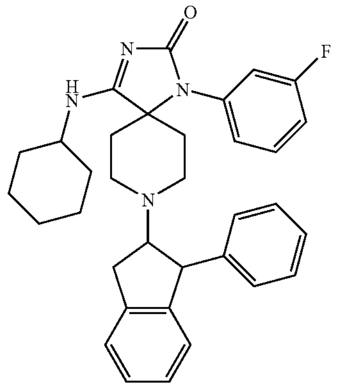 | 4-(cyclohexylamino)-1-(3-fluorophenyl)-8-(1-phenyl-2,3-dihydro-1H-inden-2-yl)-1,3,8-triazaspiro[4.5]dec-3-en-2-one | 537.3 |
| 7-36 | 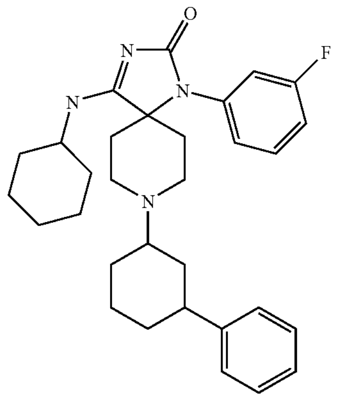 | 4-(cyclohexylamino)-1-(3-fluorophenyl)-8-(3-phenylcyclohexyl)-l,3,8-triazaspiro[4.5]dec-3-en-2-one | 503.3 |

TABLE 3-continued

Compounds (or salts thereof) Synthesized According to Schemes 5 and 7, using methods similar to that described for Examples (5-3)-(5-5) and (7-2)-(7-3).

| EX | Structure | Chemical Name | Mass spec |
|---|---|---|---|
| 7-37 | 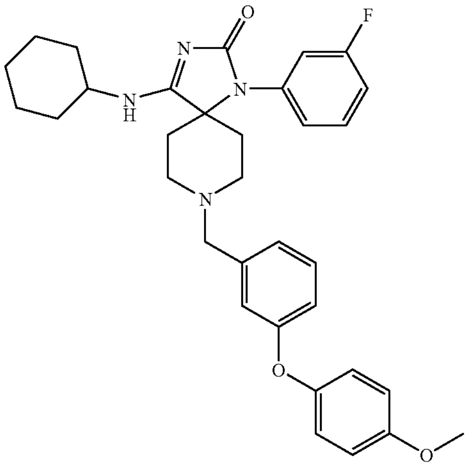 | 4-(cyclohexylamino)-1-(3-fluorophenyl)-8-[3-(4-methoxyphenoxy)benzyl]-1,3,8-triazaspiro[4.5]dec-3-en-2-one | 557.2942 |
| 7-38 | 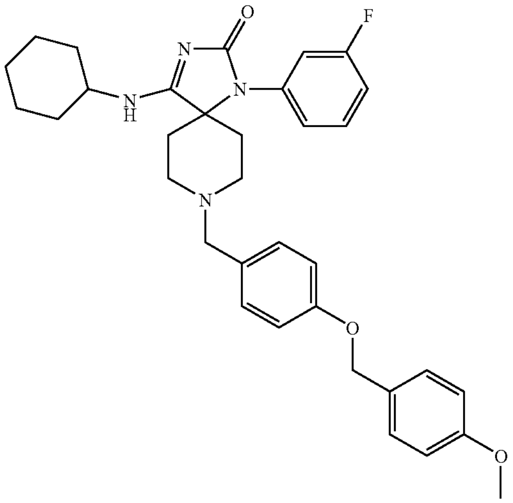 | 4-(cyclohexylamino)-1-(3-fluorophenyl)-8-{4-[(4-methoxybenzyl)oxy]benzyl}-1,3,8-triazaspiro[4.5]dec-3-en-2-one | 571.3099 |
| 7-39 | 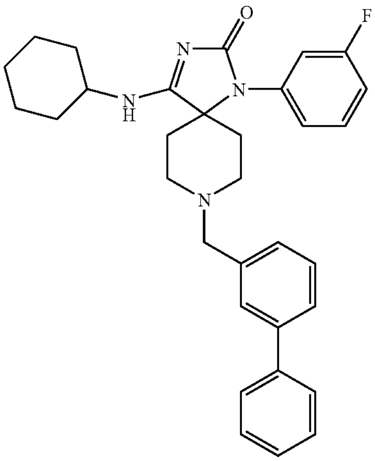 | 8-(biphenyl-3-ylmethyl)-4-(cyclohexylamino)-1-(3-fluorophenyl)-1,3,8-triazaspiro[4.5]dec-3-en-2-one | 511.2866 |

TABLE 3-continued

Compounds (or salts thereof) Synthesized According to Schemes 5 and 7, using methods similar to that described for Examples (5-3)–(5-5) and (7-2)–(7-3).

| EX | Structure | Chemical Name | Mass spec |
|---|---|---|---|
| 7-40 | 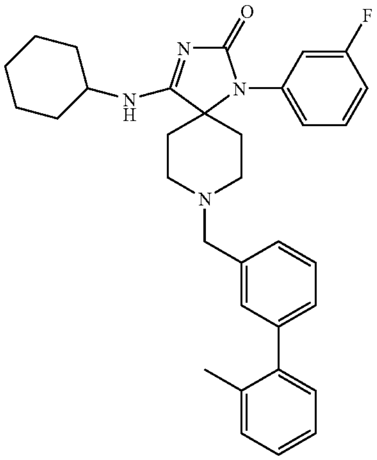 | 4-(cyclohexylamino)-1-(3-fluorophenyl)-8-[(2'-methylbiphenyl-3-yl)methyl]-1,3,8-triazaspiro[4.5]dec-3-en-2-one | 525.3 |
| 7-41 | 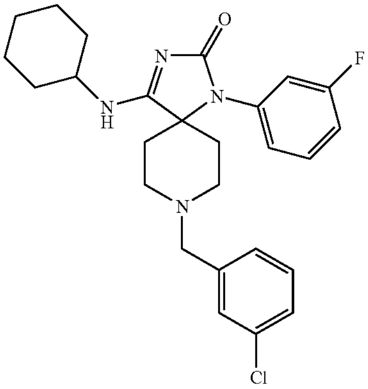 | 8-(3-chlorobenzyl)-4-(cyclohexylamino)-1-(3-fluorophenyl)-1,3,8-triazaspiro[4.5]dec-3-en-2-one | 469.2 |
| 7-42 | 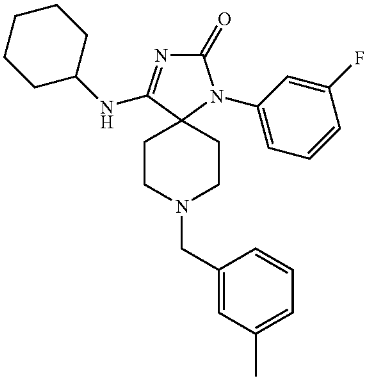 | 4-(cyclohexyl amino)-1-(3-fluorophenyl)-8-(3-methylbenzyl)-1,3,8-triazaspiro[4.5]dec-3-en-2-one | 449.2 |

TABLE 3-continued

| Compounds (or salts thereof) Synthesized According to Schemes 5 and 7, using methods similar to that described for Examples (5-3)-(5-5) and (7-2)-(7-3). | | | |
|---|---|---|---|
| EX | Structure | Chemical Name | Mass spec |
| 7-43 | 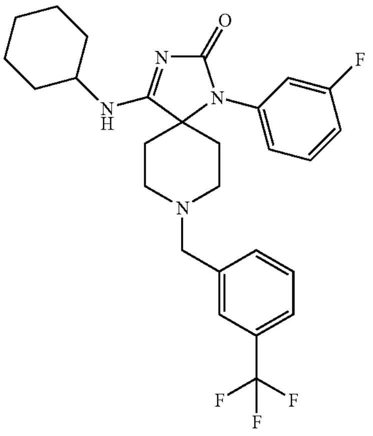 | 4-(cyclohexylamino)-1-(3-fluorophenyl)-8-[3-(trifluoromethyl)benzyl]-1,3,8-triazaspiro[4.5]dec-3-en-2-one | 503.3 |
| 7-44 | 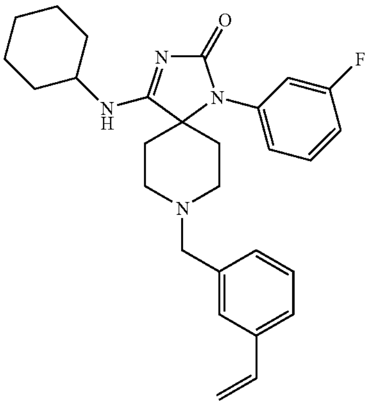 | 4-(cyclohexylamino)-1-(3-fluorophenyl)-8-(3-vinylbenzyl)-1,3,8-triazaspiro[4.5]dec-3-en-2-one | 461.2 |
| 7-45 | 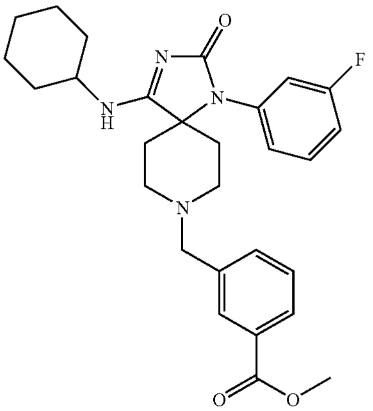 | methyl 3-{[4-(cyclohexylamino)-1-(3-fluorophenyl)-2-oxo-1,3,8-triazaspiro[4.5]dec-3-en-8-yl]methyl}benzoate | 493.2 |

TABLE 3-continued

| Compounds (or salts thereof) Synthesized According to Schemes 5 and 7, using methods similar to that described for Examples (5-3)-(5-5) and (7-2)-(7-3). | | | |
|---|---|---|---|
| EX | Structure | Chemical Name | Mass spec |
| 7-46 | 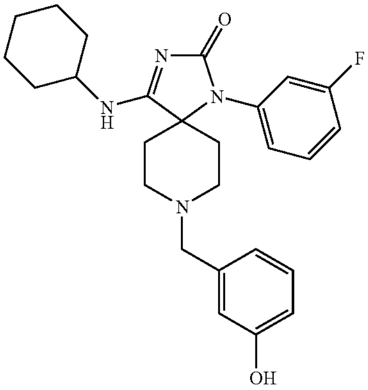 | 4-(cyclohexylamino)-1-(3-fluorophenyl)-8-(3-hydroxybenzyl)-1,3,8-triazaspiro[4.5]dec-3-en-2-one | 451.2 |
| 7-47 | 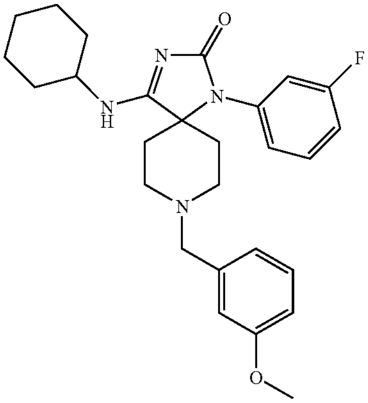 | 4-(cyclohexylamino)-1-(3-fluorophenyl)-8-(3-methoxybenzyl)-1,3,8-triazaspiro[4.5]dec-3-en-2-one | 465.2 |
| 7-48 | 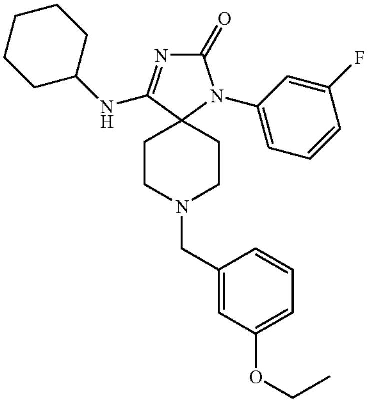 | 4-(cyclohexylamino)-8-(3-ethoxybenzyl)-1-(3-fluorophenyl)-1,3,8-triazaspiro[4.5]dec-3-en-2-one | 479.2 |

TABLE 3-continued

Compounds (or salts thereof) Synthesized According to Schemes 5 and 7, using methods similar to that described for Examples (5-3)-(5-5) and (7-2)-(7-3).

| EX | Structure | Chemical Name | Mass spec |
|---|---|---|---|
| 7-49 | 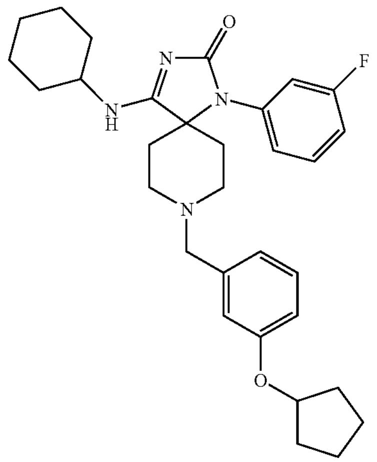 | 4-(cyclohexylamino)-8-[3-(cyclopentyloxy)benzyl]-1-(3-fluorophenyl)-1,3,8-triazaspiro[4.5]dec-3-en-2-one | 519.3 |
| 7-50 | 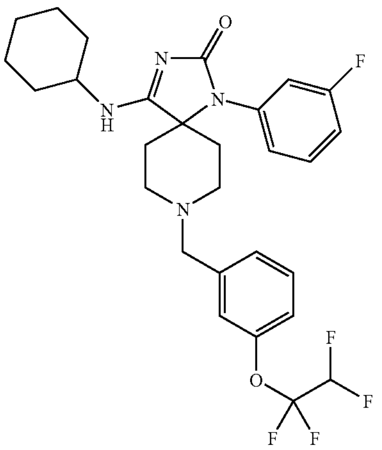 | 4-(cyclohexylamino)-1-(3-fluorophenyl)-8-[3-(1,1,2,2-tetrafluoroethoxy)benzyl]-1,3,8-triazaspiro[4.5]dec-3-en-2-one | 551.2 |
| 7-51 | 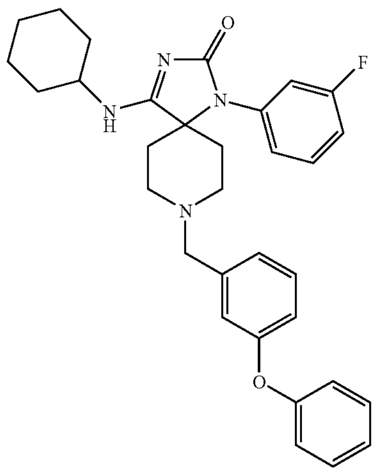 | 4-(cyclohexylamino)-1-(3-fluorophenyl)-8-(3-phenoxybenzyl)-1,3,8-triazaspiro[4.5]dec-3-en-2-one | 527.2 |

TABLE 3-continued

| Compounds (or salts thereof) Synthesized According to Schemes 5 and 7, using methods similar to that described for Examples (5-3)-(5-5) and (7-2)-(7-3). | | | |
|---|---|---|---|
| EX | Structure | Chemical Name | Mass spec |
| 7-52 | 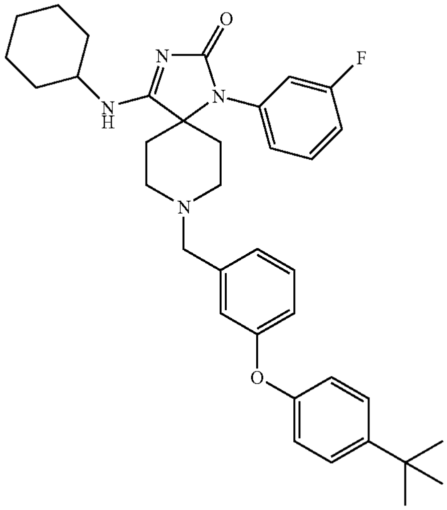 | 8-[3-(4-tert-butylphenoxy)benzyl]-4-(cyclohexylamino)-1-(3-fluorophenyl)-1,3,8-triazaspiro[4.5]dec-3-en-2-one | 583.3 |
| 7-53 | 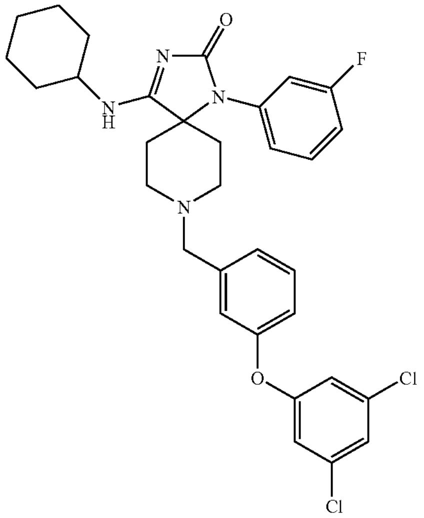 | 4-(cyclohexylamino)-8-[3-(3,5-dichlorophenoxy)benzyl]-1-(3-fluorophenyl)-1,3,8-triazaspiro[4.5]dec-3-en-2-one | 595.2 |
| 7-54 | 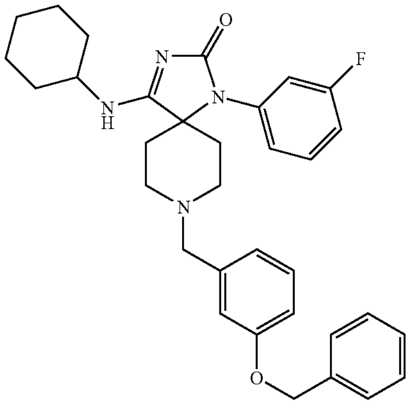 | 8-[3-(benzyloxy)benzyl]-4-(cyclohexylamino)-1-(3-fluorophenyl)-1,3,8-triazaspiro[4.5]dec-3-en-2-one | 541.3 |

TABLE 3-continued

Compounds (or salts thereof) Synthesized According to Schemes 5 and 7, using methods similar to that described for Examples (5-3)-(5-5) and (7-2)-(7-3).

| EX | Structure | Chemical Name | Mass spec |
|---|---|---|---|
| 7-55 | 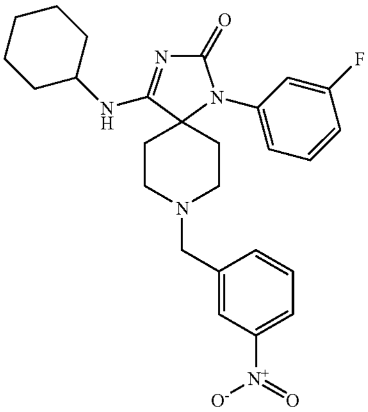 | 4-(cyclohexylamino)-1-(3-fluorophenyl)-8-(3-nitrobenzyl)-1,3,8-triazaspiro[4.5]dec-3-en-2-one | 480.2 |
| 7-56 | 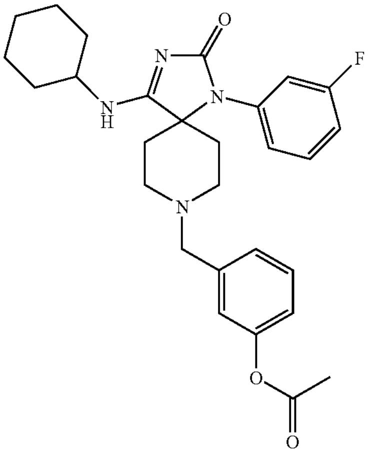 | 3-{[4-(cyclohexylamino)-1-(3-fluorophenyl)-2-oxo-1,3,8-triazaspiro[4.5]dec-3-en-8-yl]methyl}phenyl acetate | 493.2 |
| 7-57 | 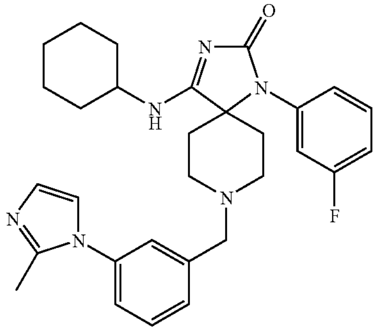 | 4-(cyclohexylamino)-1-(3-fluorophenyl)-8-[3-(2-methyl-1H-imidazol-1-yl)benzyl]-1,3,8-triazaspiro[4.5]dec-3-en-2-one | 515.2 |
| 7-58 | 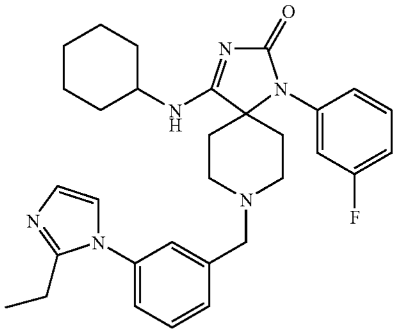 | 4-(cyclohexylamino)-8-[3-(2-ethyl-1H-imidazol-1-yl)benzyl]-1-(3-fluorophenyl)-1,3,8-triazaspiro[4.5]dec-3-en-2-one | 529.3 |

TABLE 3-continued

| Compounds (or salts thereof) Synthesized According to Schemes 5 and 7, using methods similar to that described for Examples (5-3)-(5-5) and (7-2)-(7-3). | | | |
|---|---|---|---|
| EX | Structure | Chemical Name | Mass spec |
| 7-59 | 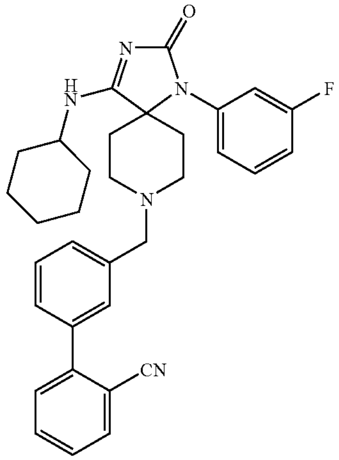 | 3'-{[4-(cyclohexylamino)-1-(3-fluorophenyl)-2-oxo-1,3,8-triazaspiro[4.5]dec-3-en-8-yl]methyl}biphenyl-2-carbonitrile | 536.3 |
| 7-60 | 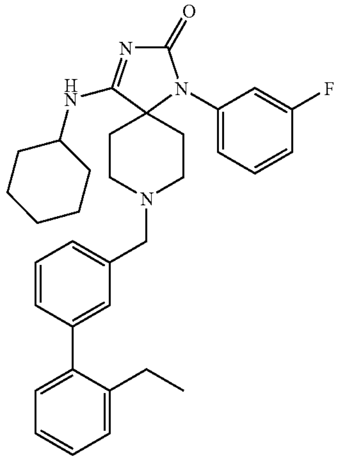 | 4-(cyclohexylamino)-8-[(2'-ethylbiphenyl-3-yl)methyl]-1-(3-fluorophenyl)-1,3,8-triazaspiro[4.5]dec-3-en-2-one | 539.3 |
| 7-61 | 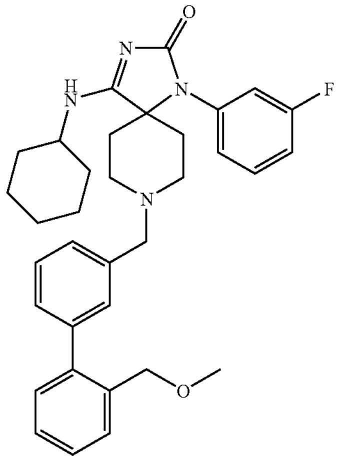 | 4-(cyclohexylamino)-1-(3-fluorophenyl)-8-{[2'-(methoxymethyl)biphenyl-3-yl]methyl}-1,3,8-triazaspiro[4.5]dec-3-en-2-one | 555.3 |

TABLE 3-continued

| Compounds (or salts thereof) Synthesized According to Schemes 5 and 7, using methods similar to that described for Examples (5-3)–(5-5) and (7-2)–(7-3). | | | |
|---|---|---|---|
| EX | Structure | Chemical Name | Mass spec |
| 7-62 | 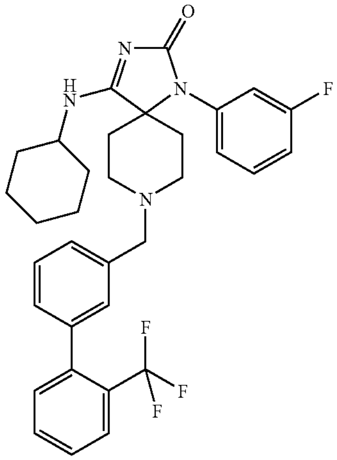 | 4-(cyclohexylammo)-1-(3-fluorophenyl)-8-{[2'-(trifluoromethyl)biphenyl-3-yl]methyl}-1,3,8-triazaspiro[4.5]dec-3-en-2-one | 579.2 |
| 7-63 | 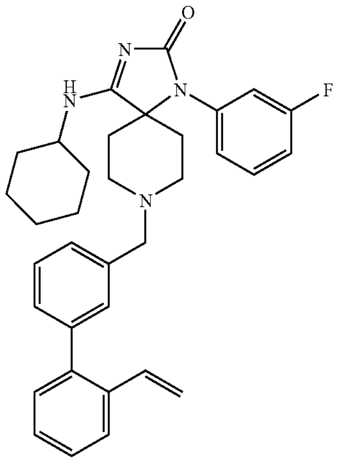 | 4-(cyclohexylamino)-1-(3-fluorophenyl)-8-[(2'-vinylbiphenyl-3-yl)methyl]-1,3,8-triazaspiro[4.5]dec-3-en-2-one | 537.3 |
| 7-64 | 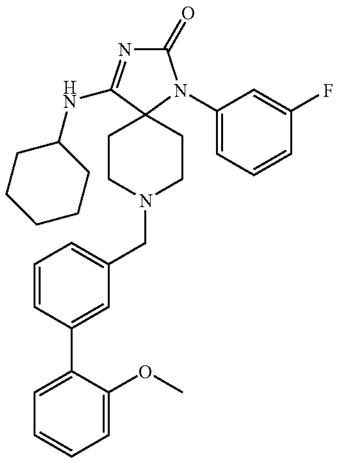 | 4-(cyclohexylamino)-1-(3-fluorophenyl)-8-[(2'-methoxybiphenyl-3-yl)methyl]-1,3,8-triazaspiro[4.5]dec-3-en-2-one | 541.3 |

TABLE 3-continued

Compounds (or salts thereof) Synthesized According to Schemes 5 and 7, using methods similar to that described for Examples (5-3)-(5-5) and (7-2)-(7-3).

| EX | Structure | Chemical Name | Mass spec |
|---|---|---|---|
| 7-65 | 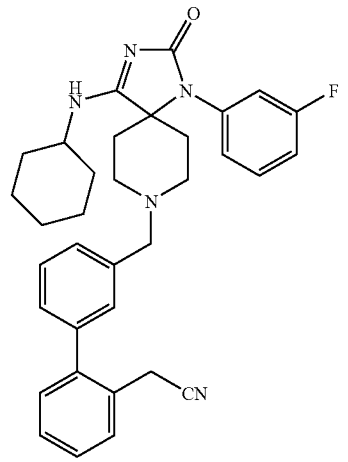 | (3'-{[4-(cyclohexylamino)-1-(3-fluorophenyl)-2-oxo-1,3,8-triazaspiro[4.5]dec-3-en-8-yl]methyl}biphenyl-2-yl)acetonitrile | 550.3 |
| 7-66 | 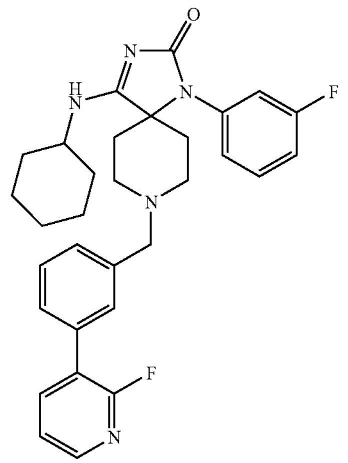 | 4-(cyclohexylamino)-1-(3-fluorophenyl)-8-[3-(2-fluoropyridin-3-yl)benzyl]-1,3,8-triazaspiro[4.5]dec-3-en-2-one | 530.2 |
| 7-67 | 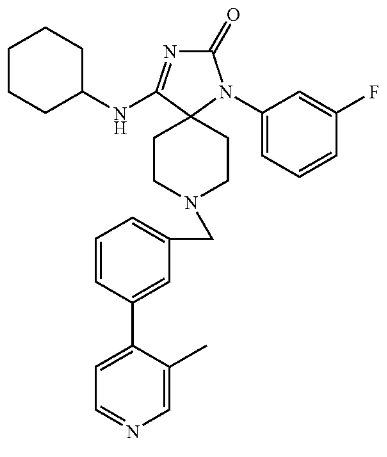 | 4-(cyclohexylamino)-1-(3-fluorophenyl)-8-[3-(3-methylpyridin-4-yl)benzyl]-1,3,8-triazaspiro[4.5]dec-3-en-2-one | 526.2 |

TABLE 3-continued

| Compounds (or salts thereof) Synthesized According to Schemes 5 and 7, using methods similar to that described for Examples (5-3)-(5-5) and (7-2)-(7-3). | | | |
|---|---|---|---|
| EX | Structure | Chemical Name | Mass spec |
| 7-68 | 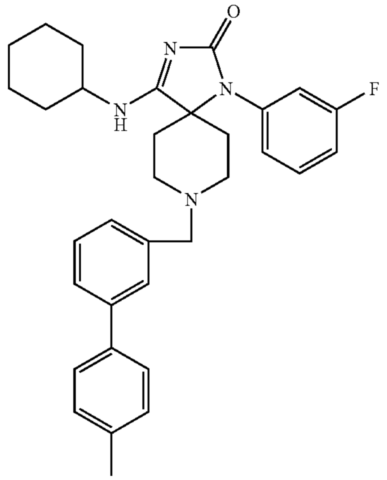 | 4-(cyclohexylamino)-1-(3-fluorophenyl)-8-[(4'-methylbiphenyl-3-yl)methyl]-1,3,8-triazaspiro[4.5]dec-3-en-2-one | 525.3 |
| 7-69 | 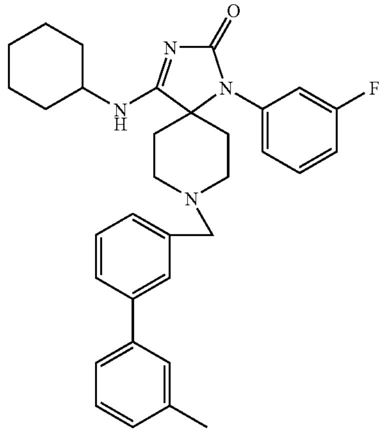 | 4-(cyclohexylamino)-1-(3-fluorophenyl)-8-[(3'-methylbiphenyl-3-yl)methyl]-1,3,8-triazaspiro[4.5]dec-3-en-2-one | 525.3 |
| 7-70 | 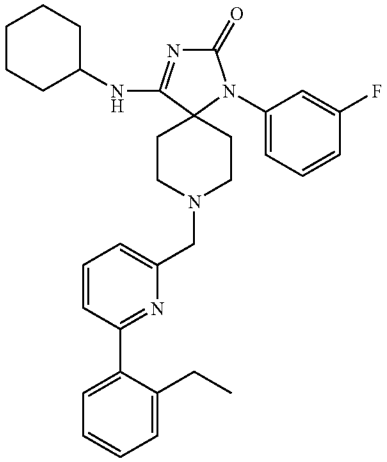 | 4-(cyclohexylamino)-8-{[6-(2-ethylphenyl)pyridin-2-yl]methyl}-1-(3-fluorophenyl)-1,3,8-triazaspiro[4.5]dec-3-en-2-one | 540.3 |

TABLE 3-continued

Compounds (or salts thereof) Synthesized According to Schemes 5 and 7, using methods similar to that described for Examples (5-3)–(5-5) and (7-2)–(7-3).

| EX | Structure | Chemical Name | Mass spec |
|---|---|---|---|
| 7-71 | 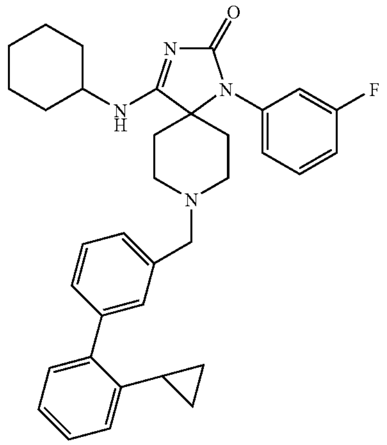 | 4-(cyclohexylamino)-8-[(2'-cyclopropylbiphenyl-3-yl)methyl]-1-(3-fluorophenyl)-1,3,8-triazaspiro[4.5]dec-3-en-2-one | 551.3 |
| 7-72 | 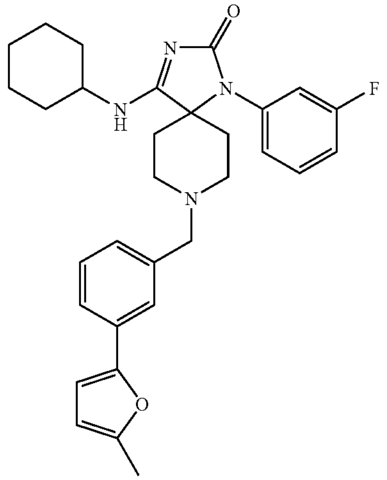 | 4-(cyclohexylamino)-1-(3-fluorophenyl)-8-[3-(5-methyl-2-furyl)benzyl]-1,3,8-triazaspiro[4.5]dec-3-en-2-one | 515.2 |
| 7-73 | 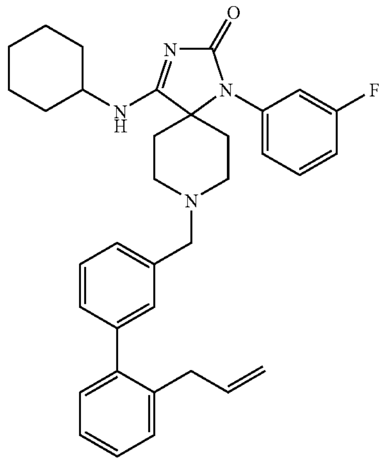 | 8-[(2'-allylbiphenyl-3-yl)methyl]-4-(cyclohexylamino)-1-(3-fluorophenyl)-1,3,8-triazaspiro[4.5]dec-3-en-2-one | 551.3 |

TABLE 3-continued

| Compounds (or salts thereof) Synthesized According to Schemes 5 and 7, using methods similar to that described for Examples (5-3)–(5-5) and (7-2)–(7-3). | | | |
|---|---|---|---|
| EX | Structure | Chemical Name | Mass spec |
| 7-74 | 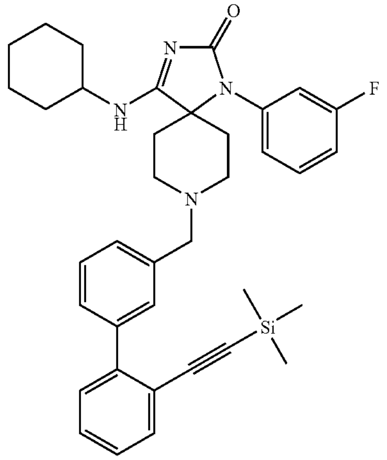 | 4-(cyclohexylamino)-1-(3-fluorophenyl)-8-({2'-[(trimethylsilyl)ethynyl]biphenyl-3-yl}methyl)-1,3,8-triazaspiro[4.5]dec-3-en-2-one | 607.3 |
| 7-75 | 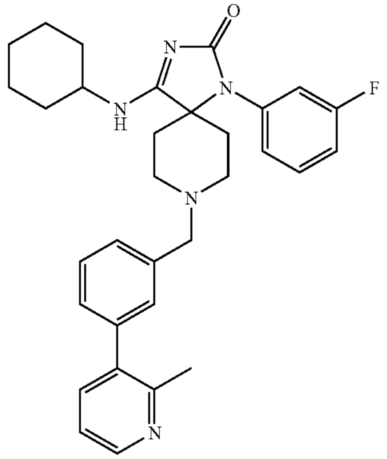 | 4-(cyclohexylamino)-1-(3-fluorophenyl)-8-[3-(2-methylpyridin-3-yl)benzyl]-1,3,8-triazaspiro[4.5]dec-3-en-2-one | 526.3 |
| 7-76 | 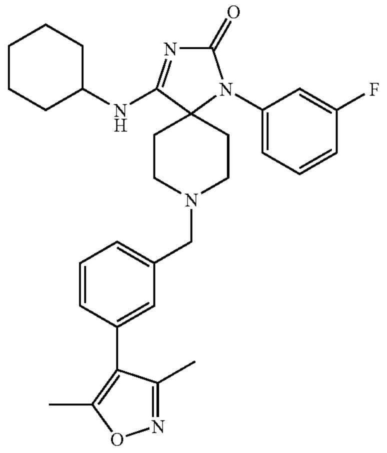 | 4-(cyclohexylamino)-8-[3-(3,5-dimethylisoxazol-4-yl)benzyl]-1-(3-fluorophenyl)-1,3,8-triazaspiro[4.5]dec-3-en-2-one | 530.3 |

TABLE 3-continued

Compounds (or salts thereof) Synthesized According to Schemes 5 and 7, using methods similar to that described for Examples (5-3)–(5-5) and (7-2)–(7-3).

| EX | Structure | Chemical Name | Mass spec |
| --- | --- | --- | --- |
| 7-77 | 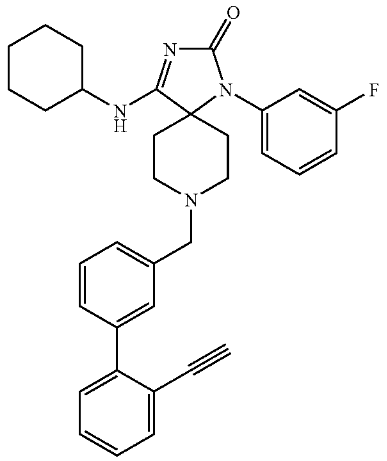 | 4-(cyclohexylamino)-8-[(2'-ethynylbiphenyl-3-yl)methyl]-1-(3-fluorophenyl)-1,3,8-triazaspiro[4.5]dec-3-en-2-one | 535.2 |
| 7-78 | 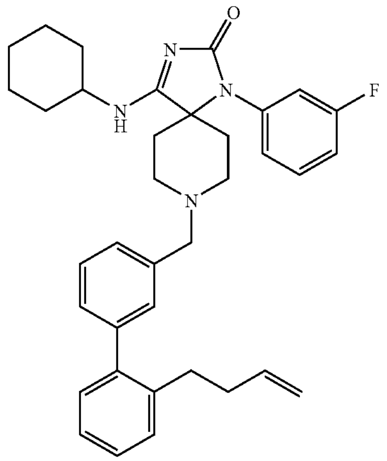 | 8-[(2'-but-3-en-1-ylbiphenyl-3-yl)methyl]-4-(cyclohexylamino)-1-(3-fluorophenyl)-1,3,8-triazaspiro[4.5]dec-3-en-2-one | 565.3 |
| 7-79 | 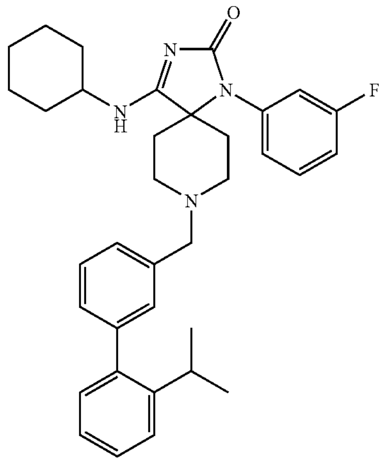 | 4-(cyclohexylamino)-1-(3-fluorophenyl)-8-[(2'-isopropylbiphenyl-3-yl)methyl]-1,3,8-triazaspiro[4.5]dec-3-en-2-one | 553.3 |

TABLE 3-continued

Compounds (or salts thereof) Synthesized According to Schemes 5 and 7, using methods similar to that described for Examples (5-3)–(5-5) and (7-2)–(7-3).

| EX | Structure | Chemical Name | Mass spec |
|---|---|---|---|
| 7-80 | 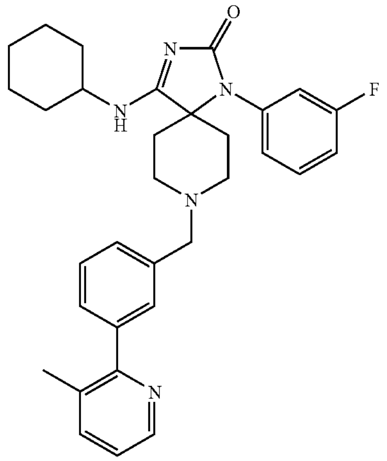 | 4-(cyclohexylamino)-1-(3-fluorophenyl)-8-[3-(3-methylpyridin-2-yl)benzyl]-1,3,8-triazaspiro[4.5]dec-3-en-2-one | 526.3 |
| 7-81 | 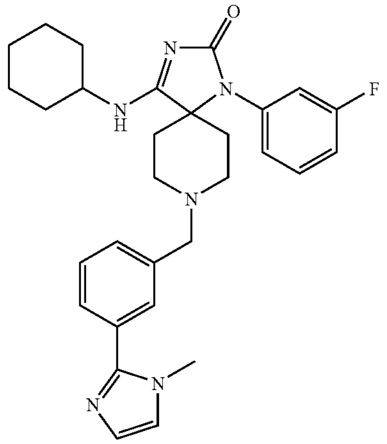 | 4-(cyclohexylamino)-1-(3-fluorophenyl)-8-[3-(1-methyl-1H-imidazol-2-yl)benzyl]-1,3,8-triazaspiro[4.5]dec-3-en-2-one | 515.3 |
| 7-82 | 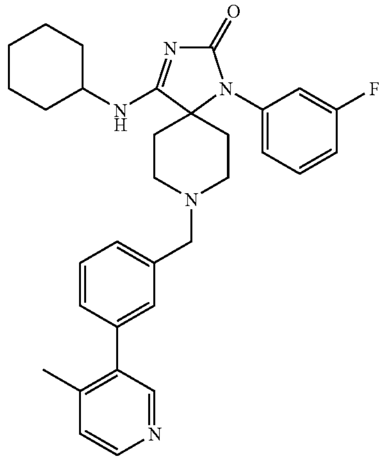 | 4-(cyclohexylamino)-1-(3-fluorophenyl)-8-[3-(4-methylpyridin-3-yl)benzyl]-1,3,8-triazaspiro[4.5]dec-3-en-2-one | 526.3 |

TABLE 3-continued

| Compounds (or salts thereof) Synthesized According to Schemes 5 and 7, using methods similar to that described for Examples (5-3)-(5-5) and (7-2)-(7-3). | | | |
|---|---|---|---|
| EX | Structure | Chemical Name | Mass spec |
| 7-83 | 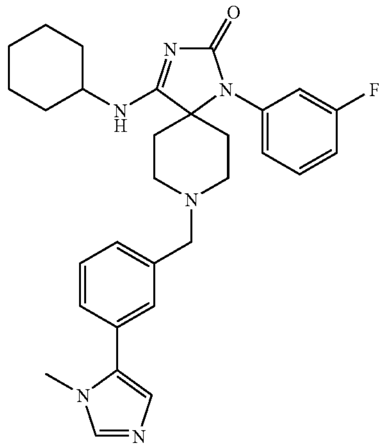 | 4-(cyclohexylamino)-1-(3-fluorophenyl)-8-[3-(1-methyl-1H-imidazol-5-yl)benzyl]-1,3,8-triazaspiro[4.5]dec-3-en-2-one | 515.2 |
| 7-84 | 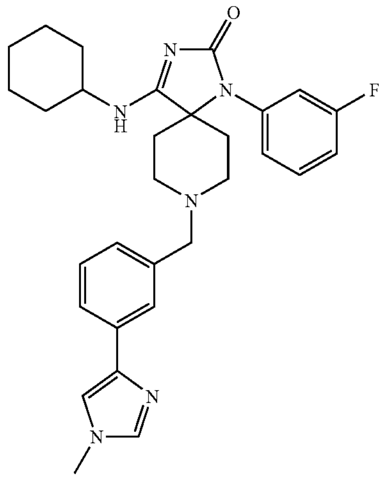 | 4-(cyclohexylamino)-1-(3-fluorophenyl)-8-[3-(1-methyl-1H-imidazol-4-yl)benzyl]-1,3,8-triazaspiro[4.5]dec-3-en-2-one | 515.3 |
| 7-85 | 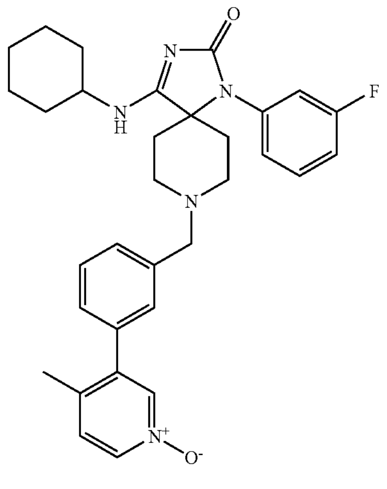 | 4-(cyclohexylamino)-1-(3-fluorophenyl)-8-[3-(4-methyl-1-oxidopyridin-3-yl)benzyl]-1,3,8-triazaspiro[4.5]dec-3-en-2-one | 542.3 |

TABLE 3-continued

| Compounds (or salts thereof) Synthesized According to Schemes 5 and 7, using methods similar to that described for Examples (5-3)–(5-5) and (7-2)–(7-3). | | | |
|---|---|---|---|
| EX | Structure | Chemical Name | Mass spec |
| 7-86 | 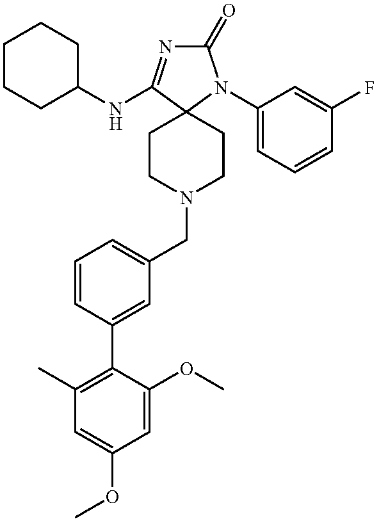 | 4-(cyclohexylamino)-8-[(2',4'-dimethoxy-6'-methyibiphenyl-3-yl)methyl]-1-(3-fluorophenyl)-1,3,8-triazaspiro[4.5]dec-3-en-2-one | 585.3 |
| 7-87 | 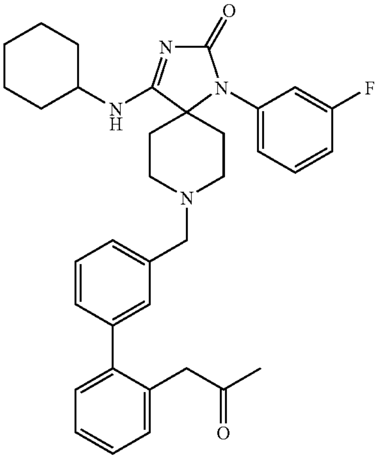 | 4-(cyclohexylamino)-1-(3-fluorophenyl)-8-{[2'-(2-methylprop-2-en-1-yl)biphenyl-3-yI]methyl}-1,3,8-triazaspiro[4.5]dec-3-en-2-one | 565.3 |
| 7-88 | 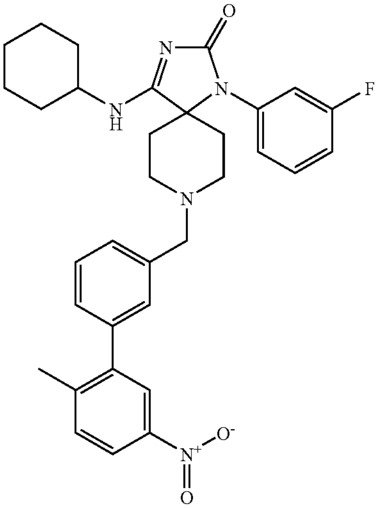 | 4-(cyclohexylamino)-1-(3-fluorophenyl)-8-[(2'-methyl-5'-nitrobiphenyl-3-yl)methyl]-1,3,8-triazaspiro[4.5]dec-3-en-2-one | 570.3 |

TABLE 3-continued

| Compounds (or salts thereof) Synthesized According to Schemes 5 and 7, using methods similar to that described for Examples (5-3)-(5-5) and (7-2)-(7-3). | | | |
|---|---|---|---|
| EX | Structure | Chemical Name | Mass spec |
| 7-89 | 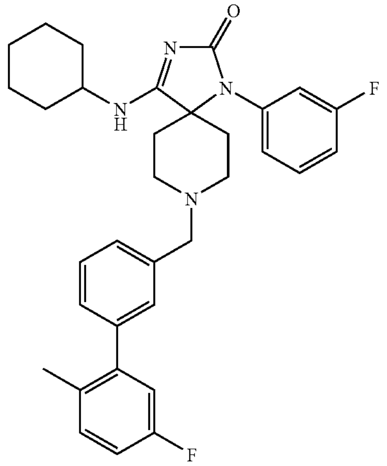 | 4-(cyclohexylamino)-8-[(5-fluoro-2'-methylbiphenyl-3-yl)methyl]-1-(3-fluorophenyl)-1,3,8-triazaspiro[4.5]dec-3-en-2-one | 543.2 |
| 7-90 | 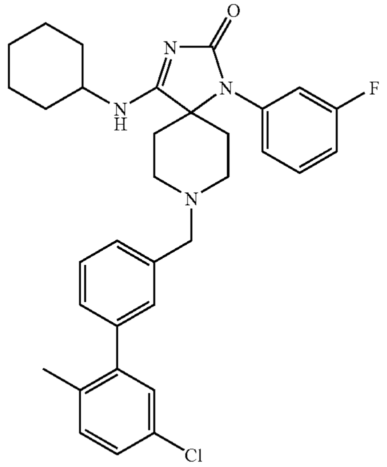 | 8-[(5'-chloro-2'-methylbiphenyl-3-yl)methyl]-4-(cyclohexylamino)-1-(3-fluorophenyl)-1,3,8-triazaspiro[4.5]dec-3-en-2-one | 559.2 |
| 7-91 | 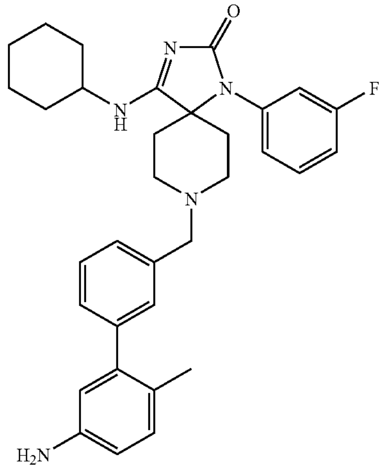 | 8-[(5'-amino-2'-methylbiphenyl-3-yl)methyl]-4-(cyclohexylamino)-1-(3-fluorophenyl)-1,3,8-triazaspiro[4.5]dec-3-en-2-one | 540.3 |

TABLE 3-continued

| Compounds (or salts thereof) Synthesized According to Schemes 5 and 7, using methods similar to that described for Examples (5-3)–(5-5) and (7-2)–(7-3). | | | |
|---|---|---|---|
| EX | Structure | Chemical Name | Mass spec |
| 7-92 | 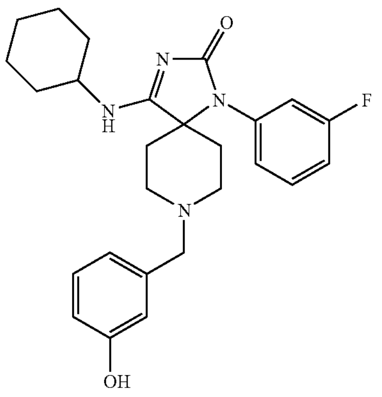 | 4-(cyclohexylamino)-1-(3-fluorophenyl)-8-(3-hydroxybenzyl)-1,3,8-triazaspiro[4.5]dec-3-en-2-one | 451 |
| 7-93 | 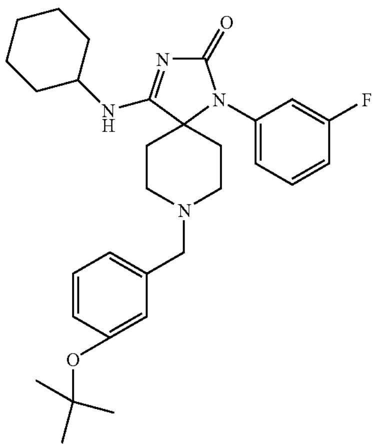 | 8-(3-tert-butoxybenzyl)-4-(cyclohexylamino)-1-(3-fluorophenyl)-1,3,8-triazaspiro[4.5]dec-3-en-2-one | 507 |
| 7-94 | 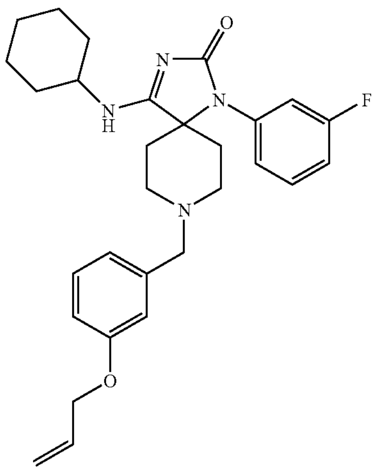 | 8-[3-(allyloxy)benzyl]-4-(cyclohexylamino)-1-(3-fluorophenyl)-1,3,8-triazaspiro[4.5]dec-3-en-2-one | 491 |

TABLE 3-continued

Compounds (or salts thereof) Synthesized According to Schemes 5 and 7, using methods similar to that described for Examples (5-3)–(5-5) and (7-2)–(7-3).

| EX | Structure | Chemical Name | Mass spec |
|---|---|---|---|
| 7-95 | 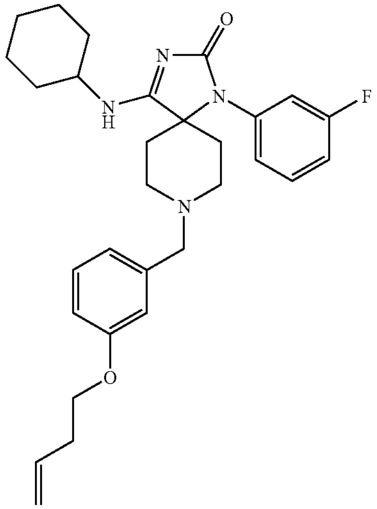 | 8-[3-(but-3-enyloxy)benzyl]-4-(cyclohexyl amino)-1-(3-fluorophenyl)-1,3,8-triazaspiro[4.5]dec-3-en-2-one | 505 |
| 7-96 | 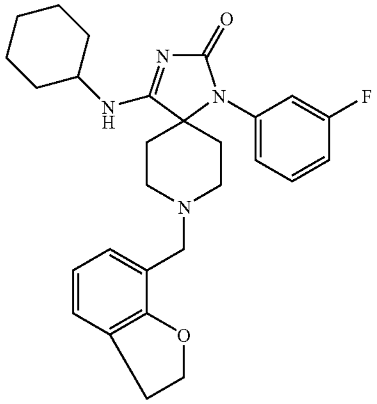 | 4-(cyclohexylamino)-8-(2,3-dihydro-1-benzofuran-7-ylmethyl)-1-(3-fluorophenyl)-1,3,8-triazaspiro[4.5]dec-3-en-2-one | 477 |
| 7-97 | 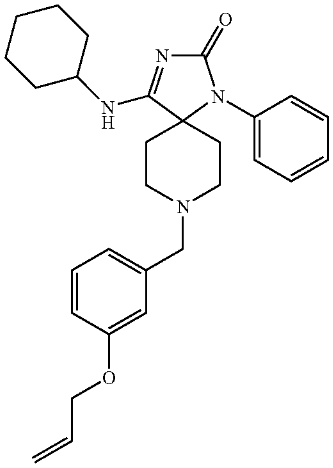 | 8-[3-(allyloxy)benzyl]-4-(cyclohexylamino)-1-phenyl-1,3,8-triazaspiro[4.5]dec-3-en-2-one | 473 |

TABLE 3-continued

| Compounds (or salts thereof) Synthesized According to Schemes 5 and 7, using methods similar to that described for Examples (5-3)–(5-5) and (7-2)–(7-3). | | | |
|---|---|---|---|
| EX | Structure | Chemical Name | Mass spec |
| 7-98 | 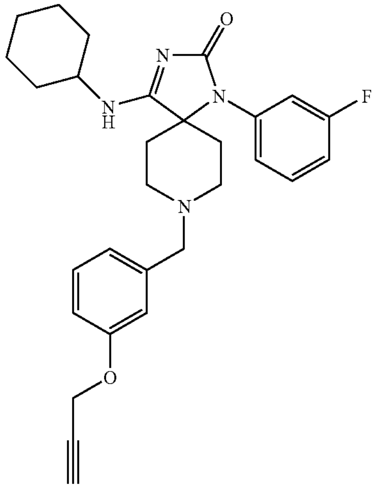 | 4-(cyclohexylamino)-1-(3-fluorophenyl)-8-[3-(prop-2-ynyloxy)benzyl]-1,3,8-triazaspiro[4.5]dec-3-en-2-one | 489 |
| 7-99 | 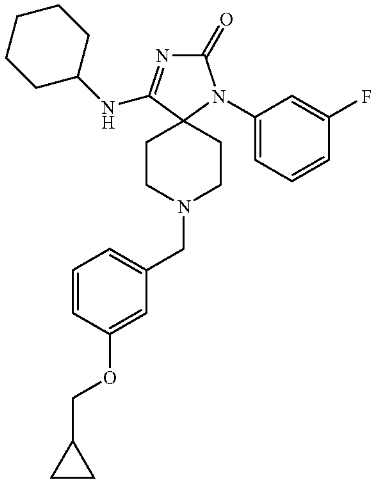 | 4-(cyclohexylamino)-8-[3-(cyclopropylmethoxy)benzyl]-1-(3-fluorophenyl)-1,3,8-triazaspiro[4.5]dec-3-en-2-one | 505 |
| 7-100 | 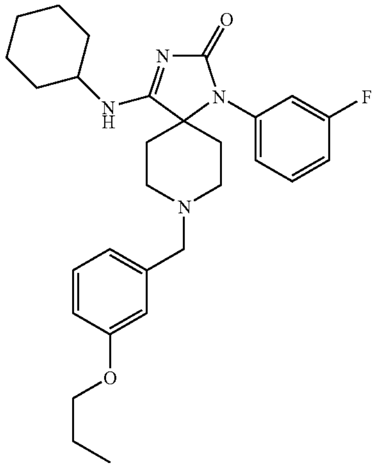 | 4-(cyclohexylamino)-1-(3-fluorophenyl)-8-(3-propoxybenzyl)-1,3,8-triazaspiro[4.5]dec-3-en-2-one | 493 |

TABLE 3-continued

| Compounds (or salts thereof) Synthesized According to Schemes 5 and 7, using methods similar to that described for Examples (5-3)–(5-5) and (7-2)–(7-3). | | | |
|---|---|---|---|
| EX | Structure | Chemical Name | Mass spec |
| 7-101 | 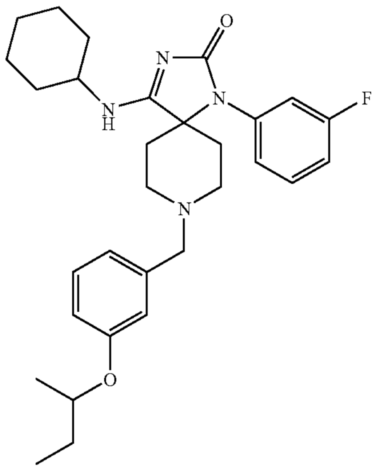 | 8-(3-sec-butoxybenzyl)-4-(cyclohexylamino)-1-(3-fluorophenyl)-1,3,8-triazaspiro[4.5]dec-3-en-2-one | 507 |
| 7-102 | 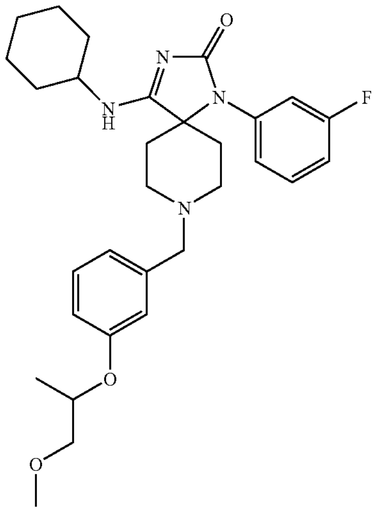 | 4-(cyclohexylamino)-1-(3-fluorophenyl)-8-[3-(2-methoxy-1-methylethoxy)benzyl]-1,3,8-triazaspiro[4.5]dec-3-en-2-one | 523 |
| 7-103 | 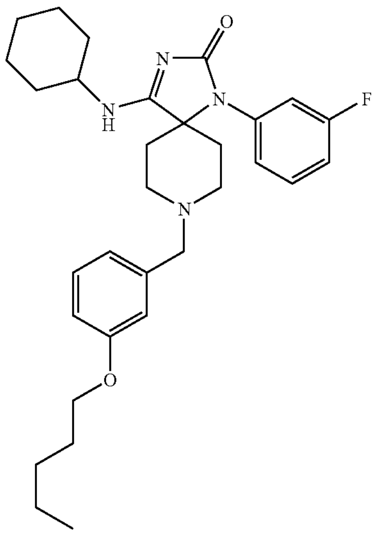 | 4-(cyclohexylamino)-1-(3-fluorophenyl)-8-[3-(pentyloxy)benzyl]-1,3,8-triazaspiro[4.5]dec-3-en-2-one | 521 |

TABLE 3-continued

| Compounds (or salts thereof) Synthesized According to Schemes 5 and 7, using methods similar to that described for Examples (5-3)–(5-5) and (7-2)–(7-3). | | | |
|---|---|---|---|
| EX | Structure | Chemical Name | Mass spec |
| 7-104 | 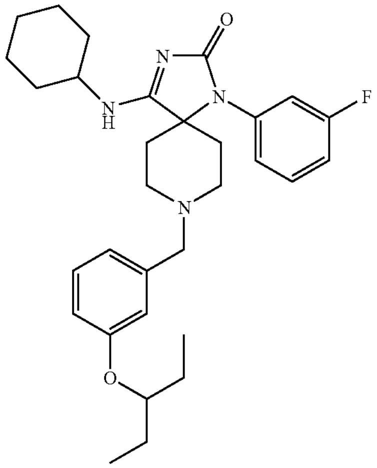 | 4-(cyclohexylamino)-8-[3-(1-ethylpropoxy)benzyl]-1-(3-fluorophenyl)-1,3,8-triazaspiro[4.5]dec-3-en-2-one | 521 |
| 7-105 | 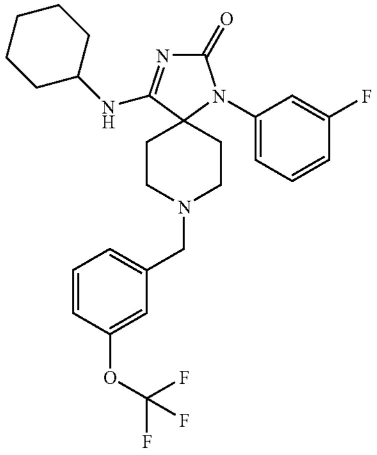 | 4-(cyclohexylamino)-1-(3-fluorophenyl)-8-[3-(trifluoromethoxy)benzyl]-1,3,8-triazaspiro[4.5]dec-3-en-2-one | 519 |
| 7-106 | 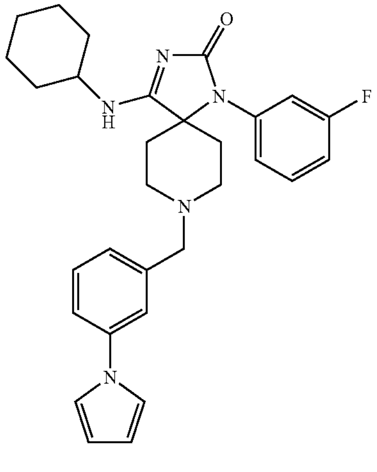 | 4-(cyclohexylamino)-1-(3-fluorophenyl)-8-[3-(1H-pyrrol-1-yl)benzyl]-1,3,8-triazaspiro[4.5]dec-3-en-2-one | 500.1 |

TABLE 3-continued

Compounds (or salts thereof) Synthesized According to Schemes 5 and 7, using methods similar to that described for Examples (5-3)-(5-5) and (7-2)-(7-3).

| EX | Structure | Chemical Name | Mass spec |
|---|---|---|---|
| 7-107 | 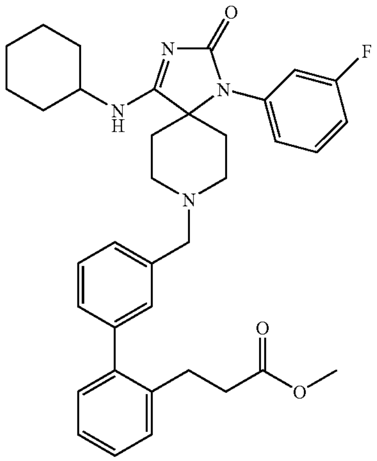 | methyl 3-(3'-{[4-(cyclohexylamino)-1-(3-fluorophenyl)-2-oxo-1,3,8-triazaspiro[4.5]dec-3-en-8-yl]methyl}biphenyl-2-yl)propanoate | 597.5 |
| 7-108 | 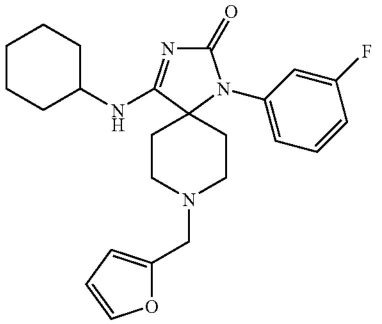 | 4-(cyclohexylamino)-1-(3-fluorophenyl)-8-(2-furylmethyl)-1,3,8-triazaspiro[4.5]dec-3-en-2-one | 425.1 |
| 7-109 | 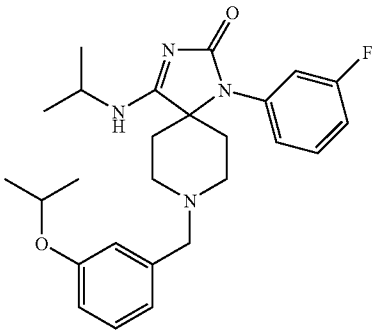 | 1-(3-fluorophenyl)-8-(3-isopropoxybenzyl)-4-(isopropylamino)-1,3,8-triazaspiro[4.5]dec-3-en-2-one | 453.2 |

Scheme 8 describes a method for preparation of compounds containing an aminopyridine $R^3$ substituent, such as Examples (8-1)-(8-4). Examples (8-1)-(8-4) are depicted in enamine form, but may also exist in tautomeric imine form.

Scheme 8
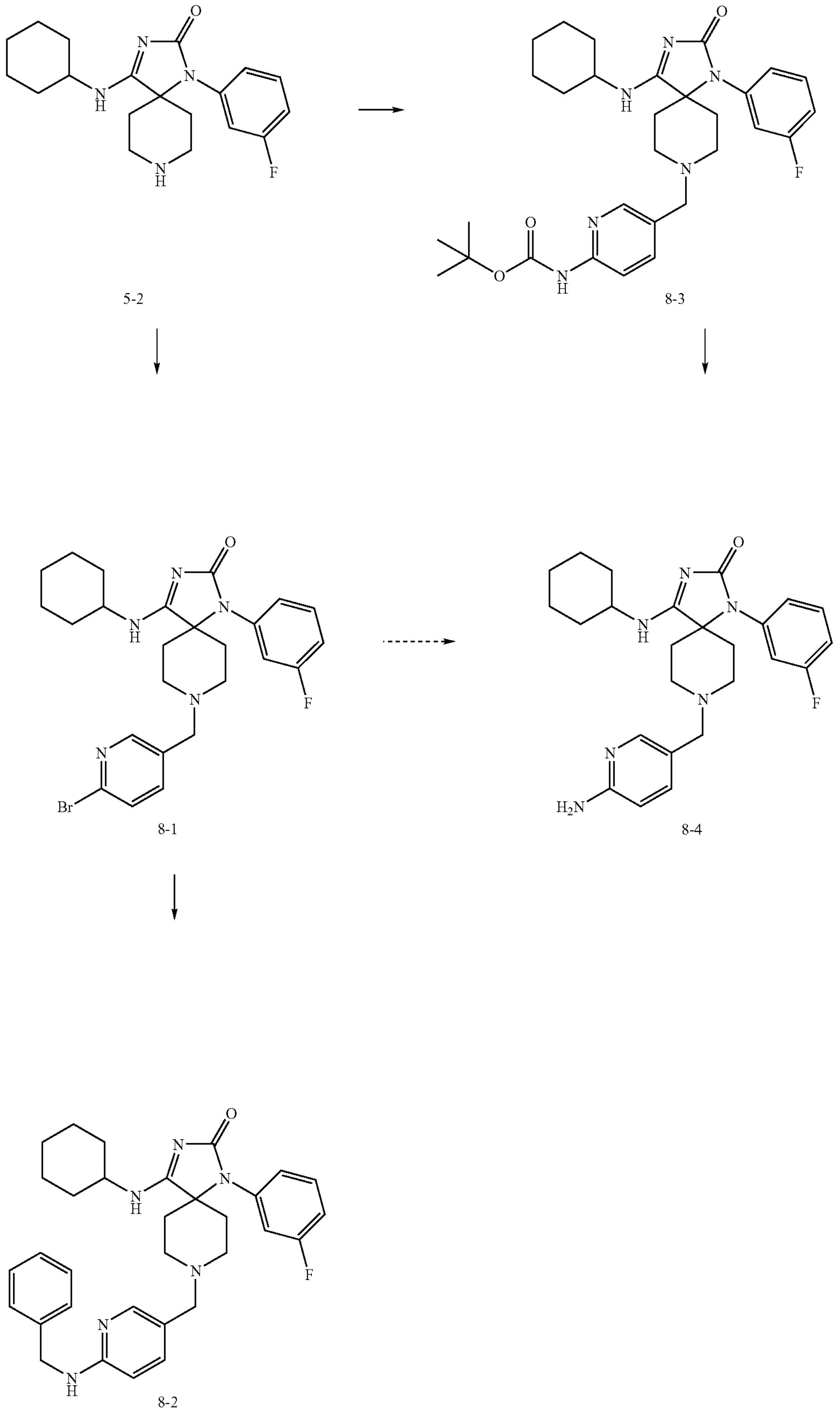
5-2
8-3
8-1
8-4
8-2

Example (8-1)

8-[(6-bromopyridin-3-yl)methyl]-4-(cyclohexylamino)-1-(3-fluorphenyl)-1,3,8-triazaspiro[4.5]dec-3-en-2-one (8-1)

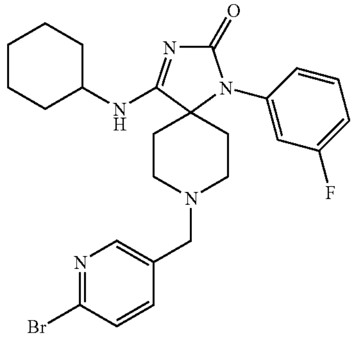

Example (8-1) was prepared in the same manner as Intermediate 5-3, electrospray mass spectrum M+H=418.2.

Example (8-2)

8-{[6-(Benzylamino)pyridin-3-yl]methyl}-4-(cyclohexylamino)-1-(3-fluorophenyl)-1,3,8-triazaspiro[4.5]dec-3-en-2-one (8-2)

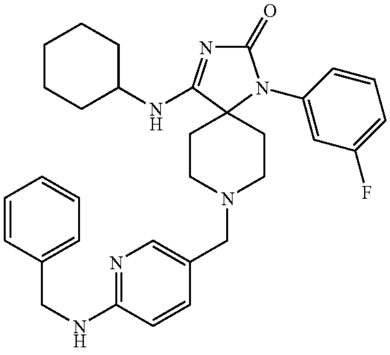

To a 600 μL dried degassed toluene suspension of 27 mg (0.052 mmol) 8-[(6-bromopyridin-3-yl)methyl]-4-(cyclohexylamino)-1-(3-fluorophenyl)-1,3,8-triazaspiro[4.5]dec-3-en-2-one (8-1, prepared in the same manner as Intermediate 5-3), 9 mg (0.094 mmol) sodium t-butoxide, 2 mg (0.003 mmol) racemic-2,2'-bis(diphenylphosphino)-1,1'-binaphthyl (BINAP), and 2 mg (0.003 mmol) tris(dibenzylideneacetone) dipalladium (0) was added 29 μL (0.262 mmol) benzylamine. The reaction vessel was capped and warmed to 110° C. overnight. The clear toluene layer was decanted and the residue extracted (2× hot toluene). The combined organic extracts were concentrated to dryness in vacuo, the residue dissolved in 900 μL DMF and purified by preparative HPLC (5→95% $CH_3CN/H_2O$ over 30 m, 0.05% added TFA, C18 PRO YMC 20×150 mm) to afford, after lyophilization, 8-{[6-(benzylamino)pyridinium-3-yl]methyl}-4-(cyclohexylamino)-1-(3-fluorophenyl)-2-oxo-1,3-diaza-8-azoniaspiro[4.5]dec-3-ene bis(trifluoroacetate) as a white fluffy solid. $^1$H NMR ($CD_3OD$ with $K_2CO_3$, 400 MHz): δ 7.70 (s, 1H), 7.34 (m, 5H), 7.23 (m, 2H), 7.08 (m, 3H), 6.47 (d, J=8.60 Hz, 1H), 4.49 (s, 2H), 3.77 (m, 1H), 3.28 (s, 2H), 2.68 (m, 2H), 2.12 (m, 4H), 2.00 (m, 4H), 1.80 (m, 2H), 1.68 (m, 1H), 1.33 (m, 5H). High resolution mass spec (FT/ICR): calc M+H=541.3086. found 541.3103

Example (8-3)

tert-Butyl 5-{[4-(cyclohexylamino)-1-(3-fluorophenyl)-2-oxo-1,3,8-triazaspiro[4.5]dec-3-en-8-yl]methyl}pyridin-2-ylcarbamate (8-3)

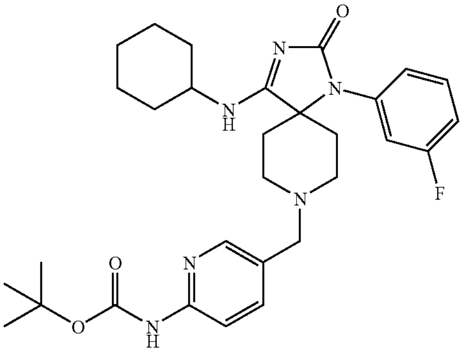

To a solution of 188 mg (0.45 mmol) 4-(cyclohexylammonio)-1-(3-fluorophenyl)-2-oxo-1,3-diaza-8-azoniaspiro[4.5]dec-3-ene dihydrochloride (5-2) and 136 mg (0.473 mmol) tert-butyl 5-(bromomethyl)pyridin-2-ylcarbamate (prepared in a manner similar to that described in PCT application WO 00/0665570, substituting Methanesulfonicanhydredl/lutidine/LiBr/THF 0-55° C. in the bromination step) in 2.5 mL DMF was added 399 mg (2.89 mmol) granular potassium carbonate and the mixture stirred vigorously at 55° C. overnight. The reaction mixture was treated with 30 mL $H_2O$ and extracted with EtOAc (3×25 mL). The combined extracts were washed with $H_2O$ (1×20 mL), brine (1×20 mL), dried over $Na_2SO_4$, filtered, and concentrated to dryness in vacuo to give a crude oily solid (390 mg). Purification by automated flash chromatography (0-6% MeOH in $CH_2Cl_2$ over 20 m) afforded tert-butyl 5-{[4-(cyclohexylamino)-1-(3-fluorophenyl)-2-oxo-1,3,8-triazaspiro[4.5]dec-3-en-8-yl]methyl}pyridin-2-ylcarbamate as a white solid. $^1$H NMR (DMSO, 400 MHz): δ 9.67 (s, 1H), 8.09 (d, J=7.78 Hz, 1H), 7.97 (s, 1H), 7.69 (d, J=8.42 Hz 1H), 7.46 (dd, J=8.52, 2.10 Hz 1H), 7.36 (m, 1H), 7.14 (m, 2H), 7.07 (d, J=8.15 Hz 1H), 3.68 (m, 1H), 3.22 (s, 2H), 2.53 (m, 2H), 2.09 (m, 2H), 1.82 (m, 4H), 1.73 (m, 1H), 1.61 (m, 1H), 1.47 (s, 9H), 1.29 (m, 5H), 1.12 (m, 1H). High resolution mass spec (FT/ICR): calc M+H=551.3141. found 551.3157

Example (8-4)

8-[(6-aminopyridin-3-yl)methyl]-4-(cyclohexylamino)-1-(3-fluorophenyl)-2-oxo-1,3,8-triazaspiro[4.5]dec-3-ene (8-4)

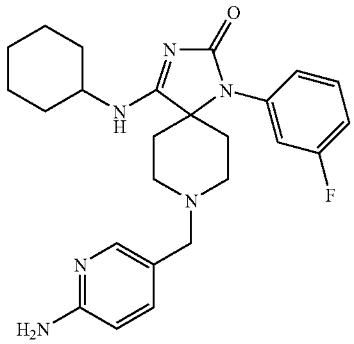

To a suspension of 64 mg (0.116 mmol) tert-butyl 5-{[4-(cyclohexylamino)-1-(3-fluorophenyl)-2-oxo-1,3,8-triazaspiro[4.5]dec-3-en-8-yl]methyl}pyridin-2-ylcarbamate in 1.5 mL EtOAc at 0° C. was bubbled in HCl gas until the solvent was saturated. The reaction was stirred in the cold for 30 min and concentrated in vacuo. The solid residue was reconcentrated to dryness (2× ethyl ether) and dried under high vacuum to give 8-[(6-aminopyridinium-3-yl)methyl]-4-(cyclohexylamino)-1-(3-fluorophenyl)-2-oxo-1,3-diaza-8-azoniaspiro[4.5]dec-3-ene dichloride dichloride as a fine white solid. $^{1}$H NMR ($CD_3OD$ with $K_2CO_3$, 400 MHz): δ 7.65 (s, 1H), 7.41 (m, 1H), 7.27 (dd, J=8.48, 2.34 Hz 1H), 7.16 (m 1H), 7.07 (m, 2H), 6.51 (d, J=8.52 Hz, 1H), 3.77 (m, 1H), 3.28 (s, 2H), 2.68 (m, 2H), 2.13 (m, 4H), 1.99 (m, 4H), 1.80 (m, 2H), 1.68 (m, 1H), 1.34 (m, 5H). High resolution mass spec (FT/ICR) calc M+H=451.2616. found 451.2617.

The aminopyridine Examples (8-5)-(8-25) listed below in Table 4 were prepared in a manner similar to that described in Scheme 8. Examples (8-5)-(8-25) and their pharmaceutically acceptable salts are depicted in enamine form, but may also exist in tautomeric imine form. Example (8-26) was prepared in the same manner as (8-5)-(8-25) starting with 8-[(6-bromophenyl)methyl]-4-(cyclohexylamino)-1-(3-fluorophenyl)-1,3,8-triazaspiro[4.5]dec-3-en-2-one.

TABLE 4

Compounds (or salts thereof) Synthesized According to Scheme 8

| EX | Structure | Chemical Name | Mass spec |
|---|---|---|---|
| 8-5 | 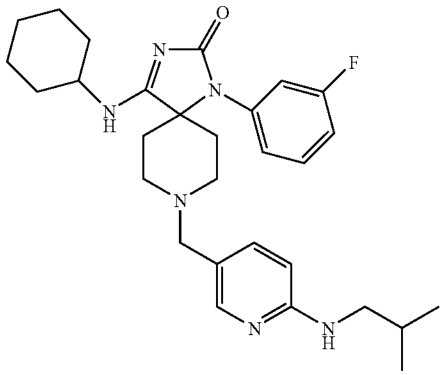 | 4-(cyclohexylamino)-1-(3-fluorophenyl)-8-{[6-(isobutylamino)pyridin-3-yl]methyl}-1,3,8-triazaspiro[4.5]dec-3-en-2-one | 507.4 |
| 8-6 | 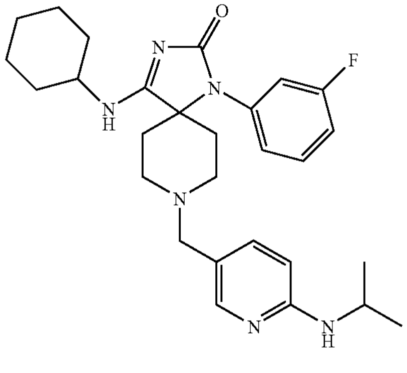 | 4-(cyclohexylamino)-1-(3-fluorophenyl)-8-{[6-(isopropylamino)pyridin-3-yl]methyl}-1,3,8-triazaspiro[4.5]dec-3-en-2-one | 493.2 |

TABLE 4-continued

Compounds (or salts thereof) Synthesized According to Scheme 8

| EX | Structure | Chemical Name | Mass spec |
|---|---|---|---|
| 8-7 | 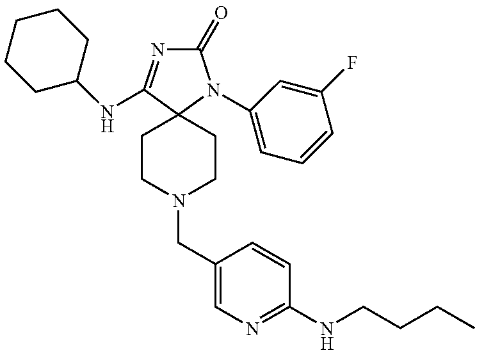 | 8-{[6-(butylamino)pyridin-3-yl]methyl}-4-(cyclohexylamino)-1-(3-fluorophenyl)-1,3,8-triazaspiro[4.5]dec-3-en-2-one | 507.4 |
| 8-8 | 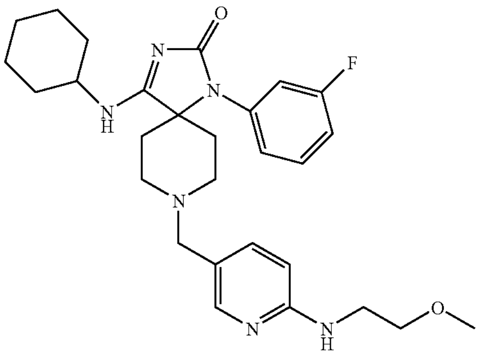 | 4-(cyclohexylamino)-1-(3-fluorophenyl)-8-({6-[(2-methoxyethyl)amino]pyridin-3-yl}methyl)-1,3,8-triazaspiro[4.5]dec-3-en-2-one | 509.3 |
| 8-9 | 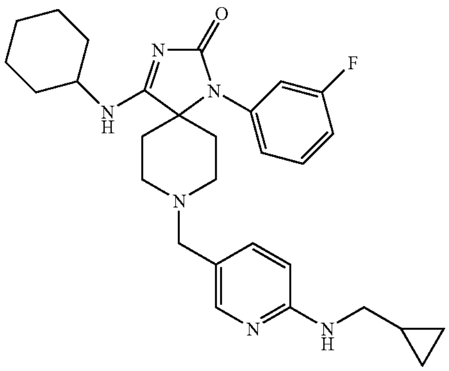 | 4-(cyclohexylamino)-8-({6-[(cyclopropylmethyl)amino]pyridin-3-yl}methyl)-1-(3-fluorophenyl)-1,3,8-triazaspiro[4.5]dec-3-en-2-one | 505.3 |
| 8-10 | 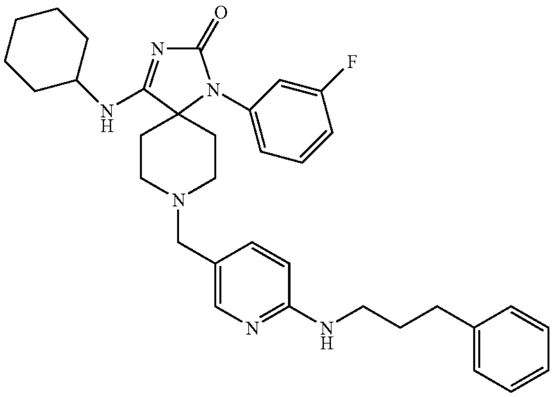 | 4-(cyclohexylamino)-1-(3-fluorophenyl)-8-({6-[(3-phenylpropyl)amino]pyridin-3-yl}methyl)-1,3,8-triazaspiro[4.5]dec-3-en-2-one | 569.3 |

TABLE 4-continued

| Compounds (or salts thereof) Synthesized According to Scheme 8 | | | |
|---|---|---|---|
| EX | Structure | Chemical Name | Mass spec |
| 8-12 | 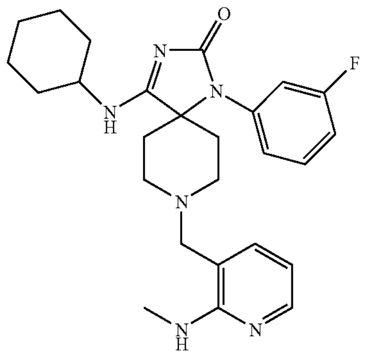 | 4-(cyclohexylamino)-1-(3-fluorophenyl)-8-{[2-(methylamino)pyridin-3-yl]methyl}-1,3,8-triazaspiro[4.5]dec-3-en-2-one | 465.2 |
| 8-13 | 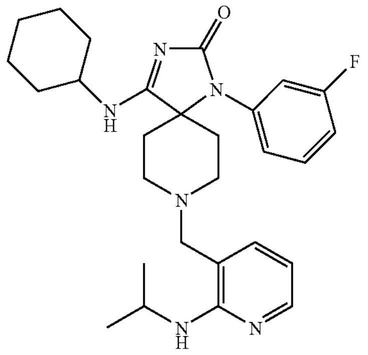 | 4-(cyclohexylamino)-1-(3-fluorophenyl)-8-{[2-(isopropylamino)pyridin-3-yl]methyl}-1,3,8-triazaspiro[4.5]dec-3-en-2-one | 493.3 |
| 8-15 | 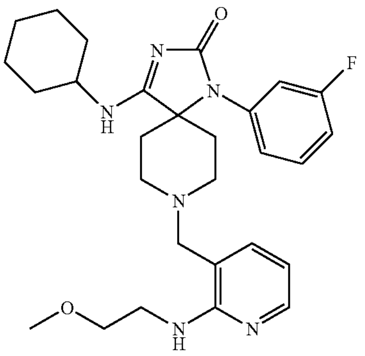 | 4-(cyclohexylamino)-1-(3-fluorophenyl)-8-({2-[(2-methoxyethyl)amino]pyridin-3-yl}methyl)-1,3,8-triazaspiro[4.5]dec-3-en-2-one | 509.2 |
| 8-16 | 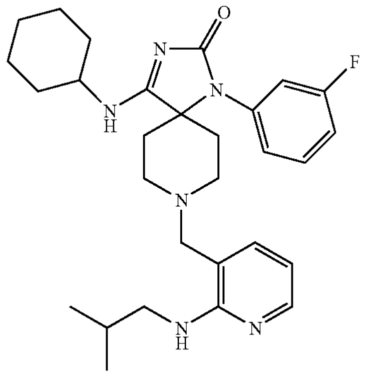 | 4-(cyclohexylamino)-1-(3-fluorophenyl)-8-{[2-(isobutylamino)pyridin-3-yl]methyl}-1,3,8-triazaspiro[4.5]dec-3-en-2-one | 507.3 |

TABLE 4-continued

| Compounds (or salts thereof) Synthesized According to Scheme 8 | | | |
|---|---|---|---|
| EX | Structure | Chemical Name | Mass spec |
| 8-17 | 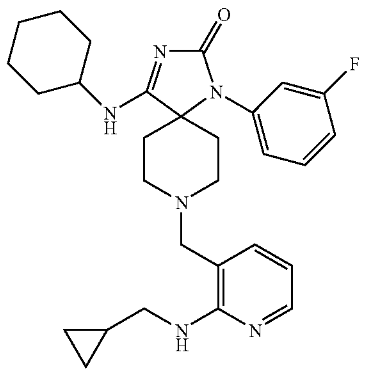 | 4-(cyclohexylamino)-8-({2-[(cyclopropylmethyl)amino]pyridin-3-yl}methyl)-1-(3-fluorophenyl)-1,3,8-triazaspiro[4.5]dec-3-en-2-one | 505.3 |
| 8-18 | 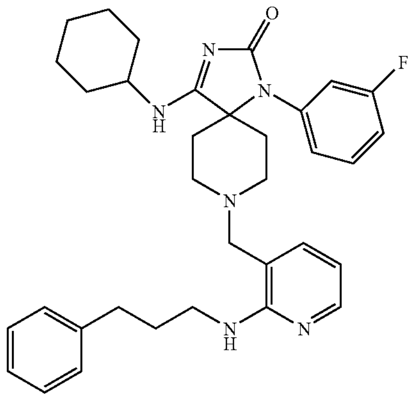 | 4-(cyclohexylamino)-1-(3-fluorophenyl)-8-({2-[(3-phenylpropyl) amino]pyridin-3-yl}methyl)-1,3,8-triazaspiro[4.5]dec-3-en-2-one | 569.3 |
| 8-19 | 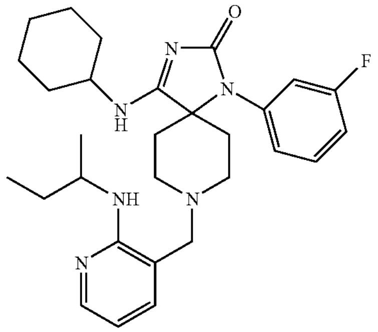 | 8-{[2-(sec-butylamino)pyridin-3-yl]methyl}-4-(cyclohexylamino)-1-(3-fluorophenyl)-1,3,8-triazaspiro[4.5]dec-3-en-2-one | 507.3 |
| 8-20 | 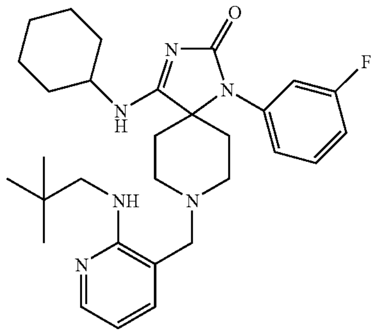 | 4-(cyclohexylamino)-8-({2-[(2,2-dimethylpropyl)amino]pyridin-3-yl}methyl)-1-(3-fluorophenyl)-1,3,8-triazaspiro[4.5]dec-3-en-2-one | 521.1 |

TABLE 4-continued

| Compounds (or salts thereof) Synthesized According to Scheme 8 | | | |
|---|---|---|---|
| EX | Structure | Chemical Name | Mass spec |
| 8-21 | 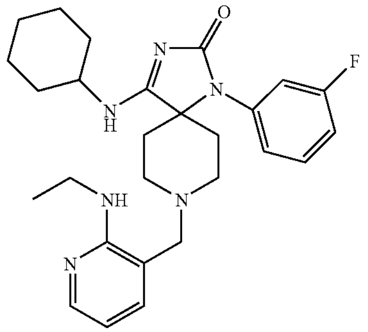 | 4-(cyclohexylamino)-8-([2-(ethylamino)pyridin-3-yl]methyl}-1-(3-fluorophenyl)-1,3,8-triazaspiro[4.5]dec-3-en-2-one | 479.3 |
| 8-22 | 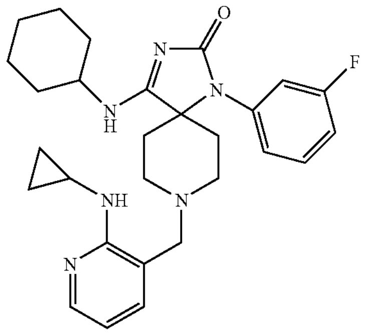 | 4-(cyclohexylamino)-8-{[2-(cyclopropylamino)pyridin-3-yl]methyl}-1-(3-fluorophenyl)-1,3,8-triazaspiro[4.5]dec-3-en-2-one | 491.3 |
| 8-23 | 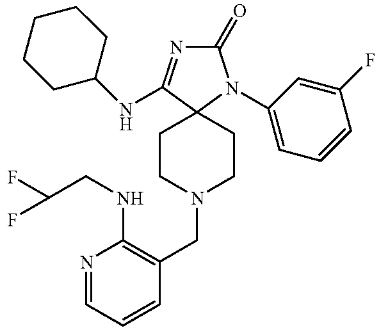 | 4-(cyclohexylamino)-8-({2-[(2,2-difluoroethyl)amino]pyridin-3-yl}methyl)-1-(3-fluorophenyl)-1,3,8-triazaspiro[4.5]dec-3-en-2-one | 515.4 |
| 8-24 | 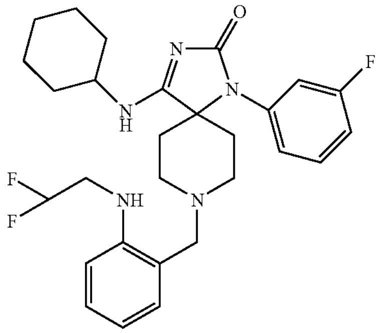 | 4-(cyclohexylamino)-8-{2-[(2,2-difluoroethyl)amino]benzyl}-1-(3-fluorophenyl)-1,3,8-triazaspiro[4.5]dec-3-en-2-one | 514.1 |

A representative procedure for elaboration of the $R^3$ substituent, as depicted in Scheme 3 below, can be used in the synthesis of various compounds of the invention, including Examples (9-4)-(9-11) below. Examples (9-4)-(9-11) are depicted below in enamine form, but may also exist in tautomeric imine form, as described above Scheme 9
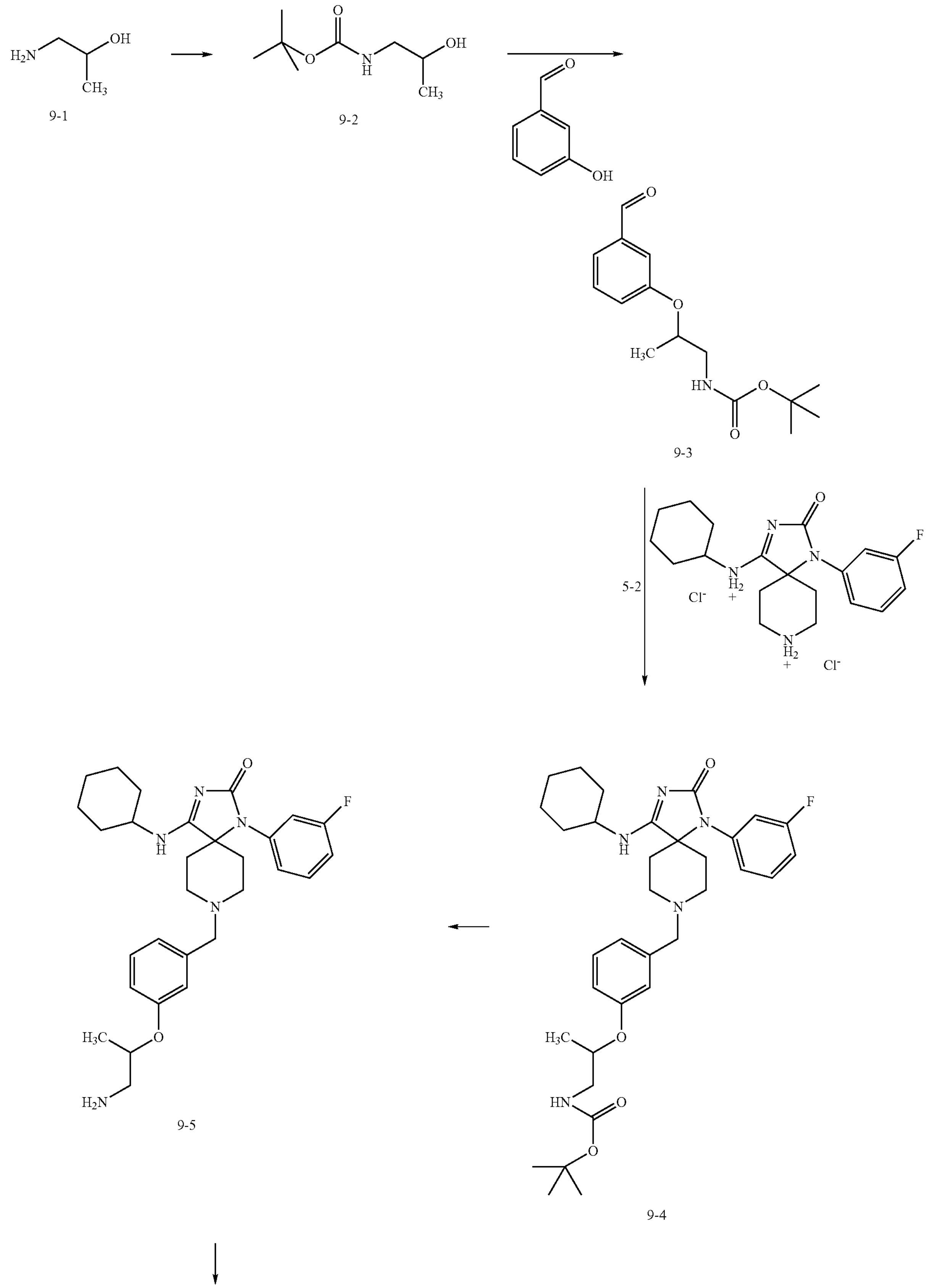

-continued

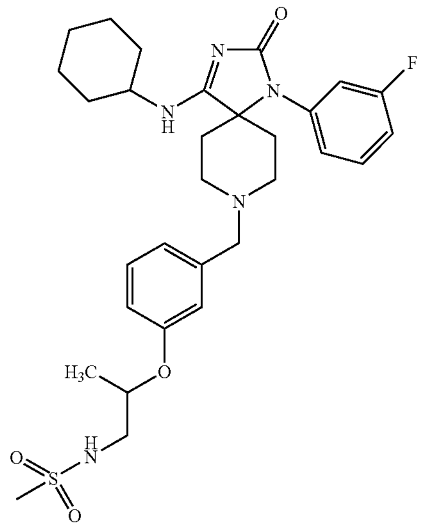

9-6

Example 9-4 tert-Butyl 2-(3-{[4-(cyclohexylamino)-1-(3-fluorophenyl)-2-oxo-1,3,8-triazaspiro[4.5]dec-3-en-8-yl]methyl}phenoxy)propylcarbamate

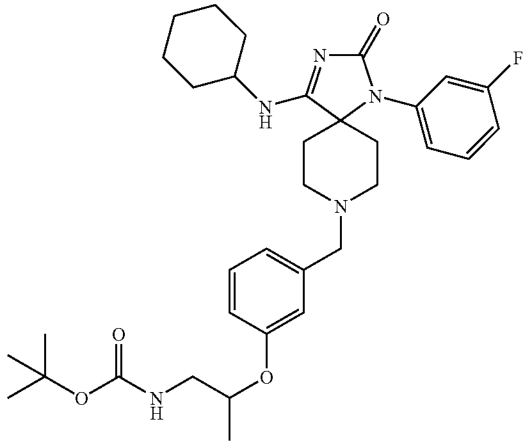

Step 1: tert-Butyl 2-hydroxypropylcarbamate (9-2)

tert-Butyl 2-hydroxypropylcarbamate (2): *Biorg. Med. Chem.*, 6, 1998 2405-2419

Added Boc anhydride (8.19 g, 37.4 mmole) in $CH_2Cl_2$ (30 mL) to a solution of 1-amino-2-propanol in 77 mL of 10% Et3N in MeOH. Let stir at rt under Argon. After 6 hr, concentrated in vacuo. Purified on a 120 g redisep column eluting with 1-1 EtOAc Hex. Concentrated clean fractions in vacuo.

Step 2: t-Butyl 2,3-(formylphenoxy)propylcarbamate (9-3)

t-Butyl 2,3-(formylphenoxy)propylcarbamate

Dissolved triphenylphosphine (0.805 g, 3.07 mmole), 3-hydroxybenzaldehyde (0.25 g, 2.047 mmole) and t-butyl 2-hydroxypropylcarbamate (0.395 g, 2.25 mmole) in dry toluene (5 mL) at rt. Added ADDP (azodicarbonyldipiperdine) (0.755 g, 3.07 mmole) at once. Warmed quickly to 80° C. After 5 hr, cooled to rt. Diluted with $CH_2Cl_2$ and filtered off solids, washing with $CH_2Cl_2$. Concentrated filtrate in vacuo. Dissolved in 50 mL $CH_2Cl_2$. Washed with 1 N NaOH (2×20 mL), and then with brine. Dried over $Na_2SO_4$, filtered and conc in vacuo. Purified using a 120 g isco redisep column eluting with 5% EtOAc to 25% EtOAc in hexanes to give the aldehyde.

tert-Butyl 2-(3-{[4-(cyclohexylamino)-1-(3-fluorophenyl)-2-oxo-1,3,8-triazaspiro[4.5]dec-3-en-8-yl]methyl}phenoxy)propylcarbamate (9-4)

t-Butyl 2,3-(formylphenoxy)propylcarbamate and 4-(cyclohexylamino)-1-(3-fluorophenyl)-2-oxo-1,3-triazaspiro[4.5]dec-3-ene dihydrochloride salt (5-2) were coupled using a procedure similar to that described for Example (5-6).

$^1$H NMR ($CDCl_3$, 400 Mh), δ 7.98 (bd, J=8.05 Hz, 1H); 7.35 (m, 1H); 7.24 (m, 1H); 7.03 (m, 2H); 6.97 (m, 1H); 6.82 (m, 3H); 4.88 (bs, 1H); 4.50 (bs, 1H); 3.97 (m, 1H); 3.49 (s, 2H); 3.44 (m, 2H); 3.25 (m, 1H); 2.78 (m, 2H); 2.44 (m, 2H); 2.07 (m, 4H); 1.95 (m, 2H); 1.72 (m, 3H); 1.44 (s, 9H); 1.39 (m, 2H); 1.27 (d, J=6.0 Hz, 3H); 1.19 (m, 3H).

Mass Spec (m+1)=608.

Example 9-5

8-[3-(2-amino-1-methylethoxy)benzyl]-4-(cyclohexylamino)-1-(3-fluorophenyl)-1,3,8-triazaspiro[4.5]dec-3-en-2-one (9-5)

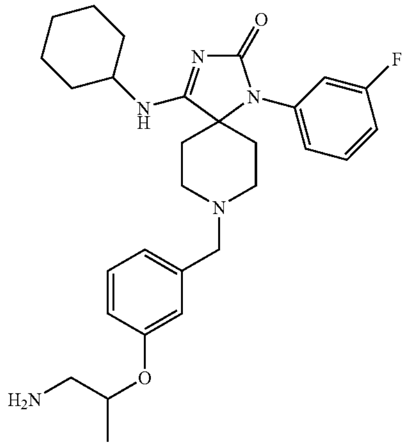

Added 2 mL of TFA to an ice cold solution of (4) (0.103 g, 0.169 mmole) in 5 mL $CH_2Cl_2$ at rt while magnetically stirring. After 15 min the reaction was concentrated in vacuo. The residue was dissolved in $CH_3CN$, then purified on the Gilson reverse phase 100×30 mm YMC J-sphere column, eluting with 10-60% $CH_3CN$ in $H_2O$ with 0.1% TFA. Concentrated appropriate fractions in vacuo on the Genie vac. The dry fractions were partitioned between $NaHCO_3$ (aq), and $CH_2Cl_2$, separated, and the aqueous layer was washed with $CH_2Cl_2$. The combined organic layers were washed with brine, dried over $Na_2SO_4$, filtered and concentrated in vacuo to yield 0.123 mg. NMR in $CDCl_3$ showed an impurity present. Repeated the above purification until there were no impurities present to yield the product.

$^1$H NMR ($CDCl_3$, 400 Mh), δ 8.01 (bd, J=8.5 Hz, 1H); 7.35 (m, 1H); 7.25 (m, 1H); 7.01 (m, 3H); 6.86 (d, J=9.3 Hz, 1H); 6.81 (m, 2H); 4.37 (q, J=5.8, 5.4, 1H); 3.97 (m, 1H); 3.51 (d, J=2.4 Hz, 2H); 2.9 (m, 2H); 2.79 (m, 4H); 2.41 (m, 2H); 2.13 (m, 2H); 2.03 (m, 4H); 1.72 (m, 2H); 1.65 (m, 1H); 1.45 (m, 2H); 1.28 (d, J=6.0 Hz, 3H); 1.24 (m, 3H).

Mass spec (m+1)=508

8-[3-(2-amino-1-(R)— methylethoxy)benzyl]-4-(cyclohexylamino)-1-(3-fluorophenyl)-1,3,8-triazaspiro[4.5]dec-3-en-2-one and 8-[3-(2-amino-1-(S)-methylethoxy)benzyl]-4-(cyclohexylamino) 1-(3-fluorophenyl)-1,3,8-triazaspiro[4.5]dec-3-en-2-one (9-5 and 9-5)

The racemic mixture of 8-[3-(2-amino-1-methylethoxy)benzyl]-4-(cyclohexylamino)-1-(3-fluorophenyl)-1,3,8-triazaspiro[4.5]dec-3-en-2-one (100 mg) was submitted for separation via chiral chromatography. The compound was eluted with 20% EtOH in Hexanes with 1 mL/L of DEA on a Chiral Pak AD column. Mass spec (m+1)=508

Example 9-6

N-[4-(3-{[4-(cyclohexylamino)-1-(3-fluorophenyl)-2-oxo-1,3,8-triazaspiro[4.5]dec-3-en-8-yl]methyl}phenoxy)butyl]methanesulfonamide. (9-6)

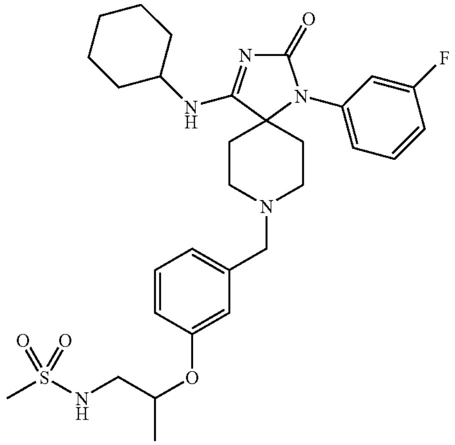

Methanesulfonyl chloride (0.019 mL, 0.245 mmole) was added dropwise to a solution of 8-{3-[(6-aminohexyl)oxy]benzyl}-4-(cyclohexylamino)-1-(3-fluorophenyl)-1,3,8-triazaspiro[4.5]dec-3-en-2-one (0.116 mg, 0.222 mmole) in 5 mL $CH_2Cl_2$ at rt, and Et3N (0.034 mL, 0.245 mmole. After stirring for 0.5 hr at rt, the reaction was concentrated in vacuo. The residue was redissolved in $CH_2Cl_2$, washed with $H_2O$, and then brine. Dried over $Na_2SO_4$, filtered and conc in vacuo. The residue was purified on a 40 g silica gel column eluting with 100% $CH_2Cl_2$ saturated with ammonia to 4% MeOH in $CH_2Cl_2$ saturated with ammonia. The clean fractions were combined and concentrated in vacuo to yield the product.

$^1$H NMR ($CDCl_3$, 400 Mh), o 7.73 (bd, J=8.0 Hz, 1H); 7.35 (dd, J=8.1, 14.6 Hz, 1H); 7.23 (m, 1H); 7.01 (m, 3H); 6.83 (m, 3H); 4.70 (m, 1H); 4.55 (m, 1H); 3.97 (m, 1H); 3.49 (d, J=3.8 Hz, 2H); 3.41 (m, 1H); 3.27 (m, 1H); 2.99 (s, 3H); 2.74 (m, 2H); 2.40 (m, 2H); 2.09 (m, 4H); 1.97 (m, 2H); 1.72 (m, 3H); 1.41 (m, 2H); 1.30 (d, J=6.1 Hz, 3H); 1.24 (m, 3H).

Mass spec (m+1)=600

TABLE 5

The following compounds (or salts thereof) of Table 5 were prepared by methods similar to that described for 9-4, 9-5, and 9-6, utilizing the appropriate reagents.

| Ex # | Structure | Chemical Name | Mass Spec |
|---|---|---|---|
| 9-7 | 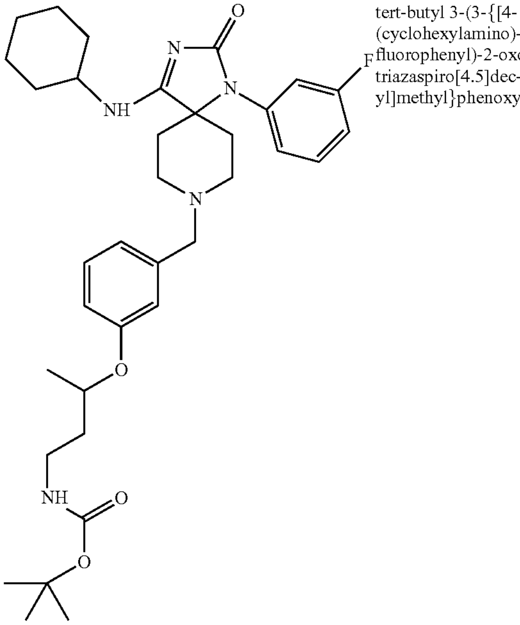 | tert-butyl 3-(3-{[4-(cyclohexylamino)-1-(3-fluorophenyl)-2-oxo-1,3,8-triazaspiro[4.5]dec-3-en-8-yl]methyl}phenoxy)butylcarbamate | 622 |
| 9-8 | 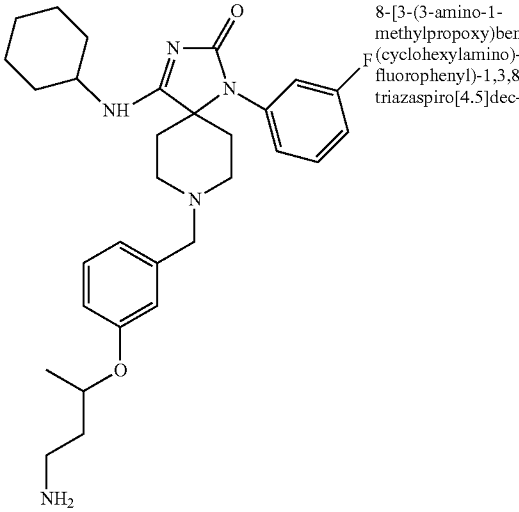 | 8-[3-(3-amino-1-methylpropoxy)benzyl]-4-(cyclohexylamino)-1-(3-fluorophenyl)-1,3,8-triazaspiro[4.5]dec-3-en-2-one | 522 |

TABLE 5-continued

| The following compounds (or salts thereof) of Table 5 were prepared by methods similar to that described for 9-4, 9-5, and 9-6, utilizing the appropriate reagents. | | | |
|---|---|---|---|
| Ex # | Structure | Chemical Name | Mass Spec |
| 9-9 | 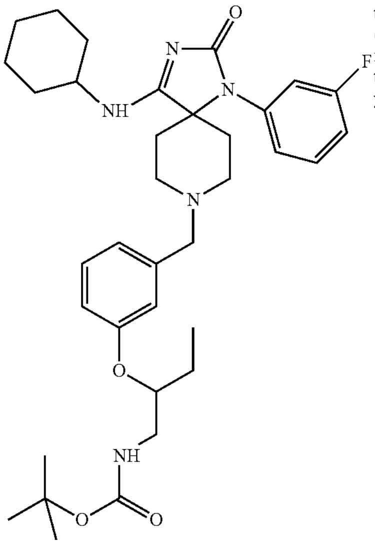 | tert-butyl 2-(3-{[4-(cyclohexylamino)-1-(3-fluorophenyl)-2-oxo-1,3,8-triazaspiro[4.5]dec-3-en-8-yl]methyl}phenoxy)butylcarbamate | 622 |
| 9-10 | 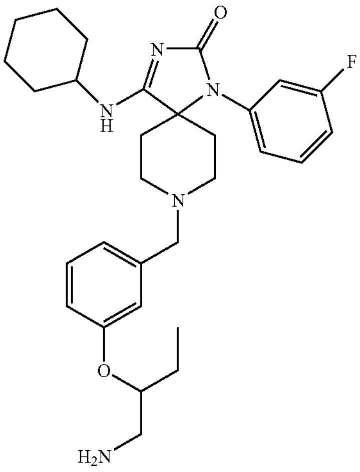 | 8-{3-[1-(aminomethyl)propoxy]benzyl}-4-(cyclohexylamino)-1-(3-fluorophenyl)-1,3,8-triazaspiro[4.5]dec-3-en-2-one | 522 |
| 9-11 | 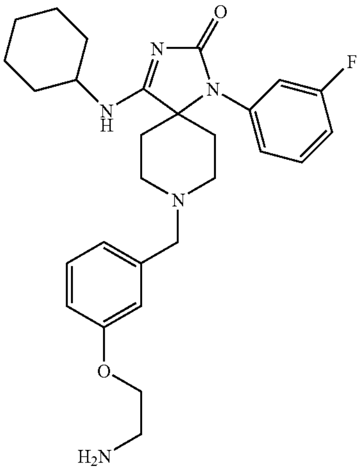 | 8-[3-(2-aminoethoxy)benzyl]-4-(cyclohexylamino)-1-(3-fluorophenyl)-1,3,8-triazaspiro[4.5]dec-3-en-2-one | 494 |

A representative procedure for elaboration of the $R^3$ substituent, as depicted in Scheme 10 below, can be used in the synthesis of various compounds of the invention, including Examples (10-1)-(10-3) below. Examples (10-1)-(10-3) are depicted below in enamine form, but may also exist in tautomeric imine form, as described above Scheme 10

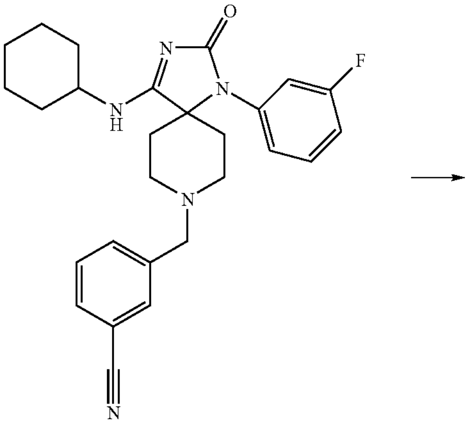

10-1

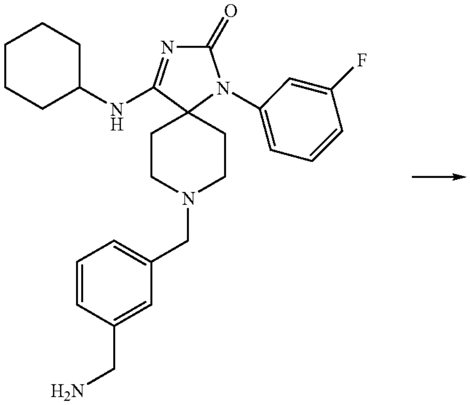

10-2

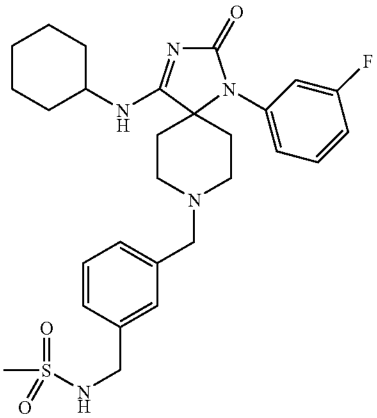

10-3

Example 10-2

8-[3-(aminomethyl)benzyl]-4-(cyclohexylamino)-1-(3-fluorophenyl)-1,3,8-triazaspiro[4.5]dec-3-en-2-one

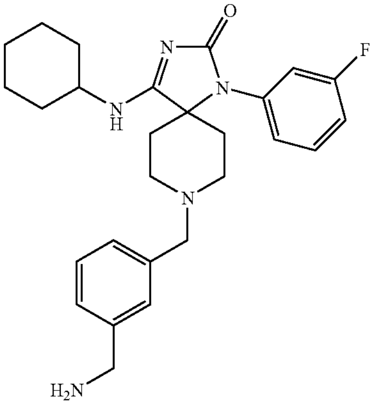

A 50 mL EtOH suspension of 0.470 g (1.02 mmol) 8-[3-cyanobenzyl]-4-(cyclohexylamino)-1-(3-fluorophenyl)-1,3,8-triazaspiro[4.5]dec-3-en-2-one (Example (7-12)) and a small amount of Raney Nickel (in water) was first evacuated and flushed with $N_2$ 3 times then put under a $H_2$ balloon and allowed to stir overnight. The catalyst was filtered and the filtrate concentrated in vacuo to pure product.

$^1$H NMR (400 MHz, $CDCl_3$) δ 7.98-8.0 (m, 1H), 7.28-7.52 (m, 4H), 7.20-7.24 (m, 1H), 7.12-7.14 (m, 1H), 6.97-7.04 (m, 2H), 4.70 (s, 2H), 3.95-4.05 (m, 1H), 3.69-3.73 (m, 1H), 2.74-2.81 (m, 2H), 2.4-2.46 (m, 2H), 2.05-2.14 (m, 4H), 1.92-2.03 (m, 2H), 1.35-1.75 (m, 9H).

exact MS found 464.2806 theory 464.2820

Example 10-3

N-(3-{[4-(cyclohexylamino)-1-(3-fluorophenyl)-2-oxo-1,3,8-triazaspiro[4.5]dec-3-en-8-yl]methyl}benzyl)methanesulfonamide

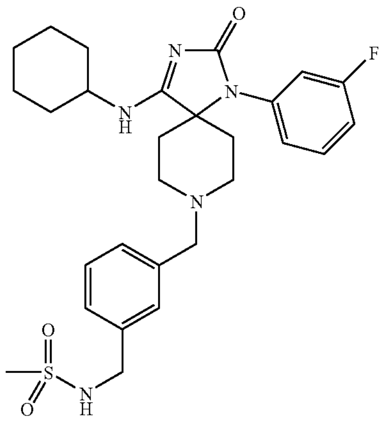

A 2 mL $CH_2Cl_2$ suspension of 0.05 g (0.11 mmol) 4-(cyclohexylamino)-8-[3-(aminomethyl)benzyl]-1-(3-fluorophenyl)-1,3,8-triazaspiro[4.5]dec-3-en-2-one (Example (7-12)), 0.02 mL (0.22 mmol) methanesulfonyl chloride and excess $K_2CO_3$ was allowed to stir at rt overnight. The reaction was filtered and concentrated. The remaining oil was dissolved in 0.5 mL $CH_2Cl_2$ and purified on an Isco automated system affixed with a Biotage Flash 25(S) cartridge eluted at 20 mL/min with 0-5% MeOH in $CH_2Cl_2$ over 15 min and hold at 5% MeOH for 30 min. The product eluted second, pure by HPLC/MS and NMR. $^1H$ NMR (400 MHz, $CDCl_3$) δ 7.79-7.83 (m, 1H), 7.45-7.54 (m, 2H), 7.33-7.4 (m, 2H), 7.12-7.14 (m, 1H), 6.96-7.05 (m, 3H), 4.31-4.39 (m, 1H), 3.92-4.05 (m, 1H), 3.48-3.52 (m, 1H), 2.65-2.80 (m, 2H), 2.4-2.50 (m, 2H), 1.90-2.20 (m, 6H), 1.62-1.8 (m, 4H), 1.55 (s, 3H), 1.30-1.50 (m, 2H), 1.15-1.30 (m, 4H). MS 542.4

A representative procedure for elaboration of the $R^3$ substituent, as depicted in Scheme 11 below, can be used in the synthesis of various compounds of the invention, including Examples (11-2)-(11-8) below. Examples (11-2)-(11-8) are depicted below in enamine form, but may also exist in tautomeric imine form, as described above Scheme 11

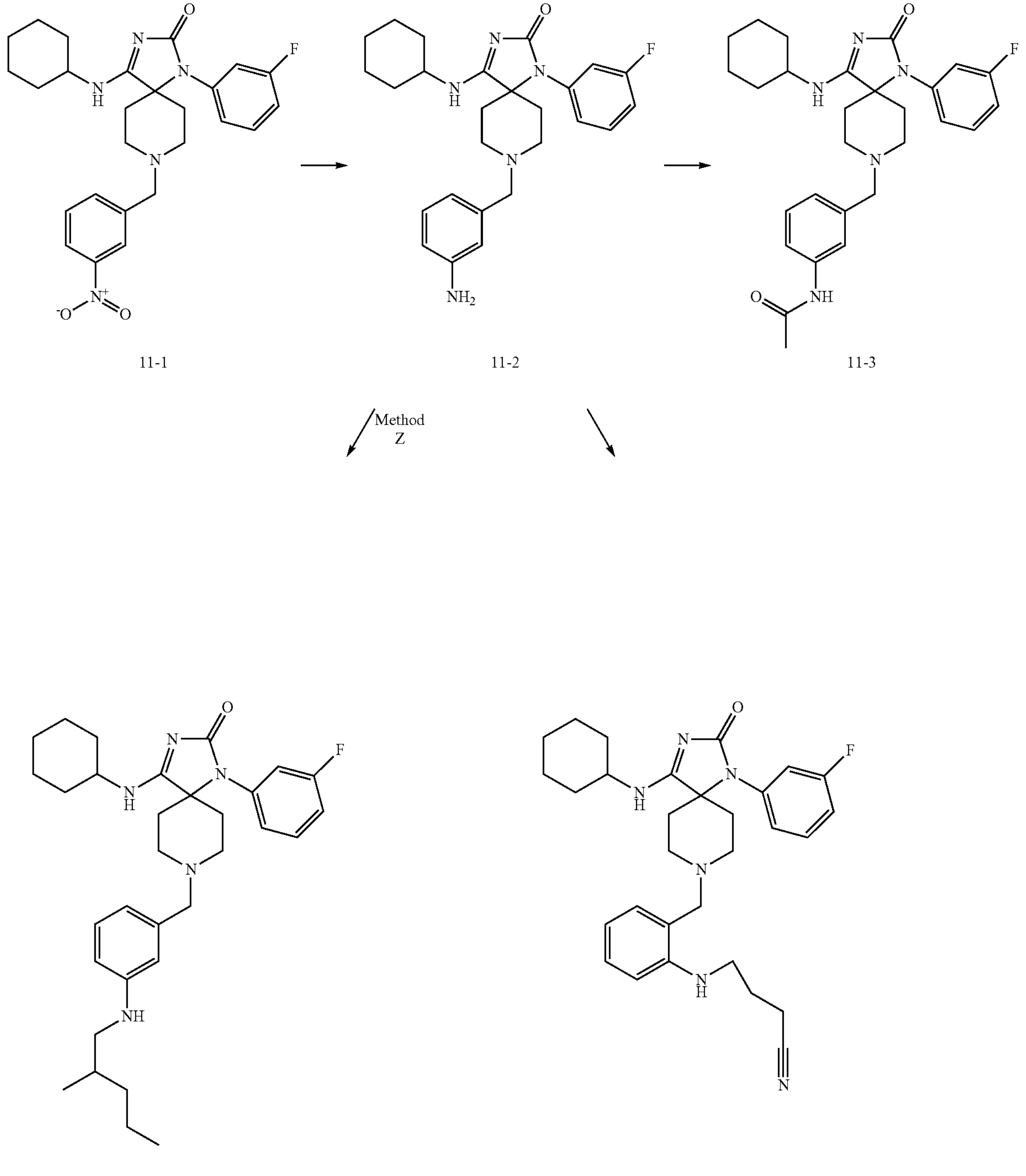

11-1 11-2 11-3

11-5 11-8

Example 11-2

8-(3-aminobenzyl)-4-(cyclohexylamino)-1-(3-fluorophenyl)-1,3,8-triazaspiro[4.5]dec-3-en-2-one

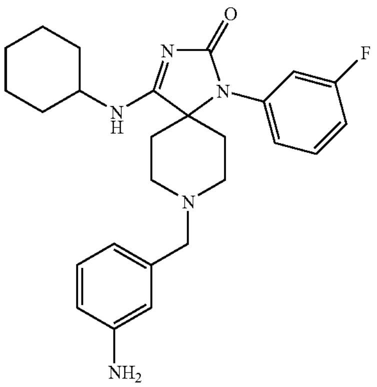

A 100 mL EtOH solution of 1.0 g (2.1 mmol) 8-(3-nitrobenzyl)-4-(cyclohexylamino)-1-(3-fluorophenyl)-1,3,8-triazaspiro[4.5]dec-3-en-2-one (example 104) and 0.57 g (2.5 mmol) $SnCl_2$ dihydrate was heated to reflux and allowed to stir overnight. HPLC/MS showed complete conversion so the reaction mixture was filtered through celite washed with EtOH then the filtrate was concentrated. The remaining oil was partitioned between 3N NaOH and EtOAc. A thick white precipitate formed in the aqueous layer. The organic layer was washed with brine, dried over $Na_2SO_4$, filtered and concentrated to pure product.

$^1$H NMR (400 MHz, $CDCl_3$) δ 8.09-8.11 (m, 1H), 7.32-7.36 (m, 1H), 7.10-7.13 (m, 1H), 6.96-7.03 (m, 3H), 6.60-6.63 (m, 2H), 6.53 (s, 1H), 3.95-4.0 (m, 1H), 3.43 (s, 2H), 2.75-2.80 (m, 2H), 2.37-2.42 (m, 2H), 1.93-2.12 (m, 5H), 1.64-1.75 (m, 3H), 1.35-1.41 (m, 2H), 1.16-1.27 (m, 4H).

MS 450.4

Example 11-3

N-(3-{[4-(cyclohexylamino)-1-(3-fluorophenyl)-2-oxo-1,3,8-triazaspiro[4.5]dec-3-en-8-yl]methyl}phenyl)acetamide

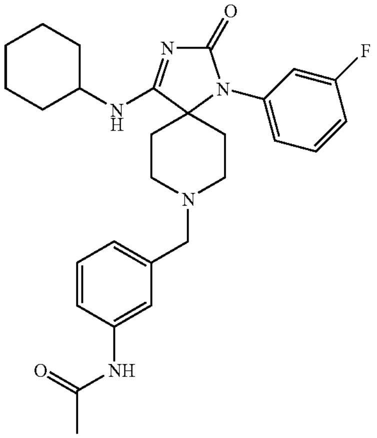

A 2 mL $CH_2Cl_2$ suspension of 0.05 g (0.11 mmol) 4-(cyclohexylamino)-8-[3-aminobenzyl]-1-(3-fluorophenyl)-1,3,8-triazaspiro[4.5]dec-3-en-2-one, 0.1 mL (0.11 mmol) acetyl chloride and excess $K_2CO_3$ was allowed to stir at rt overnight. The reaction was filtered and concentrated then the remaining oil was dissolved in 1 mL $CH_2Cl_2$ and purified on an Isco automated system affixed with a Biotage Flash 25(S) cartridge eluted at 20 mL/min with 0-5% MeOH in $CH_2Cl_2$ over 15 min and hold at 5% MeOH for 30 min. The product eluted second, pure by HPLC/MS and NMR.

$^1$H NMR (400 MHz, $CDCl_3$) δ 7.88-7.90 (m, 1H), 7.63-7.70 (m, 2H), 7.30-7.35 (m, 1H), 7.19-7.24 (m, 1H), 6.92-7.04 (m, 4H), 3.90-3.94 (m, 1H), 3.47 (s, 2H), 2.72-2.78 (m, 2H), 2.29-2.36 (m, 4H), 2.14 (s, 3H), 1.98-2.1 (m, 6H), 1.62-1.73 (m, 2H), 1.13-1.41 (m, 4H). MS 492.4

Example 11-4

N-(3-{[4-(cyclohexylamino)-1-(3-fluorophenyl)-2-oxo-1,3,8-triazaspiro[4.5]dec-3-en-8-yl]methyl}phenyl)methanesulfonamide

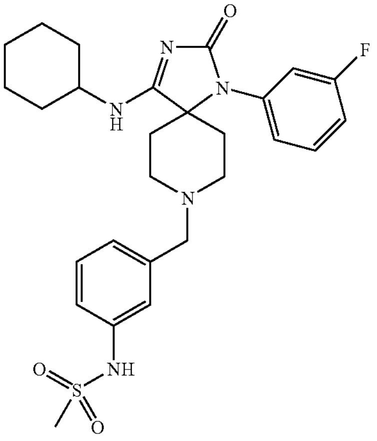

Produced by the method for Example 11-3 above but substituting sulfonyl chloride for acetyl chloride. $^1$H NMR (400 MHz, $CDCl_3$) δ 7.60-7.62 (m, 1H), 7.30-7.38 (m, 2H), 7.20 (s, 1H), 7.12-7.14 (m, 1H), 6.96-7.07 (m, 4H), 3.92-3.96 (m, 1H), 3.51 (s, 2H), 3.00 (s, 3H), 2.69-2.75 (m, 2H), 2.36-2.43 (m, 2H), 1.97-2.14 (m, 6H), 1.68-1.74 (m, 2H), 1.16-1.42 (m, 6H).

MS 528.1

Example 11-5

4-(cyclohexylamino)-1-(3-fluorophenyl)-8-{3-[(2-methylpentyl)amino]benzyl}-1,3,8-triazaspiro[4.5]dec-3-en-2-one

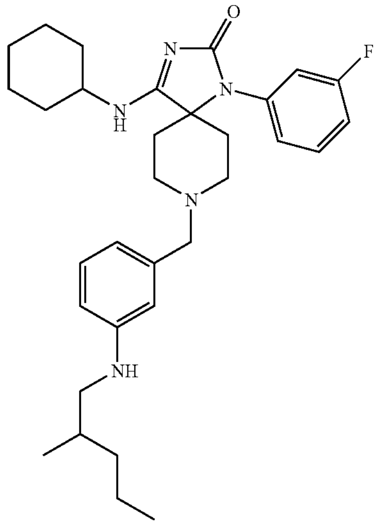

Method Z: A 5 ml dichloroethane suspension of 0.05 g (0.11 mmol) 4-(cyclohexylamino)-8-8-[3-aminobenzyl]-1-(3-fluorophenyl)-1,3,8-triazaspiro[4.5]dec-3-en-2-one (Example 11-2), 0.01 mL (0.13 mmol) 2-methylpentan-1-al, 0.05 mL HOAc, and 0.05 g (0.22 mmol) sodium triacetoxyborohydride was allowed to stir at rt overnight. The reaction was quenched with saturated aqueous $NaHCO_3$, diluted with $CH_2Cl_2$ and allowed to stir vigorously for 15 min. The organic layer was washed with brine, dried over $Na_2SO_4$, filtered and concentrated. The remaining oil was purified on an Isco automated system affixed with a Biotage Flash 25(S) cartridge eluted with 5% MeOH in $CH_2Cl_2$ at 20 mL/min for 30 min. The product eluted second.

$^1$H NMR (400 MHz, $CDCl_3$) δ 8.22-8.24 (m, 1H), 7.31-7.37 (m, 1H), 7.11-7.15 (m, 1H), 6.94-7.02 (m, 3H), 6.52-6.56 (m, 2H), 6.43 (s, 1H), 3.94-3.97 (m, 1H), 3.65-3.70 (m, 1H), 3.45 (s, 2H), 3.00-3.06 (m, 1H), 2.77-2.90 (m, 3H), 2.39-2.45 (m, 2H), 1.87-2.14 (m, 7H), 1.64-1.74 (m, 3H), 1.13-1.44 (m, 8H), 0.89-0.97 (m, 6H). MS 534.3

Example 11-6

4-(cyclohexylamino)-1-(3-fluorophenyl)-8-[3-(isopropylamino)benzyl]-1,3,8-triazaspiro[4.5]dec-3-en-2-one

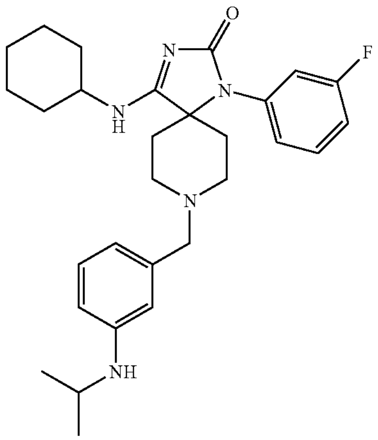

This compound was produced using Method Z substituting acetone for the aldehyde. $^1$H NMR (400 MHz, $CDCl_3$) δ 8.18-8.2 (m, 1H), 7.31-7.36 (m, 1H), 7.11-7.14 (m, 1H), 6.96-7.03 (m, 3H), 6.50-6.54 (m, 2H), 6.41 (s, 1H), 3.94-3.97 (m, 1H), 3.59-3.65 (m, 1H), 3.45 (s, 2H), 2.77-2.83 (m, 2H), 2.38-2.44 (m, 2H), 1.91-2.13 (m, 3H), 1.63-1.75 (m, 3H), 1.34-1.43 (m, 2H), 1.14-1.25 (m, 6H).

MS 492.4

Example 11-7

4-(cyclohexylamino)-1-(3-fluorophenyl)-8-[2-(isopropylamino)benzyl]-1,3,8-triazaspiro[4.5]dec-3-en-2-one

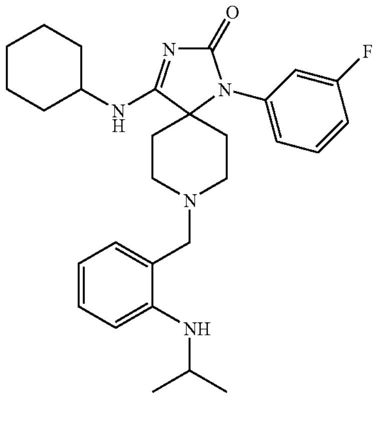

Produced using Method Z substituting acetone for the aldehyde and 8-(2-aminobenzyl)-4-(cyclohexylamino)-1-(3- fluorophenyl)-1,3,8-triazaspiro[4.5]dec-3-en-2-one (example 80) for the substrate. MS 492.4

Example 11-8

4-[(2-{[4-(cyclohexylamino)-1-(3-fluorophenyl)-2-oxo-1,3,8-triazaspiro[4.5]dec-3-en-8-yl]methyl}phenyl)amino]butanenitrile

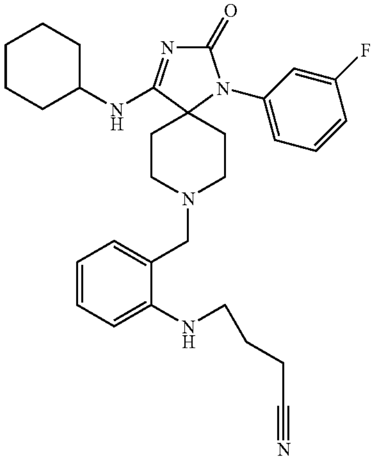

A 2 mL $CH_3CN$ suspension of 0.05 g (0.11 mmol) 8-(2-aminobenzyl)-4-(cyclohexylamino)-1-(3-fluorophenyl)-1,3,8-triazaspiro[4.5]dec-3-en-2-one (example 80), excess 4-bromobutyronitrile and $Cs_2CO_3$ was heated to 60° C. and allowed to stir for 2 days. HPLC/MS showed a small amount of product so the reaction was filtered and concentrated. The remaining oil was purified on an Isco automated system affixed with a Biotage Flash 25(M) cartridge eluted with 0-5% MeOH+0.5M $NH_3$ in $CH_2Cl_2$ over 30 min at 20 mL/min. The product eluted last.

$^1$H NMR (400 MHz, $CDCl_3$) δ 7.31-7.42 (m, 1H), 6.83-7.18 (m, 5H), 6.57-6.70 (m, 2H), 4.6-4.8 (br m, 1H), 3.57-3.97 (m, 6H), 3.28 (m, 1H), 2.65-2.70 (m, 1H), 2.39-2.58 (m, 4H), 2.21-2.25 (m, 1H), 1.67-2.08 (m, 9H), 1.26-1.43 (m, 4H).

MS 517.1

A representative procedure for elaboration of the $R^3$ substituent, as depicted in Scheme 12 below, can be used in the synthesis of various compounds of the invention, including Example (12-4) below. Example (12-4) is depicted below in enamine form, but may also exist in tautomeric imine form, as described above Scheme 12

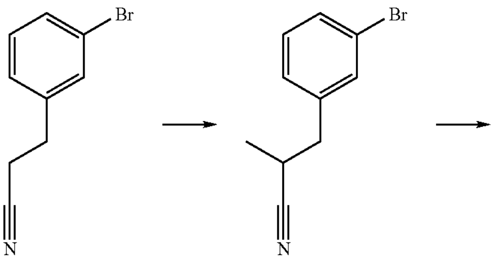

12-1 12-2

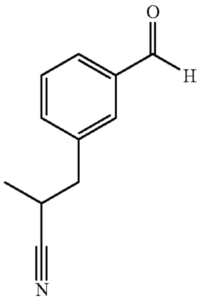

12-3

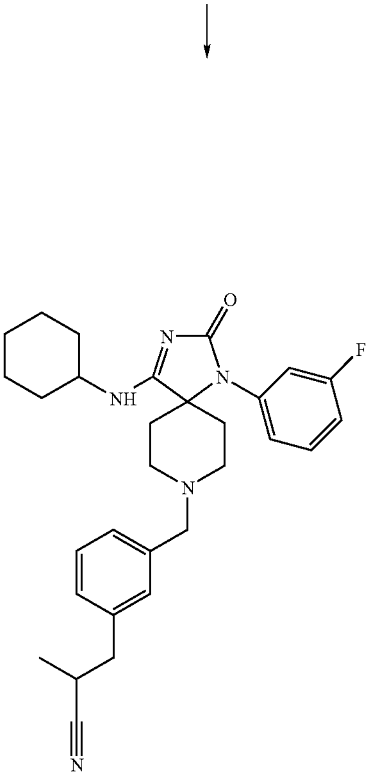

12-4

Example 12-4

3-(3-{[4-(cyclohexylamino)-1-(3-fluorophenyl)-2-oxo-1,3,8-triazaspiro[4.5]dec-3-en-8-yl]methyl}phenyl)-2-methylpropanenitrile (12-4)

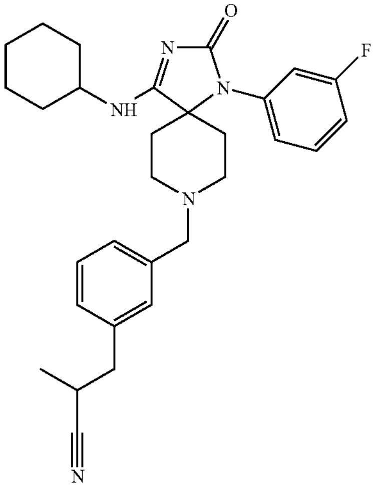

Step 1: 3-(3-bromophenyl)-2-methylpropanenitrile (12-2)

To a 10 mL THF solution of 2.5 mL (5 mmol) LDA (2M in THF) on a dry ice-acetone bath went 0.7 mL (4.76 mmol) 3-bromopropionitrile (9-1) dropwise. The solution was allowed to stir for 15 min, then transferred by cannula to a 10 mL THF solution of 0.31 mL (5 mmol) MeI also cooled to −78° C. The bath was removed and the reaction was allowed to warm to rt and stir for 30 min. The reaction was quenched with saturated aqueous $NH_4Cl$ and the product was extracted into EtOAc. The organic layer was dried over $Na_2SO_4$, filtered and concentrated. The remaining oil was dissolved in 1 mL $CH_2Cl_2$ and purified on an Isco automated system affixed with a Biotage Flash 40(M) cartridge eluted with 50-100% EtOAc in hexane. The product eluted last. MS 224.0 NB#212867-102

Step 2: 3-(3-formylphenyl)-2-methylpropanenitrile (12-3)

A 3-neck flask equipped with a condenser and 2 septa was flushed with $N_2$, then the flask was charged with 0.6 g (2.7 mmol) 3-(3-bromophenyl)-2-methylpropionitrile (9-2), 0.275 g (4 mmol) sodium formate, 0.155 g (0.13 mmol) tetrakis(triphenylphosphine)Palladium and flushed with CO from a balloon for 5 min. The solids were suspended in 10 mL DMF and CO continued to bubble into the liquid. The flask was heated in an oil bath at 100' for 20 min then 110' while stirring. The color changed from yellow to a deep orange color after 1.5 h, and HPLC/MS analysis showed no starting material and one major product. The reaction was cooled and quenched with brine. The product was extracted into EtOAc, dried over $Na_2SO_4$, filtered and concentrated. The product was dissolved in 1 mL $CH_2Cl_2$ and purified on an Isco automated system affixed with a Biotage Flash 25(M) cartridge eluted with 0-50% EtOAc in hexane at 25 mL/min over 15 min and hold for 30 min. The product eluted last. MS 174.1 NB#212867-104

Step 3: 3-(3-{[4-(cyclohexylamino)-1-(3-fluorophenyl)-2-oxo-1,3,8-triazaspiro[4.5]dec-3-en-8-yl]methyl}phenyl)-2-methylpropanenitrile (12-4)

To a 20 mL dichloroethane solution of 0.35 g (0.92 mmol) 4-(cyclohexylamino)-1-(3-fluorophenyl)-1,3,8-triazaspiro[4.5]dec-3-en-2-one and 0.25 mL (1.4 mmol) DIEA went 0.16 g (0.92 mmol) 3-(3-formylphenyl)-2-methylpropanenitrile (9-3). The suspension was allowed to stir for 10 min then 0.4 g (1.9 mmol) sodium triacetoxyborohydride was added and the reaction was allowed to stir at rt overnight. HPLC/MS showed no starting material so the reaction was quenched with 100 mL sat $NaHCO_3$ and diluted with $CH_2Cl_2$. The organic layer was washed with brine, dried over $Na_2SO_4$, filtered and concentrated. The remaining oil was purified on an Isco automated system affixed with a Biotage Flash 25(M) cartridge eluted with 5% MeOH+0.5M $NH_3$ in $CH_2Cl_2$ at 25 mL/min over 30 min. The product eluted second.

$^1H$ NMR (400 MHz, $CDCl_3$) δ 7.80-7.82 (d, 1H J=8 Hz), 7.28-7.37 (m, 2H), 7.14-7.19 (m, 3H), 6.96-7.04 (m, 3H), 3.94-3.97 (m, 1H), 3.51 (s, 2H), 2.84-2.87 (m, 3H), 2.71-2.78 (m, 2H), 2.34-2.41 (m, 2H), 1.97-2.11 (m, 6H), 1.65-1.75 (m, 3H), 1.33-1.41 (m, 5H), 1.17-1.25 (m, 3H).

MS 502.0

Scheme 13

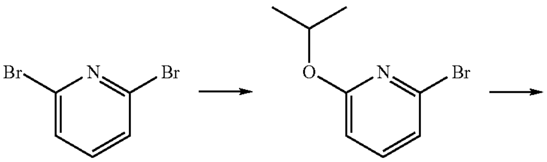

13-1

13-2

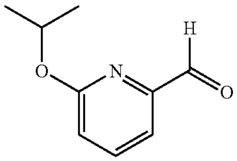

13-3

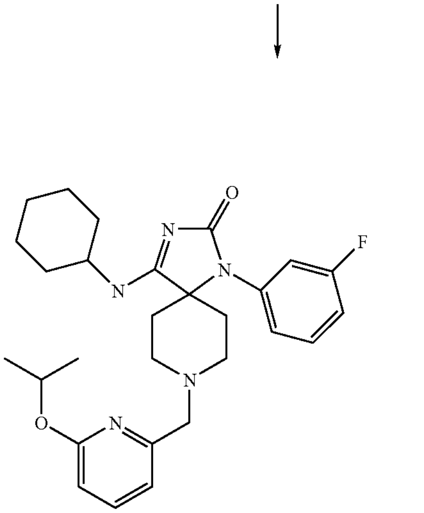

13-4

A representative procedure for elaboration of the $R^3$ substituent, as depicted in Scheme 13 below, can be used in the synthesis of various compounds of the invention, including Examples (13-4)-(13-5) below. Examples (13-4)-(13-5) are depicted below in enamine form, but may also exist in tautomeric imine form, as described above Example 13-4

4-(cyclohexylamino)-1-(3-fluorophenyl)-8-[(6-isopropoxypyridin-2-yl)methyl]-1,3,8-triazaspiro[4.5]dec-3-en-2-one

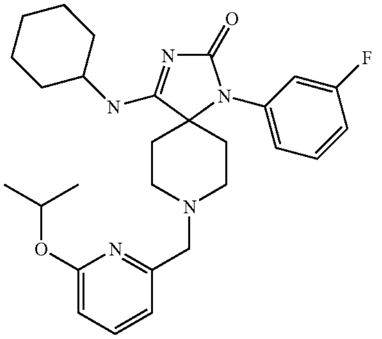

Step 1: 2-bromo-6-isopropoxypyridine

The compound was prepared in a manner similar to that described in WO 02/076983 (page 80). Dry isopropanol (25 mL, 42.2 mmole) was placed in an oven-dried 250 ml 3 necked flask under nitrogen, sodium spheres (0.5 g, 21.1 mmol) were added and the reaction was heated to 80° C. to dissolve the sodium. 2,6 dibromopyridine (10 g, 42.2 mmole) was added as a solid and the reaction was heated at 95° C. After heating for ~2.5 hr the reaction was cooled and partitioned between ether and water. The organic layer was evaporated to give a solid plus oil, the mixture was suspended in hexanes, cooled, and filtered to remove the solid. The filtrate was evaporated carefully and chromatographed on silica eluting with hexanes to give the product as a clear, colorless oil.

$^1$H NMR (400 MHz, $CDCl_3$) δ 8.23 (d, J=7.8 Hz, 1H), 7.53 (t, J=8.2 Hz, 1H), 7.33 (dd, J=8.0, 14.7 Hz, 1H), 7.0 (m, 3H), 6.75 (d, J=7.2 Hz, 1H), 6.60 (d, J=8.3 Hz, 1H), 5.22 (m, 1H), 3.93 (m, 1H), 3.59 (s, 2H), 2.90 (m, 2H), 2.55 (m, 2H), 2.12 (m, 2H), 2.0 (m, 4H), 1.7-1.5 (m, 4H), 1.4-1.3 (m, 2H), 1.33 (d, J=6.2 Hz, 6H), 1.15 (m, 3H).

LCMS (m+1)=215.1, 217.1

Step 2: 6-isopropoxypyridine-2-carbaldehyde 6-isopropoxypyridine-2-carbaldehyde was prepared in a manner similar to that described in D. L. Comins, M. O. Killpack, *J. Org. Chem.* 1990 55 69-73 for the methoxy analog. 2-bromo-6-isopropoxypyridine (1 g, 4.6 mmole) was dissolved in 10 ml dry THF under argon, cooled to −78° C. and treated with added 2.5 M n-Butyl lithium (1.9 mL, 4.8 mmole) keeping the temperature of the reaction below −65° C. After the reaction had stirred 45 min DMF (0.717 mL, 9.25 mmole) was added, again keeping temp below −60° C., the reaction was stirred for 15 min, then quenched with saturated bicarbonate solution. The layers were separated, the aqueous extracted with $CHCl_3$, the organic layers dried over $Na_2SO_4$, filtered and evap carefully, and the residue chromatographed in 0-50% Ether/hexanes to give the product as an oil. LCMS (m+1)=165.2

Step 3: 4-(cyclohexylamino)-1-(3-fluorophenyl)-8-[(6-isopropoxypyridin-2-yl)methyl]-1,3,8-triazaspiro[4.5]dec-3-en-2-one. This compound was prepare in a manner similar to that described for example (5-6) using the intermediate from scheme 13 step 2 and compound (5-2).

LCMS (m+1)=494.1

Example 13-5

8-[(6-sec-butoxypyridin-2-yl)methyl]-4-(cyclohexylamino)-1-(3-fluorophenyl)-1,3,8-triazaspiro[4.5]dec-3-en-2-one

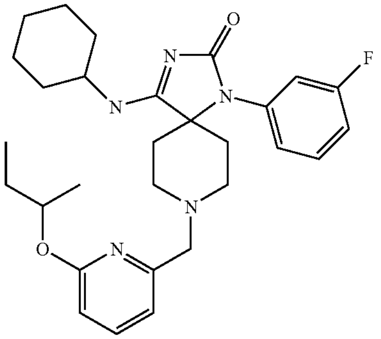

8-[(6-sec-butoxypyridin-2-yl)methyl]-4-(cyclohexylamino)-1-(3-fluorophenyl)-1,3,8-triazaspiro[4.5]dec-3-en-2-one was prepared in a manner similar to that described for Example 134 except that dichloroethane was used in the final step.

LCMS (m+1)=508.1

Scheme 14A depicts a method for preparing 8-Benzyl-1-phenyl-4-thioxo-1,3,8-triazaspiro[4.5]decan-2-one 14A-5 intermediates useful for making compounds of the invention. The commercially available 14A-1 may be alkylated with an appropriate alkyl halide like benzyl chloride using a suitable base like potassium carbonate in a suitable solvent like acetonitrile to afford 14A-2. A similar method is described by M. E. Kopach et. al. *J. Org. Chem.* 2003 68 5739-5741. A modified Strecker reaction of A-2 yields 14A-3; and followed by the treatment of chlorosulfonyl isocyanate in methylene chloride to afford 14A-4. A similar method is described by P. L. Feldman and M. F. Brackeen *J. Org. Chem.* 1990, 55, 4207-4209 at reference therein. 14A-5 is obtained by the thiolation of 14A-4 by $Na_2S$. The treatment of the intermediates 14A-5 with various amines in a suitable solvent like in DMSO or DMF with heat yields the invention compounds 14A-6.

Scheme 14A

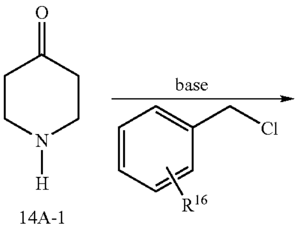

14A-1

-continued
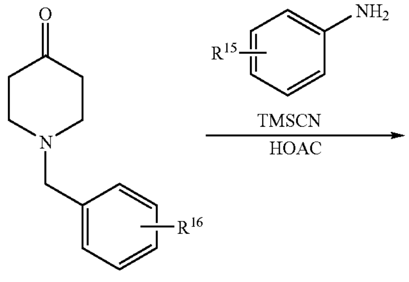
14A-2
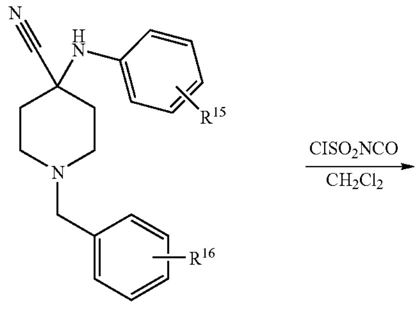
14A-3
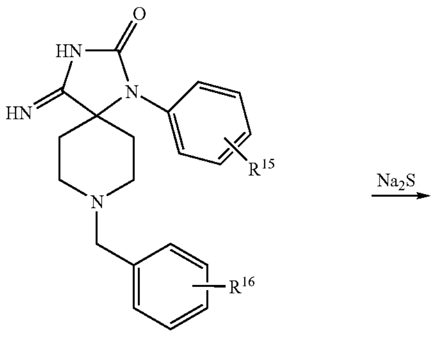
14A-4
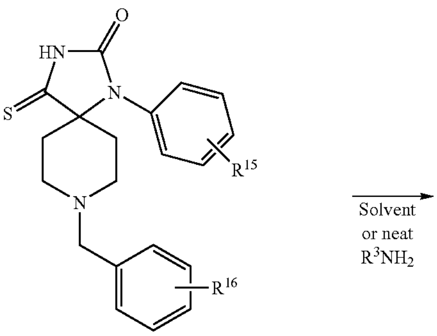
14A-5
-continued
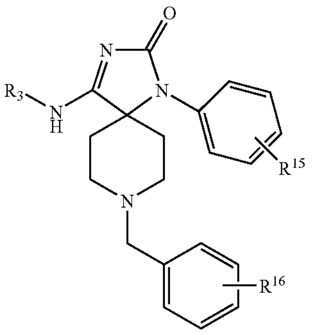
14A-6
Scheme 14
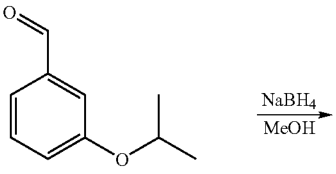
14-1
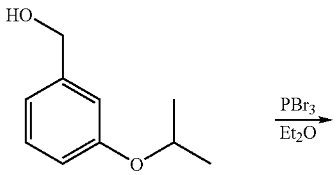
14-2
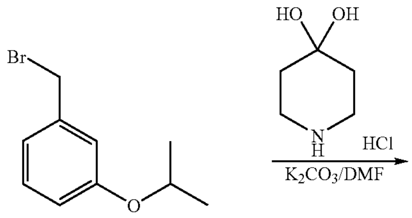
14-3
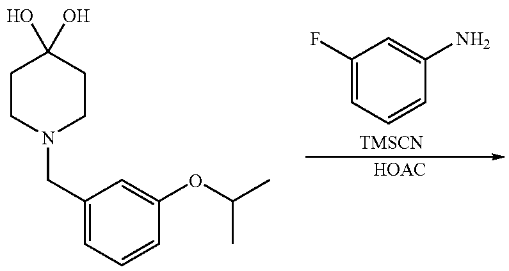
14-4

-continued

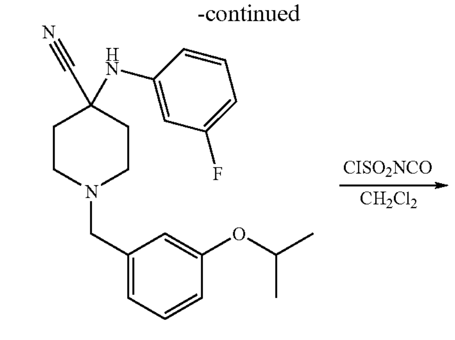

14-5

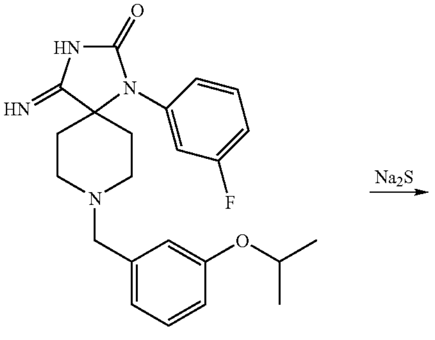

14-6

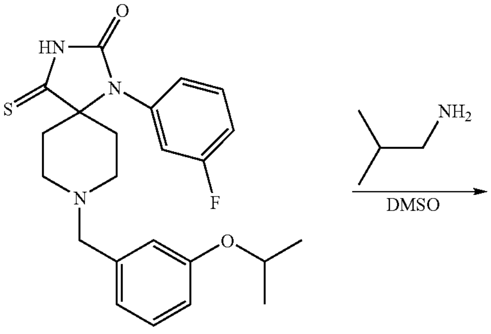

14-7

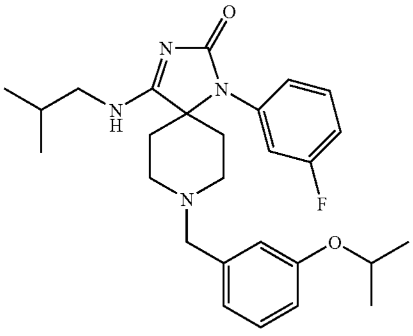

14-8

Example 14

1-(3-Fluorophenyl)-4-isobutylamino-8-(3-isopropoxy-benzyl)-1,3,8-triaza-spiro[4.5]dec-3-en-2-one (14-8)

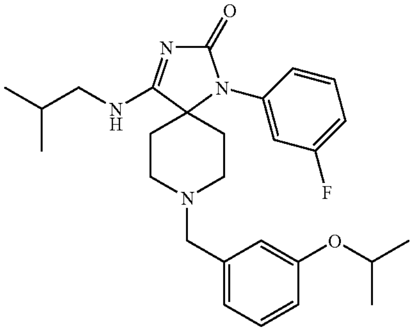

Step 1: 3-Isopropoxy-benzylbromide (14-3)

To a solution of 3-Isopropoxy-benzaldehyde 14-1 (20 g, 122 mmol) in methanol (400 mL), sodium borohydride (5 g) is added in several portions at 0° C. The resulting mixture is then stirred at rt for 3 h. The reaction is quenched by addition of saturated $NH_4OH$. Extracted (EtOAc), concentrated, a colorless oil 14-2 (MH+, 166) is obtained and use without purification. Re-dissolve (3-Isopropoxy-phenyl)-methanol 14-2 in ether (244 mL) $PBr_3$ (11.5 mL, 122 mmol) is added dropwise at 0° C. The reaction mixture is stirred at 0° C. then rt for 3 h, quenched (MeOH), extracted (EtOAc), concentrated, a colorless oil 14-3 is obtained. (MH+, 288)

Step 2: 1-(3-Isopropoxy-benzyl)-piperidin-4-one monohydrate (14-4)

A mixture of 4-piperidone hydrochloride monohydrate (19.52 g, 127.12 mmol), 1-Bromomethyl-3-isopropoxy-benzene (19.41 g, 84.76 mmol) and $K_2CO_3$ in DMF (150 mL) is stirred at rt for 16 hr. Solvent is removed in vacco, the residue is extract (EtOAc/Brine), dried ($Na_2SO_4$), concentrated, and purified by chromatography (silica gel, EtoAc/hexanes, 2/3) to afford 14-4. (MH+, 266)

Step 3: 4-(3-Fluoro-phenyl)-1-(3-isopropoxy-benzyl)-piperidine-4-carbonitrile (14-5)

To a solution of 1-(3-Isopropoxy-benzyl)-piperidin-4-one monohydrate 14-4 (7.98 g, 30 mmol) and aniline (3.67 g, 33 mmol) in glacial acetic acid (30 mL) is added TMSCN (2.98 g, 30 mmol) dropwise over a 10 min period, maintaining the temperature below 40° C. The reaction mixture is stirred an additional 30 min and than poured into a cold $NH_4OH$ mixture (30 mL $NH_4OH$ and 30 g of ice). Additional of $NH_4OH$ is slowly added until pH=10 is reach. Extracted ($CHCl_3$), Dried ($Na_2SO_4$), Concentrated, and Purified by silica gel to afford 14-5. LCMS (MH+ 368.3)

Step 4: 1-(3-Fluoro-phenyl)-8-(3-isopropoxy-benzyl)-4-thioxo-1,3,8-triaza-spiro[4.5]decan-2-one (14-7)

The 4-(3-Fluoro-phenyl)-1-(3-isopropoxy-benzyl)-piperidine-4-carbonitrile 14-5 (5.28 g, 15.0 mmole) was dissolved into chloroform (15 mL). The solution was stirred and cooled to 0° C., at which point chlorosulfonyl isocyanate (Acros, 1.75 mL, 20.1 mmole, 1.25 eq) was added dropwise, causing formation of a large amount of white precipitate. The ice bath was removed, and the slurry was stirred hard with a magnetic stirrer for 10 min. LCMS (MH+ 411.2) indicated consumption of the nitrile at this point. Water (15 mL) was added, and the heterogeneous mixture was stirred hard at rt for 1 hr. In a 500 mL Erlenmeyer flask (used to accommodate a large stir bar), sodium sulfide (anhydrous, Aldrich, 22.5 g, 288 mmole) was dissolved into water (200 mL) and cooled to an internal temperature below 0° C. with an ice/isopropanol bath. Acetic acid (approx 28 mL) was added dropwise to the stirred solution, over a period of about 10 min, ensuring that the internal temperature stayed close to 0° C. (During the addition, there is a formation of a large amount of light-colored precipitate and the mixture becomes thick. The thickness diminishes as the addition of acetic acid nears completion.) The addition was stopped when pH paper indicated that the pH was ~6, and the solution had assumed a slight greenish color. At this point, the above slurry of imine was added to the sulfide solution, using dichloromethane (~30 mL) to assist the transfer. Isopropanol (50 mL) was added, and the flask was sealed with a balloon, removed from the ice bath, and stirred hard for 16 hr. The reaction was then diluted with dichloromethane, and washed with water plus sufficient saturated sodium bicarbonate solution to ensure basic pH. The organic layer was then removed, and the aqueous layer was extracted with 2× dichloromethane. The combined organic layers were dried ($MgSO_4$), filtered, and concentrated to a yellow solid. The solid was resuspended into dichloromethane, and deposited onto silica gel for chromatography. The sample was purified by flash chromatography over silica gel using a Combiflash system (80 g column), with 50% ethyl acetate/hexanes as the eluent (product Rf~0.25), providing the product 14-7.

LCMS (MH+ 428.2).

Step 6: 1-(3-Fluorophenyl)-4-isobutylamino-8-(3-isopropoxy-benzyl)-1,3,8-triaza-spiro[4.5]dec-3-en-2-one (14-8)

To a solution of 1-(3-Fluoro-phenyl)-8-(3-isopropoxy-benzyl)-4-thioxo-1,3,8-triaza-spiro[4.5]decan-2-one SNS-1 (21.4 mg, 0.05 mmol) in DMSO (1 mL) was added isobutyl amine (36.5 mg, 0.5 mmol). The reaction mixture was heated at 110° C. for 12 hr. The crude was purified by preparative HPLC to provide (14-8).

$^1H$ NMR ($CD_3OD$): δ 7.29 (br s, 1H), 7.18 (m, 1H), 7.05 (m, 3H), 6.90 (d, J=8.31 Hz, 1H), 6.76 (br m, 2H), 4.50 (m, 1H), 4.06 (br s, 2H), 3.00-3.20 (br, 2H), 2.2-2.8 (br, 4H), 1.92 (br, 1H), 1.19 (d, J=5.87 Hz), 0.86 (m, 6H). EI-MS m/z: 467.25 (MH+).

TABLE 6

The following compounds (or salts thereof) of table 6 were prepared in a manner similar to that described for scheme 14.

| Example # | Structure | Chemical Name | Mass Spec |
|---|---|---|---|
| 14-9 | 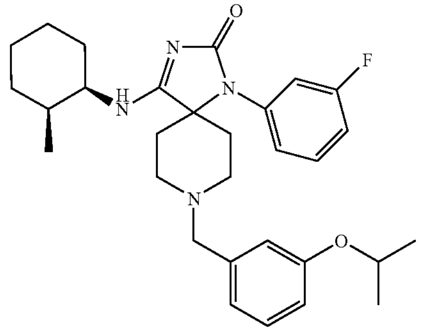 | 1-(3-Fluoro-phenyl)-8-(3-isopropoxy-benzyl)-4-(2-methyl-cyclohexylamino)-2-oxo-1,3-diaza-8-azonia-spiro[4.5]dec-3-ene | 507.3 |
| 14-10 | 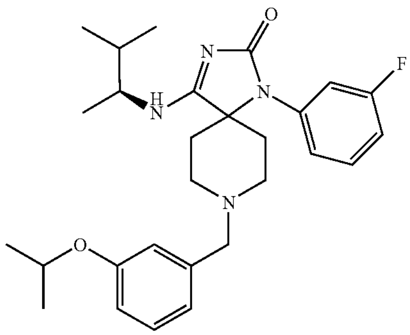 | 4-(1,2-Dimethyl-propylamino)-1-(3-fluoro-phenyl)-8-(3-isopropoxy-benzyl)-2-oxo-1,3-diaza-8-azonia-spiro[4.5]dec-3-ene | 481.25 |

TABLE 6-continued

The following compounds (or salts thereof) of table 6 were prepared in a manner similar to that described for scheme 14.

| Example # | Structure | Chemical Name | Mass Spec |
|---|---|---|---|
| 14-11 | 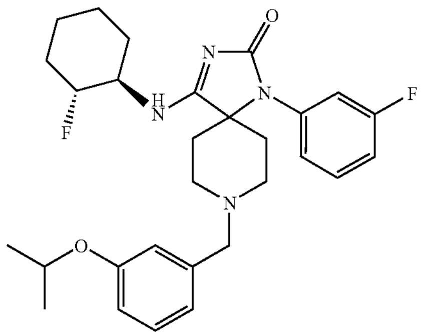 | 4-(2-Fluoro-cyclohexylamino)-1-(3-fluoro-phenyl)-8-(3-isopropoxy-benzyl)-2-oxo-1,3-diaza-8-azonia-spiro[4.5]dec-3-ene | 511.2 |
| 14-12 | 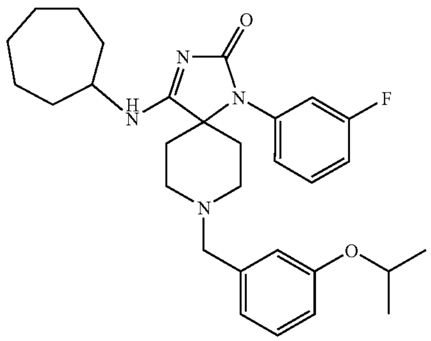 | 4-Cycloheptylamino-1-(3-fluoro-phenyl)-8-(3-isopropoxy-benzyl)-2-oxo-1,3-diaza-8-azonia-spiro[4.5]dec-3-ene | 507.3 |
| 14-13 | 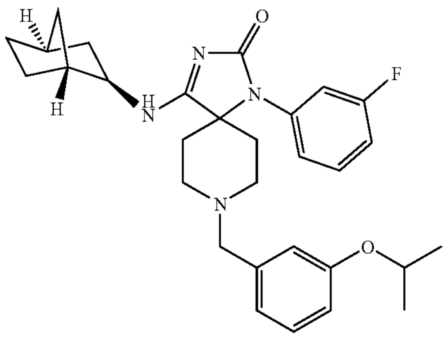 | 4-(Bicyclo[2.2.1]hept-2-ylamino)-1-(3-fluoro-phenyl)-8-(3-isopropoxy-benzyl)-2-oxo-1,3-diaza-8-azonia-spiro[4.5]dec-3-ene | 505.3 |
| 14-14 | 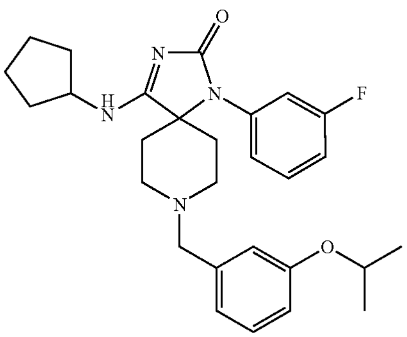 | 4-Cyclopentylamino-1-(3-fluoro-phenyl)-8-(3-isopropoxy-benzyl)-2-oxo-1,3-diaza-8-azonia-spiro[4.5]dec-3-ene | 479.25 |

TABLE 6-continued

| The following compounds (or salts thereof) of table 6 were prepared in a manner similar to that described for scheme 14. | | | |
|---|---|---|---|
| Example # | Structure | Chemical Name | Mass Spec |
| 14-15 | 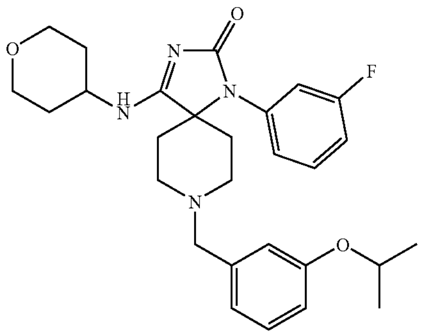 | 1-(3-Fluoro-phenyl)-8-(3-isopropoxy-benzyl)-2-oxo-4-(tetrahydro-pyran-4-ylamino)-1,3-diaza-8-azonia-spiro[4.5]dec-3-ene | 495.25 |
| 14-16 | 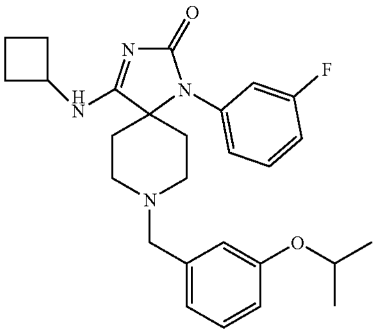 | 4-Cyclobutylamino-1-(3-fluoro-phenyl)-8-(3-isopropoxy-benzyl)-2-oxo-1,3-diaza-8-azonia-spiro[4.5]dec-3-ene | 465.3 |
| 14-17 | 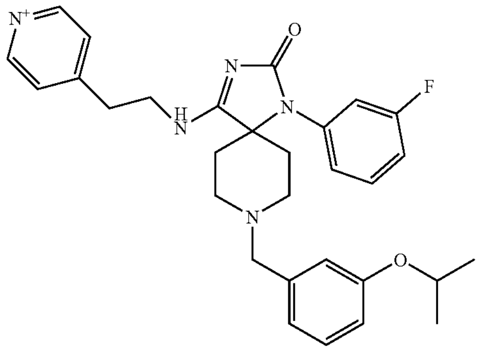 | 1-(3-Fluoro-phenyl)-8-(3-isopropoxy-benzyl)-2-oxo-4-(2-pyridin-4-yl-ethylamino)-1,3-diaza-8-azonia-spiro[4.5]dec-3-ene | 516.3 |
| 14-18 | 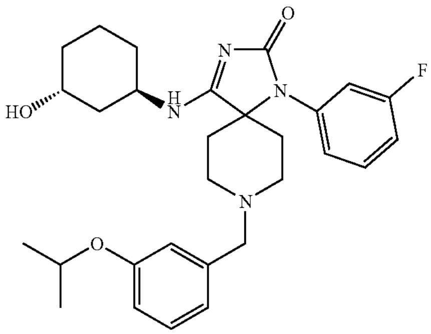 | 1-(3-Fluoro-phenyl)-4-(3-hydroxy-cyclohexylamino)-8-(3-isopropoxy-benzyl)-2-oxo-1,3-diaza-8-azonia-spiro[4.5]dec-3-ene | 509.35 |

TABLE 6-continued

| The following compounds (or salts thereof) of table 6 were prepared in a manner similar to that described for scheme 14. | | | |
|---|---|---|---|
| Example # | Structure | Chemical Name | Mass Spec |
| 14-19 | 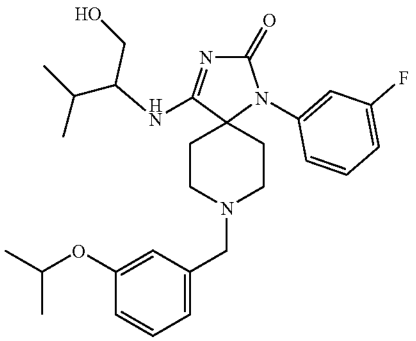 | 1-(3-Fluoro-phenyl)-4-(1-hydroxymethyl-2-methyl-propylamino)-8-(3-isopropoxy-benzyl)-2-oxo-1,3-diaza-8-azonia-spiro[4.5]dec-3-ene | 497.25 |
| 14-20 | 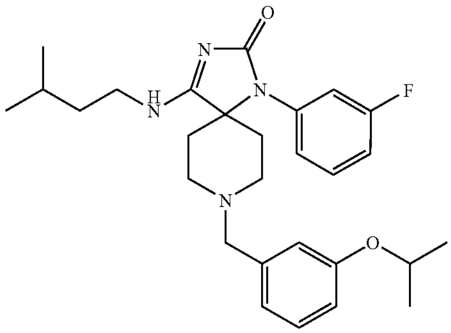 | 1-(3-Fluoro-phenyl)-8-(3-isopropoxy-benzyl)-4-(3-methyl-butylamino)-2-oxo-1,3-diaza-8-azonia-spiro[4.5]dec-3-ene | 481.3 |
| 14-21 | 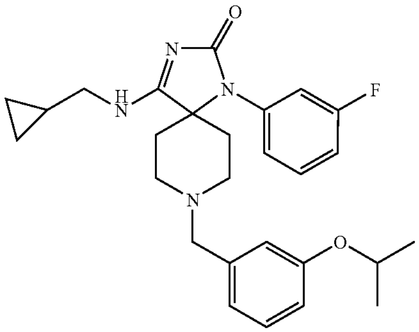 | 4-(Cyclopropylmethyl-amino)-1-(3-fluoro-phenyl)-8-(3-isopropoxy-benzyl)-2-oxo-1,3-diaza-8-azonia-spiro[4.5]dec-3-ene | 465.3 |
| 14-22 | 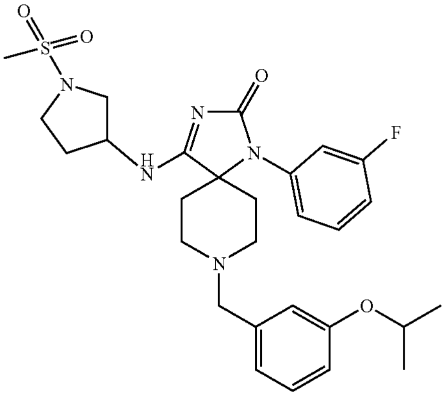 | 1-(3-Fluoro-phenyl)-8-(3-isopropoxy-benzyl)-4-(1-methanesulfonyl-pyrrolidin-3-ylamino)-2-oxo-1,3-diaza-8-azonia-spiro[4.5]dec-3-ene | 558.3 |

TABLE 6-continued

The following compounds (or salts thereof) of table 6 were prepared in a manner similar to that described for scheme 14.

| Example # | Structure | Chemical Name | Mass Spec |
|---|---|---|---|
| 14-23 | 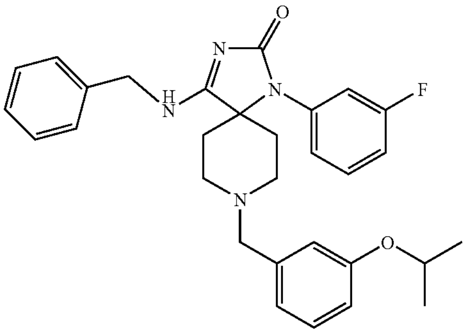 | 4-Benzylamino-1-(3-fluoro-phenyl)-8-(3-isopropoxy-benzyl)-2-oxo-1,3-diaza-8-azonia-spiro[4.5]dec-3-ene | 501.3 |
| 14-24 | 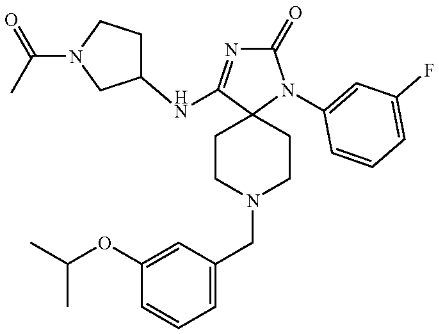 | 4-(1-Acetyl-pyrrolidin-3-ylamino)-1-(3-fluoro-phenyl)-8-(3-isopropoxy-benzyl)-2-oxo-1,3-diaza-8-azonia-spiro[4.5]dec-3-ene | 522.3 |
| 14-25 | 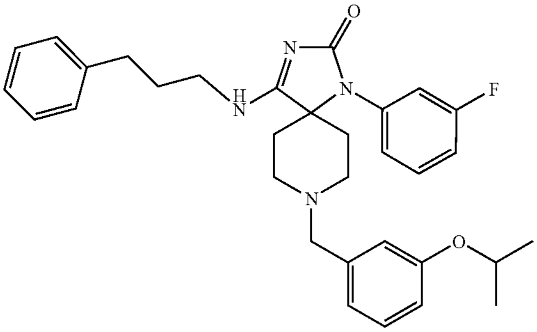 | 1-(3-Fluoro-phenyl)-8-(3-isopropoxy-benzyl)-2-oxo-4-(3-phenyl-propylamino)-1,3-diaza-8-azonia-spiro[4.5]dec-3-ene | 529.3 |
| 14-26 | 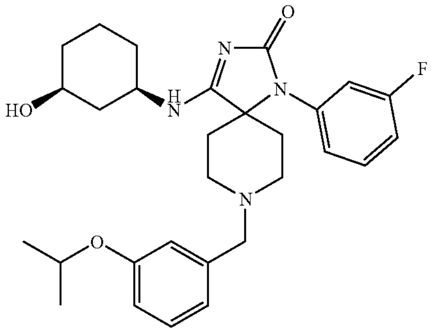 | 1-(3-Fluoro-phenyl)-4-(3-hydroxy-cyclohexylamino)-8-(3-isopropoxy-benzyl)-2-oxo-1,3-diaza-8-azonia-spiro[4.5]dec-3-ene | 509.35 |

TABLE 6-continued

The following compounds (or salts thereof) of table 6 were prepared in a manner similar to that described for scheme 14.

| Example # | Structure | Chemical Name | Mass Spec |
|---|---|---|---|
| 14-27 | 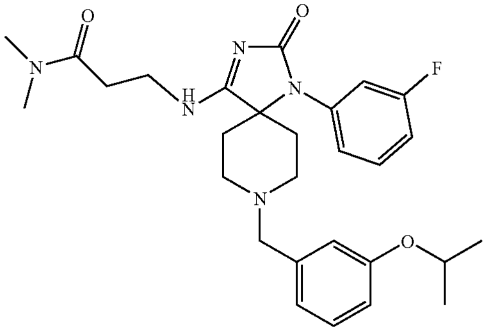 | 4-(2-Dimethylcarbamoyl-ethylamino)-1-(3-fluoro-phenyl)-8-(3-isopropoxy-benzyl)-2-oxo-1,3-diaza-8-azonia-spiro[4.5]dec-3-ene | 510.3 |
| 14-28 | 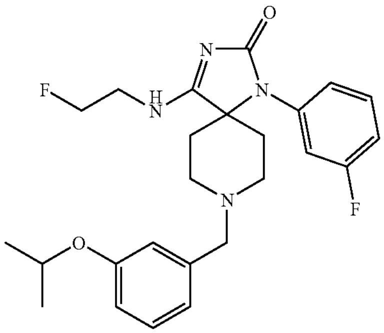 | 4-(2-Fluoro-ethylamino)-1-(3-fluoro-phenyl)-8-(3-isopropoxy-benzyl)-2-oxo-1,3-diaza-8-azonia-spiro[4.5]dec-3-ene | 457 |
| 14-29 | 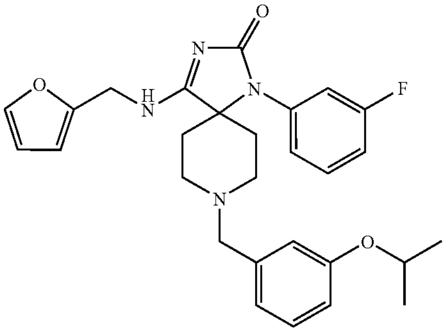 | 1-(3-Fluoro-phenyl)-4-[(furan-2-ylmethyl)-amino]-8-(3-isopropoxy-benzyl)-2-oxo-1,3-diaza-8-azonia-spiro[4.5]dec-3-ene | 491.2 |
| 14-30 | 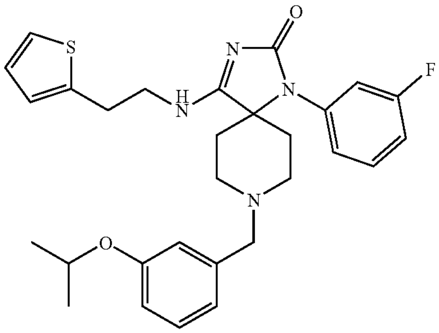 | 1-(3-Fluoro-phenyl)-8-(3-isopropoxy-benzyl)-2-oxo-4-(2-thiophen-2-yl-ethylamino)-1,3-diaza-8-azonia-spiro[4.5]dec-3-ene | 521 |

TABLE 6-continued

| The following compounds (or salts thereof) of table 6 were prepared in a manner similar to that described for scheme 14. | | | |
|---|---|---|---|
| Example # | Structure | Chemical Name | Mass Spec |
| 14-31 | 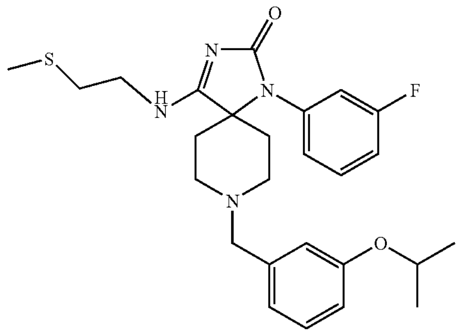 | 1-(3-Fluoro-phenyl)-8-(3-isopropoxy-benzyl)-4-(2-methylsulfanyl-ethylamino)-2-oxo-1,3-diaza-8-azonia-spiro[4.5]dec-3-ene | 485.2 |
| 14-32 | 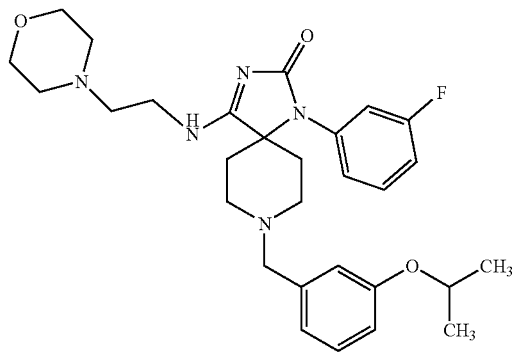 | 1-(3-Fluoro-phenyl)-8-(3-isopropoxy-benzyl)-4-(2-morpholin-4-yl-ethylamino)-2-oxo-1,3-diaza-8-azonia-spiro[4.5]dec-3-ene | 524.35 |
| 14-33 | 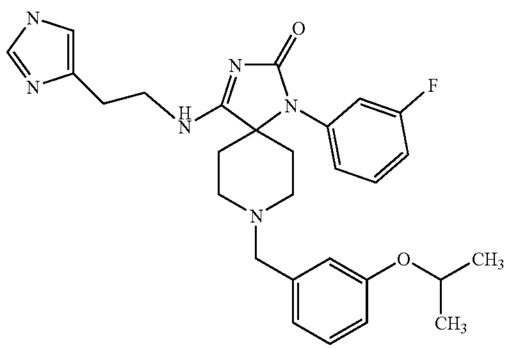 | 1-(3-Fluoro-phenyl)-4-[2-(1H-imidazol-4-yl)-ethylamino]-8-(3-isopropoxy-benzyl)-2-oxo-1,3-diaza-8-azonia-spiro[4.5]dec-3-ene | 504.6 |

TABLE 6-continued

| The following compounds (or salts thereof) of table 6 were prepared in a manner similar to that described for scheme 14. | | | |
|---|---|---|---|
| Example # | Structure | Chemical Name | Mass Spec |
| 14-34 | 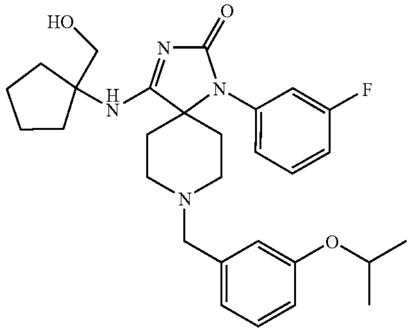 | 1-(3-Fluoro-phenyl)-4-(1-hydroxymethyl-cyclopentylamino)-8-(3-isopropoxy-benzyl)-2-oxo-1,3-diaza-8-azonia-spiro[4.5]dec-3-ene | 509.35 |
| 14-35 | 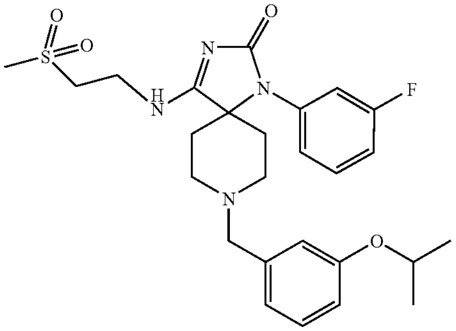 | 1-(3-Fluoro-phenyl)-8-(3-isopropoxy-benzyl)-4-(2-methanesulfonyl-ethylamino)-2-oxo-1,3-diaza-8-azonia-spiro[4.5]dec-3-ene | 517.25 |
| 14-36 | 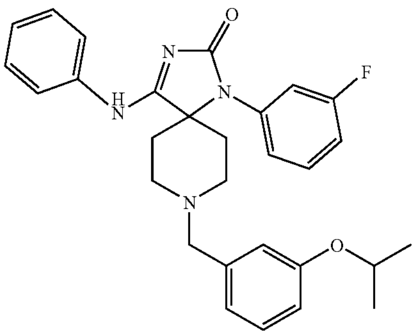 | 1-(3-Fluoro-phenyl)-8-(3-isopropoxy-benzyl)-2-oxo-4-phenylamino-1,3-diaza-8-azonia-spiro[4.5]dec-3-ene | 487.2 |

$R^2$ elaboration can be prepared by the methods described in Scheme 3, Scheme 14-A with various substituted aniline or by Suzuki coupling of 15-1 with a various of boronic acid or boronate ester. A representative procedure for elaboration of the $R^2$ substituent, as depicted in Scheme 15 below, can be used in the synthesis of various compounds of the invention, including Examples (15-2)-(15-42) below. The boronate ester can be prepared as describe in Scheme 15-A. Examples (15-2)-(15-42) are depicted below in enamine form, but may also exist in tautomeric imine form, as described above.

Scheme 15

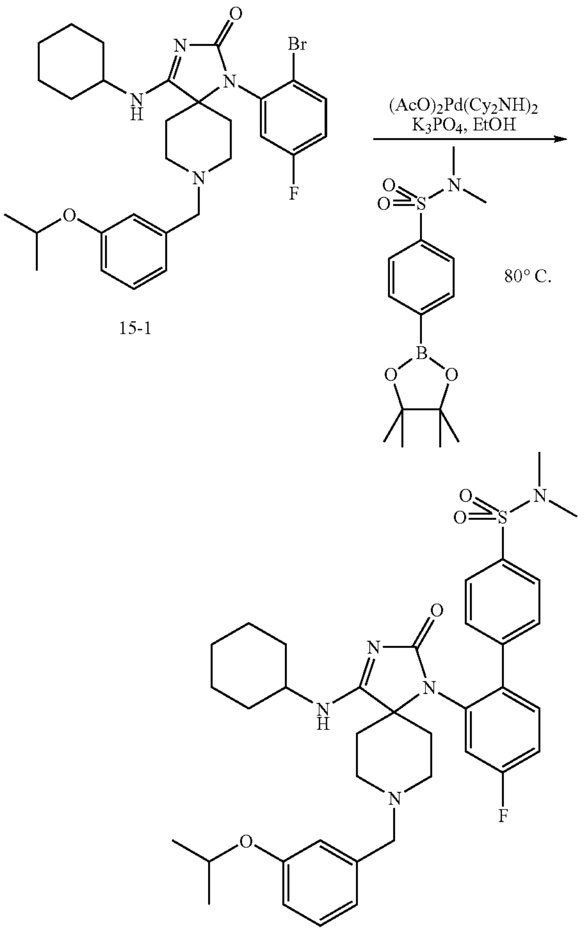

15-1

15-2

Scheme 15-A: General Procedure for Synthesis of Boronate Esters from Aryl Halides

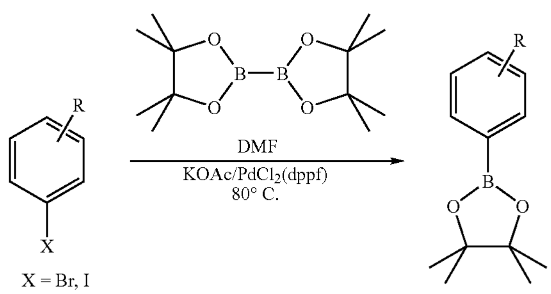

X = Br, I

15-A-1

15-A-2

This procedure is based on conditions developed by Miyaura et. al. (*J. Org. Chem.* 1995, 60, 7508-7510). The aryl halide 15-A-1 (0.20 mmol, 1 eq), potassium acetate (0.60 mmol, 3 eq.), bis(pinacolato)diboron (0.18 mmol, 0.9 eq.) and $PdCl_2$(dppf) (0.020 mmol, 0.1 eq.) were added to a round bottom flask. Dry DMF (3 ml) was added, and the flask was flushed with nitrogen, then capped. The resultant mixture was stirred and placed into an 80° C. oil bath. The reaction was followed by LCMS. Upon consumption of aryl bromide (several hours), the reaction mixture was extracted with ethyl acetate/water 3-4 times, then washed with brine twice. The resultant organic solution was dried over $MgSO_4$ and concentrated to afford crude boronate ester 15-A-2, which was used directly for the subsequent Suzuki coupling reactions. A series of representative Procedure for Synthesis of Boronate Esters from Aryl Halides is described in Scheme 15-B-E Scheme 15-B

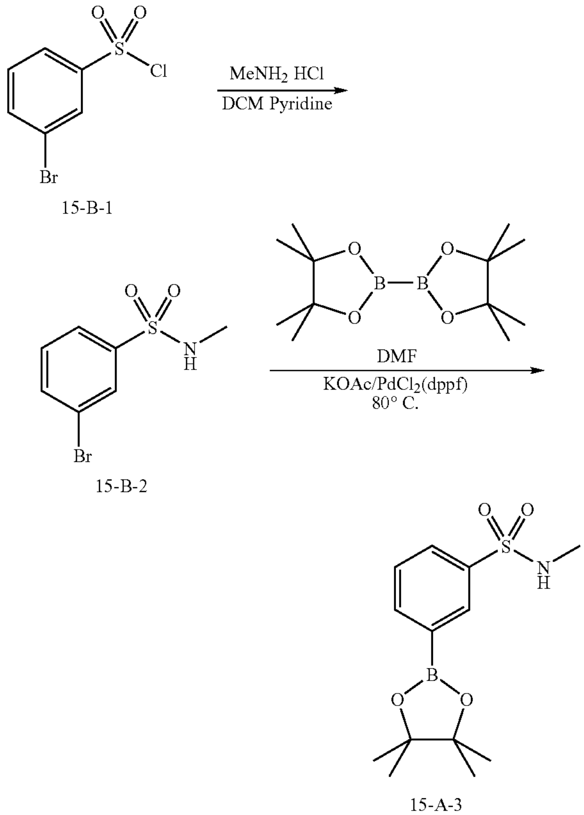

15-B-1

15-B-2

15-A-3

Compound 15-B-1 (0.230 g 0.90 mmol) was added to a stirred solution of methylamine hydrochloride (0.091 g 1.35 mmol) and pyridine (0.364 ml 4.50 mmol) in dichloromethane (10 ml) at 0° C. The reaction mixture was allowed to warm to room temperature and the reaction was followed by LCMS. Upon consumption of starting material (about 3 hrs), the mixture was extracted twice with diethyl ether/saturated sodium bicarbonate solution. The organic solution was washed twice with an aqueous sodium dihydrogen phosphate (pH=3-4) solution, twice with brine, and then the organic solution was dried over $MgSO_4$ and concentrated to afford the crude sulfonamide 15-B-2.

The crude 15-B-2 (0.050 g, 0.20 mmol), potassium acetate (0.059 g 0.60 mmol), bis(pinacolato)diboron (0.046 g, 0.18 mmol) and $PdCl_2$(dppf) (0.016 g 0.020 mmol) were added to a round bottom flask. Dry DMF (3 ml) was then added, and the flask was flushed with nitrogen, then capped. The resultant mixture was stirred and placed into an 80° C. oil bath. The reaction was followed by LCMS. Upon consumption of starting material, the reaction mixture was extracted with ethyl acetate/water 3-4 times, then washed with brine twice. The resultant organic solution was dried over $MgSO_4$ and concentrated to afford crude boronate ester 15-B-3 which was used directly for the Suzuki coupling without further purification, to provide Example 15-35. The Suzuki coupling was carried out using the standard conditions already described with the Boykin catalyst.

Scheme 15-C

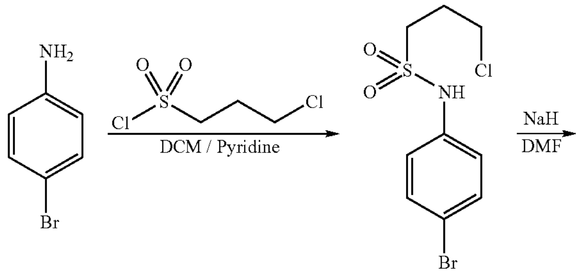

15-C-1

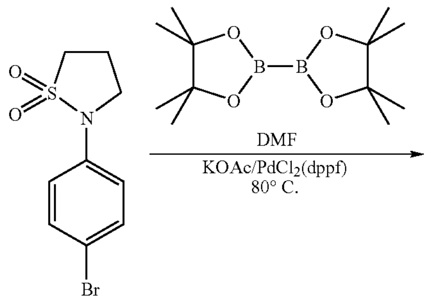

15-C-2

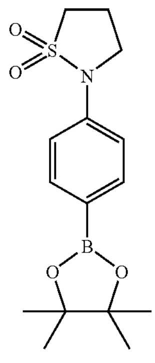

15-C-3

3-Chloropropylsulfonyl chloride (1.200 g, 0.00678 mol) was added dropwise to a stirred solution of p-bromoaniline (1.032 g 0.00600 mol) and pyridine (5 ml) in dichloromethane (90 ml) at 0° C. under nitrogen. The mixture was allowed to warm to rt and stirred overnight. The resultant mixture was concentrated and extracted with $Et_2O$/aqueous sodium dihydrogen phosphate (pH=3-4) solution. The organic solution was then washed twice with saturated sodium bicarbonate solution, twice with brine, then dried with $MgSO_4$ and concentrated to afford crude 15-C-1 (1.630 g 87%).

Crude 15-C-1 (1.630 g, 0.0052 mol) was dissolved in 10 ml DMF. The resultant solution was added dropwise to a stirred mixture of NaH 60% dispersion in mineral oil (0.480 g, 0.0104 mol) and DMF (30 ml) at 0° C. The reaction mixture was allowed to warm up to rt and stirred overnight. Upon completion, the reaction was quenched with saturated $NH_4Cl$ aqueous solution and extracted twice with diethyl ether. The resultant ethereal solution was washed twice with an aqueous sodium dihydrogen phosphate (pH=3-4) solution, then twice with a saturated $NaHCO_3$ aqueous solution, then twice with brine. The organic solution was dried over $MgSO_4$ and concentrated to afford crude 15-C-2 (1.295 g, 90%).

Crude 15-C-2 (0.156 g, 0.566 mmol), potassium acetate (0.167 g, 1.698 mmol), bis(pinacolato)diboron (0.144 g, 0.509 mmol), and $PdCl_2$(dppf) (0.046 g, 0.0566 mmol) were added to a round bottom flask. Dry DMF (10 ml) was then added and the flask was flushed with nitrogen. The resultant mixture was stirred and placed into an 80° C. oil bath. The reaction was followed by LCMS. Upon consumption of starting material (1-2 hr), the reaction mixture was diluted with ethyl acetate, washed twice with water and twice with brine. The resultant organic solution was then dried over $MgSO_4$ and concentrated to afford the crude boronate ester 15-c-3, which was used directly for the next step without further purification. The Suzuki coupling was carried out using the standard conditions already described with the Boykin catalyst. See example 15-36 as product.

Scheme 15-D

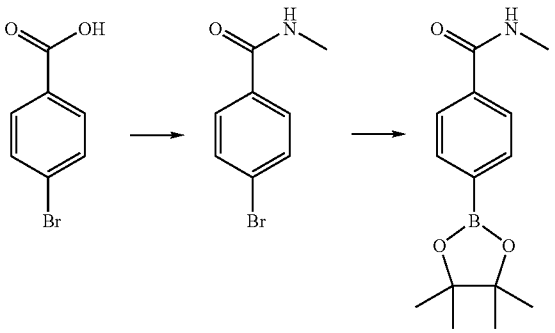

15-D-1 15-D-2

To a solution of 4-bromobenzoic acid (402.0 mg, 2 mmol) in DMF (10 mL), was added HATU (836.5 mg, 2.2 mmol) and DIEA (697.0 μL, 4 mmol). After stirring for 5 minutes at room temperature, methylamine hydrochloride salt (135.0 mg, 2 mmol) was added. The solution was stirred at rt overnight. The reaction mixture was diluted with water and extracted two times with ethyl acetate. The combined extract was washed with saturated sodium bicarbonate, 1M HCl and brine, dried over magnesium sulfate, filtered and concentrated to dryness to provide 15-D-1 (181.1 mg, 42.0%) as white crystals.

A solution of 15-D-1 (107.0 mg, 0.5 mmol), bis(pinacolato)diboron (139.7 mg, 0.55 mmol) and potassium acetate (245.4 mg, 2.5 mmol) in 2.5 mL DMF, was purged with nitrogen gas, then $PdCl_2$(dppf) (11.0 mg, 0.015 mmol) was added. The solution was heated at 80° C. for two hr, then cooled to rt. The reaction was quenched with water, then extracted twice with ethyl acetate. The organic solution was washed with water, then with saturated sodium bicarbonate, then with brine. The organic solution was then dried over magnesium sulfate, filtered and concentrated to dryness to provide boronate ester 15-D-2 (91.1 mg, 61.0%). The final compound, example 15-14, was prepared from the boronate ester 15-D-2 using the representative Suzuki coupling conditions and the Boykin catalyst.

Scheme 15-E

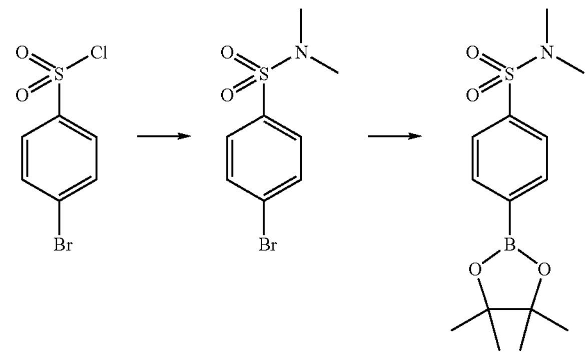

15-E-1 15-E-2

4-Bromophenylsulfonyl chloride (3.33 g, 13.0 mmol, 1.0 eq.) and dimethylamine hydrochloride (1.58 g, 19.4 mmol, 1.49 eq.) were weighed into a flask. THF (25 mL) was added, followed by DIEA (5.2 mL, 29.9 mmol, 2.3 eq.). The reaction was stirred hard at rt for 5.5 h, then diluted with diethyl ether, washed with 1N hydrochloric acid, then with saturated sodium bicarbonate solution. The resulting solution was dried over magnesium sulfate, filtered and concentrated to provide the crude product. The crude material was purified by recrystallization from methylene chloride:hexanes to provide the sulfonamide 15-E-1 (1.1788 g, 34%).

The N,N-dimethyl-4-bromophenyl sulfonamide above (0.486 g, 1.84 mmol, 1.0 eq.), the bis(pinacolato)diboron (538.5 mg, 2.12 mmol, 1.15 eq.), potassium acetate (881.2 mg, 8.98 mmol, 4.88 eq.), and the $PdCl_2$(dppf) (11.0 mg, 0.015 mmol) were weighed into a 20 mL scintillation vial. DMF (6 mL) was added, the vial was flushed with nitrogen, capped, and placed to stir in an 80 deg C. aluminum block. After 2 hr, the reaction was cooled to rt, diluted with diethyl ether, and washed with water. The organic solution was dried over magnesium sulfate, filtered, and concentrated. The crude product was purified by flash chromatography over silica gel (20% ethyl acetate/hexanes) to provide the desired boronate ester 15-E-2 (256.2 mg, 45%), which was used in preparation of example 15-2 describe in below.

Example 15

2'-[4-Cyclohexylamino-8-(3-isopropoxy-benzyl)-2-oxo-1,3,8-triaza-spiro[4.5]dec-3-en-1-yl]-4'-fluoro-biphenyl-4-sulfonic acid dimethylamide (15-2)

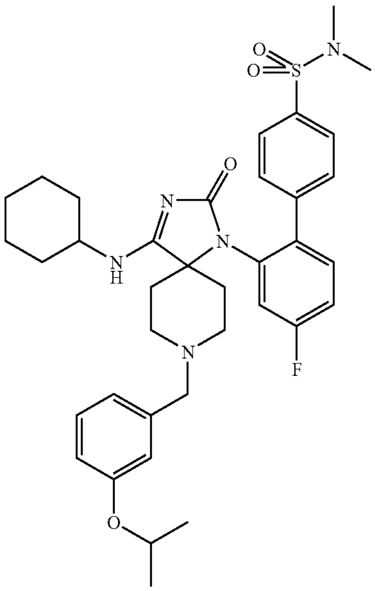

Step 1:

Step 2: 2'-[4-Cyclohexylamino-8-(3-isopropoxy-benzyl)-2-oxo-1,3,8-triaza-spiro[4.5]dec-3-en-1-yl]-4'-fluoro-biphenyl-4-sulfonic acid dimethylamide (15-2)

The bromide (15-1, prepared in a manner similar to that described for Example 14) (60.4 mg, 0.106 mmol, 1.0 eq.), the boronic acid (51.8 mg, 0.166 mmol, 1.57 eq.), the palladium catalyst (26.7 mg, 0.045 mmol, 0.43 eq. For catalyst preparation, see Boykin et. al, *J. Org. Chem.* 2004, 69, 13, 4330-4335), and the tribasic potassium phosphate (70.6 mg, 0.333 mmol, 3.1 eq.) were weighed into a I dram vial. A magnetic stir bar was added, followed by absolute ethanol (1 mL). The vial was capped, and placed to stir in a 90° C. aluminum block over a hot plate. When the reaction showed black palladium precipitate (approximately 3 hr), the reaction was cooled to rt. The reaction was then filtered through celite, and the resulting solution was purified directly by reverse phase HPLC in acetonitrile: water with 0.1% TFA, to provide the desired diaryl product as the TFA salt. $^1$H NMR (400 MHz, MeOH-d4): δ 7.83 (d, J=8.3 Hz, 2H), 7.59 (m, 2H), 7.33 (m, 4H), 7.11 (br s, 1H), 6.84 (m, 2H), 4.75-4.50 (m, 1H), 4.14 (s, 2H), 2.68 (s, 6H), 2.50-2.00 (m, 2H), 2.00-1.60 (m, 6H), 1.50-1.20 (m, 10H). EI-MS m/z: 676 $(M+H)^+$.

TABLE 7

| The compounds (or salts thereof) in table 7 were prepared in a manner similar to that described for Schemes 14 and 15. | | | |
|---|---|---|---|
| Example # | Structure | Chemical Name | Mass Spec |
| 15-3 | 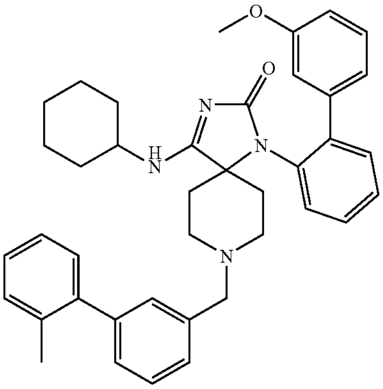 | 4-Cyclohexylamino-1-(3'-methoxy-biphenyl-2-yl)-8-(2'-methyl-biphenyl-3-ylmethyl)-2-oxo-1,3-diaza-8-azonia-spiro[4.5]dec-3-ene | 613.3 |
| 15-4 | 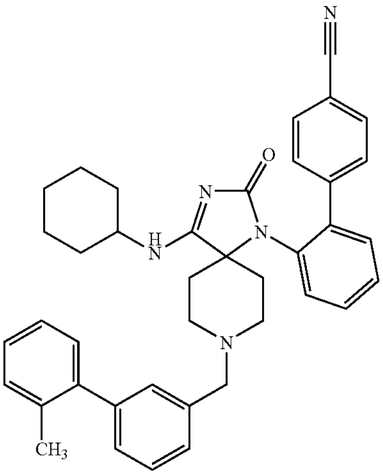 | 1-(4'-Cyano-biphenyl-2-yl)-4-cyclohexylamino-8-(2'-methyl-biphenyl-3-ylmethyl)-2-oxo-1,3-diaza-8-azonia-spiro[4.5]dec-3-ene | 608.35 |
| 15-5 | 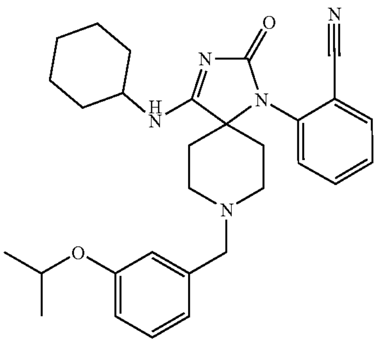 | 1-(2-Cyano-phenyl)-4-cyclohexylamino-8-(3-isopropoxy-benzyl)-2-oxo-1,3-diaza-8-azonia-spiro[4.5]dec-3-ene | 500.1 |

TABLE 7-continued

The compounds (or salts thereof) in table 7 were prepared in a manner similar to that described for Schemes 14 and 15.

| Example # | Structure | Chemical Name | Mass Spec |
|---|---|---|---|
| 15-6 | 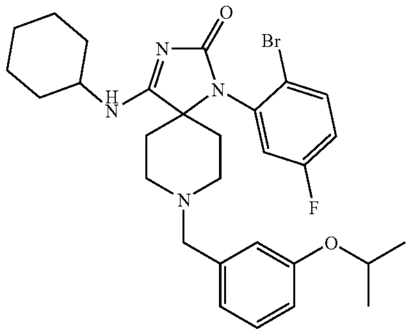 | 1-(2-Bromo-5-fluoro-phenyl)-4-cyclohexylamino-8-(3-isopropoxy-benzyl)-2-oxo-1,3-diaza-8-azonia-spiro[4.5]dec-3-ene | 573.15 |
| 15-7 | 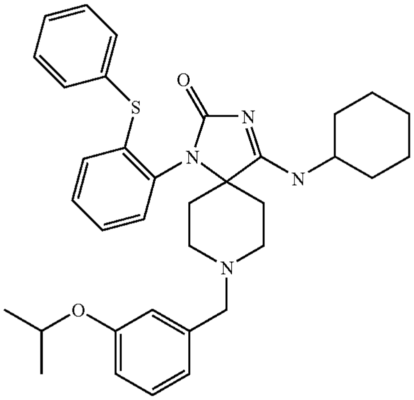 | 4-Cyclohexylamino-8-(3-isopropoxy-benzyl)-2-oxo-1-(2-phenylsulfanyl-phenyl)-1,3-diaza-8-azonia-spiro[4.5]dec-3-ene | 583.35 |
| 15-8 | 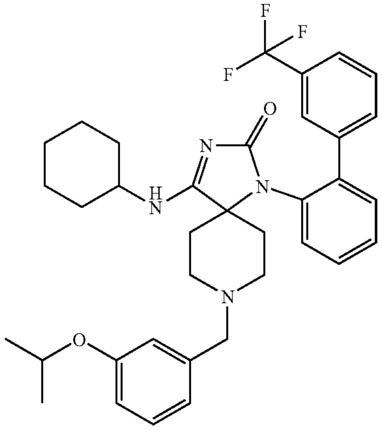 | 4-Cyclohexylamino-8-(3-isopropoxy-benzyl)-2-oxo-1-(3'-trifluoromethyl-biphenyl-2-yl)-1,3-diaza-8-azonia-spiro[4.5]dec-3-ene | 619.35 |

TABLE 7-continued

The compounds (or salts thereof) in table 7 were prepared in a manner similar to that described for Schemes 14 and 15.

| Example # | Structure | Chemical Name | Mass Spec |
|---|---|---|---|
| 15-9 | 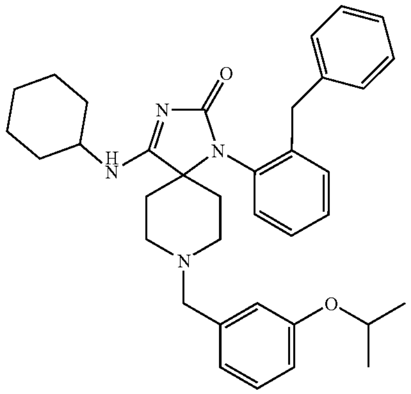 | 1-(2-Benzyl-phenyl)-4-cyclohexylamino-8-(3-isopropoxy-benzyl)-2-oxo-1,3-diaza-8-azonia-spiro[4.5]dec-3-ene | 565.35 |
| 15-10 | 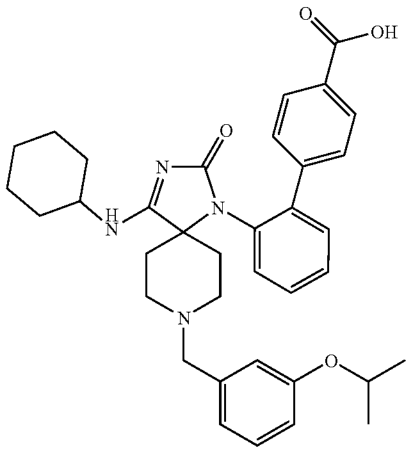 | 1-(4'-Carboxy-biphenyl-2-yl)-4-cyclohexylamino-8-(3-isopropoxy-benzyl)-2-oxo-1,3-diaza-8-azonia-spiro[4.5]dec-3-ene | 595.35 |
| 15-11 | 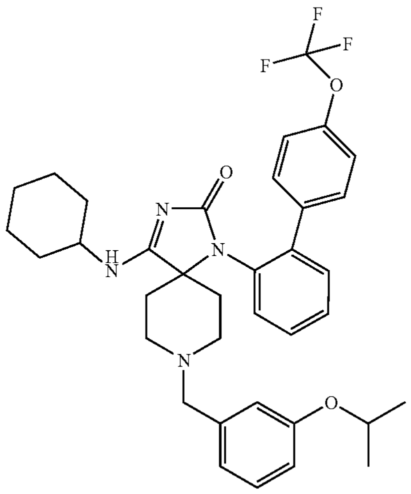 | 4-Cyclohexylamino-8-(3-isopropoxy-benzyl)-2-oxo-1-(4'-trifluoromethoxy-biphenyl-2-yl)-1,3-diaza-8-azonia-spiro[4.5]dec-3-ene | 635.25 |

TABLE 7-continued

The compounds (or salts thereof) in table 7 were prepared in a manner similar to that described for Schemes 14 and 15.

| Example # | Structure | Chemical Name | Mass Spec |
|---|---|---|---|
| 15-12 | 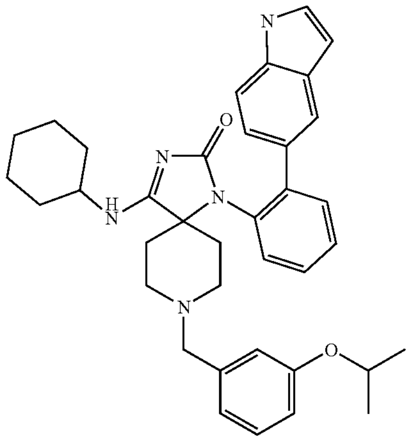 | 4-Cyclohexylamino-1-[2-(1H-indol-5-yl)-phenyl]-8-(3-isopropoxy-benzyl)-2-oxo-1,3-diaza-8-azonia-spiro[4.5]dec-3-ene | 590.4 |
| 15-13 | 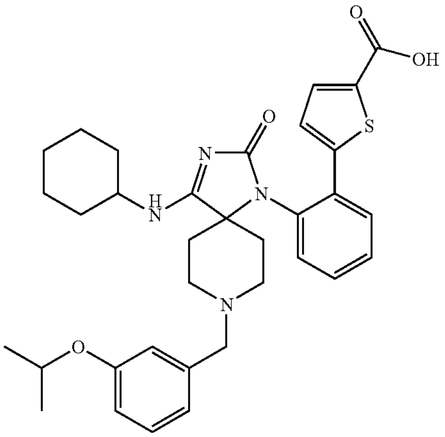 | 1-[2-(5-Carboxy-thiophen-2-yl)-phenyl]-4-cyclohexylamino-8-(3-isopropoxy-benzyl)-2-oxo-1,3-diaza-8-azonia-spiro[4.5]dec-3-ene | 601.3 |
| 15-14 | 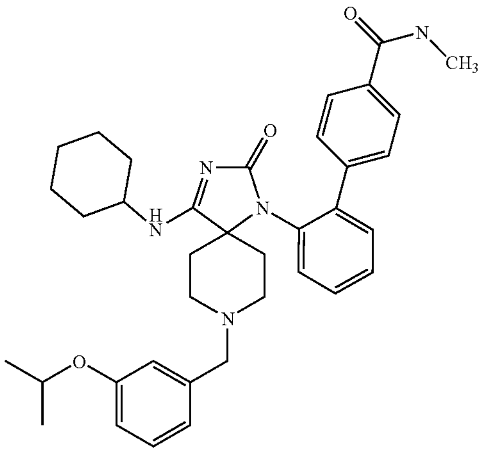 | 4-Cyclohexylamino-8-(3-isopropoxy-benzyl)-1-(4'-methylcarbamoyl-biphenyl-2-yl)-2-oxo-1,3-diaza-8-azonia-spiro[4.5]dec-3-ene | 608.35 |

TABLE 7-continued

| The compounds (or salts thereof) in table 7 were prepared in a manner similar to that described for Schemes 14 and 15. | | | |
|---|---|---|---|
| Example # | Structure | Chemical Name | Mass Spec |
| 15-15 | 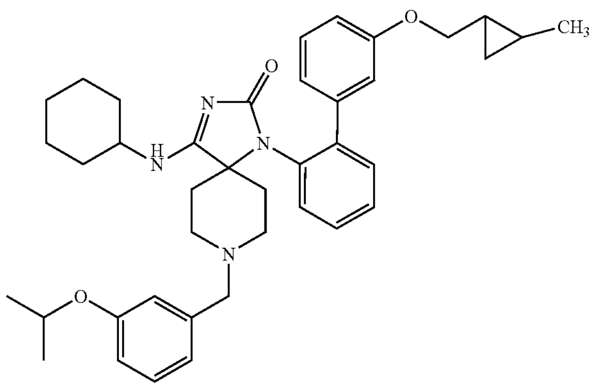 | 4-Cyclohexylamino-8-(3-isopropoxy-benzyl)-1-[3'-(2-methyl-cyclopropylmethoxy)-biphenyl-2-yl]-1,3,8-triaza-spiro[4.5]dec-3-en-2-one | 635.4 |
| 15-16 | 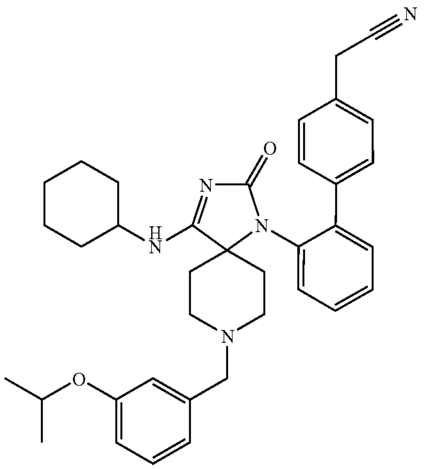 | 1-(4'-Cyanomethyl-biphenyl-2-yl)-4-cyclohexylamino-8-(3-isopropoxy-benzyl)-2-oxo-1,3-diaza-8-azonia-spiro[4.5]dec-3-ene | 590.25 |
| 15-17 | 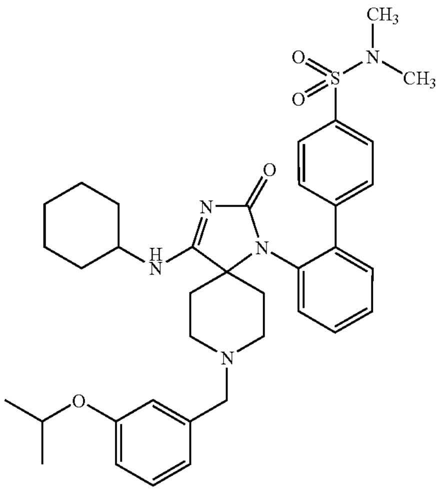 | 4-Cyclohexylamino-1-(4'-dimethylsulfamoyl-biphenyl-2-yl)-8-(3-isopropoxy-benzyl)-2-oxo-1,3-diaza-8-azonia-spiro[4.5]dec-3-ene | 658.35 |

TABLE 7-continued

The compounds (or salts thereof) in table 7 were prepared in a manner similar to that described for Schemes 14 and 15.

| Example # | Structure | Chemical Name | Mass Spec |
|---|---|---|---|
| 15-18 | 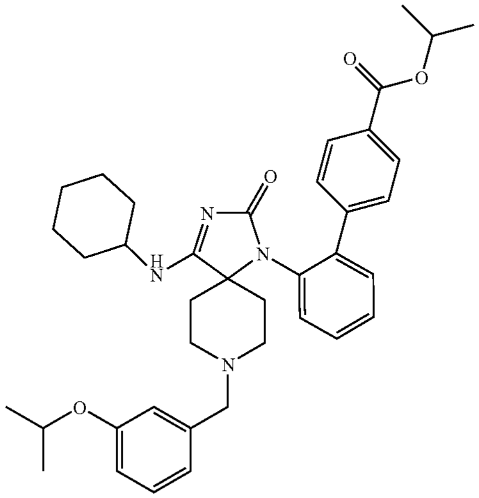 | 4-Cyclohexylamino-8-(3-isopropoxy-benzyl)-1-(4'-isopropoxycarbonyl-biphenyl-2-yl)-2-oxo-1,3-diaza-8-azonia-spiro[4.5]dec-3-ene | 637.35 |
| 15-19 | 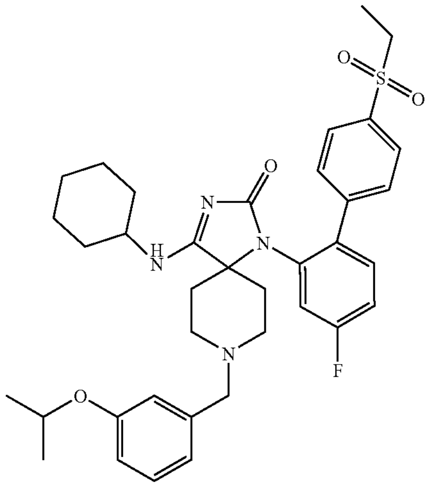 | 4-Cyclohexylamino-1-(4'-ethanesulfonyl-4-fluoro-biphenyl-2-yl)-8-(3-isopropoxy-benzyl)-2-oxo-1,3-diaza-8-azonia-spiro[4.5]dec-3-ene | 661.35 |
| 15-20 | 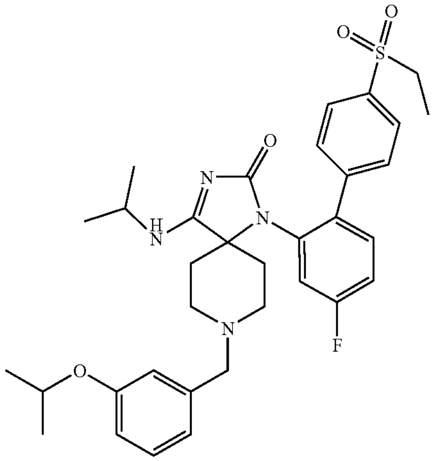 | 1-(4'-Ethanesulfonyl-4-fluoro-biphenyl-2-yl)-8-(3-isopropoxy-benzyl)-4-isopropylamino-2-oxo-1,3-diaza-8-azonia-spiro[4.5]dec-3-ene | 621.3 |

TABLE 7-continued

| The compounds (or salts thereof) in table 7 were prepared in a manner similar to that described for Schemes 14 and 15. | | | |
|---|---|---|---|
| Example # | Structure | Chemical Name | Mass Spec |
| 15-21 | 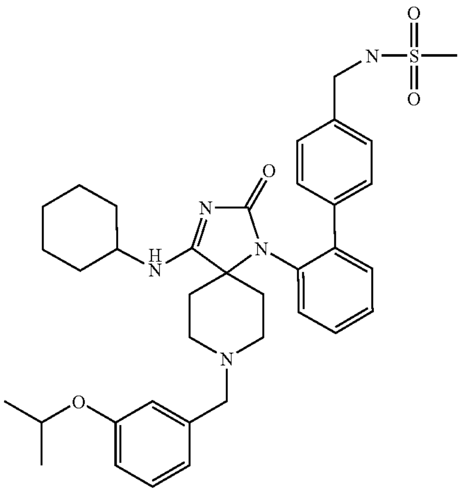 | 4-Cyclohexylamino-8-(3-isopropoxy-benzyl)-1-[4'-(methanesulfonylamino-methyl)-biphenyl-2-yl]-2-oxo-1,3-diaza-8-azonia-spiro[4.5]dec-3-ene | 658.35 |
| 15-22 | 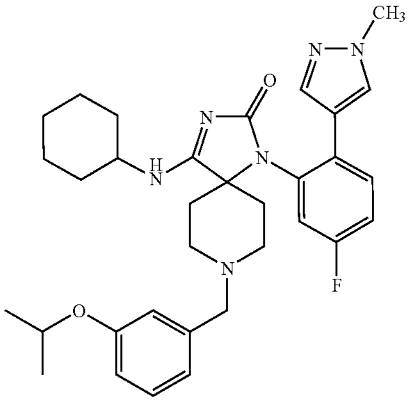 | 4-Cyclohexylamino-1-[5-fluoro-2-(1-methyl-1H-pyrazol-4-yl)-phenyl]-8-(3-isopropoxy-benzyl)-1,3,8-triaza-spiro[4.5]dec-3-en-2-one | 573.3 |
| 15-23 | 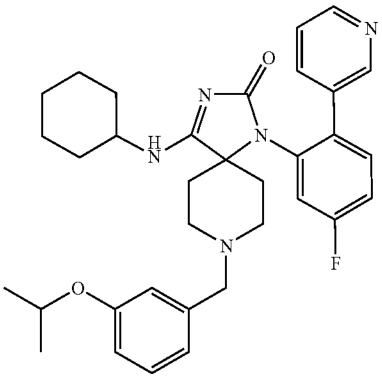 | 4-Cyclohexylamino-1-(5-fluoro-2-pyridin-3-yl-phenyl)-8-(3-isopropoxy-benzyl)-2-oxo-1,3-diaza-8-azonia-spiro[4.5]dec-3-ene | 570.3 |

TABLE 7-continued

| The compounds (or salts thereof) in table 7 were prepared in a manner similar to that described for Schemes 14 and 15. | | | |
|---|---|---|---|
| Example # | Structure | Chemical Name | Mass Spec |
| 15-24 | 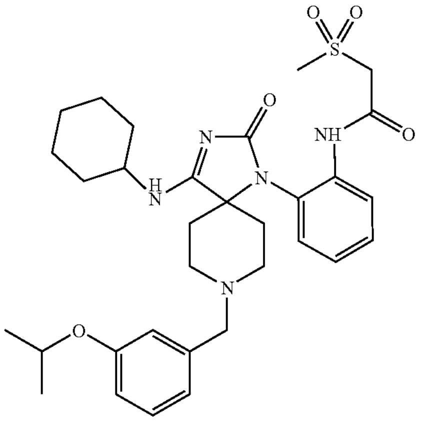 | 4-Cyclohexylamino-8-(3-isopropoxy-benzyl)-1-[2-(2-methanesulfonyl-acetylamino)-phenyl]-2-oxo-1,3-diaza-8-azonia-spiro[4.5]dec-3-ene | 610.3 |
| 15-25 | 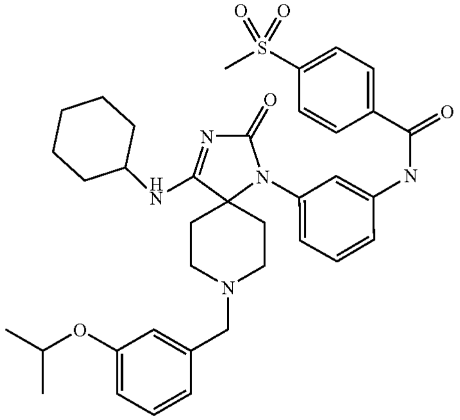 | 4-Cyclohexylamino-8-(3-isopropoxy-benzyl)-1-[3-(4-methanesulfonyl-benzoylamino)-phenyl]-2-oxo-1,3-diaza-8-azonia-spiro[4.5]dec-3-ene | 672.3 |
| 15-26 | 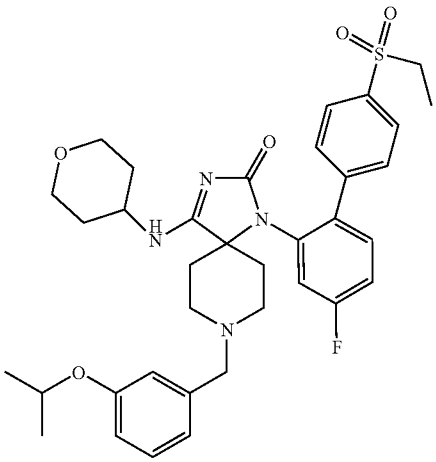 | 1-(4'-Ethanesulfonyl-4-fluoro-biphenyl-2-yl)-8-(3-isopropoxy-benzyl)-2-oxo-4-(tetrahydro-pyran-4-ylamino)-1,3-diaza-8-azonia-spiro[4.5]dec-3-ene | 663.3 |

TABLE 7-continued

The compounds (or salts thereof) in table 7 were prepared in a manner similar to that described for Schemes 14 and 15.

| Example # | Structure | Chemical Name | Mass Spec |
|---|---|---|---|
| 15-27 | 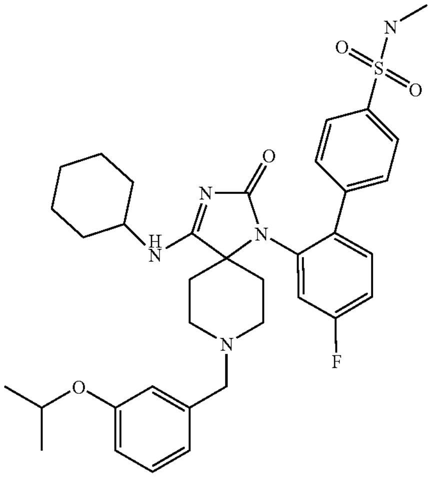 | 4-Cyclohexylamino-1-(4-fluoro-4'-methylsulfamoyl-biphenyl-2-yl)-8-(3-isopropoxy-benzyl)-2-oxo-1,3-diaza-8-azonia-spiro[4.5]dec-3-ene | 662.25 |
| 15-28 | 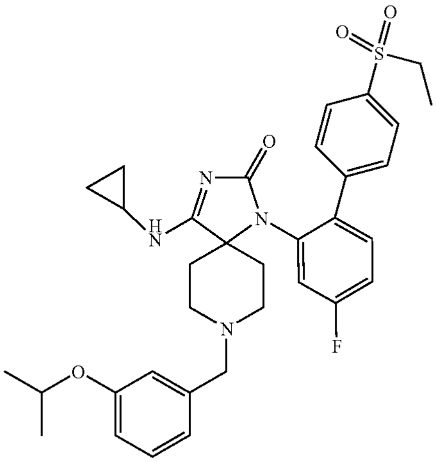 | 4-Cyclopropylamino-1-(4'-ethanesulfonyl-4-fluoro-biphenyl-2-yl)-8-(3-isopropoxy-benzyl)-2-oxo-1,3-diaza-8-azonia-spiro[4.5]dec-3-ene | 619.2 |
| 15-29 | 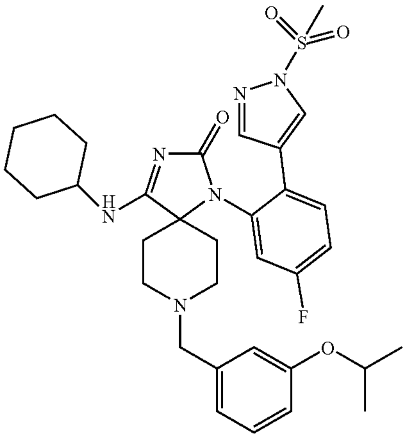 | 4-Cyclohexylamino-1-[5-fluoro-2-(1-methanesulfonyl-1H-pyrazol-4-yl)-phenyl]-8-(3-isopropoxy-benzyl)-2-oxo-1,3-diaza-8-azonia-spiro[4.5]dec-3-ene | 637.3 |

TABLE 7-continued

| The compounds (or salts thereof) in table 7 were prepared in a manner similar to that described for Schemes 14 and 15. | | | |
|---|---|---|---|
| Example # | Structure | Chemical Name | Mass Spec |
| 15-30 | 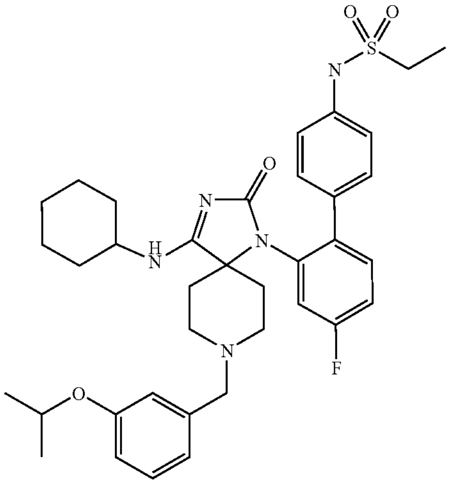 | Ethanesulfonic acid {2'-[4-cyclohexylamino-8-(3-isopropoxy-benzyl)-2-oxo-1,3,8-triaza-spiro[4.5]dec-3-en-1-yl]-4'-fluoro-biphenyl-4-yl}-amide | 676.35 |
| 15-31 | 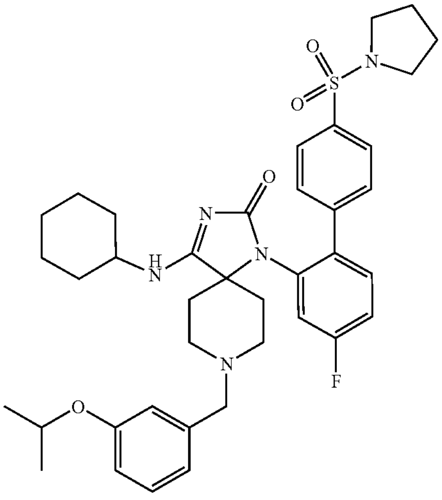 | 4-Cyclohexylamino-1-[4-fluoro-4'-(pyrrolidine-1-sulfonyl)-biphenyl-2-yl]-8-(3-isopropoxy-benzyl)-2-oxo-1,3-diaza-8-azonia-spiro[4.5]dec-3-ene | 702.3 |
| 15-32 | 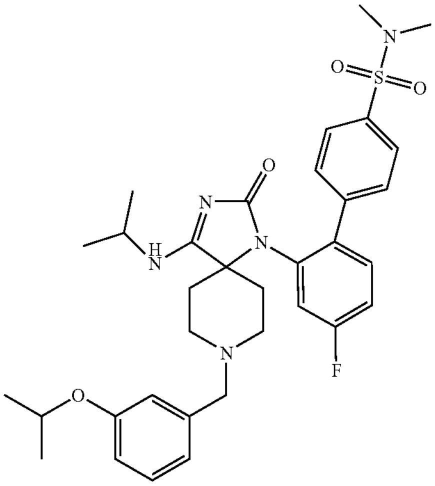 | 1-(4'-Dimethylsulfamoyl-4-fluoro-biphenyl-2-yl)-8-(3-isopropoxy-benzyl)-4-isopropylamino-2-oxo-1,3-diaza-8-azonia-spiro[4.5]dec-3-ene | 636.3 |

TABLE 7-continued

| The compounds (or salts thereof) in table 7 were prepared in a manner similar to that described for Schemes 14 and 15. | | | |
|---|---|---|---|
| Example # | Structure | Chemical Name | Mass Spec |
| 15-33 | 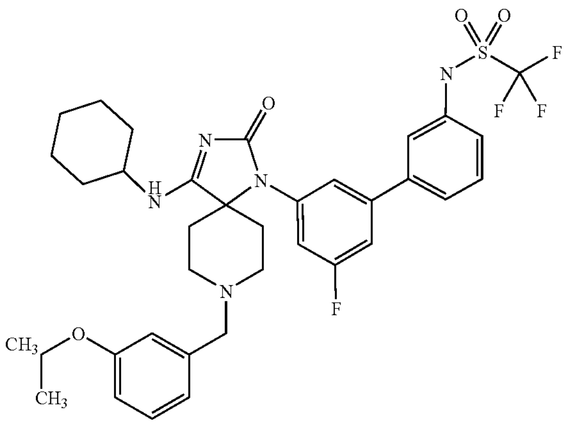 | 4-Cyclohexylamino-1-(5-fluoro-3'-trifluoromethanesulfonylamino-biphenyl-3-yl)-8-(3-isopropoxy-benzyl)-2-oxo-1,3-diaza-8-azonia-spiro[4.5]dec-3-ene | 716.3 |
| 15-34 | 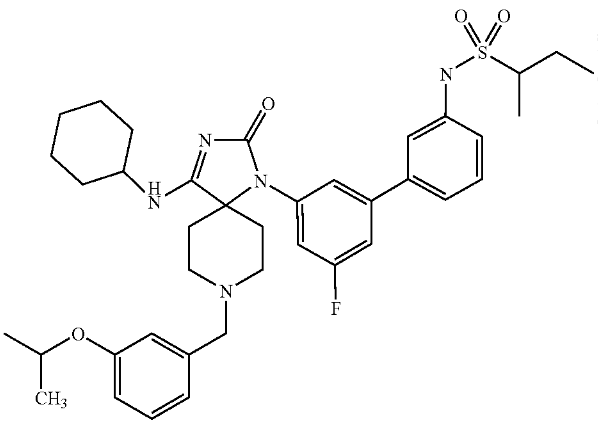 | 1-[3'-(Butane-2-sulfonylamino)-5-fluoro-biphenyl-3-yl]-4-cyclohexylamino-8-(3-isopropoxy-benzyl)-2-oxo-1,3-diaza-8-azonia-spiro[4.5]dec-3-ene | 704.3 |
| 15-35 | 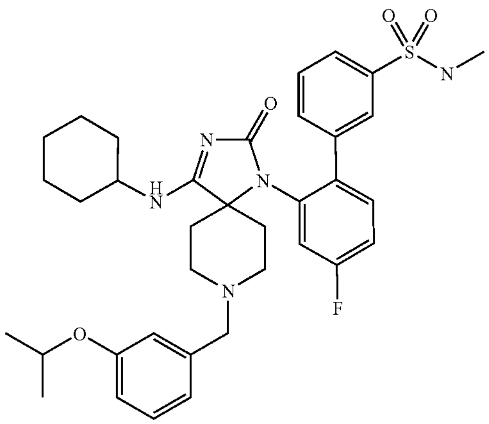 | 2'-[4-Cyclohexylamino-8-(3-isopropoxy-benzyl)-2-oxo-1,3,8-triaza-spiro[4.5]dec-3-en-1-yl]-4'-fluoro-biphenyl-3-sulfonic acid methylamide | 662.25 |

TABLE 7-continued

The compounds (or salts thereof) in table 7 were prepared in a manner similar to that described for Schemes 14 and 15.

| Example # | Structure | Chemical Name | Mass Spec |
|---|---|---|---|
| 15-36 | 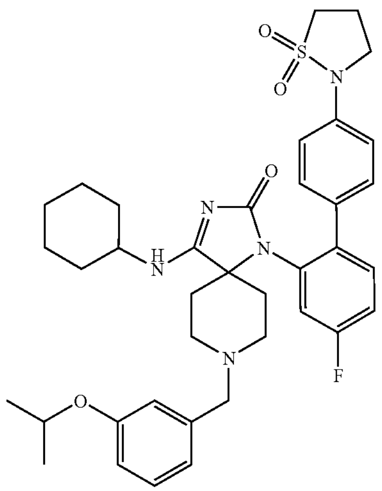 | 4-Cyclohexylamino-1-[4'-(1,1-dioxo-1,6-isothiazolidin-2-yl)-4-fluoro-biphenyl-2-yl]-8-(3-isopropoxy-benzyl)-1,3,8-triaza-spiro[4.5]dec-3-en-2-one | 688.3 |
| 15-37 | 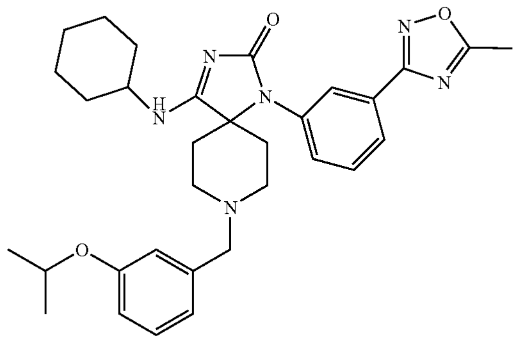 | 4-Cyclohexylamino-8-(3-isopropoxy-benzyl)-1-[3-(5-methyl-[1,2,4]oxadiazol-3-yl)-phenyl]-2-oxo-1,3-diaza-8-azonia-spiro[4.5]dec-3-ene | 577.25 |
| 15-38 | 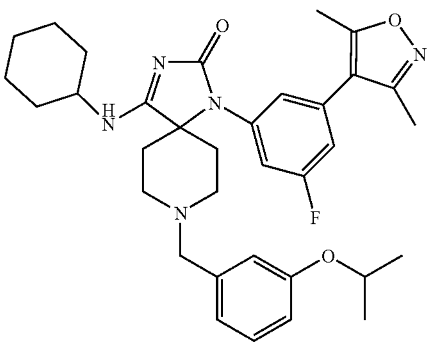 | 4-Cyclohexylamino-1-[3-(3,5-dimethyl-isoxazol-4-yl)-5-fluoro-phenyl]-8-(3-isopropoxy-benzyl)-2-oxo-1,3-diaza-8-azonia-spiro[4.5]dec-3-ene | 588.35 |

TABLE 7-continued

The compounds (or salts thereof) in table 7 were prepared in a manner similar to that described for Schemes 14 and 15.

| Example # | Structure | Chemical Name | Mass Spec |
|---|---|---|---|
| 15-39 | 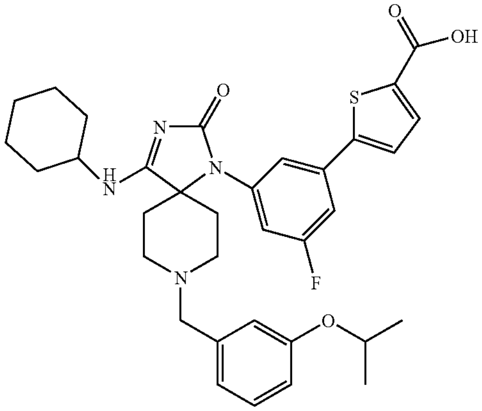 | 1-[3-(5 -Carboxy-thiophen-2-yl)-5-fluoro-phenyl]-4-cyclohexylamino-8-(3-isopropoxy-benzyl)-2-oxo-1,3-diaza-8-azonia-spiro[4.5]dec-3-ene | 619.3 |
| 15-40 | 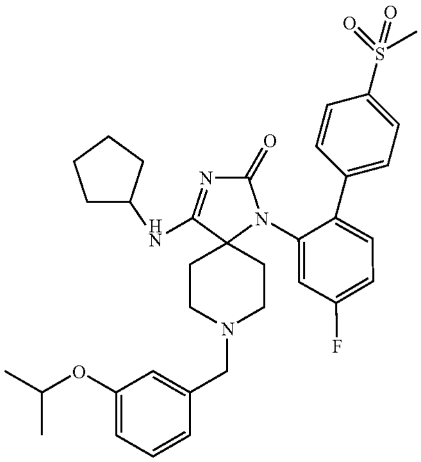 | 4-Cyclopentylamino-1-(4-fluoro-4'-methanesulfonyl-biphenyl-2-yl)-8-(3-isopropoxy-benzyl)-2-oxo-1,3-diaza-8-azonia-spiro[4.5]dec-3-ene | 633.3 |
| 15-41 | 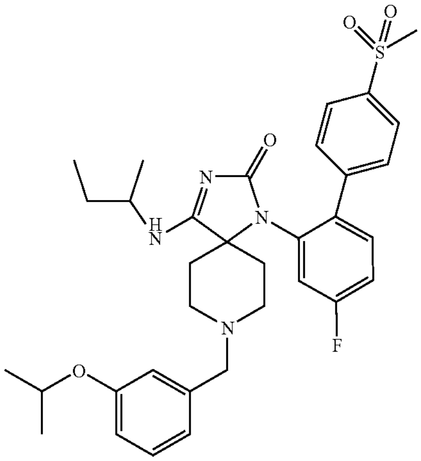 | 4-sec-Butylamino-1-(4-fluoro-4'-methanesulfonyl-biphenyl-2-yl)-8-(3-isopropoxy-benzyl)-2-oxo-1,3-diaza-8-azonia-spiro[4.5]dec-3-ene | 621.3 |

TABLE 7-continued

| The compounds (or salts thereof) in table 7 were prepared in a manner similar to that described for Schemes 14 and 15. | | | |
|---|---|---|---|
| Example # | Structure | Chemical Name | Mass Spec |
| 15-42 | 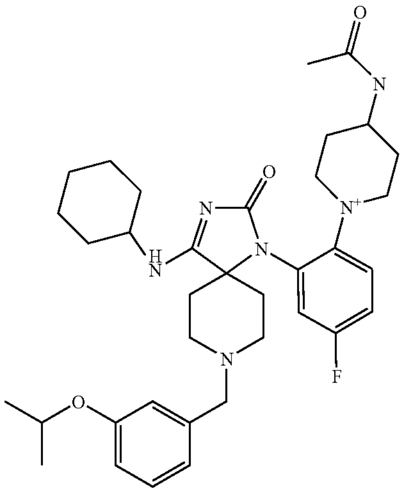 | 1-[2-(4-Acetylamino-piperidin-1-yl)-5-fluoro-phenyl]-4-cyclohexylamino-8-(3-isopropoxy-benzyl)-2-oxo-1,3-diaza-8-azonia-spiro[4.5]dec-3-ene | 633.3 |
| 15-43 | 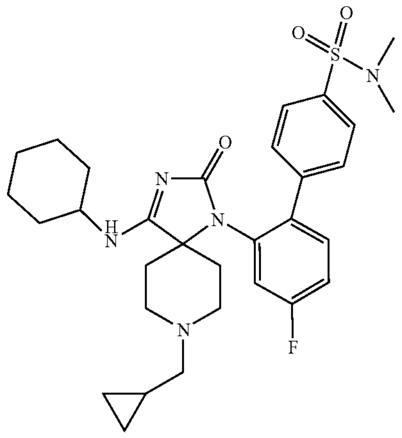 | 4-Cyclohexylamino-8-cyclopropylmethyl-1-(4'-dimethylsulfamoyl-4-fluoro-biphenyl-2-yl)-2-oxo-1,3-diaza-8-azonia-spiro[4.5]dec-3-ene | 582.3 |
| 15-44 | 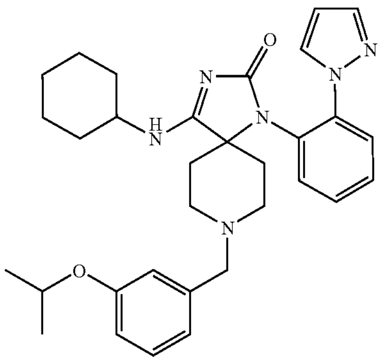 | 4-Cyclohexylamino-8-(3-isopropoxy-benzyl)-1-(2-pyrazol-1-yl-phenyl)-1,3,8-triaza-spiro[4.5]dec-3-en-2-one | 541.35 |

TABLE 7-continued

The compounds (or salts thereof) in table 7 were prepared in a manner similar to that described for Schemes 14 and 15.

| Example # | Structure | Chemical Name | Mass Spec |
| --- | --- | --- | --- |
| 15-45 | 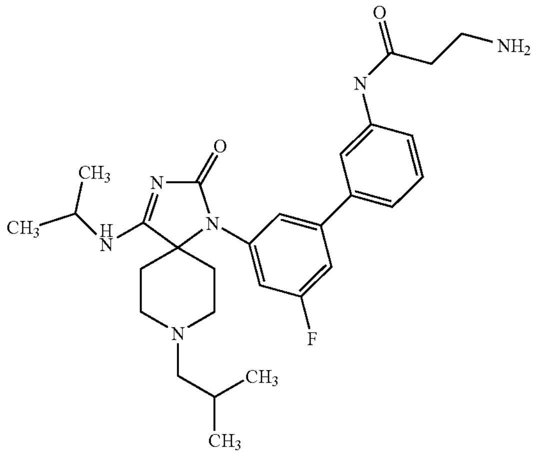 | 1-[3'-(3-Amino-propionylamino)-5-fluoro-biphenyl-3-yl]-8-isobutyl-4-isopropylamino-2-oxo-1,3-diaza-8-azonia-spiro[4.5]dec-3-ene hydrochloride | 523.3 |

Example 15-46

4-Cyclohexylamino-8-cyclopropylmethyl-1-(4'-dimethylsulfamoyl-4-fluoro-biphenyl-2-yl)-2-oxo-1,3-diaza-8-azonia-spiro[4.5]dec-3-ene trifluoroacetate

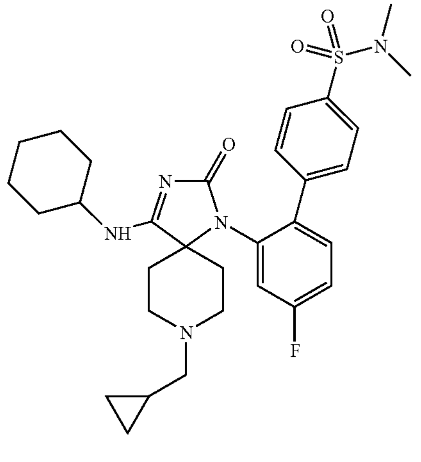

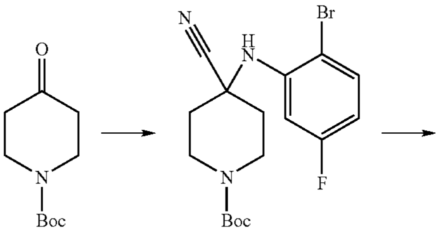

-continued

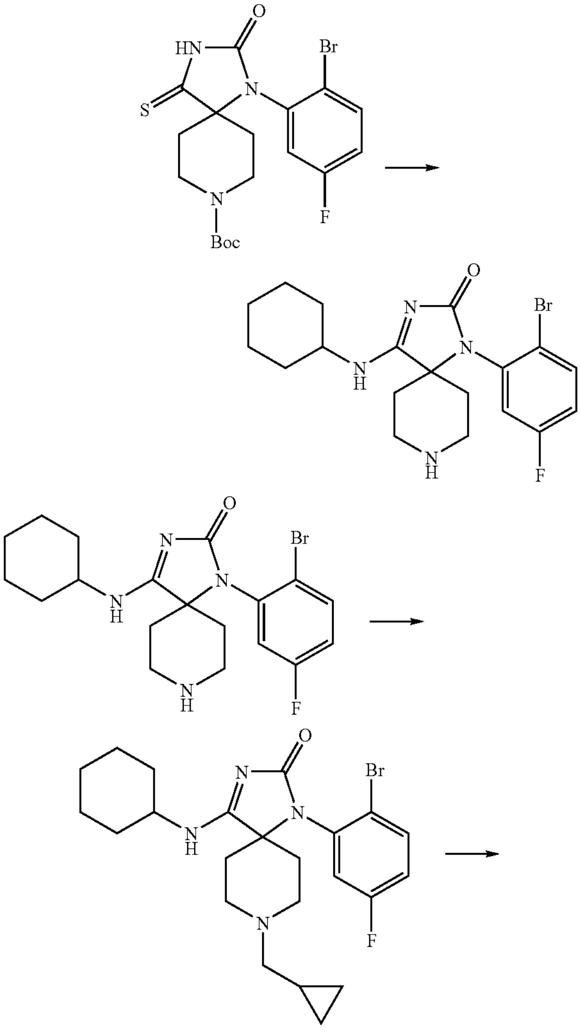

-continued

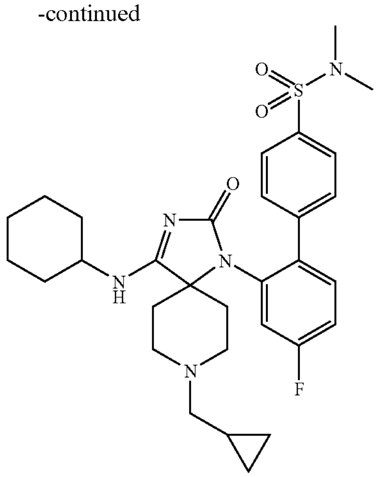

The N-(t-butyloxycarbonyl)-4-piperidone (10.13 g, 50.8 mmol, 1.0 eq) and the 2-bromo-5-fluoroaniline (11.60 g, 61.0 mmol, 1.2 eq.) were weighed into a flask. Acetic acid (75 mL) was added, followed by trimethylsilyl cyanide (7.75 mL, 58.1 mmol, 1.14 eq.). The mixture was stirred at rt for 24 hr, and was then added to a mixture of 200 mL ice and 200 mL saturated ammonium hydroxide solution. The resulting mixture was extracted twice with methylene chloride, and the organic solution was dried over magnesium sulfate, filtered, and concentrated to provide 22.57 g of crude product. This amino nitrile was converted to the thiohydantoin via the standard procedure already described.

Crude thiol from the standard thiolation conditions (8.47 g, 17.5 mmol, 1.0 eq.) and cyclohexylamine (8.0 mL, 70 mmol, 4.0 eq.) were dissolved into DMSO (32 mL). The solution was stirred and heated to 115° C. in an oil bath for 24 hr, then cooled to rt. The resulting solution was diluted with diethyl ether, and washed with 1 N hydrochloric acid, then dried over magnesium sulfate, filtered and concentrated. The crude aminohydantoin was purified by filtration through a 600 mL silica plug in 2 L fritted funnel, using 70% ethyl acetate in hexanes, followed by 100% ethyl acetate, as the elution solvents. This procedure yielded (2.0971 g, 23%) of the desired product as a dark green semi-solid.

A portion of the aminohydantoin (528.6 mg) was dissolved into dioxane (4 mL). A 4N solution of hydrogen chloride in dioxane (5 mL) was added, and the reaction was left to sit for 3 hr, then concentrated. The crude product was treated with dichloromethane, and washed with saturated sodium bicarbonate solution. The organic solution was dried over magnesium sulfate, filtered and concentrated. The crude free base was then purified by flash chromatography over silica gel using 5% of 2N ammonia(methanol): 95% dichloromethane to provide the desired, deprotected piperidine (241 mg, 56%).

To the deprotected piperidine (127.0 mg, 0.3 mmol) in DMF (3 mL) was added potassium carbonate (45.6 mg, 0.33 mmol), followed by cyclopropane methyl bromide (32.3 μL, 0.33 mmol). The solution was heated at 80° C. for 15 hours, cooled to rt and then quenched with water. The product was extracted three times with ethyl acetate, washed with water, then with aqueous 1M HCl, and then with brine. The organic solution was dried over magnesium sulfate, filtered, and concentrated to dryness. The product was purified using prep-TLC (elution with 1% methanol/99% ethyl acetate) to provide the cyclopropylmethyl piperidine aryl bromide (52.6 mg, 36.8%).

The final compound example 15-43 MS (MH+) 582.3 was prepared from the above aryl bromide via the standard Suzuki coupling conditions already described, using the Boykin catalyst.

Example 15-47

4-Cyclohexylamino-8-(3-isopropoxy-benzyl)-1-[3-(5-methyl-[1,2,4]oxadiazol-3-yl)-phenyl]-2-oxo-1,3-diaza-8-azonia-spiro[4.5]dec-3-ene trifluoroacetate

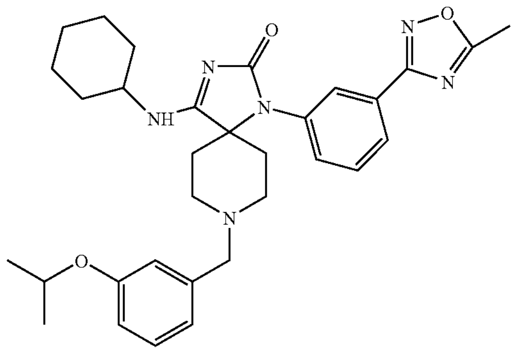

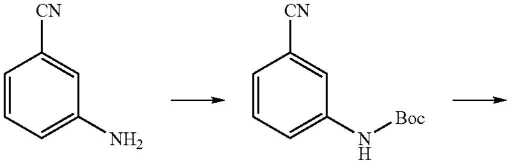

A

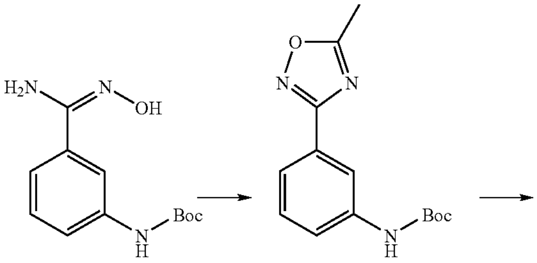

B

C

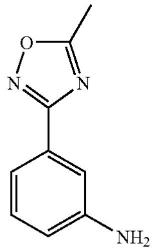

D

To a solution of 3-amino-benzonitrile (4.7 g, 40.0 mmol) in 200 mL THF, was added triethylamine (5.6 mL, 40.0 mmol), followed by di-tert-butyl dicarbonate (8.7 g, 40.0 mmol). After two days of heating at reflux, the solution was cooled, then partitioned between water and ethyl acetate. The product was extracted three times with ethyl acetate, washed with aqueous 1M HCl and brine, dried over magnesium sulfate, filtered, and concentrated to dryness. The product was purified using silica gel chromatography (elution with 10% hexane/90% ethyl acetate) to provide A (8.31 g, 93.2%).

A combined solution of A (6.54 g, 30 mmol), 50% w/w aqueous hydroxylamine (3.6 mL, 60 mmol), and 60 mL ethanol was refluxed for three hours. Ethanol was removed under high vacuum to yield B (7.3 g, 96.9%) as a brittle foam.

A solution of B (1.7 g, 7.0 mmol), acetyl chloride (746.5 µL, 10.5 mmol) in 35.0 mL pyridine was refluxed for one day. Pyridine was removed under high vacuum. The crude material was partitioned between ethyl acetate and water. The product was extracted three times with ethyl acetate, washed with aqueous 1M HCl, then with brine, and then dried over magnesium sulfate, filtered, and concentrated to dryness. The product was purified using silica gel chromatography (elution with 15% hexane/85% ethyl acetate) to provide C. Removal of the Boc protecting group was accomplished by stirring a solution of C in 50 mL of 4M HCl/dioxane for 30 minutes at rt. Dioxane was evaporated in vacuo to yield the aniline hydrochloric salt D (944.8 mg, 64.3%) as an off-white solid. The aniline was converted to the desired product Example 15-47 MS (MH+) 577.25 using the standard Ugi reaction conditions as described in Scheme 3.

Example 15-48

1-[2-(4-Acetylamino-piperidin-1-yl)-5-fluoro-phenyl]-4-cyclohexylamino-8-(3-isopropoxy-benzyl)-2-oxo-1,3-diaza-8-azonia-spiro[4.5]dec-3-ene trifluoroacetate

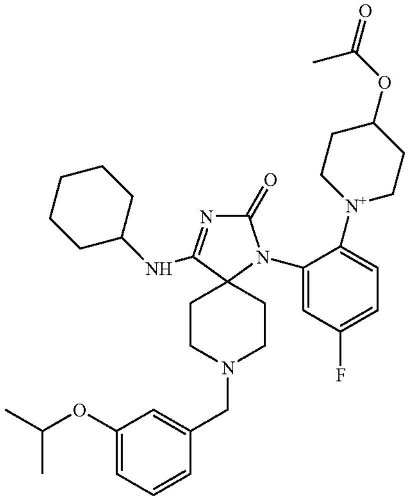

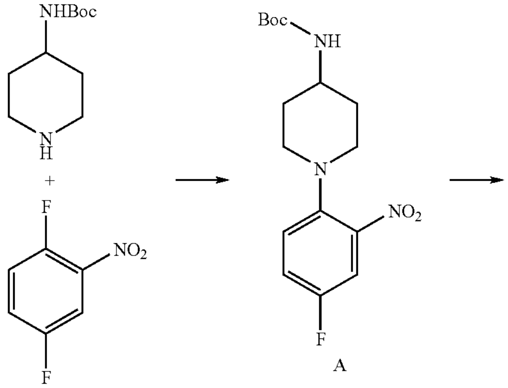

A

-continued

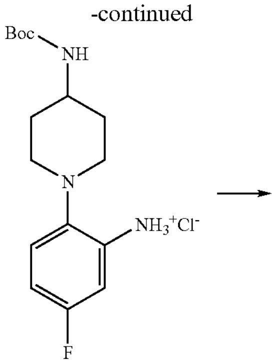

B

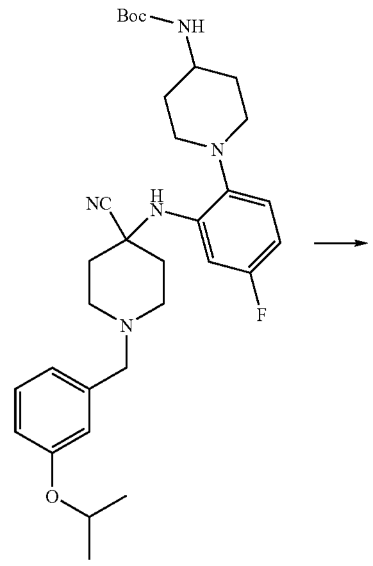

C

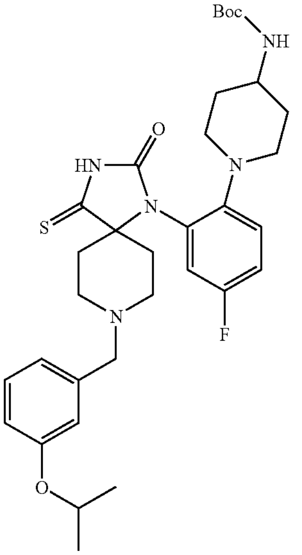

D

-continued

D

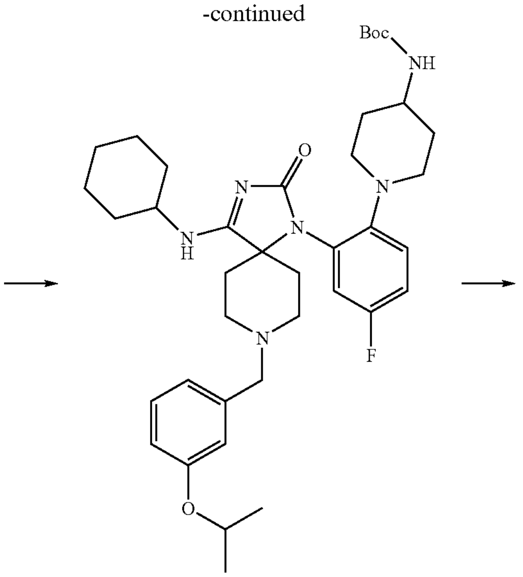

E

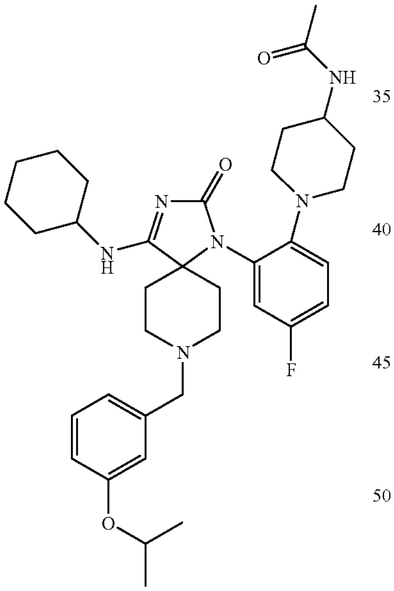

F 4-t-butoxycarbonylamino-piperidine (804.4 mg, 4.02 mmol, 1.0 eq.) and 2,5-difluoronitrobenzene (679.5 mg, 4.27 mmol, 1.06 eq.) were dissolved into DMSO (4 mL) in a 20 mL scintillation vial with a stir bar. Diusopropylethylamine (DIEA, 1 mL, 7.75 mmol, 1.93 eq.) was added, and the vial was capped and placed to stir in a 70° C. aluminum block for 3.5 h. The solution was then cooled to rt, diluted with diethyl ether, and washed with 1N hydrochloric acid. The organic solution was dried over $MgSO_4$, filtered, and concentrated to provide the aryl piperidine A (1.5261 g, 112%), which was carried on directly to the next step.

To a solution of A (339.36 mg, 1.0 mmol) in 2.5 mL methanol and 2.5 mL water, was added ammonium chloride (266.5 mg, 5 mmol), followed by zinc dust (327 mg, 5 mmol). The reaction mixture was stirred at room temperature for one hour, then filtered through a celite plug. Hydrochloric acid (1 mmol) was added to the free amine to obtain the amine hydrochloride salt. The filtrate was concentrated to yield B (307.5 mg, 89.0%) as a white solid.

To an ice-cold solution of 1-(3-Isopropoxy-benzyl)-piperidine-4,4-diol (132.5 mg, 0.5 mmol) and B (169.9 mg, 0.55 mmol) in glacial acetic acid (0.5 mL), was added slowly trimethylsilyl cyanide (73.4 μL, 0.55 mmol). The reaction mixture was kept at 0° C. for 5 min then allowed to warm to rt over 30 min. The resulting mixture was quenched with a saturated ammonium hydroxide:ice mixture until the pH reached 10, and was then extracted twice with dichloromethane. The combined dichloromethane extracts were washed with brine, dried over magnesium sulfate and concentrated. The crude material was purified by preparative TLC (20% ethyl acetate/60% hexanes) to provide C (234.5 mg, 83.0%) as an oily residue.

To an ice cold solution of C (234.5 mg, 0.415 mmol) in 1.5 mL chloroform, was added dropwise chlorosulfonyl isocyanate (39.7 μL, 0.46 mmol). The reaction was stirred at rt for 30 min, then quenched by addition of 830 μL of water. The reaction mixture was stirred for another one hr at rt, then added to a 0° C. aqueous solution of $H_2S$ (622.5 mg $Na_2S$+313.0 mL $H_2O$+622.5-650.0 μL acetic acid), which was prepared immediately before use. The resulting mixture was stirred at room temperature for 24 hr, then made alkaline with saturated sodium bicarbonate solution until pH>7, then extracted two times with ethyl acetate. The combined extracts was washed with brine, dried over magnesium sulfate and concentrated. The crude material was purified by preparative TLC (40% ethylacetate/60% hexane) to provide D (98.8 mg, 38.0%) as an oil residue.

To a solution of D (98.8 mg, 0.158 mmol) in 2 mL DMSO was added cyclohexyl amine (200 μL, 1.58 mmol). The reaction mixture was heated at 110° C. for two days. The crude product was purified by preparative reverse phase HPLC to provide E (59.7 mg, 54.7%) as the TFA salt, a fine yellow powder after being lyophilized.

Boc removal of E (30 mg, 0.43 mmol) was carried out using 0.5 ml 25% TFA/DCM at rt for 10 min. The TFA amine salt was dried in vacuo and redissolved in 0.5 mL tetrahydrofuran. Triethylamine (0.09 mmol, 12.5 μL) was added to the reaction solution, followed by acetyl chloride (~4.0 μL, 0.052 mmol), and the reaction was then stirred at rt for 15 min. The crude reaction was purified by preparative reverse phase HPLC and lyophilized to provide 15-45 (6.4 mg, 23.6%) MS (MH+) 633.3, as a fine yellow powder.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:

1. A compound of formula (I):

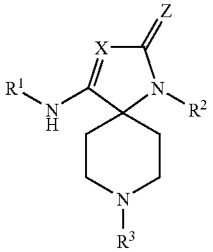

or its tautomer (I')

(I')

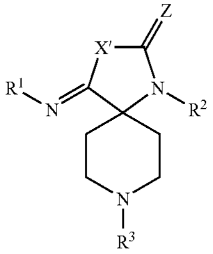

wherein:

X is N;

X' is NH;

Z is O;

$R^1$ is selected from the group consisting of (3) —$C_{0-6}$ alkyl-$C_{6-10}$ aryl, (5) —$C_{0-6}$ alkyl-$C_{3-12}$ carbocyclic, said $R^1$ carbocyclic moiety is substituted with one or more (a) —$OR^4$, (b) ═O, (c) halogen, (d) cyano, (e) —C(═O)—$NR^4R^{4'}$, (f) —$C_{1-6}$ alkyl, wherein said alkyl is optionally substituted with one or more (I) halogen, (II) —OH, and (III) —$C_{6-10}$ aryl, (g) —$NR^4$—$SO_2$—$R^{4'}$, (h) —$SO_2$—$R^4$, (i) —$NR^4$—C(═O)—$R^{4'}$, (j) —C(═O)—$OR^4$, (k) —$NR^4R^{4'}$, (l) —C(═O)—$R^4$, and (m) —$SO_2$—$NR^4R^{4'}$, and said $R^1$ aryl is optionally substituted with one or more (a) halogen, (b) —$C_{1-6}$ alkyl, (c) —$C_{2-6}$ alkenyl, (d) —$C_{2-6}$ alkynyl, (e) —$C_{0-3}$ alkyl-$C_{6-10}$ aryl, (f) cyano, (g) —O—$C_{0-3}$ alkyl-$C_{6-10}$ aryl, (h) —O—$R^4$, (i) —C(═O)—$NR^4R^{4'}$, (j) —$NR^4R^{4'}$, (k) -$Q^2$-$R^7$, and (l) —$C_{0-3}$ alkyl-$C_{5-12}$ heteroaryl, $Q^2$ is selected from the group consisting of (a) —C(═O)—, (b) —C(═O)—O—, (c) —C(═O)—$NR^8$—, (d) —$NR^8$—C(═O)—, (e) —$S(═O)_n$—, (f) —$Si(R^8R^9)$—, (g) —$S(═O)_2$—$R^8$—, (h) —$R^8$—$S(═O)_2$—, (i) —O—C(═O)—, (j) —$NR^8$—C(═O)—O—, (k) —$SO_2$—$NR^4$—, (l) —$NR^4SO_2$—, (m) —$NR^4$— wherein n is 0, 1 or 2;

$R^2$ is selected from the group consisting of (4) —$C_{0-6}$ alkyl-$C_{6-10}$ aryl, and said $R^2$ aryl is optionally substituted with one or more (a) —$OR^{10}$, (b) halogen, (c) -cyano, (d) —$NO_2$, (e) -$Q^4$-$C_{1-6}$ alkyl, (f) —$C_{1-6}$ alkyl, wherein said alkyl is optionally substituted with one or more (I) halogen, and (II) cyano, (g) —$C_{0-3}$ alkyl-$C_{6-10}$ aryl, wherein said aryl is optionally substituted with one or more (I) halogen, (II) —$C_{1-6}$ alkyl, (III) —$C_{2-6}$ alkenyl, (IV) —$C_{2-6}$ alkynyl, (V) —O—$C_{1-6}$ alkyl, (VI) —$SO_2$—$C_{1-6}$ alkyl, (VII) cyano, (VIII) —$C_{3-8}$ cycloalkyl, (IX) —$NO_2$, (X) —$SO_2$—$NR^4R^{4'}$ (h) —$SO_2$—$C_{1-6}$ alkyl, (i) —$SO_2$—$NR^4R^{4'}$, (j) —$NR^4R^{4'}$, (k) —$C_{3-8}$ cycloalkyl, (l) —$C_{2-6}$ alkenyl, (m) —NHC(═O)—$C_{1-6}$ alkyl, wherein said alkyl is optionally substituted with one or more (I) —$NR^4R^{4'}$ (II) OH (III) —$SO_2R^4$, and (IV) —$NHSO_2R^4$, (n) —NHC(═O)—$C_{0-3}$ alkyl-$C_{6-10}$ aryl, wherein said aryl is optionally substituted with one or more (I) $NR^4R^{4'}$, (II) OH, (III) —$SO_2R^4$, and (IV) —$NHSO_2R^4$, (o) —$C_{0-3}$ alkyl-$C_{5-12}$ heteroaryl, wherein said heteroaryl is optionally substituted with one or more (I) halogen, (II) —$C_{1-6}$ alkyl, and (III) ═O, (p) —$S(═O)_m$—$C_{0-6}$ alkyl-$C_{6-10}$ aryl, (q) —$CO_2$—$R^4$, (r) $—C(=O)—NR^4R^{4'}$,
(s) $—C_{0-6}$ alkyl—$NR^4SO_2—R^4$,
(t) $—O—C_{2-6}$ alkenyl,
and m is 0, 1 or 2;
and $Q^4$ is selected from the same group as $Q^2$;
$R^3$ is selected from the group consisting of
(2) $—C_{0-3}$ alkyl-$C_{6-10}$ aryl,
and said $R^3$ aryl is optionally substituted with one or more
(a) $—OR^{12}$,
(b) $—NR^4R^{4'}$,
(c) halogen,
(d) cyano,
(f) $—NO_2$,
(g) $-Q^6-R^4$, and
(h) $—C_{1-6}$ alkyl, wherein said alkyl is optionally substituted with one or more
(I) halogen,
(II) cyano,
(III) $—C_{1-6}$ alkyl,
(IV) $—O—C_{1-6}$ alkyl,
(V) $—C_{3-8}$ cycloalkyl,
(VI) $—C(=O)—C_{1-6}$ alkyl,
(i) $—C_{2-6}$ alkenyl,
(j) $—C_{2-6}$ alkynyl,
(k) $—C_{0-3}$ alkyl-$C_{5-12}$ heteroaryl,
(l) $—O—C_{2-6}$ alkenyl,
(m) $—C_{0-3}$ alkyl-$C_{6-10}$ aryl, wherein said aryl moiety is optionally substituted with one or more
(I) $—C_{1-6}$ alkyl,
(II) $—C_{2-6}$ alkenyl,
(III) $—C_{2-6}$ alkynyl,
(IV) halogen,
(V) cyano,
(VI) $—C_{3-8}$ cycloalkyl, and
(VII) $NO_2$,
and $R^{12}$ is selected from the group consisting of
(I) hydrogen,
(II) $—C_{1-6}$ alkyl,
(III) $—C_{2-6}$ alkenyl,
(IV) $—C_{2-6}$ alkynyl,
(V) $—C_{3-8}$ cycloalkyl, and
(VI) $—C_{0-3}$ alkyl-$C_{6-10}$ aryl,
and said $R^{12}$ alkyl, alkenyl and alkynyl moiety is optionally substituted with one or more
(A) halogen,
(B) hydroxyl,
(C) cyano,
(D) $—O—C_{1-6}$ alkyl, wherein said alkyl is optionally substituted with one or more halogen,
(E) $—NR^4R^{4'}$,
(F) $—NR^4—S(=O)_2—R^{4'}$,
(G) $—NR^4—C(=O)—R^{4'}$,
(H) $—NR^4—C(=O)—OR^{4'}$,
(I) $—S(=O)_2—NR^4—$,
and said $R^{10}$ cycloalkyl moiety is optionally substituted with one or more
(A) halogen,
(B) hydroxyl,
(C) -cyano,
(D) $—O—Cl_{1-6}$ alkyl, and
(E) $—C_{1-6}$ alkyl, wherein said alkyl is optionally substituted one or more halogen;
and said $R^{12}$ aryl moiety is optionally substituted with one or more
(A) halogen,
(B) cyano,
(C) $—O—C_{1-6}$ alkyl, and
(D) $—C_{1-6}$ alkyl, wherein said alkyl is optionally substituted one or more halogen;
$Q^6$ is selected from the same group as $Q^2$;
$R^4$ and $R^{4'}$ are selected from the group consisting of
(1) hydrogen,
(2) $—C_{1-8}$ alkyl, wherein said alkyl is optionally substituted with
(a) halogen,
(b) $—C_{3-8}$ cycloalkyl
(c) $—CO_2C_{1-6}$ alkyl
(d) $—OC_{1-6}$ alkyl, wherein said alkyl is optionally substituted with one or more
(I) halogen, or
(II) cyano,
(3) $—C_{2-8}$ alkenyl, and
(4) $—C_{0-3}$ alkyl-$C_{6-10}$aryl;
$R^5$ is selected from the group consisting of
(1) hydrogen,
(2) $—C_{1-6}$ alkyl,
(3) halogen, and
(4) $—CO_2—R^4$,
$R^6$, $R^7$, $R^8$, $R^9$, $R^{10}$ and $R^{11}$ are independently selected from the group consisting of:
(1) hydrogen,
(2) $—C_{1-6}$ alkyl,
(3) $—C_{3-8}$ cycloalkyl,
(4) $—C_{0-3}$ alkyl-$C_{6-10}$ aryl,
wherein said alkyl is optionally substituted with one or more
(A) halogen,
(B) hydroxyl,
(C) cyano,
(D) $—O—C_{1-6}$ alkyl, wherein said alkyl is optionally substituted with one or more
halogen,
and said cycloalkyl and aryl are optionally substituted with one or more
(A) halogen,
(B) hydroxyl,
(C) cyano,
(D) $—O—C_{1-6}$ alkyl, and
(E) $—C_{1-6}$ alkyl, wherein said alkyl is optionally substituted one or more halogen;
provided that when X is N; Z is O; and $R^2$ is unsubstituted phenyl, then $R^3$ is not unsubstituted benzyl;
and pharmaceutically acceptable salts thereof, and individual enantiomers and diastereomers thereof.

2. The compound of claim 1 wherein $R^1$is $—C_{0-3}$ alkyl-$C_{3-12}$ carbocyclic, wherein said alkyl or carbocyclic is substituted as in claim 1.

3. The compound of claim 1 wherein $R^1$ is $—C_{0-3}$ alkyl-$C_{6-10}$ aryl, and said aryl moiety is optionally substituted with one or more
(a) halogen, or
(b) $—C_{1-6}$ alkyl.

4. The compound of claim 1 wherein $R^2$ is: $—C_{0-3}$ alkyl-$C_{6-10}$ aryl, wherein said aryl moiety is optionally substituted as in claim 1.

5. The compound of claim 4, wherein $R^2$ is phenyl or benzyl, and said phenyl or benzyl are optionally substituted as in claim 1.

6. The compound of claim 1 which is a compound of formula (II)

(II)

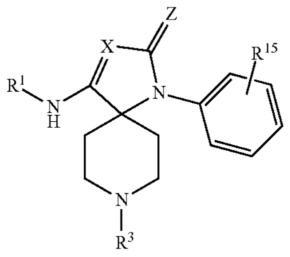

or its tautomer (II')

(II')

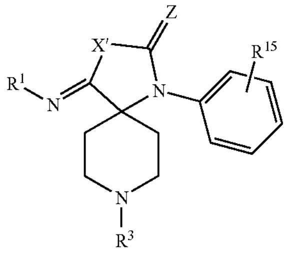

and pharmaceutically acceptable salts thereof, and individual enantiomers and diasteromers thereof, wherein X, X', Z, $R^1$ and $R^3$ are as defined in claim 1, and $R^{15}$ is selected from the group consisting of (a) —$OR^{10}$,
(b) halogen,
(c) -cyano,
(d) -$Q^4$-$C_{1-6}$ alkyl,
(e) —$C_{1-6}$ alkyl, wherein said alkyl is optionally substituted with one or more
(I) halogen, and
(II) cyano,
(f) —$C_{0-3}$-alkyl-$C_{6-10}$ aryl, wherein said aryl is optionally substituted with one or more
(I) halogen,
(II) —$C_{1-6}$ alkyl,
(V) —O—$C_{1-6}$ alkyl,
(VI) —$SO_2$—$C_{1-6}$ alkyl,
(VII) cyano,
(VIII) —$C_{3-8}$ cycloalkyl,
(X) —$SO_2$—$NR^4R^{4'}$
(g) —$SO_2$—$C_{1-6}$ alkyl,
(h) —$SO_2$—$NR^4R^{4'}$,
(i) —$C_{3-8}$ cycloalkyl,
(j) —NHC(═O)—$C_{1-6}$ alkyl, wherein said alkyl is optionally substituted with one or more
(I) —$NR^4R^{4'}$
(II) OH
(III) —$SO_2R^4$, and
(IV) —$NHSO_2R^4$,
(k) —$C_{0-3}$ alkyl-$C_{5-12}$ heteroaryl, wherein said heteroaryl is optionally substituted with one or more
(I) halogen,
(II) —$C_{1-6}$ alkyl, and
(III) ═O,
(l) —S(═O)$_m$—$C_{0-6}$ alkyl-$C_{6-10}$ aryl,
(m) —$CO_2$—$R^4$,
(n) —C(═O)—$NR^4R^{4'}$,
(o) —$C_{0-6}$ alkyl-$NR^4SO_2$—$R^4$.

7. The compound of claim 6 wherein $R^3$ is selected from the group consisting of
(1) —$C_{0-3}$ alkyl-$C_{6-10}$ aryl,
and said aryl is optionally substituted with one or more
(a) —$OR^{12}$,
(b) —$NR^4R^{4'}$,
(c) halogen,
(d) cyano,
(e) —$NO_2$,
(f) -$Q^6$-$R^4$, and
(g) —$C_{1-6}$ alkyl, wherein said alkyl is optionally substituted with one or more
(I) halogen,
(II) cyano,
(III) —$C_{1-6}$ alkyl,
(IV) —O—$C_{1-6}$ alkyl,
(V) —$C_{3-8}$ cycloalkyl,
(VI) —C(═O)—$C_{1-6}$ alkyl,
(h) —$C_{2-6}$ alkenyl,
(i) —$C_{2-6}$ alkynyl,
(j) —$C_{0-3}$ alkyl-$C_{5-12}$ heteroaryl,
(k) —$C_{0-3}$ alkyl-$C_{6-10}$ aryl, and said aryl moiety is optionally substituted with one or more
(I) —$C_{1-6}$ alkyl,
(II) —$C_{2-6}$ alkenyl,
(III) —$C_{2-6}$ alkynyl,
(IV) halogen,
(V) cyano,
(VI) —$C_{3-8}$ cycloalkyl, and
(VII) $NO_2$.

8. The compound of claim 7 wherein $R^3$ is benzyl, which is optionally substituted with one or more
(a) —$OR^{12}$,
(b) $NR^4R^{4'}$,
(c) halogen,
(d) cyano,
(f) —$NO_2$,
(g) -$Q^6$-$R^4$, and
(h) —$C_{1-6}$ alkyl, wherein said alkyl is optionally substituted with one or more
(I) halogen,
(II) cyano,
(III) —$C_{1-6}$ alkyl,
(IV) —O—$C_{1-6}$ alkyl,
(V) —$C_{3-8}$ cycloalkyl,
(VI) —C(═O) —$C_{1-6}$ alkyl,
(i) —$C_{2-6}$ alkenyl,
(j) —$C_{2-6}$ alkynyl,
(k) —$C_{0-3}$ alkyl-$C_{5-12}$ heteroaryl,
(l) —$C_{0-3}$ alkyl-$C_{6-10}$ aryl, and said aryl moiety is optionally substituted with one or more
(I) —$C_{1-6}$ alkyl,
(II) —$C_{2-6}$ alkenyl,
(III) —$C_{2-6}$ alkynyl,
(IV) halogen,
(V) cyano,
(VI) —$C_{3-8}$ cycloalkyl, and
(VII) $NO_2$.

9. The compound of claim 1 which is a compound of formula (III)

(III)

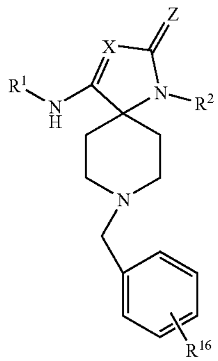

or its tautomer (III')

(III')

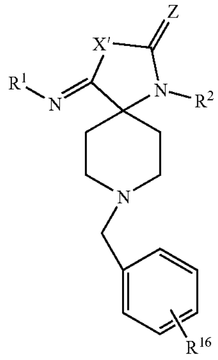

and pharmaceutically acceptable salts thereof, and individual enantiomers and diastereomers thereof, wherein X, X', Z, $R^1$, and $R^2$ are as defined in claim 1, and $R^{16}$ is selected from the group consisting of (a) —$OR^{12}$, (b) $NR^4R^{4'}$, (c) halogen, (d) cyano, (f) —$NO_2$, (g) -$Q^6$-$R^4$, and (h) —$C_{1-6}$ alkyl, wherein said alkyl is optionally substituted with one or more (I) halogen, (II) cyano, (III) —$C_{1-6}$ alkyl, (IV) —O—$C_{1-6}$ alkyl, (V) —$C_{3-8}$ cycloalkyl, (VI) —C(═O)—$C_{1-6}$ alkyl, (i) —$C_{2-6}$ alkenyl, (j) —$C_{2-6}$ alkynyl, (k) —$C_{0-3}$ alkyl-$C_{5-12}$ heteroaryl, (l) —$C_{0-3}$ alkyl-$C_{6-10}$ aryl, wherein said aryl moiety is optionally substituted with one or more (I) —$C_{1-6}$ alkyl, (II) —$C_{2-6}$ alkenyl, (III) —$C_{2-6}$ alkynyl, (IV) halogen, (V) cyano, (VI) —$C_{3-8}$ cycloalkyl, and (VII) $NO_2$.

10. A pharmaceutical composition comprising a compound of claim 1 and a pharmaceutically acceptable carrier.

11. A compound which is selected from the group consisting of:

8-benzyl-4-(benzylamino)-1-phenyl-1,3,8-triazaspiro[4.5]dec-3-en-2-one;

8-benzyl-4-(cyclohexylamino)-1-methyl-1,3,8-triazaspiro[4.5]dec-3-en-2-one;

8-benzyl-4-(cyclohexylamino)-1-(3-fluorophenyl)-1,3,8-triazaspiro[4.5]dec-3-en-2-one;

8-benzyl-4-(cyclohexylamino)-1-(3-methylbutyl)-1,3,8-triazaspiro[4.5]dec-3-en-2-one;

8-benzyl-4-(tert-butylamino)-1-phenyl-1,3,8-triazaspiro[4.5]dec-3-en-2-one;

8-benzyl-4-(isopropylamino)-1-phenyl-1,3,8-triazaspiro[4.5]dec-3-en-2-one;

8-benzyl-4-(cyclohexylamino)-1-(3-pyridyl)-1,3,8-triazaspiro[4.5]dec-3-en-2-one;

8-benzyl-4-(butylamino)-1-phenyl-1,3,8-triazaspiro[4.5]dec-3-en-2-one;

8-benzyl-4-(cyclohexylamino)-1-(3,5-dimethylphenyl)-1,3,8-triazaspiro[4.5]dec-3-en-2-one;

8-benzyl-4-(1-methylbutylamino)-1-phenyl-1,3,8-triazaspiro[4.5]dec-3-en-2-one;

8-benzyl-4-(cyclohexylamino)-1-(4-chlorophenyl)-1,3,8-triazaspiro[4.5]dec-3-en-2-one;

8-benzyl-4-(cyclohexylamino)-1-(4-methoxyphenyl)-1,3,8-triazaspiro[4.5]dec-3-en-2-one;

8-benzyl-4-(cyclohexylamino)-1-(4-methoxy-3-fluorophenyl)-1,3,8-triazaspiro[4.5]dec-3-en-2-one;

8-benzyl-4-(cyclohexylamino)-1-(3,4-difluorophenyl)-1,3,8-triazaspiro[4.5]dec-3-en-2-one;

8-benzyl-4-(cyclohexylamino)-1-(3-trifluoromethylphenyl)-1,3,8-triazaspiro[4.5]dec-3-en-2-one;

8-benzyl-4-(cyclohexylamino)-1-(2-methylphenyl)-1,3,8-triazaspiro[4.5]dec-3-en-2-one;

8-benzyl-4-(cyclohexylamino)-1-(3-methoxyphenyl)-1,3,8-triazaspiro[4.5]dec-3-en-2-one;

8-benzyl-4-(cyclohexylamino)-1-(3,4-dichlorophenyl)-1,3,8-triazaspiro[4.5]dec-3-en-2-one;

8-benzyl-4-(cyclohexylamino)-1-(4-trifluoromethylphenyl)-1,3,8-triazaspiro[4.5]dec-3-en-2-one;

8-benzyl-4-(cyclohexylamino)-1-(3-chlorophenyl)-1,3,8-triazaspiro[4.5]dec-3-en-2-one;

8-benzyl-4-(cyclohexylamino)-1-(2-chlorophenyl)-1,3,8-triazaspiro[4.5]dec-3-en-2-one;

8-benzyl-4-(cyclohexylamino)-1-(2,4-dichlorophenyl)-1,3,8-triazaspiro[4.5]dec-3-en-2-one;

8-benzyl-4-(cyclohexylamino)-1-(3-cyanophenyl)-1,3,8-triazaspiro[4.5]dec-3-en-2-one;

8-benzyl-4-(cyclohexylamino)-1-(2-trifluoromethyl-4-methoxyphenyl)-1,3,8-triazaspiro[4.5]dec-3-en-2-one;

8-benzyl-4-(cyclohexylamino)-1-(2-methyl-4-methoxyphenyl)-1,3,8-triazaspiro[4.5]dec-3-en-2-one;

8-benzyl-4-(cyclohexylamino)-1-(1,3-benzodioxo-5-yl)-1,3,8-triazaspiro[4.5]dec-3-en-2-one;

8-benzyl-4-(cyclohexylamino)-1-(4-acetylaminophenyl)-1,3,8-triazaspiro[4.5]dec-3-en-2-one;

8-benzyl-4-(cyclohexylamino)-1-(3,5-difluorophenyl)-1,3,8-triazaspiro[4.5]dec-3-en-2-one;

8-benzyl-4-((2-phenethyl)amino)-1-(3-fluorophenyl)-1,3,8-triazaspiro[4.5]dec-3-en-2-one;

8-benzyl-4-(cyclohexylamino)-1-(4-pentanoylaminophenyl)-1,3,8-triazaspiro[4.5]dec-3-en-2-one;

8-benzyl-4-(cyclohexylamino)-1-(4-(4-dimethylamino) butanoylaminophenyl)-1,3,8-triazaspiro[4.5]dec-3-en-2-one;

N-{4-[8-benzyl-4-(cyclohexylamino)-2-oxo-1,3,8-triazaspiro[4.5]dec-3-en-1-yl]phenyl}butanamide;

N-{4-[8-benzyl-4-(cyclohexylamino)-2-oxo-1,3,8-triazaspiro[4.5]dec-3-en-1-yl]phenyl}-3-hydroxypropanamide;

ethyl N-[8-benzyl-1-(3-fluorophenyl)-2-oxo-1,3,8-triazaspiro[4.5]dec-3-en-4-yl]-beta-alaninate;

8-benzyl-4-(cyclohexylamino)-1-[3'-(methylsulfonyl)biphenyl-2-yl]-1,3,8-triazaspiro[4.5]dec-3-en-2-one;

8-benzyl-4-(isopropylamino)-1-phenyl-1,3,8-triazaspiro[4.5]dec-3-en-2-one;

N-{4-[8-benzyl-4-(cyclohexylamino)-2-oxo-1,3,8-triazaspiro[4.5]dec-3-en-1-yl]-2-chlorophenyl}acetamide;

8-(3-Bromobenzyl)-4-(cyclohexylamino)-1-(3-fluorophenyl)-1,3,8-triazaspiro[4.5]dec-3-en-2-one;

4-(cyclohexylamino)-1-(3-fluorophenyl)-8-{3-[(1-methylprop-2-enyl)oxy]benzyl}-1,3,8-triazaspiro[4.5]dec-3-en-2-one;

4-(cyclohexylamino)-1-(3-fluorophenyl)-8-(3-isopropoxybenzyl)-1,3,8-triazaspiro[4.5]dec-3-en-2-one;

4-methyl-1-(3-fluorophenyl)-2-oxo-1,3,8-triazaspiro[4.5]dec-3-ene;

1-(3-fluorophenyl)-4-(methylamino)-8-[(2'-methylbiphenyl-3-yl)methyl]-1,3,8-triazaspiro[4.5]dec-3-en-2-one;

8-benzyl-1-(3-fluorophenyl)-4-(methylamino)-1,3,8-triazaspiro[4.5]dec-3-en-2-one;

N-(4-{[1-(3-fluorophenyl)-4-(methylamino)-2-oxo-1,3,8-triazaspiro[4.5]dec-3-en-8-yl]methyl}phenyl)acetamide;

4-(cyclohexylamino)-1-(3-fluorophenyl)-8-[(2'-vinyl-1,1'-biphenyl-3-yl)methyl]-1,3,8-triazaspiro[4.5]dec-3-en-2-one;

4-(cyclohexylamino)-1-(3-fluorophenyl)-8-[3-(4-methylpyridin-3-yl)benzyl]-1,3,8-triazaspiro[4.5]dec-3-en-2-one;

8-benzyl-4-(cyclohexylamino)-1-(3-fluorophenyl)-1,3,8-triazaspiro[4.5]dec-3-en-2-one;

8-(2-trifluoromethoxybenzyl)-4-(cyclohexylamino)-1-(3-fluorophenyl)-1,3,8-triazaspiro[4.5]dec-3-en-2-one;

4-(cyclohexylamino)-8-[2-(difluoromethoxy)benzyl]-1-(3-fluorophenyl)-1,3,8-triazaspiro[4.5]dec-3-en-2-one;

8-[2-(tert-butylthio)benzyl]-4-(cyclohexylamino)-1-(3-fluorophenyl)-1,3,8-triazaspiro[4.5]dec-3-en-2-one;

8-[2-methylbenzyl]-4-(cyclohexylamino)-1-(3-fluorophenyl)-1,3,8-triazaspiro[4.5]dec-3-en-2-one;

8-[2-nitrobenzyl]-4-(cyclohexylamino)-1-(3-fluorophenyl)-1,3,8-triazaspiro[4.5]dec-3-en-2-one;

N-(4-{[4-(cyclohexylamino)-1-(3-fluorophenyl)-2-oxo-1,3,8-triazaspiro[4.5]dec-3-en-8-yl]methyl}phenyl)acetamide;

8-[4-cyanobenzyl]-4-(cyclohexylamino)-1-(3-fluorophenyl)-1,3,8-triazaspiro[4.5]dec-3-en-2-one;

8-[3-cyanobenzyl]-4-(cyclohexylamino)-1-(3-fluorophenyl)-1,3,8-triazaspiro[4.5]dec-3-en-2-one;

8-[2-propoxybenzyl]-4-(cyclohexylamino)-1-(3-fluorophenyl)-1,3,8-triazaspiro[4.5]dec-3-en-2-one;

8-[3-phenylpropyl]-4-(cyclohexylamino)-1-(3-fluorophenyl)-1,3,8-triazaspiro[4.5]dec-3-en-2-one;

8-[3-fluorobenzyl]-4-(cyclohexylamino)-1-(3-fluorophenyl)-1,3,8-triazaspiro[4.5]dec-3-en-2-one;

8-[2-cyanobenzyl]-4-(cyclohexylamino)-1-(3-fluorophenyl)-1,3,8-triazaspiro[4.5]dec-3-en-2-one;

4-(cyclohexylamino)-1-(3-fluorophenyl)-8-(2-thienylmethyl)-1,3,8-triazaspiro[4.5]dec-3-en-2-one;

4-(cyclohexylamino)-1-(3-fluorophenyl)-8-(1-phenylethyl)-1,3,8-triazaspiro[4.5]dec-3-en-2-one;

8-[(2-benzyl-1H-indol-7-yl)methyl]-4-(cyclohexylamino)-1-(3-fluorophenyl)-1,3,8-triazaspiro[4.5]dec-3-en-2-one;

8-[(2-benzyl-2,3-dihydro-1H-indol-7-yl)methyl]-4-(cyclohexylamino)-1-(3-fluorophenyl)-1,3,8-triazaspiro[4.5]dec-3-en-2-one;

4-(cyclohexylamino)-1-(3-fluorophenyl)-8-(1H-pyrrol-2-ylmethyl)-1,3,8-triazaspiro[4.5]dec-3-en-2-one;

4-(cyclohexylamino)-1-(3-fluorophenyl)-8-(1H-indol-2-ylmethyl)-1,3,8-triazaspiro[4.5]dec-3-en-2-one;

8-[(3-aminopyridin-4-yl)methyl]-4-(cyclohexylamino)-1-(3-fluorophenyl)-1,3,8-triazaspiro[4.5]dec-3-en-2-one;

4-(cyclohexylamino)-1-(3-fluorophenyl)-8-(quinolin-6-ylmethyl)-1,3,8-triazaspiro[4.5]dec-3-en-2-one;

4-(cyclohexylamino)-1-(3-fluorophenyl)-8-(1,2,3,4-tetrahydroquinolin-6-ylmethyl)-1,3,8-triazaspiro[4.5]dec-3-en-2-one;

4-(cyclohexylamino)-1-(3-fluorophenyl)-8-(1H-indol-7-ylmethyl)-1,3,8-triazaspiro[4.5]dec-3-en-2-one;

8-[(2-aminopyridin-3-yl)methyl]-4-(cyclohexylamino)-1-(3-fluorophenyl)-1,3,8-triazaspiro[4.5]dec-3-en-2-one;

4-(cyclohexylamino)-1-(3-fluorophenyl)-8-(1H-indol-5-ylmethyl)-1,3,8-triazaspiro[4.5]dec-3-en-2-one;

4-(cyclohexylamino)-8-(2,3-dihydro-1H-indol-5-ylmethyl)-1-(3-fluorophenyl)-1,3,8-triazaspiro[4.5]dec-3-en-2-one;

8-(2-aminobenzyl)-4-(cyclohexylamino)-1-(3-fluorophenyl)-1,3,8-triazaspiro[4.5]dec-3-en-2-one;

4-(cyclohexylamino)-8-(2,3-dihydro-1H-indol-7-ylmethyl)-1-(3-fluorophenyl)-1,3,8-triazaspiro[4.5]dec-3-en-2-one;

4-(cyclohexylamino)-8-(2,3-dihydro-1H-inden-2-yl)-1-(3-fluorophenyl)-triazaspiro[4.5]dec-3-en-2-one;

4-(cyclohexylamino)-1-(3-fluorophenyl)-8-(3-phenylcyclohexyl)-1,3,8-triazaspiro[4.5]dec-3-en-2-one;

4-(cyclohexylamino)-1-(3-fluorophenyl)-8-(1-phenyl-2,3-dihydro-1H-inden-2-yl)-1,3,8-triazaspiro[4.5]dec-3-en-2-one;

4-(cyclohexylamino)-1-(3-fluorophenyl)-8-(3-phenylcyclohexyl)-1,3,8-triazaspiro[4.5]dec-3-en-2-one;

4-(cyclohexylamino)-1-(3-fluorophenyl)-8-[3-(4-methoxyphenoxy)benzyl]-1,3,8-triazaspiro[4.5]dec-3-en-2-one;

4-(cyclohexylamino)-1-(3-fluorophenyl)-8-{4-[(4-methoxybenzyl)oxy]benzyl}-1,3,8-triazaspiro[4.5]dec-3-en-2-one;

8-(biphenyl-3-ylmethyl)-4-(cyclohexylamino)-1-(3-fluorophenyl)-1,3,8-triazaspiro[4.5]dec-3-en-2-one;

4-(cyclohexylamino)-1-(3-fluorophenyl)-8-[(2'-methylbiphenyl-3-yl)methyl]-1,3,8-triazaspiro[4.5]dec-3-en-2-one;

8-(3-chlorobenzyl)-4-(cyclohexylamino)-1-(3-fluorophenyl)-1,3,8-triazaspiro[4.5]dec-3-en-2-one;

4-(cyclohexylamino)-1-(3-fluorophenyl)-8-(3-methylbenzyl)-1,3,8-triazaspiro[4.5]dec-3-en-2-one;

4-(cyclohexylamino)-1-(3-fluorophenyl)-8-[3-(trifluoromethyl)benzyl]-1,3,8-triazaspiro[4.5]dec-3-en-2-one;

4-(cyclohexylamino)-1-(3-fluorophenyl)-8-(3-vinylbenzyl)-1,3,8-triazaspiro[4.5]dec-3-en-2-one;

methyl 3-{[4-(cyclohexylamino)-1-(3-fluorophenyl)-2-oxo-1,3,8-triazaspiro[4.5]dec-3-en-8-yl]methyl}benzoate;

4-(cyclohexylamino)-1-(3-fluorophenyl)-8-(3-hydroxybenzyl)-1,3,8-triazaspiro[4.5]dec-3-en-2-one;

4-(cyclohexylamino)-1-(3-fluorophenyl)-8-(3-methoxy-benzyl)-1,3,8-triazaspiro[4.5]dec-3-en-2-one;

4-(cyclohexylamino)-8-(3-ethoxybenzyl)-1-(3-fluorophenyl)-1,3,8-triazaspiro[4.5]dec-3-en-2-one;

4-(cyclohexylamino)-8-[3-(cyclopentyloxy)benzyl]-1-(3-fluorophenyl)-1,3,8-triazaspiro[4.5]dec-3-en-2-one;

4-(cyclohexylamino)-1-(3-fluorophenyl)-8-[3-(1,1,2,2-tetrafluoroethoxy)benzyl]-1,3,8-triazaspiro[4.5]dec-3-en-2-one;

4-(cyclohexylamino)-1-(3-fluorophenyl)-8-(3-phenoxy-benzyl)-1,3,8-triazaspiro[4.5]dec-3-en-2-one;

8-[3-(4-tert-butylphenoxy)benzyl]-4-(cyclohexylamino)-1-(3-fluorophenyl)-1,3,8-triazaspiro[4.5]dec-3-en-2-one;

4-(cyclohexylamino)-8-[3-(3,5-dichlorophenoxy)benzyl]-1-(3-fluorophenyl)-1,3,8-triazaspiro[4.5]dec-3-en-2-one;

8-[3-(benzyloxy)benzyl]-4-(cyclohexylamino)-1-(3-fluorophenyl)-1,3,8-triazaspiro[4.5]dec-3-en-2-one;

4-(cyclohexylamino)-1-(3-fluorophenyl)-8-(3-nitrobenzyl)-1,3,8-triazaspiro[4.5]dec-3-en-2-one;

3-{[4-(cyclohexylamino)-1-(3-fluorophenyl)-2-oxo-1,3,8-triazaspiro[4.5]dec-3-en-8-yl]methyl}phenyl acetate;

4-(cyclohexylamino)-1-(3-fluorophenyl)-8-[3-(2-methyl-1H-imidazol-1-yl)benzyl]-1,3,8-triazaspiro[4.5]dec-3-en-2-one;

4-(cyclohexylamino)-8-[3-(2-ethyl-1H-imidazol-1-yl)benzyl]-1-(3-fluorophenyl)-1,3,8-triazaspiro[4.5]dec-3-en-2-one;

3'-{[4-(cyclohexylamino)-1-(3-fluorophenyl)-2-oxo-1,3,8-triazaspiro[4.5]dec-3-en-8-yl]methyl}biphenyl-2-carbonitrile;

4-(cyclohexylamino)-8-[(2'-ethylbiphenyl-3-yl)methyl]-1-(3-fluorophenyl)-1,3,8-triazaspiro[4.5]dec-3-en-2-one;

4-(cyclohexylamino)-1-(3-fluorophenyl)-8-{[2'-(methoxymethyl)biphenyl-3-yl]methyl}-1,3,8-triazaspiro[4.5]dec-3-en-2-one;

4-(cyclohexylamino)-1-(3-fluorophenyl)-8-{[2'-(trifluoromethyl)biphenyl-3-yl]methyl}-1,3,8-triazaspiro[4.5]dec-3-en-2-one;

4-(cyclohexylamino)-1-(3-fluorophenyl)-8-[(2'-vinylbiphenyl-3-yl)methyl]-1,3,8-triazaspiro[4.5]dec-3-en-2-one;

4-(cyclohexylamino)-1-(3-fluorophenyl)-8-[(2'-methoxy-biphenyl-3-yl)methyl]-1,3,8-triazaspiro[4.5]dec-3-en-2-one;

(3'-{[4-(cyclohexylamino)-1-(3-fluorophenyl)-2-oxo-1,3,8-triazaspiro[4.5]dec-3-en-8-yl]methyl}biphenyl-2-yl)acetonitrile;

4-(cyclohexylamino)-1-(3-fluorophenyl)-8-[3-(2-fluoro-pyridin-3-yl)benzyl]-1,3,8-triazaspiro[4.5]dec-3-en-2-one;

4-(cyclohexylamino)-1-(3-fluorophenyl)-8-[3-(3-methylpyridin-4-yl)benzyl]-1,3,8-triazaspiro[4.5]dec-3-en-2-one;

4-(cyclohexylamino)-1-(3-fluorophenyl)-8-[(4'-methylbiphenyl-3-yl)methyl]-1,3,8-triazaspiro[4.5]dec-3-en-2-one;

4-(cyclohexylamino)-1-(3-fluorophenyl)-8-[(3'-methylbiphenyl-3-yl)methyl]-1,3,8-triazaspiro[4.5]dec-3-en-2-one;

4-(cyclohexylamino)-8-{[6-(2-ethylphenyl)pyridin-2-yl]methyl}-1-(3-fluorophenyl)-1,3,8-triazaspiro[4.5]dec-3-en-2-one;

4-(cyclohexylamino)-8-[(2'-cyclopropylbiphenyl-3-yl)methyl]-1-(3-fluorophenyl)-1,3,8-triazaspiro[4.5]dec-3-en-2-one;

4-(cyclohexylamino)-1-(3-fluorophenyl)-8-[3-(5-methyl-2-furyl)benzyl]-1,3,8-triazaspiro[4.5]dec-3-en-2-one;

8-[(2'-allylbiphenyl-3-yl)methyl]-4-(cyclohexylamino)-1-(3-fluorophenyl)-1,3,8-triazaspiro[4.5]dec-3-en-2-one;

4-(cyclohexylamino)-1-(3-fluorophenyl)-8-({2'-[(trimethylsilyl)ethynyl]biphenyl-3-yl}methyl)-1,3,8-triazaspiro[4.5]dec-3-en-2-one;

4-(cyclohexylamino)-1-(3-fluorophenyl)-8-[3-(2-methylpyridin-3-yl)benzyl]-1,3,8-triazaspiro[4.5]dec-3-en-2-one;

4-(cyclohexylamino)-8-[3-(3,5-dimethylisoxazol-4-yl)benzyl]-1-(3-fluorophenyl)-1,3,8-triazaspiro[4.5]dec-3-en-2-one;

4-(cyclohexylamino)-8-[(2'-ethynylbiphenyl-3-yl)methyl]-1-(3-fluorophenyl)-1,3,8-triazaspiro[4.5]dec-3-en-2-one;

8-[(2'-but-3-en-1-ylbiphenyl-3-yl)methyl]-4-(cyclohexylamino)-1-(3-fluorophenyl)-1,3,8-triazaspiro[4.5]dec-3-en-2-one;

4-(cyclohexylamino)-1-(3-fluorophenyl)-8-[(2'-isopropylbiphenyl-3-yl)methyl]-1,3,8-triazaspiro[4.5]dec-3-en-2-one;

4-(cyclohexylamino)-1-(3-fluorophenyl)-8-[3-(3-methylpyridin-2-yl)benzyl]-1,3,8-triazaspiro[4.5]dec-3-en-2-one;

4-(cyclohexylamino)-1-(3-fluorophenyl)-8-[3-(1-methyl-1H-imidazol-2-yl)benzyl]-1,3,8-triazaspiro[4.5]dec-3-en-2-one;

4-(cyclohexylamino)-1-(3-fluorophenyl)-8-[3-(4-methylpyridin-3-yl)benzyl]-1,3,8-triazaspiro[4.5]dec-3-en-2-one;

4-(cyclohexylamino)-1-(3-fluorophenyl)-8-[3-(1-methyl-1H-imidazol-5-yl)benzyl]-1,3,8-triazaspiro[4.5]dec-3-en-2-one;

4-(cyclohexylamino)-1-(3-fluorophenyl)-8-[3-(1-methyl-1H-imidazol-4-yl)benzyl]-1,3,8-triazaspiro[4.5]dec-3-en-2-one;

4-(cyclohexylamino)-1-(3-fluorophenyl)-8-[3-(4-methyl-1-oxidopyridin-3-yl)benzyl]-1,3,8-triazaspiro[4.5]dec-3-en-2-one;

4-(cyclohexylamino)-8-[(2',4'-dimethoxy-6'-methylbiphenyl-3-yl)methyl]-1-(3-fluorophenyl)-1,3,8-triazaspiro[4.5]dec-3-en-2-one;

4-(cyclohexylamino)-1-(3-fluorophenyl)-8-[2'-(2-methylprop-2-en-1-yl)biphenyl-3-yl]methyl-1,3,8-triazaspiro[4.5]dec-3-en-2-one;

4-(cyclohexylamino)-1-(3-fluorophenyl)-8-[(2'-methyl-5'-nitrobiphenyl-3-yl)methyl]-1,3,8-triazaspiro[4.5]dec-3-en-2-one;

4-(cyclohexylamino)-8-[(5'-fluoro-2'-methylbiphenyl-3-yl)methyl]-1-(3-fluorophenyl)-1,3,8-triazaspiro[4.5]dec-3-en-2-one;

8-[(5'-chloro-2'-methylbiphenyl-3-yl)methyl]-4-(cyclohexylamino)-1-(3-fluorophenyl)-1,3,8-triazaspiro[4.5]dec-3-en-2-one;

8-[(5'-amino-2'-methylbiphenyl-3-yl)methyl]-4-(cyclohexylamino)-1-(3-fluorophenyl)-1,3,8-triazaspiro[4.5]dec-3-en-2-one;

4-(cyclohexylamino)-1-(3-fluorophenyl)-8-(3-hydroxy-benzyl)-1,3,8-triazaspiro[4.5]dec-3-en-2-one;

8-(3-tert-butoxybenzyl)-4-(cyclohexylamino)-1-(3-fluorophenyl)-1,3,8-triazaspiro[4.5]dec-3-en-2-one;

8-[3-(allyloxy)benzyl]-4-(cyclohexylamino)-1-(3-fluorophenyl)-1,3,8-triazaspiro[4.5]dec-3-en-2-one;

8-[3-(but-3-enyloxy)benzyl]-4-(cyclohexylamino)-1-(3-fluorophenyl)-1,3,8-triazaspiro[4.5]dec-3-en-2-one;

4-(cyclohexylamino)-8-(2,3-dihydro-1-benzofuran-7-ylmethyl)-1-(3-fluorophenyl)-1,3,8-triazaspiro[4.5]dec-3-en-2-one;

8-[3-(allyloxy)benzyl]-4-(cyclohexylamino)-1-phenyl-1,3,8-triazaspiro[4.5]dec-3-en-2-one;

4-(cyclohexylamino)-1-(3-fluorophenyl)-8-[3-(prop-2-ynyloxy)benzyl]-1,3,8-triazaspiro[4.5]dec-3-en-2-one;

4-(cyclohexylamino)-8-[3-(cyclopropylmethoxy)benzyl]-1-(3-fluorophenyl)-1,3,8-triazaspiro[4.5]dec-3-en-2-one;

4-(cyclohexylamino)-1-(3-fluorophenyl)-8-(3-propoxybenzyl)-1,3,8-triazaspiro[4.5]dec-3-en-2-one;

8-(3-sec-butoxybenzyl)-4-(cyclohexylamino)-1-(3-fluorophenyl)-1,3,8-triazaspiro[4.5]dec-3-en-2-one;

4-(cyclohexylamino)-1-(3-fluorophenyl)-8-[3-(2-methoxy-1-methylethoxy)benzyl]-1,3,8-triazaspiro[4.5]dec-3-en-2-one;

4-(cyclohexylamino)-1-(3-fluorophenyl)-8-[3-(pentyloxy)benzyl]-1,3,8-triazaspiro[4.5]dec-3-en-2-one;

4-(cyclohexylamino)-8-[3-(1-ethylpropoxy)benzyl]-1-(3-fluorophenyl)-1,3,8-triazaspiro[4.5]dec-3-en-2-one;

4-(cyclohexylamino)-1-(3-fluorophenyl)-8-[3-(trifluoromethoxy)benzyl]-1,3,8-triazaspiro[4.5]dec-3-en-2-one;

4-(cyclohexylamino)-1-(3-fluorophenyl)-8-[3-(1H-pyrrol-1-yl)benzyl]-1,3,8-triazaspiro[4.5]dec-3-en-2-one;

methyl 3-(3'-{[4-(cyclohexylamino)-1-(3-fluorophenyl)-2-oxo-1,3,8-triazaspiro[4.5]dec-3-en-8-yl]methyl}biphenyl-2-yl)propanoate;

4-(cyclohexylamino)-1-(3-fluorophenyl)-8-(2-furylmethyl)-1,3,8-triazaspiro[4.5]dec-3-en-2-one;

1-(3-fluorophenyl)-8-(3-isopropoxybenzyl)-4-(isopropylamino)-1,3,8-triazaspiro[4.5]dec-3-en-2-one;

8-[(6-bromopyridin-3-yl)methyl]-4-(cyclohexylamino)-1-(3-fluorphenyl)-1,3,8-triazaspiro[4.5]dec-3-en-2-one;

8-{[6-(Benzylamino)pyridin-3-yl]methyl}-4-(cyclohexylamino)-1-(3-fluorophenyl)-1,3,8-triazaspiro[4.5]dec-3-en-2-one;

tert-Butyl 5-{[4-(cyclohexylamino)-1-(3-fluorophenyl)-2-oxo-1,3,8-triazaspiro[4.5]dec-3-en-8-yl]methyl}pyridin-2-ylcarbamate;

8-[(6-aminopyridin-3-yl)methyl]-4-(cyclohexylamino)-1-(3-fluorophenyl)-2-oxo-1,3,8-triazaspiro[4.5]dec-3-ene;

4-(cyclohexylamino)-1-(3-fluorophenyl)-8-{[6-(isobutylamino)pyridin-3-yl]methyl}-1,3,8-triazaspiro[4.5]dec-3-en-2-one;

4-(cyclohexylamino)-1-(3-fluorophenyl)-8-{[6-(isopropylamino)pyridin-3-yl]methyl}-1,3,8-triazaspiro[4.5]dec-3-en-2-one;

8-{[6-(butylamino)pyridin-3-yl]methyl}-4-(cyclohexylamino)-1-(3-fluorophenyl)-1,3,8-triazaspiro[4.5]dec-3-en-2-one;

4-(cyclohexylamino)-1-(3-fluorophenyl)-8-({6-[(2-methoxyethyl)amino]pyridin-3-yl}methyl)-1,3,8-triazaspiro[4.5]dec-3-en-2-one;

4-(cyclohexylamino)-8-({6-[(cyclopropylmethyl)amino]pyridin-3-yl}methyl)-1-(3-fluorophenyl)-1,3,8-triazaspiro[4.5]dec-3-en-2-one;

4-(cyclohexylamino)-1-(3-fluorophenyl)-8-({6-[(3-phenylpropyl)amino]pyridin-3-yl}methyl)-1,3,8-triazaspiro[4.5]dec-3-en-2-one;

4-(cyclohexylamino)-1-(3-fluorophenyl)-8-{[2-(methylamino)pyridin-3-yl]methyl}-1,3,8-triazaspiro[4.5]dec-3-en-2-one;

4-(cyclohexylamino)-1-(3-fluorophenyl)-8-{[2-(isopropylamino)pyridin-3-yl]methyl}-1,3,8-triazaspiro[4.5]dec-3-en-2-one;

4-(cyclohexylamino)-1-(3-fluorophenyl)-8-({2-[(2-methoxyethyl)amino]pyridin-3-yl}methyl)-1,3,8-triazaspiro[4.5]dec-3-en-2-one;

4-(cyclohexylamino)-1-(3-fluorophenyl)-8-{[2-(isobutylamino)pyridin-3-yl]methyl}-1,3,8-triazaspiro[4.5]dec-3-en-2-one;

4-(cyclohexylamino)-8-({2-[(cyclopropylmethyl)amino]pyrid in-3-yl}methyl)-1-(3-fluorophenyl)-1,3,8-triazaspiro[4.5]dec-3-en-2-one;

4-(cyclohexylamino)-1-(3-fluorophenyl)-8-({2-[(3-phenylpropyl)amino]pyridin-3-yl}methyl)-1,3,8-triazaspiro[4.5]dec-3-en-2-one;

8-{[2-(sec-butylamino)pyridin-3-yl]methyl}-4-(cyclohexylamino)-1-(3-fluorophenyl)-1,3,8-triazaspiro[4.5]dec-3-en-2-one;

4-(cyclohexylamino)-8-({2-[(2,2-dimethylpropyl)amino]pyridin-3-yl}methyl)-1-(3-fluorophenyl)-1,3,8-triazaspiro[4.5]dec-3-en-2-one;

4-(cyclohexylamino)-8-{[2-(ethylamino)pyridin-3-yl]methyl}-1-(3-fluorophenyl)-1,3,8-triazaspiro[4.5]dec-3-en-2-one;

4-(cyclohexylamino)-8-{[2-(cyclopropylamino)pyridin-3-yl]methyl}-1-(3-fluorophenyl)-1,3,8-triazaspiro[4.5]dec-3-en-2-one;

4-(cyclohexylamino)-8-({2-[(2,2-difluoroethyl)amino]pyridin-3-yl}methyl)-1-(3-fluorophenyl)-1,3,8-triazaspiro[4.5]dec-3-en-2-one;

4-(cyclohexylamino)-8-{2-[(2,2-difluoroethyl)amino]benzyl}-1-(3-fluorophenyl)-1,3,8-triazaspiro[4.5]dec-3-en-2-one;

tert-Butyl 2-(3-{[4-(cyclohexylamino)-1-(3-fluorophenyl)-2-oxo-1,3,8-triazaspiro[4.5]dec-3-en-8-yl]methyl}phenoxy)propylcarbamate;

8-[3-(2-amino-1-methylethoxy)benzyl]-4-(cyclohexylamino)-1-(3-fluorophenyl)-1,3,8-triazaspiro[4.5]dec-3-en-2-one;

N-[4-(3-{[4-(cyclohexylamino)-1-(3-fluorophenyl)-2-oxo-1,3,8-triazaspiro[4.5]dec-3-en-8-yl]methyl}phenoxy)butyl]methanesulfonamide;

tert-butyl 3-(3-{[4-(cyclohexylamino)-1-(3-fluorophenyl)-2-oxo-1,3,8-triazaspiro[4.5]dec-3-en-8-yl]methyl}phenoxy)butylcarbamate;

8-[3-(3-amino-1-methylpropoxy)benzyl]-4-(cyclohexylamino)-1-(3-fluorophenyl)-1,3,8-triazaspiro[4.5]dec-3-en-2-one;

tert-butyl 2-(3-{[4-(cyclohexylamino)-1-(3-fluorophenyl)-2-oxo-1,3,8-triazaspiro[4.5]dec-3-en-8-yl]methyl}phenoxy)butylcarbamate;

8-{3-[1-(aminomethyl)propoxy]benzyl}-4-(cyclohexylamino)-1-(3-fluorophenyl)-1,3,8-triazaspiro[4.5]dec-3-en-2-one;

8-[3-(2-aminoethoxy)benzyl]-4-(cyclohexylamino)-1-(3-fluorophenyl)-1,3,8-triazaspiro[4.5]dec-3-en-2-one;

8-[3-(aminomethyl)benzyl]-4-(cyclohexylamino)-1-(3-fluorophenyl)-1,3,8-triazaspiro[4.5]dec-3-en-2-one;

8-(3-aminobenzyl)-4-(cyclohexylamino)-1-(3-fluorophenyl)-1,3,8-triazaspiro[4.5]dec-3-en-2-one;

N-(3-{[4-(cyclohexylamino)-1-(3-fluorophenyl)-2-oxo-1,3,8-triazaspiro[4.5]dec-3-en-8-yl]methyl}phenyl)acetamide;

N-(3-{[4-(cyclohexylamino)-1-(3-fluorophenyl)-2-oxo-1,3,8-triazaspiro[4.5]dec-3-en-8-yl]methyl}phenyl) methane sulfonamide;

4-(cyclohexylamino)-1-(3-fluorophenyl)-8-{3-[(2-methylpentyl)amino]benzyl}-1,3,8-triazaspiro[4.5]dec-3-en-2-one;

4-(cyclohexylamino)-1-(3-fluorophenyl)-8-[3-(isopropylamino)benzyl]-1,3,8-triazaspiro[4.5]dec-3-en-2-one;

4-(cyclohexylamino)-1-(3-fluorophenyl)-8-[2-(isopropylamino)benzyl]-1,3,8-triazaspiro[4.5]dec-3-en-2-one;

4-[(2-{[4-(cyclohexylamino)-1-(3-fluorophenyl)-2-oxo-1,3,8-triazaspiro[4.5]dec-3-en-8-yl]methyl}phenyl) amino]butanenitrile;

3-(3-{[4-(cyclohexylamino)-1-(3-fluorophenyl)-2-oxo-1,3,8-triazaspiro[4.5]dec-3-en-8-yl]methyl}phenyl)-2-methylpropanenitrile;

4-(cyclohexylamino)-1-(3-fluorophenyl)-8-[(6-isopropoxypyridin-2-yl)methyl]-1,3,8-triazaspiro[4.5]dec-3-en-2-one;

8-[(6-sec-butoxypyridin-2-yl)methyl]-4-(cyclohexylamino)-1-(3-fluorophenyl)-1,3,8-triazaspiro[4.5]dec-3-en-2-one;

1-(3-Fluorophenyl)-4-isobutylamino-8-(3-isopropoxy-benzyl)-1,3,8-triaza-spiro[4.5]dec-3-en-2-one;

1-(3-Fluorophenyl)-8-(3-isopropoxy-benzyl)-4-(2-methyl-cyclohexylamino)-2-oxo-1,3-diaza-8-azonia-spiro[4.5]dec-3-ene;

4-(1,2-Dimethyl-propylamino)-1-(3-fluorophenyl)-8-(3-isopropoxy-benzyl)-2-oxo-1,3-diaza-8-azonia-spiro[4.5]dec-3-ene;

4-(2-Fluoro-cyclohexylamino)-1-(3-fluorophenyl)-8-(3-isopropoxy-benzyl)-2-oxo-1,3-diaza-8-azonia-spiro[4.5]dec-3-ene;

4-Cycloheptylamino-1-(3-fluorophenyl)-8-(3-isopropoxy-benzyl)-2-oxo-1,3-diaza-8-azonia-spiro[4.5]dec-3-ene;

4-(Bicyclo[2.2.1]hept-2-ylamino)-1-(3-fluorophenyl)-8-(3-isopropoxy-benzyl)-2-oxo-1,3-diaza-8-azonia-spiro[4.5]dec-3-ene;

4-Cyclopentylamino-1-(3-fluorophenyl)-8-(3-isopropoxy-benzyl)-2-oxo-1,3-diaza-8-azonia-spiro[4.5]dec-3-ene;

1-(3-Fluorophenyl)-8-(3-isopropoxy-benzyl)-2-oxo-4-(tetrahydro-pyran-4-ylamino)-1,3-diaza-8-azonia-spiro[4.5]dec-3-ene;

4-Cyclobutylamino-1-(3-fluorophenyl)-8-(3-isopropoxy-benzyl)-2-oxo-1,3-diaza-8-azonia-spiro[4.5]dec-3-ene;

1-(3-Fluoro-phenyl)-8-(3-isopropoxy-benzyl)-2-oxo-4-(2-pyridin-4-yl-ethylamino)-1,3-diaza-8-azonia-spiro[4.5]dec-3-ene;

1-(3-Fluorophenyl)-4-(3-hydroxy-cyclohexylamino)-8-(3-isopropoxy-benzyl)-2-oxo-1,3-diaza-8-azonia-spiro[4.5]dec-3-ene;

1-(3-Fluorophenyl)-4-(1-hydroxymethyl-2-methyl-propylamino)-8-(3-isopropoxy-benzyl)-2-oxo-1,3-diaza-8-azonia-spiro[4.5]dec-3-ene;

1-(3-Fluorophenyl)-8-(3-isopropoxy-benzyl)-4-(3-methyl-butylamino)-2-oxo-1,3-diaza-8-azonia-spiro[4.5]dec-3-ene;

4-(Cyclopropylmethyl-amino)-1-(3-fluorophenyl)-8-(3-isopropoxy-benzyl)-2-oxo-1,3-diaza-8-azonia-spiro[4.5]dec-3-ene;

1-(3-Fluorophenyl)-8-(3-isopropoxy-benzyl)-4-(1-methanesulfonyl-pyrrolidin-3-ylamino)-2-oxo-1,3-diaza-8-azonia-spiro[4.5]dec-3-ene;

4-Benzylamino-1-(3-fluorophenyl)-8-(3-isopropoxy-benzyl)-2-oxo-1,3-diaza-8-azonia-spiro[4.5]dec-3-ene;

4-(1-Acetyl-pyrrolidin-3-ylamino)-1-(3-fluorophenyl)-8-(3-isopropoxy-benzyl)-2-oxo-1,3-diaza-8-azonia-spiro[4.5]dec-3-ene;

1-(3-Fluorophenyl)-8-(3-isopropoxy-benzyl)-2-oxo-4-(3-phenyl-propylamino)-1,3-diaza-8-azonia-spiro[4.5]dec-3-ene;

1-(3-Fluorophenyl)-4-(3-hydroxy-cyclohexylamino)-8-(3-isopropoxy-benzyl)-2-oxo-1,3-diaza-8-azonia-spiro[4.5]dec-3-ene;

4-(2-Dimethylcarbamoyl-ethylamino)-1-(3-fluorophenyl)-8-(3-isopropoxy-benzyl)-2-oxo-1,3-diaza-8-azonia-spiro[4.5]dec-3-ene;

4-(2-Fluoro-ethylamino)-1-(3-fluorophenyl)-8-(3-isopropoxy-benzyl)-2-oxo-1,3-diaza-8-azonia-spiro[4.5]dec-3-ene;

1-(3-Fluorophenyl)-4-[(furan-2-ylmethyl)-amino]-8-(3-isopropoxy-benzyl)-2-oxo-1,3-diaza-8-azonia-spiro[4.5]dec-3-ene;

1-(3-Fluorophenyl)-8-(3-isopropoxy-benzyl)-2-oxo-4-(2-thiophen-2-yl-ethylamino)-1,3-diaza-8-azonia-spiro[4.5]dec-3-ene;

1-(3-Fluorophenyl)-8-(3-isopropoxy-benzyl)-4-(2-methylsulfanyl-ethylamino)-2-oxo-1,3-diaza-8-azonia-spiro[4.5]dec-3-ene;

1-(3-Fluorophenyl)-8-(3-isopropoxy-benzyl)-4-(2-morpholin-4-yl-ethylamino)-2-oxo-1,3-diaza-8-azonia-spiro[4.5]dec-3-ene;

1-(3-Fluorophenyl)-4-[2-(1H-imidazol-4-yl)-ethylamino]-8-(3-isopropoxy-benzyl)-2-oxo-1,3-diaza-8-azonia-spiro[4.5]dec-3-ene;

1-(3-Fluorophenyl)-4-(1-hydroxymethyl-cyclopentylamino)-8-(3-isopropoxy-benzyl)-2-oxo-1,3-diaza-8-azonia-spiro[4.5]dec-3-ene;

1-(3-Fluorophenyl)-8-(3-isopropoxy-benzyl)-4-(2-methanesulfonyl-ethylamino)-2-oxo-1,3-diaza-8-azonia-spiro[4.5]dec-3-ene;

1-(3-Fluorophenyl)-8-(3-isopropoxy-benzyl)-2-oxo-4-phenylamino-1,3-diaza-8-azonia-spiro[4.5]dec-3-ene;

2'-[4-Cyclohexylamino-8-(3-isopropoxy-benzyl)-2-oxo-1,3,8-triaza-spiro[4.5]dec-3-en-1-yl]-4'-fluoro-biphenyl-4-sulfonic acid dimethylamide;

4-Cyclohexylamino-1-(3'-methoxy-biphenyl-2-yl)-8-(2'-methyl-biphenyl-3-ylmethyl)-2-oxo-1,3-diaza-8-azonia-spiro[4.5]dec-3-ene;

1-(4'-Cyano-biphenyl-2-yl)-4-cyclohexylamino-8-(2'-methyl-biphenyl-3-ylmethyl)-2-oxo-1,3-diaza-8-azonia-spiro[4.5]dec-3-ene;

1-(2-Cyano-phenyl)-4-cyclohexylamino-8-(3-isopropoxy-benzyl)-2-oxo-1,3-diaza-8-azonia-spiro[4.5]dec-3-ene;

1-(2-Bromo-5-fluorophenyl)-4-cyclohexylamino-8-(3-isopropoxy-benzyl)-2-oxo-1,3-diaza-8-azonia-spiro[4.5]dec-3-ene;

4-Cyclohexylamino-8-(3-isopropoxy-benzyl)-2-oxo-1-(2-phenylsulfanyl-phenyl)-1,3-diaza-8-azonia-spiro[4.5]dec-3-ene;

4-Cyclohexylamino-8-(3-isopropoxy-benzyl)-2-oxo-1-(3'-trifluoromethyl-biphenyl-2-yl)-1,3-diaza-8-azonia-spiro[4.5]dec-3-ene;

1-(2-Benzyl-phenyl)-4-cyclohexylamino-8-(3-isopropoxy-benzyl)-2-oxo-1,3-diaza-8-azonia-spiro[4.5]dec-3-ene;

1-(4'-Carboxy-biphenyl-2-yl)-4-cyclohexylamino-8-(3-isopropoxy-benzyl)-2-oxo-1,3-diaza-8-azonia-spiro[4.5]dec-3-ene;

4-Cyclohexylamino-8-(3-isopropoxy-benzyl)-2-oxo-1-(4'-trifluoromethoxy-biphenyl-2-yl)-1,3-diaza-8-azonia-spiro[4.5]dec-3-ene;

4-Cyclohexylamino-1-[2-(1H-indol-5-yl)-phenyl]-8-(3-isopropoxy-benzyl)-2-oxo-1,3-diaza-8-azonia-spiro[4.5]dec-3-ene;

1-[2-(5-Carboxy-thiophen-2-yl)-phenyl]-4-cyclohexylamino-8-(3-isopropoxy-benzyl)-2-oxo-1,3-diaza-8-azonia-spiro[4.5]dec-3-ene;

4-Cyclohexylamino-8-(3-isopropoxy-benzyl)-1-(4'-methylcarbamoyl-biphenyl-2-yl)-2-oxo-1,3-diaza-8-azonia-spiro[4.5]dec-3-ene;

4-Cyclohexylamino-8-(3-isopropoxy-benzyl)-1-[3'-(2-methyl-cyclopropylmethoxy)-biphenyl-2-yl]-1,3,8-triaza-spiro[4.5]dec-3-en-2-one;

1-(4'-Cyanomethyl-biphenyl-2-yl)-4-cyclohexylamino-8-(3-isopropoxy-benzyl)-2-oxo-1,3-diaza-8-azonia-spiro[4.5]dec-3-ene;

4-Cyclohexylamino-1-(4'-dimethylsulfamoyl-biphenyl-2-yl)-8-(3-isopropoxy-benzyl)-2-oxo-1,3-diaza-8-azonia-spiro[4.5]dec-3-ene;

4-Cyclohexylamino-8-(3-isopropoxy-benzyl)-1-(4'-isopropoxycarbonyl-biphenyl-2-yl)-2-oxo-1,3-diaza-8-azonia-spiro[4.5]dec-3-ene;

4-Cyclohexylamino-1-(4'-ethanesulfonyl-4-fluoro-biphenyl-2-yl)-8-(3-isopropoxy-benzyl)-2-oxo-1,3-diaza-8-azonia-spiro[4.5]dec-3-ene;

1-(4'-Ethanesulfonyl-4-fluoro-biphenyl-2-yl)-8-(3-isopropoxy-benzyl)-4-isopropylamino-2-oxo-1,3-diaza-8-azonia-spiro[4.5]dec-3-ene;

4-Cyclohexylamino-8-(3-isopropoxy-benzyl)-1-[4'-(methanesulfonylamino-methyl)-biphenyl-2-yl]-2-oxo-1,3-diaza-8-azonia-spiro[4.5]dec-3-ene;

4-Cyclohexylamino-1-[5-fluoro-2-(1-methyl-1H-pyrazol-4-yl)-phenyl]-8-(3-isopropoxy-benzyl)-1,3,8-triaza-spiro[4.5]dec-3-en-2-one;

4-Cyclohexylamino-1-(5-fluoro-2-pyridin-3-yl-phenyl)-8-(3-isopropoxy-benzyl)-2-oxo-1,3-diaza-8-azonia-spiro[4.5]dec-3-ene;

4-Cyclohexylamino-8-(3-isopropoxy-benzyl)-1-[2-(2-methanesulfonyl-acetylamino)-phenyl]-2-oxo-1,3-diaza-8-azonia-spiro[4.5]dec-3-ene;

4-Cyclohexylamino-8-(3-isopropoxy-benzyl)-1-[4-methanesulfonyl-benzoylamino)-phenyl]-2-oxo-1,3-diaza-8-azonia-spiro[4.5]dec-3-ene;

1-(4'-Ethanesulfonyl-4-fluoro-biphenyl-2-yl)-8-(3-isopropoxy-benzyl)-2-oxo-4-(tetrahydro-pyran-4-ylamino)-1,3-diaza-8-azonia-spiro[4.5]dec-3-ene;

4-Cyclohexylamino-1-(4-fluoro-4'-methylsulfamoyl-biphenyl-2-yl)-8-(3-isopropoxy-benzyl)-2-oxo-1,3-diaza-8-azonia-spiro[4.5]dec-3-ene;

4-Cyclopropylamino-1-(4'-ethanesulfonyl-4-fluoro-biphenyl-2-yl)-8-(3-isopropoxy-benzyl)-2-oxo-1,3-diaza-8-azonia-spiro[4.5]dec-3-ene;

4-Cyclohexylamino-1-[5-fluoro-2-(1-methanesulfonyl-1H-pyrazol-4-yl)-phenyl]-8-(3-isopropoxy-benzyl)-2-oxo-1,3-diaza-8-azonia-spiro[4.5]dec-3-ene;

Ethanesulfonic acid {2'-[4-cyclohexylamino-8-(3-isopropoxy-benzyl)-2-oxo-1,3,8-triaza-spiro[4.5]dec-3-en-1-yl]-4'-fluoro-biphenyl-4-yl}-amide;

4-Cyclohexylamino-1-[4-fluoro-4'-(pyrrolidine-1-sulfonyl)-biphenyl-2-yl]-8-(3-isopropoxy-benzyl)-2-oxo-1,3-diaza-8-azonia-spiro[4.5]dec-3-ene;

1-(4'-Dimethylsulfamoyl-4-fluoro-biphenyl-2-yl)-8-(3-isopropoxy-benzyl)-4-isopropylamino-2-oxo-1,3-diaza-8-azonia-spiro[4.5]dec-3-ene;

4-Cyclohexylamino-1-(5-fluoro-3'-trifluoromethanesulfonylamino-biphenyl-3-yl)-8-(3-isopropoxy-benzyl)-2-oxo-1,3-diaza-8-azonia-spiro[4.5]dec-3-ene;

1-[3'-(Butane-2-sulfonylamino)-5-fluoro-biphenyl-3-yl]-4-cyclohexylamino-8-(3-isopropoxy-benzyl)-2-oxo-1,3-diaza-8-azonia-spiro[4.5]dec-3-ene;

2'-[4-Cyclohexylamino-8-(3-isopropoxy-benzyl)-2-oxo-1,3,8-triaza-spiro[4.5]dec-3-en-1-yl]-4'-fluoro-biphenyl-3-sulfonic acid methylamide;

4-Cyclohexylamino-1-[4'-(1,1-dioxo-1,6-isothiazolidin-2-yl)-4-fluoro-biphenyl-2-yl]-8-(3-isopropoxy-benzyl)-1,3,8-triaza-spiro[4.5]dec-3-en-2-one;

4-Cyclohexylamino-8-(3-isopropoxy-benzyl)-1-[3-(5-methyl-[1,2,4]oxadiazol-3-yl)-phenyl]-2-oxo-1,3-diaza-8-azonia-spiro[4.5]dec-3-ene;

4-Cyclohexylamino-1-[3-(3,5-dimethyl-isoxazol-4-yl)-5-fluoro-phenyl]-8-(3-isopropoxy-benzyl)-2-oxo-1,3-diaza-8-azonia-spiro[4.5]dec-3-ene;

1-[3-(5-Carboxy-thiophen-2-yl)-5-fluorophenyl]-4-cyclohexylamino-8-(3-isopropoxy-benzyl)-2-oxo-1,3-diaza-8-azonia-spiro[4.5]dec-3-ene;

4-Cyclopentylamino-1-(4-fluoro-4'-methanesulfonyl-biphenyl-2-yl)-8-(3-isopropoxy-benzyl)-2-oxo-1,3-diaza-8-azonia-spiro[4.5]dec-3-ene;

4-sec-Butylamino-1-(4-fluoro-4'-methanesulfonyl-biphenyl-2-yl)-8-(3-isopropoxy-benzyl)-2-oxo-1,3-diaza-8-azonia-spiro[4.5]dec-3-ene;

1-[2-(4-Acetylamino-piperidin-1-yl)-5-fluorophenyl]-4-cyclohexylamino-8-(3-isopropoxy-benzyl)-2-oxo-1,3-diaza-8-azonia-spiro[4.5]dec-3-ene;

4-Cyclohexylamino-8-cyclopropylmethyl-1-(4'-dimethylsulfamoyl-4-fluoro-biphenyl-2-yl)-2-oxo-1,3-diaza-8-azonia-spiro[4.5]dec-3-ene;

4-Cyclohexylamino-8-(3-isopropoxy-benzyl)-1-(2-pyrazol-1-yl-phenyl)-1,3,8-triaza-spiro[4.5]dec-3-en-2-one;

N-{3'-fluoro-5'-[8-isobutyl-4-(isopropylamino)-2-oxo-1,3,8-triazaspiro[4.5]dec-3-en-1-yl]biphenyl-3-yl}-β-alaninamide[15-45]

2'-[4-(cyclohexylamino)-8-(cyclopropylmethyl)-2-oxo-1,3,8-triazaspiro[4.5]dec-3-en-1-yl]-4'-fluoro-N,N-dimethylbiphenyl-4-sulfonamide[15-46]

4-(cyclohexylamino)-8-(3-isopropoxybenzyl)-1-[3-(5-methyl-1,2,4-oxadiazol-3-yl)phenyl]-1,3,8-triazaspiro[4.5]dec-3-en-2-one; and N-(1-{2-[4-(cyclohexylamino)-8-(3-isopropoxybenzyl)-2-oxo-1,3,8-triazaspiro[4.5]dec-3-en-1-yl]-4-fluorophenyl}piperidin-4-yl)acetamide;

and pharmaceutically acceptable salts thereof.

* * * * *